(12) United States Patent
Mochly-Rosen et al.

(10) Patent No.: US 6,423,684 B1
(45) Date of Patent: *Jul. 23, 2002

(54) WD-40 DERIVED PEPTIDES AND USES THEREOF

(75) Inventors: Daria Mochly-Rosen, Menlo Park; Dorit Ron, San Francisco, both of CA (US)

(73) Assignee: The Board of Trustees of the Leland Stanford Junior University, Stanford, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/487,072

(22) Filed: Jun. 7, 1995

Related U.S. Application Data

(63) Continuation-in-part of application No. 08/190,802, filed on Feb. 1, 1994, now Pat. No. 5,519,003.

(30) Foreign Application Priority Data

Jan. 31, 1995 (WO) ................................. pct/us95/01210

(51) Int. Cl.⁷ .......................... A61K 38/16; A61K 38/00
(52) U.S. Cl. ................................ 514/7; 514/12; 435/4; 435/7.1; 435/7.8; 435/15; 435/194; 436/501; 530/300; 530/350; 530/352
(58) Field of Search .......................... 514/7, 12; 435/4, 435/7.1, 7.8, 15, 194; 436/501; 530/300, 350, 352

(56) References Cited

U.S. PATENT DOCUMENTS

| | | | |
|---|---|---|---|
| 5,283,173 A | 2/1994 | Fields et al. | 435/6 |
| 5,352,660 A | 10/1994 | Pawson | 514/12 |

FOREIGN PATENT DOCUMENTS

| | | |
|---|---|---|
| WO | WO 95/21252 | 1/1995 |

OTHER PUBLICATIONS

Dalrymple, M.A. et al., "The Product of the PRP4 Gene of *S. cerevisiae* Shows Homology to β Subunits of G Proteins," *Cell* 58: 811–812 (1989).

Dynlacht, B.D. et al., "The dTAF80 subunit of *Drosphila* TFIID contains β–transducin repeats," *Nature* 363: 176–179 (1993).

Fong, H.K.W. et al., "Repetitive segmental structure of the transducin β subunit: Homology with the CDC4 gene and identification of related mRNAs," *Proc. Natl. Acad. Sci. USA* 83:2162–2166 (1986).

Guillemot, F. et al., "Physical linkage of a guanine nucleotide–binding protein–related gene to the chicken major histocompatibility complex," *Proc. Natl. Acad. Sci. USA* 86: 4594–459 (1989).

Keleher, C.A. et al., "Ssn6–Tup 1 Is a General Repressor of Transcription in Yeast," *Cell* 68: 709–719 (1992).

Mochly–Rosen, D. et al., "Identification of intracellular receptor proteins for activated protein kinase C," *Proc. Natl Acad. Sci USA* 88: 3997–4000 (1991).

Mochly–Rosen, D. et al., "Intracellular Receptors for Activated Protein Kinase C," *J. Biol. Chem* 266(23): 14866–14868 (1991).

Peitsch, M.C. et al., "Sequence similarity of phospholipase A2 activating protein and the G protein β–subunits: a new concept of effector protein activation in signal transduction?," *TIBS* 18(8): 292–293 (1993).

Smith, B.L. and Mochly–Rosen, D., "Inhibition of Protein Kinase C Function by Injection of Intracellular Receptors for the Enzyme," *Biochem. Biophys. Res. Comm.* 188(3): 1235–1240 (1992).

Takagaki, Y. and Manley, J.L., "A Human Polyadenylation Factor Is a G Protein β–subunit Homologue," *J. Biol. Chem* 267(33): 23471–23474.

van der voorn, L. and Ploegh, H.L., "The WD–40 repeat," *FEBS Lett.* 307(2): 131–134 (1992).

Williams, F.E. and Trumbly, R.J., "Characterization of TUP1, a Mediator of Glucose Repression in *Saccharomyces cerevisiae*," *Mol. Cell. Biol.* 10(12): 6500–6511 (1990).

Williams, F.E. et al., "The CYC8 and TUP1 Proteins Involved in Glucose Repression in *Saccharomyces cerevisiae* Are Associated in a Protein Complex," *Mol. Cell. Biol.* 11(6): 3307–3316 (1991).

Ron, D. et al. "An Autoregulatory Region in Protein Kinase C: The Pseudoanchoring Site" *Proc. Natl. Acad. Sci. USA* 92:492–496 (1995).

Ron, D. et al. "Agonists and Antagonists of Protein Kinase C Function, Derived from its Binding Proteins" *J. Biol. Chem.* 269:21395–21398 (1994).

(List continued on next page.)

*Primary Examiner*—Lisa J. Hobbs
(74) *Attorney, Agent, or Firm*—Morrison & Foerster LLP

(57) ABSTRACT

The present invention relates to a polypeptide composition effective to alter the activity of a first protein that interacts with a second protein, where the second protein contains at least one WD-40 region. The polypeptides of the present invention typically have between 4 and 50 amino acids whose sequence is the same as a sequence of the same length in the WD-40 region of the second protein. The invention further includes a method of altering the activity of the above described first protein. In one embodiment of the invention the polypeptide composition is effective to alter the activity of a protein kinase C, where the protein kinase C interacts with a second protein, and the second protein contains at least one WD-40 region (e.g., RACK1).

13 Claims, 54 Drawing Sheets

OTHER PUBLICATIONS

Ron, D. et al. "Cloning of an Intracellular Receptor for Protein Kinase C: A Homolog of the Beta Subunit of G Proteins" *Proc. Natl. Acad. Sci. USA* 91:839–843 (1994).

Ruggieri, R., et al. "MSI1, a Negative Regulator of the RAS–cAMP Pathway in Saccharomyces Cerevisiae" *Proc. Natl. Acad. Sci. USA* 86:8778–8782 (1989).

Tamaki, M. et al. "Rat Lipocortin I cDNA" *Nucleic Acids Res.* 15:7637 (1987).

Weinstat–Saslow et al., "Transnducin–like Gene Maps to the Autosomal Dominant Polycystic Kidney Disease Gene Region" *Genomics* 18:709–711 (1993).

Wallner, B., et al. "Cloning and Expression of Human Lipocortin, a Phospholipase A2 Inhibitor with Potential Anti–Inflammatory Activity" *Nature* 320:77–81 (1986).

Derwent Publications Ltd., AN 94–026226 (1994).

Mochly–Rosen et al. (1991) Intracellular Receptors for Activated Protein Kinase C: Identification of a Binding Site for the Enzyme. J. Biol. Chem. 266(23): 14866–14868.* van der Voorn et al. (1992) The WD–40 Repeat. FEBS Letters 307(2): 131–134.*

* cited by examiner

```
     1  GGCACGAGGG  GTCGCGGTGG  CAGCCGTGCG  GTGCTTGGCT  CCCTAAGCTA  TCCGGTGCCA
    61  TCCTTGTCGC  TGCGGCGACT  CGCAACATCT  GCAGCCATGA  CCGAGCAAAT  GACCCTTCGT
   121  GGGACCCTCA  AGGGCCATAA  TGGATGGGTT  ACACAGATCG  CCACCACTCC  GCAGTTCCCG
   181  GACATGATCC  TGTCGGCGTC  TCGAGACAAG  ACCATCATCA  TGTGGAAGCT  GACCAGGAT
   241  GAGACCAACT  ACGGCATACC  ACAACGTGCT  CTTCGAGGTC  ACTCCCACTT  TGTTAGCGAT
   301  GTTGTCATCT  CCCTGATGG  CCAGTTTGCC  CTCTCAGGCT  CCTGGGATGG  AACCCTACGC
   361  CTCTGGGATC  TCACAACGGG  CACTACCACG  AGACGATTTG  TCGGCCACAC  CAAGGATGTG
   421  CTGAGCGTGG  CTTTCTCCTC  TGACAACCGG  CAGATTGTCT  CTGGGTCCCG  AGACAAGACC
   481  ATTAAGTTAT  GGAATACTCT  GGGTGTCTGC  AAGTACACTG  TCCAGGATGA  GAGTCATTCA
   541  GAATGGGTGT  CTTGTGTCCG  CTTCTCCCCG  AACAGCAGCA  ACCCTATCAT  CGTCTCCTGC
   601  GGATGGGACA  AGCTGGTCAA  GGTGTGGAAT  CTGGCTAACT  GCAAGCTAAA  GACCAACCAC
   661  ATTGGCCACA  CTGGCTATCT  GAACACAGTG  ACTGTCTCTC  CAGATGGATC  CCTCTGTGCT
   721  TCTGGAGGCA  AGGATGGCCA  GGCTATGCTG  TGGGATCTCA  ATGAAGGCAA  GCACTTTTAC
   781  ACATTAGATG  GTGGAGACAT  CATCAATGCC  TTGTGCTTCA  GCCCCAACCG  CTACTGGCTC
   841  TGTGCTGCCA  CTGGCCCCAG  TATCAAGATC  TGGGACTTGG  AGGGCAAGAT  CATGGTAGAT
   901  GAACTGAAGC  AAGAAGTTAT  CAGCACCAGC  AGCAAGGCAG  AGCCACCCCA  GTGTACCTCT
   961  TTGGCTTGGT  CTGCTGATGG  CCAGACTCTG  TTTGCTGGCT  ATACCGACAA  CTTGGTGCGT
  1021  GTATGGCAGG  TGACTATTGG  TACCCGCTAA  AAGTTTATGA  CAGACTCTTA  GAAATAAACT
  1081  GGCTTTCTGA  AAAAAAAAAA  AAAAAAAAAA  AAAAA
```

Fig. 1A

```
Rat RACK1    MTEQMTLRGTLKGHNGWVTQ IATTPQFPDMILSASRDKTIIMWKLTRDETN(51)        RepeatI
             YGIPQRALRGHSHFVS  DVVISSDGQFALSGGSWDGTLRLWDLT(93)               RepeatII
             TGTTTRRFVGHTKDVL  SVAFSSDNRQIVSGSRDKTIKLWNTLG(136)              RepeatIII
             VCKYTVQDESHSEWVSCVRFSPNSSNPIIVSCGWDKLVKVWNLA(180)               RepeatIV
             NCKLKTNHIGHTGYLN  TVTVSPDGSLCASGGKDGQAMLWDL(221)                RepeatV
             NEGKHLYTLDGGDII   NALCFSPNRYWLCAATGPSIKIWDLEGKIIVDE(269)        RepeatVI
             LKQEVISTSSKAEPPQCTSLAWSADGQTLFAGYTDNLVRVWQVTIGTR(317)           RepeatVII Consensus sequence of repeats:
Rat RACK1        GHS--V----V--SSD----ILSG--D-TIKLW-L
Human Gβ2        GH---I----SVA---DG--LVTGS-D--C-IWDL
```

Fig. 1C rVI rVI
PL, Ca peptide I peptide I
PL, Ca control
peptide
PL, Ca

10μmole  5μmole  1μmole  0.5μmole

Fig. 11

Human 56 kDa protein (PWP homolog)

```
  1 mnrsrqvtcv awvrcgvake tpdkvelske evkrliaeak eklqeeggqs
 51 deeetgspse dgmqsartqa rprepledgd peddrtlddd elaeydldky
101 deecdpdaet lgesllgltv ygsndqdpyv tlkdteqyer edflikpsdn
151 livcgraeqd qcnlevhvyn qeedsfyvhh dillsaypls vewlnfdpsp
201 ddstgnyiav gnmtpvievw dldivdslep vftlgsklsk kkkkkgkkss
251 saeghtdav ldlswnkl         irnvld sasadntvilwdmslgk
291 paaslavhtd kvqtlqfhpf eaqtlisgsy dksvalydcr
331 spdeshrmwr fsgqiervtw 351 nhfspchfla stddgfvynl darsdkpift
381 lnahndeis gldlssqi        kgclvt asadkyvkiwdilgdrp
421 slvhsrdmk mgvlfcssccpdlpfiyafg gqkegl rvwdi
461 stvssvneaf grrerlvlgs arnssisgpf gsrssdtpme
501 s
```

AAC-RICH protein

```
  1  pggfqhlqqq qqqqqqqqqq qqqqqqqqtq vqqlhnqlhq qhnqqiqqqa
 51  qatqqhlqtq qylqsqihqq sqqsqlsnnl nsnskestni pktntqytnf
101  dsknldlasr yfsecstkdfi
122  gnkkkstsvawnangtkia   sbsgsdgivrvwnfd
155  plgnsnnnnnsnntss nsknnniketi
182  eikghdgsiekiswspknndlla  sbgtdkvikiwdvkigkcigtvstnsenid
235  vrwspdgdhlalidlptiktlkiykfn  geelnqvgwdnngdlilmansmgnieaykf
301  lpkstthvkhlktlyghtas iycmefdptg kylaagsadsivslwdiedm
351  mcvktfikst fpcrsvsfsf dgqfiaassf estieifhie
411  ssqpihtiecgvsslmwhptlpllayapesinennkdpsi rvfgyhs
```

Fig. 12

BETA TRCP

```
  1 megfscslqp ptaseredcn rdepprkiit ekntlrqtklangtssmivp
 51 kqrklsanye kekelcvkyf eqwsecdqve fvehlisrmchyqhghinty
101 lkpmlqrdfi talpargldh iaenilsyld akslcsaelv ckewyrvtsd
151 gmlwkklier mvrtdslwrg laerrgwgqy lfknkppdgk tppnsfyral
201 ypkiiqdiet iesnwrcgr
```

| | | | |
|---|---|---|---|
| 220 | hslqr<u>ih</u>cr | se tskgvyclqyddq | kivsglr<u>dntikiwd</u>kn tleckrv |
| 268 | lm<u>gh</u>tg | svlclqy | de rviitgs<u>dstvrvwdv</u>ntgem |
| 305 | lntl<u>ih</u>hce | avlhlrfnngmmvtcsk | dr<u>siavwdm</u>asatditlrrv |
| 351 | lv<u>gh</u>raa | vnv vdfddkyivs | asg<u>drtikvwn</u>tstcefvrt |
| 391 | ln<u>gh</u>krg | iaclqyrdrlvvs | gss<u>dntirlwdi</u>ecga |
| 427 | clrv le<u>gh</u>eel | vrc irfdnkrivs | gaydgk<u>ikvwdl</u>vaaldprapagt |
| 475 | lclrtlve<u>h</u>sgr | yfrl qfdefqi | vssshd<u>dt iliwdf</u>lndpgla |

Fig. 13 beta-prime-cop

```
    vks vdihptepwmlaslyngsvcvwnhetqtlv
 51 ktfevcdlpv raakfvarkn wvvtgaddmqirvfnyntle
```

```
 91  rvhmfeahsdyirciavhptqp     filtssddmliklwdwdkkwscsq 137  vfeghthyvmqivinpkdnnqfas   asldrtikvwqlgssspnft 181  leghekgvncidyysggdkpyl     isgaddrlvkiwdyqnkt 221  cvqtleghaq  hvscasfhpe     lpliitgsedgtvriwhsst
```

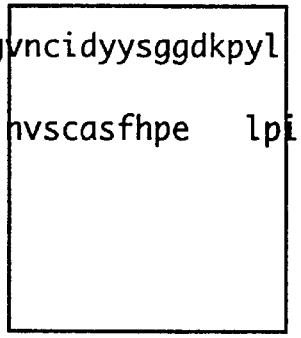

```
262 yrlestlnyg mervwcvasl rgsnnvalgy degsiivklgreepamsmda
318 ngkiiwakhs evqqanlkam gdaeikdger lplavkdmgs
351 ceiypqtiqh npngrfvvvc gdgeyiiyta malrnksfgs aqefawahds
401 seyairesns vvkifknfke kksfkpdfga esiyggfllg vrsvnglafy
451 dwentelirr ieiqpkhifw sdsgelvcia teesffilky lsekvlaaqe
501 thegvtedgi edgfevlgei qeivktglvv gdcfiytssv nrlnyyvgge
551 ivtiahldrt myllgyipkd nrlylgdkel nivsysllvs vleyqtavmr
601 rdfsmadkvl ptipkeqrtr vahflekqgf kqqaltvstd pehrfelalq
651 lgelkiayql aveaeseqkwkqlaelaisk cpfglaqecl hhaqdyggll
701 llatasgnas mvnklaegae rdgknnvafm syflqgklda clellirtgr
751 lpeaaflart ylpsqvsrvv klwrenlskv nqkaaeslad pteyenlfpg
801 lkeafvveew vkethadlwp akqyplvtpn eernvmeeak gfqpsrsaaq
851 qeldgkpasp tpvivtsqta nkeeksllel evdldnleie didttdinld
901 edildd
```

Fig. 14

CDC4 / CDC20 protein

```
  1 mgsfplaefp lrdipvpysy rvsggiassg svtalvtaag thrnsstakt
 51 vetedgeedi deyqrkraag sgestpersd fkrvkhdnhk tlhpvnlqnt
101 gaasvdndgl hnltdisnda ekllmsvddg saapstlsvn mgvashnvaa
151 pttvnaatit gsdvsnnvns atinnpmeeg alplsptass pgtttplakt
201 tktinnnnni adlieskdsi ispeylsdei fsainnnlph ayfknllfrl
251 vanmdrsels dlgtlikdnl krdlitslpf eislkifnyl qfediinslg
301 vsqnwnkiir kstslwkkll isenfvspkg fnslnlklsq kypklsqqdr
351 lrlsflenif ilknwynpkf
```

371        vpqrttlrgh mtsvitclqf     ednyvitgaddkmirvydsi 411        nkkfllqlsghdggvwalkyahg    gilvsgstdrtvrvwdi 451        kkgccthvfe ghnstvrcld iveyknikyi vtgsrdntlhvwklpkessvpdhgeehdyp 511  lvfhtpeenp yfvgvlrghmasvrtvsghg    nivvsgsydntlivwdvaqm 561            kclyilsghtdriystiydh erkrcisasmdttiriwdleniwnngecsyatnsasp 618       cak ilgamytlqghtalvgllrl    sdkflvsaaadgsirgwdan

```
661 dysrkfsyhh tnlsaittfy vsdnilvsgs enqfniynlr
701 sgklvhanil kdadqiwsvn fkgktlvaav ekdgqsflei ldfskaskin
751 yvsnpvnsss sslesistsl gltrttiip
```

Fig. 15

GBLP -CHLAMIDOMONAS HOMOLOG

```
1   maetltlratlkghtnwvtaiatpldpssntllsasrdksvlvwelerse 51  snygyarkalrghshfvddvvi  ssdgqfcltgswdgtlrlwdlntgtttr 101         rfvghtkdvlsvafs  vdnrqivsgsrdktiklwntlgeck 141       ytigepeghtewvscvrfspmttnpiivsggwdkmvkvwnlt 183   ncklknnlvghhgyvntvtv  spdgslcasggkdgiamlwdlaegkrly 231       sldagdvihclcfspnryw  lcaatqssikiwdlesksivddl 273     rpefnitskkaqvpycvslawsadgstlysgytdgqirvwavghsl
```

Fig. 16 cop-1 protein

```
1   meeistdpvv pavkpdprts svgeganrhe nddggsggse igapdldkdl
51  lcpicmqiik dafltacghs fcymciithl rnksdcpccs qhltnnqlyp
101 nflldkllkk tsarhvskta spldqfreal qrgcdvsike vdnlltllae
151 rkrkmeqeea ernmqilldf lhclrkqkvd elnevqtdlq yikedinave
201 rhridlyrar drysvklrml gddpstrnaw pheknqigfn snslsirggn
251 fvgnyqnkkv egkaqgsshg lpkkdalsgs dsqslnqstv smarkkriha
301 qfndlqecy'. qkrrqladqp nskqendksv vrregysngl adfqsvlttf
351 trysrlrvia eirhgdifhs anivssiefd rddelfatagvsrcikvfdf
```

401 ssvvnepadmqcpivemstrskls<u>d</u>lswnk heknhh<u>iassd</u>yegi<u>vtvwdv</u>

451 ttrqslmeteenekraws<u>v</u>df srte psmlv<u>sasdd</u>c k<u>vkvw</u>ctrqeasvi 501 nidmkanicc vkynpgssny iavgsadhhi 531 hyydlrnisqplhvfs<u>gh</u>kka<u>v</u>sy<u>m</u>kflsnnelas<u>d</u>st ds tl<u>rlwdv</u>

```
551 kdn lpvrtfrght neknfvgltvnseylacgse
601 ttryvyhkei trpvtshrfg spdmddaekr qvptllvrfa
651 grvivprc
```

Fig. 17

CORO PROTEIN

```
  1  mskvvrsskyrhvfabqpkkeecyqnlktk      savwdsnyvaantryiwdaagggsfa
 61  veaiphsgktTsvplfnghksavldiafh    pfnenlvgsvsedcniciwgip
111  eggltdsist plqtlsghkr kvgtisfgpv     adnvavtssgdflvktwdve
161  qgknlttveghsdmitscehngsqivtt                     ckdkkarvfd
201  prtnsivnev vchqgvknsr aifakdkvit vgfsktsere lhiydpraft
251  tplsaqvvds asgllmpfyd adnsilylag kgdgniryye lvdespyihf
301  lsefksatpq rglcflpkrc lntseceiar glkvtpftve pisfrvprks
351  difqgdiypd tyagepslta eqwsgtnae  pktvslaggf vkkasavefk
401  pvvqvqegpk nekelreeye klkirvayle seivkkdaki keltn
``` fgv

Fig. 18

Coronin (p55)

1 mskvvrsskyrhvfaaqpkkeecyqnlkvtksawdsnyvaantryfgviwdaagggsfav 61 ipheasgkttsvplfnghksdvldiafhpfnenlvgsvsedcniciwgipeggltdsist 121 plqtlsghkrkvgtisfgpvadnvavtssgdflvktwdve 161 qgknlttveghsdmitscewn hngsqivttckdkkarvfdprtnsivnev 211 vchqgvknsr aifakdkvit vgfsktsere lhiydpraft 251 tplsaqvvds asgllmpfyd adnsilylag kgdgniryye lvdespyihf 301 lsefksatpq rglcflpkrc lntseceiar glkvtpftve pisfrvprks 351 difqgdiypd tyagepslta eqwsgtnae pktvslaggf vkkasavefk 401 pvvqvqegpk nekelreeye klkirvayle seivkkdaki keltn

Fig. 19

CSTF 50kDa 1    myrtkvglkd rqqlykliis qllydgyisi anglineikp qsvcapseql 51   lhliklgmen ddtavqyaig rsdtvapgtg idlefdadvq tmspeaseye 101  tcyvtshkgp crvatysrdg qliatgsada sikildterm laksampiev 151  mmnetaqqnm 201  enhpvirtly<u>dh</u>vde<u>y</u>tclafhpte qilas<u>g</u>sr<u>d</u>ytlkl<u>fd</u>yskpsakra 210 fkyiqeaeml rsisfhpsgd filvgtqhpt lrlydintfqcfvsc 256       npqd<u>ah</u>tda icsvnyns sanmyvt<u>g</u>skdgcik<u>lwd</u>gvsnrcittf 3                                  0                                              1 ekahdgaevcsaifsknskyil ssgk<u>d</u>svak<u>lwe</u>istg rtlvrytgagls 351       grq<u>vh</u>rtq<u>a</u>vfnhte    dyvllp<u>d</u>ertislcc<u>wd</u>srtaerrn 391       llsl<u>gh</u>nnivrcivh sptnpgfmtcsd<u>d</u>frarf<u>wy</u>rrstt d

Fig. 20

G-Beta 1 bovine 1 mseldqlrqe aeqlknqird arkacadatl sqitnnidpv griqmrtrrt 51            lrghlakiya mhwgtdsrll vsasqdgkliiwds 85 yttnkvhaiplrsswvmtcayapsgnyvacggldnicsiynlktregnvrvsrela 141        ghtgylsccrfldd    nqivtssgdttcalwdietg
174    qqttttftghtgdvmslslap    dtrlfvsgacdasaklwdvregmcrq
221       tftghesdin aicffpngna  fatgsddatcrlfdlradqe
261       lmtyshdnicgitsvsfsksgrlllagyddfncnvwdal kadrag
307       vlaghdnrvsclg   vtddgmavatgswdsflkiwn

Fig. 21

G-Beta- bovine (2)

1    rnqirdarka cgdstltqit agldpvgriq 31   mrtrrtlrghla kiyamhwgtdsr    llvsa sqdgkli iwds 71   egnvryttnkvhaiplrsswvmtcayapsgnfvacggldnicsiyslktr 121  vsrelpghtg ylsccrfldd       nqiits sgdttcalwdietg
161  qqtvgfaghsg dvmslslap       dgrtfvsg acdasiklwdvr
201  dsmcrqtfighes dinavaffp     ngyafttg sddatcrlfdlradq
246  ellmyshdn iicgitsvafsrsgrlllag yddfncniwdamkgdr
291  agvlaghdn rvsclgvt          ddgmavatg swdsflkiwn

Fig. 22

G- BETA DROSOPH 1 mneldslrqe aeslknaird arkaacdtsllqaatslepigriqmrtrrt 51 lrghlak:yamhwgn dsrnlvsasqdgkli vwdshttnkv 91 haiplrsswvmtcayapsgsyvacggldnmcsiynlktregnvr 135 vsrelpghggylsccrfl ddnqivtssgdmscglwdietglqv
178 tsflghtgdvmalsla pqcktfvsgacdasaklwdiregvckq
221 tfpghesdinavtf ⁻pngqafdtgsddatcrlfdiradqe
261 lamyshdnii:cgitsvafsksgrlllagyddfncnvwdtm
301 kaersgilaghdnrvsclg vtengmavdtgswdsflrvwn

Fig. 23

G-BETA HUMAN

```
1   mteqmtlrgtlkghngwvtqiattp        qfpdmilsasrdktiimwkltrdet
51  nygipqralr ghshfvsdvvi    ssdgqfalsgswdgtlrlwdlttgtttrr
101            fvghtkdvlsvaf  ssdnrqivsgsrdktiklwntlgvcky
141         tvqdeshsewvscvrfsp nssnpiivscgwdklvkvwnla nc
183         klktnhightgylntvtv spdgslcdsggkdgqamlwdl
222             negkhlytldggdiinalcfspnrywlcaatgpsikiwdlegkiivdel
271 kqevistsskaeppqctslawsad        gqtlfpgytdnlvrvwqvtigtr
```

Fig. 24

G-Beta 2 (Human)

```
1   mseleqlrqe aeqlrnqird arkacgdstl tqitagldpv griqmrtrrt 51              lrghlakiya mhwgtds  rllvsasqdgkliiwdsyt 97  tnkvhaiplrsswvmtcayapsgnfvacggldnicsiyslktre 151             gnvrvsrelpghtgylsccrfl    ddnqiitssgdttcalwdietgqqtvgf
201             aghsgdvmslslap    dgrtfvsgdcdasiklwdvrdsmcrq
241             tfighesdinavaffpn    gyafttgsddatcrlfdlradqe
281             llmyshdniicgitsvafsrsgrlllagyddfncniwdam
321             kgdragvlaghdnrvsclgvtddgm    avatgswdsflkiwn
```

Fig. 25

G-Beta 4 (mouse)

1   mseleqlrqeaeqlrnqiqdarkacndatlvqitsnmdsv griqmrtrrt 51   lr<u>gh</u>lak|iyamhwgydsr    llvsa|s<u>q</u>dgkli<u>iwd</u>syttnkm 91   haiplrsswvmtcayapsgnyvacggldnicsiynlktregdvrvsrela 141   <u>gh</u>tgyl|sccrflddg    qiits|sg<u>d</u>ttca<u>lwdi</u>etgqqtttf
181   tg<u>h</u>sgdv|mslslspd    lktfvsg|ac<u>d</u>assk<u>lwdi</u>rdgmcrq
221   sft<u>gh</u>isdi|navsffpsg    yafatg|s<u>dd</u>atcrl<u>fd</u>lradqe
261   llly<u>sh</u>dnii|cgitsvafsksgrlllag|y<u>dd</u>fncs<u>vwd</u>alkggrs
306   gvla<u>gh</u>dnrv|sclgv    tddgmavatg|sw<u>d</u>sflr<u>iwn</u>

Fig. 26

GROUCHO PROTEIN DROSOPH

```
  1 mypspvrhpa aggpppqgpi kftiadtler ikeefnflqa hyhsiklece
 51 klsnektemq rhyvmyyems yglnvemhkq teiakrlntl inqllpflqa
101 dhqqqvlqav erakqvtmqe lnliigqqih aqqvpggppq pmgalnpfga
151 lgatmglphg pqgllnkppe hhrpdikptg legpaaaeer lrnsvspadr
201 ekyrtrspld iendskrrkd eklqedegek sdqdlvvdva nemeshsprp
251 ngehvsmevr dreslngerl ekpsssgikq erppsrsgss ssrstpslkt
301 kdmekpgtpg akartptpna aapapgvnpk qmmpqgpppa gypgapyqrp
351 adpyqrppsd paygrpppmp ydphahvrtn giphpsaltg gkpaysfhmn
401 gegslqpvpf ppdalvgvgi prharqintl shgevvcavt isnptkyvyt
451 ggkgcvkvwdisqpgnknpv sqldclqrdn yirsvkllpdgrtlivggea
501 snlsiwdlas
```

```
511    ptpri kaeltsaapacyal aspdskvcfsccsdgniavwdl 553    hneilvrqfqghtdgascidispdgsrlwtggldntvrswdlregrql
```

```
601 qqhdfssqif slgycptgdwlavgmenshv evlhaskpdk yqlhlhescv
651 lslrfaacgkwfvstgkdnl lnawrtpyga sifqsketss vlscdistdd
701 kyivtgsgdk katvyeviy
```

Fig. 27

GTP binding protein (squid)

1 mtselealrqeteqlknqirearkaaadttlamatanvepvgriqmrtrr 51 tlrghlaki|yamhwasd    srnlvs|sqdgklivwdgyttnk 91 vhaiplrssw vmtcayapsg nyvacggldn icsiyslktr egnvrvsrel 141 pghtgyl|sccrfid    dnqivt|sgdmtcalwnietgnqits
181 fgghtgdv|mslslapd    mrtfvs|gacdasaklfdirdgick
221 qtftghesdi|naityfpn    gfafat|gsddatcrlfdiradq
261 eigmyshdnii|cgitsvafsksgrlllggyddfncnvwdv
301 lkqeragvlaghdnrv|scl    gvtedgmavatgswdsflkiw n

Fig. 28

IEF SSP 9306

1 madkeaafdd aveervinee ykiwkkntpf lydlvmthal ewpsltaqwl
51 pdvtrpegkd fsihrlvlgt htsdeqnhlv iasvqlpndd aqfdashyds
101 ekgefggfgs vsgkieieik inhegevnra rympqnpcii atktpssdvl
151 vfdytkhpsk pdpsgecnpd 171 lrlrghqkeg yglswnpnlsg hllsasddhticlwdisav pkegkvvdak 221 tiftghtavv edvswhllhe slfgsvaddqklmiwdtrsn 261 ntskpshsvdahtaevnclsfnpysefilatgsadktvalwdlrnl 307 klklhsfeshkdeifqvqwsphnetilassgtdrrlnvwdls 351 kigeeqspedaedgppellfihgghtakisdf swnpne 387 pwvicsvsednimqvwqmelvldh

Fig. 29

HUMAN 12.3

```
1   mteqmtlrgtlkghngwvtqiattpqfpdm        ilsasrdktiimwkltrdet
51  nygipqralrghshfvsdvvissdgq            falsgswdgtlrlwdltt
95  gtttrrfvghtk dvlsvafssdn              rqivsgsrdktiklwntlg
137 vcky tvqdeshsewvscvrfspn              ssnpiivscgwdklvkvwnla
181 ncklktnhightgylntvtvs                 pdgslcdsggkdgqamlwdln
222        egkhlytldggdii  nalcfspnrywlcaatgpsikiwdle
263 gkiivdelkqevistsskaeppqctslawsadgqtlfpgytdnlvrvwqvtigtr
```

Fig. 30

IEF -7442 - human 1 maskemfedt veervineey kiwkkntpfl ydlvmthalq wpsltvqwlp 51 evtkpegkdy alhwlvlgth tsdeqnhlvv arvhipndda qfdashcdsd 101 kgefggfgsv tgkieceiki nhegevnrar ympqnphiia tktpssdvlv 151 fdytkhpakp dpsgecnpdl 171 rlrghqkegyglswnsnlsghllsasddhtvclwdinagpkegkivdaka
221 iftghsavvedvawhllheslfgsvaddqklmiwdtrsnt
261 tskpshlvdahtaevnclsfnpysefilatgsadktvalwdlrnlklklh
311 tfeshkdeifqvhwsphneti            lassgtdrrlnvwdlskigeeqsaedaed
361 gppellfihgghtakisdfswnpnepwvicsvsednimqiwqmaeniynd 411 eesdvttsel egqgs

Fig. 31 insulin-like growth factor binding protein complex

```
  1 malrkgglal allllswval gprslegadp gtpgeaegpa cpaacvcsyd
 51 ddadelsvfc ssrnltrlpd gvpggtqalw ldgnnlssvp paafqnlssl
101 gflnlqggql gslepqallg lenlchlhle rnqlrslalg 141 tfahtpalaslglsnnrlsrledglfeglgslwdlnlgwn slavlpdaaf
    rglgslrelv 201 lagnrlaylq palfsglael reldlsrnal raikanvfvq lprlqklyld
251 rnliaavapg aflglkalrw ldlshnrvag lledtfpgll glrvlrlshn
301 aiaslrprtf kdlhfleelq lghnrirqla ersfeglgql evltldhnql
351 qevkagaflg ltnvavmnls gnclrnlpeq vfrglgklhs lhlegsclgr
401 irphtftgls glrrlflkdn glvgieeqsl wgiaelleld ltsnqlthlp
451 hrlfqglgkl eylllsrnrl aelpadalgp lqrafwldvs hnrlealpns 501 llaplgrlry lslrnnslrt ftpqppgler lwlegnpwdc gcplkalrdf
551 alqnpsavpr fvqaicegdd cqppaytynn itcasppevv gldlrdlsea
601 hfapc
```

Fig. 32 insulin like growth factor binding protein complex - rat 1   malrtggpal vvllafwval gpchlqgtdp gasadaegpq cpvactcshd 51  dytdelsvfc ssknlthlpd dipvstralw ldgnnlssip saafqnlssl 101 dflnlqgswl rslepqallg lqnlyylhle rnrlrnlavg 141 lfthtp|laslslssnllgrleeg|lfaglshlwdlnlgwn 181 slvvlpdtvf qglgnlhelv 201 lagnkltylq palfcglgel reldlsrnal rsvkanvfvh lprlqklyld 251 rnlitavapg aflgmkalrw ldlshnrvag lmedtfpgll glhvlrlahn 301 aiaslrprtf kdlhfleelq lghnrirqlg ertfeglgql evltlndnqi 351 tevrvgafsg lfnvavmnls gnclrslper vfqgldklhs lhlehsclgh 401 vrlhtfagls glrrlflrdn sissieeqsl aglselleld lttnrlthlp 451 rqlfqglghl eylllsynql ttlsaevlgp lqrafwldis 491 hnhletlaeglfsslgrvrylslrnnslqtfspqpglerlwldanpwdcs 541 cplkalrdfa lqnpgvvprf vqtvcegddc qpvytynnit cagpanvsgl dlrdvsethf 601 vhc

Fig. 33

LIS1 (human)

```
1    mvlsqrqrde lnraiadylr sngyeeaysv fkkeaeldvn eeldkkyagl
51   lekkwtsvir lqkkvmeles klneakeeft sggplgqkrd pkewiprppe
101  kyalsghrspvtrvifhpvfsvmvsasedatikvwdyetg
151  dfertlkghtdsvqdisfdhsgkllascsadmtiklwdfqgfecir
191  tmhghdhnvssvaimpngdhivsasrdktikmwevqtgycvktf
241  tghrewvrmvrpnqdgtliascsndqtvrvwvvatkecka
291  elrehehvvecíswapessy
311  ssiseatgsetkksgkpgp      fllsasrdkt kr.iwdvstgmc
351  lmtlvghdnwvrgvlfhsggkfilscddktlrvwdyknk
391  rcmktlnahehfvtsldfhktapyvvtgsvdqtvkvwecr
```

```
1   merkdfetwl dnisvtflsl mdlqknetld hlislsgavq lrhlsnnlet
51  llkrdflkll plelsfyllk wldpqtlltc clvskqrnkv isactevwqt
101 acknlgwqid dsvqdslhwk kvylkailrm kqledheafe
```

```
141  tsslighsd rvyalyyk           dgllctgsddlsaklwdvstgqc
181  vygiqthtd a avkfde            qklvtgsfdntvacwewssgart
220  qhfrghtd avfsvdysdel           dilvsgsadfavkvwalsagtc
261  lntltghte wvtkvvlqkckvksllhspgdyill sadkyeikiwpigrei
```

```
301 nckclktlsv sedrsiclqp rlhfdgkyiv cssalglyqw
351 dfasydilrv iktpevanla llgfgdvful lfdnhylyim dlrteslisr
401 wplpeyrksk rgtsflager pg
```

Fig. 35

MSL1

1 mnqcakdith eassipidlq eryshwkknt kllydylntn stkwpsltcq 51 ffpdldttsd ehrillssft ssqkpedeti yiskistlgh ikwsslnnfd 101 mdemefkpen strfpskhlv ndisiffpng ecnrarylpq npdiiagass 151 dgaiyifdrt khgstrirqs kishpfetkl fgshgviqdv eamdtssadi 201 neatslawnl qqealllssh sngqvqvwdi kqyshenpii dlplvsinsd 251 gtavndvtwm pthdslfaac tegnavslld lrtkkeklqs 291 nrekhdggv nscrfn  yknslila sadsngrlnlwdirnmn
331 kspiatmehgtsv stlewspnfdtvlatagq edgl  vklwdtsceetifth
381 gghmlgv ndisw dahdpwlmcsv andn  svhiwkpagnlvg hs

Fig. 36

MUS MUSCULUS PROTEIN

```
  1 msshesytna aetpenisil sclgetsgal vdtktisdik tmdprvsltp
 51 ssdvtgteds svltpqstdv nsvdsyqgye gdddeedde ddkdgdsnlp
101 sledsdnfis clensyipqn vengevveeq slgrrfhpye leagevvegq
151 gggslfypye leagevveaq nvqnlfhrye leegevveaq vvqsmfpyye
201 leagevveae evqgffqrye learevigaq gggqlsrhyg leggevveat
251 avrrliqhhe leegedvddq eessemheet sedsseqydi eddslidewi
301 aletsplprp rwnvlsalrd rqlgssgrfv yeacgarlfv qrfs
```

351 lehvfe<u>gh</u>sg<u>d</u> vntvh ... fnqhgt lasgsd<u>d</u> lkvivwdw lkkrsvln

Fig. 37

```
391  fdsghknnilqakflpncnd ailamcgrdg qvrvaqlsav
401  agthmtkrlv khggashrlglepdspfrfl tsgedavvfn
451  idlrqahpas kllvikdgdk kvglytvfvn
501  panvyqfavg gqdqfmriyd qrkidenvnn gvlkkfcphh llssdypahi
551  tslmysydgt eilasynded iyifnssdsd gaqyakrykg hrnnstvkgv
601  yfygprsefv 611  msgsdcghifiweksscqiv qfleadeggt incidshpylpvldssgldhevkiwspiae 671  pskklaglkn vikinklkrd nftlrhtslf
701  lnnsmlcflms hvtqsnygrswrgirinagg gdfsdsssss eetnqes
```

Fig. 37 (con't)

ORF RB1

```
  1 mnqcakdith eassipidlqeryshwkknt kllydylntn stkwpsltcq
 51 ffpdldttsd ehrillssft ssqkpedeti yiskistlghikwsslnnfd
101 mdemefkpen strfpskhlv ndisiffpng ecnrarylpq npdiiagass
151 dgaiyifdrt khgstrirqs kishpfetkl fgshgviqdv eamdtssadi
201 neatslawnl qqealllssh sngqvqvwdi kqyshenpii dlplvsinsd
251 gtavndvtwm pthdslfaac tegnavslld lrtkkeklqs 291     nrekhdggvnscrfnykn    slildsadsngrlnlwdirnmn 331 kspiatmehgtsvstlewspnfdtvlataqqedg  lvklwdtsceetifth 381     gghmlgvndiswdah dpwlmcsvandn svhiwkpagnlvghs
```

Fig. 38

Periodic Trp protein

```
  1 misatnwvpr gfssefpeky vlddeeveri nqlaqlnldd akatleeaeg
 51 esgveddaat gssnklkdql didddlkeyn leeyddeeia dneggkdvsm
101 fpglsndsdv kfhegekged pyislpnqed sqeekqelqv ypsdnlvlaa
151 rteddvsyld iyvyddgagf hssdipveeg deadpdvarg lvrdpalyvh
201 hdlmlpafpl cvewldykvg snseeaanya aigtfdpqie iwnldcvdka
251 fpdmilgepl dnsmvslksk
```

```
271 kkkkksktgh itthhtdavl            smahnkyfrsvldstsadhtv klwdlnsgn
321 aarslasihs nkhvsssewhmlngsilltggydsrvaltdvrisdesqmskywsamagee
```

```
381 ietvtfasen iilcgtdsgn vysfdirnne nrkpvwtlka
421 hdagistlcs nkfipgmmst gamgektvkl
451 wkfplddatn tkgpsmvlsr dfdvgnvlts sfapdievag tmviggvnkv 501 lklwdvftnr svrksfksel envqarakee aqkigkssri arkytsndnp
551 dtvitiddqg edeeereggd ehddma
```

Fig. 39

PLAP 1 mhymsghsnf vsyvciipss diyphgliat ggndhnicif sldspmplyi 51 lkghkdtvcslssgkf gtllsgswdttakvwlndkcmmtl 91 qghtqavwavkilpeqglmtgsadktiklwkagrcertf 131 lghedcvrglails etefscandasirrwqitgeclevy 171 fghtnyiysisvfpnskdfvttaedrslriwkhgecaqti 211 rlpaqsiwcc cvlengdivv gasdgiirvf teseertasa 251 eeikaslsre spliakvltt eppiitpvrr tlpcrvtrsm issclsrlvs 301 tslstsdshl titalhlflt tttte

Fig. 40

RETINOBLASTOMA BINDING PROTEIN - HUMAN

```
  1 madkeaafdd aveervinee ykiwkkntpf lydlvmthal ewpsltaqwl
 51 pdvtrpegkd fsihrlvlgt htsdeqnhlv iasvqlpndd aqfdashyds
101 ekgefggfgs vsgkieieik inhegevnra rympqnpcii atktpssdvl
151 vfdytkhpsk pdpsgecnpd
171 lrlrahqkegyglswnpn   lsghllsasddhticlwdisavpkegkvvdak
221 tiftghtavvedvswhll   heslfgsvaddqklmiwdtrsn
261 ntskpshsvdahtaevnclsfnpysefildtgsadktvalwdlrnlklkl
311 hsfeshkdeifqvqwsph   netildssgtdrrlnvwdlskigeeqspedaedgppell
374 fihgghtakisdfswnpnepw   vidsvsednimqvwqmaeniyndedpegsvdpeggs
```

Fig. 41

S253 PROTEIN

```
  1 mfksktstls ydetpnsneg drnatpvnpk eksqtkhlni pgdrsrhssi
 51 adskrsssry dggysadiip aqlrfidnid ygtrlrktlh rnsvvsngyn
101 klsendrwyf dlfarkyfen yleeptyiki fkkkegleqf drmflaqelk
151 ipdvykstty qgepavanse lfknsiccct fshdgkymvi gckdgslhlw
201 kvinspvkrs emgrseksvs asranslkiq rhlasisshn gsissndlkp
251 sdqfegpskq lhlyapvfys
```

271    dvfrvfme<u>ha</u>|dildanw  skngflita|<u>m</u>dkta<u>klw</u>hper 311    kyslktfv<u>hp</u>|fvtsaiffpnddrfiitg|<u>l</u>dhrc<u>rlw</u>si

```
351 ldnevsyafd ckdlitsltl sppggeytii gtfngyiyvl lthglkfvss
401 fhvsdkstqg ttknsfhpss eygkvqhgpr itglqcffsk vdknlrlivt
451 tndskiqifd lnekkplelf kgfqsgssrh rgqflmmkne pvvftgsddh
501 wfytwkmqsf nlsaemncta phrkkrlsgs mslkgllriv snkstndecl
551 tetsnqsssh tftnssknvl qtqtvgsqai knnhyisfha hnspvtcasi
601 apdvaiknls lsndlifelt sqyfkemgqn ysesketcdn kpnhpvtetg
651 gfssnlsnvv nnvgtilitt dsqglirvfr tdilpeirkk iiekfheynl
701 fhleaagkin nhnndsilen rmderssted nefsttppsn thnsrpshdf
751 celhpnnspv isgmpsrasa ifknsifnks ngsfislksr sestsstvfg
801 phdiprvstt ypklkcdvcn gsnfecaskn piaggdsgft cadcgtilnn
851 fr
```

Fig. 42

SOF1

```
  1  mkiktikrsa ddyvpvkstq esqmprnlnp elhpferare ytkalnatkl 51  ermfakpfvgqlgyghrdgvy    aiaknygslnklatgsadgvikywnmstr 101  eefvsfkahyglvtglcvtqprfhdkkpdlksqnfmlsdsddktvklwsinvddysnkns 161  sdndsvtneeglirtfdgesafqgidshrenstfdtggakihlwdvnrlk 211  pvsdlswgad nitslkfnqn etdilastgs dnsivlydlr tnsptqkivq tmrtnaicwn 271  pmeafnfvta nedhnayyyd mrnlsrslnv fkdhvsavmd vdfsptgdei vtgsydksir 331  iyktnhghsreijyhtkrmqhvf vkysmdskyiisgsddgnvrlwrskaw 381  ersnvkttre knkleydekl kerfrhmpei krisrhrhvp qvikkaqeik 431  nielssikrr eanerrtrkdmpyiserkkq ivgtvhkyed sgrdrkrrke ddkrdtqek
```

Fig. 43

STE4 - YEAST

| | |
|---|---|
| 1 | maahqmdsit ysnnvtqqyi qpqslqdisa vedeiqnkie aarqeskqlh |
| 51 | aqinkakhki qdaslfqman kvtsltknki nlkpnivl |
| 89 | kg̲hnn kisdfrwsrdsk　　　rilsq sqd̲gfml iw̲d̲sasglkqnai |
| 131 | pldsqwvlscaispsstlvasaglnnnctiyrvskenrva |
| 171 | qnvasifkg̲htc yisdieft　　　dnahilt asgd̲mtcalw̲d̲ip |
| 211 | kakrvreysdh̲lg dvlalaipeepnlenssntfas cgsd̲gytyiw̲d̲srsp |
| 261 | savqsfyvndsdinalrffkdgmsivagsd ngainmydlr |
| 301 | sdcsiatfslfrgyeertptptymaanmey ntaqspqtlk |
| 341 | stsssyld̲nq gvvsldfsasgrlmysc ytd̲igcvvw̲d̲vlk |
| 381 | geivgkleg̲hgg rvtgvrsspdglavctgs w̲d̲stmkiw̲s̲p gyq |

Fig. 44

TRANSCRIPTION FACTOR TIIF

```
1   mslevsning gngtqlshdk rellcllkli kkyqlkstee llcqeanvss
51  velseisesd vqqvlgavlg agdanrerkh vqspaqqhkq savteanaae
101 elakfiddds fdaqhyeqay kelrtfveds ldiykhelsm vlypilvqiy
151 fkilasglre kakefiekyk cdldgyyieg lfnllllskp eellendlvv
201 ameqdkfvir msrdshslfk rhiqdrrqev vadivskylh fdtyegmarn
251 klqcvatags hlgeakrqdn kmrvyygllk evdfqtlttp apapeeeddd
301 pdapdrpkkk kpkkdpllsk ksksdpnaps idriplpelk dsdkllklka
351 lreaskrlal skdqlpsavfytvln
```

Fig. 45

376 shqgvtcaeisddstm lacgfgdssvriwsltpanvrtlkdads lreldkesadi 431 nvrmlddrsgevtrslmghtgpvyrcafapemnllscsedstirlwsll
481 twscvvtyrghvypvwdvrfaphgyyfvscsydktarlwatdsnqalrvf
531 vghlsdvdcvqfhpnsnyvdtgssdrtvrlwdnmtggsvr
571 lmtghkgsvsslafsacgryldsgsvdhniiiwdlsngsl
611 vttllrhtstvttitfsrdgtvldaagldnnltlwdfhkv
651 tedyisnhit vshhqdende dvytmrtfps knspfvslhf trrnllmcvg
701 lfks

Fig. 45 (con't)

TUP1

```
  1 mtasvsntqn klnelldair qeflqvsqea ntyrlqnqkd ydfkmnqqla
 51 emqqirntvy elelthrkmk dayeaeikhl klgleqrdhq iasltvqqqq
101 qqqqqqqvqq hlqqqqqqla aasasvpvaq qppattsata tpaantttgs
151 psafpvqasr pnlvgsqlpt ttlpvvssna qqqlpqqqlq qqqlqqqqpp
201 pqvsvaplsn taingsptsk etttlpsvka pestlketep ennntskind
251 tgsattattt tateteikpk eedatraslh qdhylvpynq ranhskpipp
301 flldldsqsv pdalkkqtnd yyilynpalp reidvelhks ldhtsvvccv
351 kfsndgeyla tgcnkttqvy rvsdgslvar lsddsaannh rnsitenntt
401 tstdnntmtt ttttittta mtsaaelakd venlntsssp
```

```
441          ssdly rsvcfspdgkfla tgaedrliriwdi enrkivmi
481          lqgheqd iysldyfpsgdklv sgsgdrtvriwdl rtgqcs
521          ltlsiedgv ttvavspgdgkyia agsldravrvwd setgflverldsene
571          sgtghkds vysvvftrdgqsvv sgsldrsvklw nlqnannksdsktpnsg
621 tcevtyighkdf vlsvattqndeyil sgskdrgvlfwd kk
```

```
661 sgnpllmlqg hrnsvisvav angsslgpey nvfatgsgdc
701 kariwkykki apn
```

Fig. 46

TUP1 HOMOLOG

```
  1  msqkqstnqn  qngthqpqpv  knqrtnnaag  ansgqqpqqq  sqgqsqqqgr
 51  sngpfsasdl  nrivleylnk  kgyhrteaml  raesgrtltp  qnkqspantk
101  tgkfpeqssi  ppnpgktakp  isnptnlssk  rdaeggivss  grleglnape
151  nyiraysmlk  nwvdssleiy  kpelsyimyp  ifiylflnlv  aknpvyarrf
201  fdrfspdfkd  fhgseinrlf  svnsidhike  nevasafqsh  kyritmsktt
251  lnlllyflne  nesiggslii  svinqhldpn  ivesvtarek  ladgikvlsd
301  sengnjkqnl  emnsvpvklg  pfpkdeefvk  eietelkikd  dqekqlnqqt
351  agdnysgann  rtllqeykam  nnekfkdntg  dddkdkikdk  iakdeekkes
401  elkvdgekkd  snlsspardi  lplppktald  lkleiqkvke  srdaikldnl
451  qlalpsvcmy
```

```
461  tfqntnkdmscldfsddcriaaag            fqdsyikiwsldgsslnnpnialnnn
511  dkdedptcktlvghsqtvystsf  spdnkyllsgsedkt  vrlwsmdthtal
561          vsykghnhpvwdvs  fsplghyfatashdqt  arlwscdhiy
601          plrifaghlrdvdcvs  fhpngcyvftgssdkt  crmwdvst
641          gdsvrlflghtdpvisi  avcpdgrwlstgsedgi  invwdigtgkr
686          lkqmrghgknaiyslsyskegnvlisggadht  vrvwdlkkattep
```

```
731  saepdepfig  ylgdvtasin  qdikeygrrr  tviptsdlva
771  sfytkktpvf  kvkfsrsnla  laggafrp
```

Fig. 47

YCU7

```
1   mvrrfrgkel aattfnghrd yvmgaffshd qekiytvskd gavfvweftk
51  rpsddddnes edddkqeevd iskyswritk khffyanqak vkcvtfhpat
101 rllavgftsg efrlydlpdf tliqqlsmgq npvntvsvnq tgewlafgss
151 klgqllvyew
```

```
161    qsesyilkqqghfds tnslay  spdgsrvv tasedgkikvwd 202    itsgfclatfeehtss vta vqfakrgqvmf ssldgtvrawdli 251 ryrnfrtftgteriqfn clavdpsgevvcags dnfdih  vwsvqt 291     gqlldalsghegp vscl sfsqensvla aswdktiriwsi
```

```
341 fgrsqqvepi evysdvlals mrpdgkevav stlkgcisif niedakqvgn
391 idcrkdiisg rfnqdrftakilndpnfllq yitvlmvwll wlvviitpfv
431 ymmfqmksc
```

Fig. 48

YCW2 PROTEIN

```
  1 mstlipppsk kqkkeaqlpr evaiipkdlp nvsikfqald tgdnvggalr
 51 vpgaisekql eellnqlngt sddpvpytfs ctiqgkkasd pvktiditdn
101 lysslikpgy nstedqitll ytpravfkvk
```

```
131     pvtrsssaiaghgstilcsafaph        tssrmvtgagdntariwdcdtqtpmh 181             tlkghynwvlcvswsp        dgeviatgsmdntirlwdpksgqc 221         lgdalrghskwitslswepihlvkpgskprlasskdgtikiwdtvsrvc 271         qytmsghtnsvscvkwggqg        llysgshdrtvrvwdinsqg
```

```
311 rcinilksha hwvnhlslst dyalrigafd htgkkpstpe
```

```
351 eaqkkalenyekickkngnse               emmvtasddytmflwnplkstkpiarmtg 401             hqklvnhvafspdgr         yivsasfdnsiklwdgr 441         dgkfistfrghiasvyqvawssdc    rllvscskdttlkvwdv 481         rtrklsvdlpgiktklyvdw        svdgkrvcsggkdkmvrlwth
```

Fig. 49

Fig. 50
YKL525

```
  1 mfksktstls ydetpnsneg drnatpvnpk eksqtkhlni pgdrsrhssi
 51 adskrsssry dggysadiip aqlrfidnid ygtrlrktlh rnsvvsngyn
101 klsendrwyf dlfdrkyfen yleeptyiki fkkkegleqf drmflaqelk
151 ipdvykstty
```

```
161 qgepavanselfknsiccct fshdgkymvi gckdgslhlwk
```

```
202 vinspvkrs emgrseksvs asranslkiq rhlasisshn gsissndlkp
```

```
251         sdqfegpskqlhly apvfysdvf    rvfmehaldildanwskngflitasmd
301 ktaklwhperkyslktfvhpd fvtsaiffpnddrfiitgcldhrcrlwsi
```

```
351 ldnevsyafd ckdlitsltl sppggeytii gtfngyiyvl lthglkfvss
401 fhvsdkstqg ttknsfhpss eygkvqhgpr itglqcffsk vdknlrlivt
451 tndskiqifd lnekkplelf kgfqsgssrh rgqflmmkne pvvftgsddh
501 wfytwkmqsf nlsaemncta phrkkrlsgs mslkgllriv snkstndecl
551 tetsnqsssh tftnssknvl qtqtvgsqai knnhyisfha hnspvtcasi
601 apdvaiknls lsndlifelt sqyfkemgqn ysesketcdn kpnhpvtetg
651 gfssnlsnvv nnvgtilitt dsqglirvfr tdilpeirkk iiekfheynl
701 fhleaagkin nhnndsilen rmderssted nefsttppsn thnsrpshdf
751 celhpnnspv isgmpsrasa ifknsifnks ngsfislksr sestsstvfg
801 phdiprvstt ypklkcdvcn gsnfecaskn piaggdsgft cadcgtilnn
851 fr
``` yrb 1410 yeast

```
  1 msqkqstnqn qngthqpqpv knqrtnnaag ansgqqpqqq sqgqsqqqgr 51 sngpfsasdl nrivleylnk kgyhrteaml raesgrtltp qnkqspantk 101 tgkfpeqssi ppnpgktakp isnptnlssk rdaeggivss grleglnape 151 nyiraysmlk nwvdssleiy kpelsyimyp ifiylflnlv aknpvyarrf 201 fdrfspdfkd fhgseinrlf svnsidhike nevasafqsh kyritmsktt 251 lnlllyflne nesiggslii svinqhldpn ivesvtarek ladgikvlsd 301 sengngkqnl emnsvpvklg pfpkdeefvk eietelkikd dqekqlnqqt 351 agdnysgann rtllqeykam nnekfkdntg dddkdkikdk iakdeekkes 401 elkvdgekkd snlsspardi lplppktald lkleiqkvke srdaikldnl 451 qlalpsvcmy tfqntnkdms cldfsddcri aaagfqdsyi kiwsldgssl 501 nnpnialnnn dkdedptckt lvghsgtvys tsfspdnkyl lsgsedktvr
```

Fig. 51

551 lwsmdthtalvsykgh nhpvwdvs fsplghyfatpshdqtarlwscdhiy 601 plrifaghlndvdcvs fhpngcyvftgssdktcrmwdvst 641 gdsvrlflghtapvisiav cpdgrwlstgsedgiinvwdigtgkrlkqmr 691 ghgknaiyslsyskegnvlisggadhtvrvwdlkkattep 731 saepdepfig ylgdvtasinqdikeygrrr tviptsdlva sfytkktpvf kvkfsrsnla laggafrp

Fig. 51 (con't)

SEQUENCE LISTING (1) GENERAL INFORMATION:

(iii) NUMBER OF SEQUENCES: 265

(2) INFORMATION FOR SEQ ID NO:1:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Peptide I (xi) SEQUENCE DESCRIPTION: SEQ ID NO:1:

```
Lys Gly Asp Tyr Glu Lys Ile Leu Val Ala Leu Cys Gly Gly Asn
1               5                   10                  15
```

(2) INFORMATION FOR SEQ ID NO:2:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Peptide, rI, Fig. 1C (xi) SEQUENCE DESCRIPTION: SEQ ID NO:2:

```
Val Thr Gln Ile Ala Thr Thr
1               5
```

(2) INFORMATION FOR SEQ ID NO:3:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Peptide rII, Fig. 1C (xi) SEQUENCE DESCRIPTION: SEQ ID NO:3:

```
Phe Val Ser Asp Val Val Ile
1               5
```

(2) INFORMATION FOR SEQ ID NO:4:

(i) SEQUENCE CHARACTERISTICS:
        (A) LENGTH: 7 amino acids
        (B) TYPE: amino acid (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: Peptide rIII, Fig. 1C (xi) SEQUENCE DESCRIPTION: SEQ ID NO:4:

Asp Val Leu Ser Val Ala Phe
1               5

(2) INFORMATION FOR SEQ ID NO:5:

(i) SEQUENCE CHARACTERISTICS:
             (A) LENGTH: 7 amino acids
             (B) TYPE: amino acid
             (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: peptide rIV, Fig. 1C (xi) SEQUENCE DESCRIPTION: SEQ ID NO:5:

Val Ser Cys Val Arg Phe Ser
1               5

(2) INFORMATION FOR SEQ ID NO:6:

(i) SEQUENCE CHARACTERISTICS:
             (A) LENGTH: 7 amino acids
             (B) TYPE: amino acid
             (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: Peptide rV, Fig. 1C (xi) SEQUENCE DESCRIPTION: SEQ ID NO:6:

Gly Tyr Leu Asn Thr Val Thr
1               5

(2) INFORMATION FOR SEQ ID NO:7:

(i) SEQUENCE CHARACTERISTICS:
             (A) LENGTH: 8 amino acids
             (B) TYPE: amino acid
             (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: Peptide rVI, Fig. 1C (xi) SEQUENCE DESCRIPTION: SEQ ID NO:7:

```
Asp Ile Ile Asn Ala Leu Cys Phe
1               5
```

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Peptide rVII, Fig. 1C (xi) SEQUENCE DESCRIPTION: SEQ ID NO:8:

```
Pro Gln Cys Thr Ser Leu Ala
1               5
```

(2) INFORMATION FOR SEQ ID NO:9:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: control peptide 1, homol. to RACK1
            261-266, LKGKIL (xi) SEQUENCE DESCRIPTION: SEQ ID NO:9:

```
Leu Lys Gly Lys Ile Leu
1               5
```

(2) INFORMATION FOR SEQ ID NO:10:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: control peptide 2, iden. to RACK1,
            265 to 270 IIVDEL (xi) SEQUENCE DESCRIPTION: SEQ ID NO:10:

```
Ile Ile Val Asp Glu Leu
1               5
```

(2) INFORMATION FOR SEQ ID NO:11:

(i) SEQUENCE CHARACTERISTICS:
        (A) LENGTH: 18 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: PKC substrate peptide, (Ser25)
                 PKC(19-36)

(xi) SEQUENCE DESCRIPTION: SEQ ID NO:11:

Arg Phe Ala Arg Lys Gly Ser Leu Arg Gln Lys Asn Val His Glu Val
1               5                  10                  15

Lys Asn (2) INFORMATION FOR SEQ ID NO:12:

(i) SEQUENCE CHARACTERISTICS:
            (A) LENGTH: 18 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: PKC Pseudosubstrate Inhibitor
                 (PCK(19-36))

(xi) SEQUENCE DESCRIPTION: SEQ ID NO:12:

Arg Phe Ala Arg Lys Gly Ala Leu Arg Gln Lys Asn Val His Glu Val
1               5                  10                  15

Lys Asn (2) INFORMATION FOR SEQ ID NO:13:

(i) SEQUENCE CHARACTERISTICS:
            (A) LENGTH: 15 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: GBH Peptide, rI, Fig. 24

(xi) SEQUENCE DESCRIPTION: SEQ ID NO:13:

Trp Val Thr Gln Ile Ala Thr Thr Pro Gln Phe Pro Asp Met Ile
1               5                  10                  15

(2) INFORMATION FOR SEQ ID NO:14:

(i) SEQUENCE CHARACTERISTICS:
            (A) LENGTH: 15 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:

(C) INDIVIDUAL ISOLATE: GBH Peptide rII, Fig. 24

(xi) SEQUENCE DESCRIPTION: SEQ ID NO:14:

Phe Val Ser Asp Val Val Ile Ser Ser Asp Gly Gln Phe Ala Leu
1               5                   10                  15

(2) INFORMATION FOR SEQ ID NO:15:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: GBH Peptide rIII, Fig. 24

(xi) SEQUENCE DESCRIPTION: SEQ ID NO:15:

Asp Val Leu Ser Val Ala Phe Ser Ser Asp Asn Arg Gln Ile Val
1               5                   10                  15

(2) INFORMATION FOR SEQ ID NO:16:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: GBH Peptide rIV, Fig. 24

(xi) SEQUENCE DESCRIPTION: SEQ ID NO:16:

Trp Val Ser Cys Val Arg Phe Ser Pro Asn Ser Ser Asn Pro Ile
1               5                   10                  15

(2) INFORMATION FOR SEQ ID NO:17:

(i) SEQUENCE CHARACTERISTICS:
        (A) LENGTH: 15 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: GBH Peptide rV, Fig. 24

(xi) SEQUENCE DESCRIPTION: SEQ ID NO:17:

Tyr Leu Asn Thr Val Thr Val Ser Pro Asp Gly Ser Leu Cys Ala
1               5                   10                  15

(2) INFORMATION FOR SEQ ID NO:18:

(i) SEQUENCE CHARACTERISTICS:
        (A) LENGTH: 15 amino acids
        (B) TYPE: amino acid (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: GBH Peptide rVI, Fig. 24

(xi) SEQUENCE DESCRIPTION: SEQ ID NO:18:

Thr Leu Asp Gly Gly Asp Ile Ile Asn Ala Leu Cys Phe Ser Pro
1               5                   10                  15

(2) INFORMATION FOR SEQ ID NO:19:

(i) SEQUENCE CHARACTERISTICS:
        (A) LENGTH: 1115 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: RACK1 DNA Sequence, Fig. 1A (xi) SEQUENCE DESCRIPTION: SEQ ID NO:19:

```
GGCACGAGGG GTCGCGGTGG CAGCCGTGCG GTGCTTGGCT CCCTAAGCTA TCCGGTGCCA      60

TCCTTGTCGC TGCGGCGACT CGCAACATCT GCAGCCATGA CCGAGCAAAT GACCCTTCGT    120

GGGACCCTCA AGGGCCATAA TGGATGGGTT ACACAGATCG CCACCACTCC GCAGTTCCCG    180

GACATGATCC TGTCGGCGTC TCGAGACAAG ACCATCATCA TGTGGAAGCT GACCAGGGAT    240

GAGACCAACT ACGGCATACC ACAACGTGCT CTTCGAGGTC ACTCCCACTT TGTTAGCGAT    300

GTTGTCATCT CCTCTGATGG CCAGTTTGCC CTCTCAGGCT CCTGGGATGG AACCCTACGC    360

CTCTGGGATC TCACAACGGG CACTACCACG AGACGATTTG TCGGCCACAC CAAGGATGTG    420

CTGAGCGTGG CTTTCTCCTC TGACAACCGG CAGATTGTCT CTGGGTCCCG AGACAAGACC    480

ATTAAGTTAT GGAATACTCT GGGTGTCTGC AAGTACACTG TCCAGGATGA GAGTCATTCA    540

GAATGGGTGT CTTGTGTCCG CTTCTCCCCG AACAGCAGCA ACCCTATCAT CGTCTCCTGC    600

GGATGGACA AGCTGGTCAA GGTGTGGAAT CTGGCTAACT GCAAGCTAAA GACCAACCAC    660

ATTGGCCACA CTGGCTATCT GAACACAGTG ACTGTCTCTC CAGATGGATC CCTCTGTGCT    720

TCTGGAGGCA AGGATGGCCA GGCTATGCTG TGGGATCTCA ATGAAGGCAA GCACCTTTAC    780

ACATTAGATG GTGGAGACAT CATCAATGCC TTGTGCTTCA GCCCCAACCG CTACTGGCTC    840

TGTGCTGCCA CTGGCCCCAG TATCAAGATC TGGGACTTGG AGGGCAAGAT CATGGTAGAT    900

GAACTGAAGC AAGAAGTTAT CAGCACCAGC AGCAAGGCAG AGCCACCCCA GTGTACCTCT    960

TTGGCTTGGT CTGCTGATGG CCAGACTCTG TTTGCTGGCT ATACCGACAA CTTGGTGCGT   1020

GTATGGCAGG TGACTATTGG TACCCGCTAA AAGTTTATGA CAGACTCTTA GAAATAAACT   1080

GGCTTTCTGA AAAAAAAAAA AAAAAAAAAA AAAAA                              1115
```

(2) INFORMATION FOR SEQ ID NO:20:

(i) SEQUENCE CHARACTERISTICS:
        (A) LENGTH: 96 base pairs (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (C) INDIVIDUAL ISOLATE: RACK1 rI DNA Sequence, Fig. 1A (xi) SEQUENCE DESCRIPTION: SEQ ID NO:20:

GGCCATAATG GATGGGTTAC ACAGATCGCC ACCACTCCGC AGTTCCCGGA CATGATCCTG        60

TCGGCGTCTC GAGACAAGAC CATCATCATG TGGAAG        96

(2) INFORMATION FOR SEQ ID NO:21:

(i) SEQUENCE CHARACTERISTICS:
            (A) LENGTH: 94 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (C) INDIVIDUAL ISOLATE: RACK1 rII DNA Sequence (xi) SEQUENCE DESCRIPTION: SEQ ID NO:21:

GGTCACTCCC ACTTTGTTAG CGATGTTGTC ATCTCCTCTG ATGGCCAGTT TGCCCTCTCA        60

GGCTCCTGGG ATGGAACCCT ACGCCTCTGG GATC        94

(2) INFORMATION FOR SEQ ID NO:22:

(i) SEQUENCE CHARACTERISTICS:
            (A) LENGTH: 93 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (C) INDIVIDUAL ISOLATE: RACK1 rIII DNA Sequence, Fig. 1A (xi) SEQUENCE DESCRIPTION: SEQ ID NO:22:

GGCCACACCA AGGATGTGCT GAGCGTGGCT TTCTCCTCTG ACAACCGGCA GATTGTCTCT        60

GGGTCCCGAG ACAAGACCAT TAAGTTATGG AAT        93

(2) INFORMATION FOR SEQ ID NO:23:

(i) SEQUENCE CHARACTERISTICS:
            (A) LENGTH: 99 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (C) INDIVIDUAL ISOLATE: RACK1 rIV DNA Sequence, Fig. 1A (xi) SEQUENCE DESCRIPTION: SEQ ID NO:23:

```
AGTCATTCAG AATGGGTGTC TTGTGTCCGC TTCTCCCCGA ACAGCAGCAA CCCTATCATC    60

GTCTCCTGCG GATGGGACAA GCTGGTCAAG GTGTGGAAT                            99
```

(2) INFORMATION FOR SEQ ID NO:24:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: RACK1 rV DNA Sequence, Fig. 1A (xi) SEQUENCE DESCRIPTION: SEQ ID NO:24:

```
GGCCACACTG GCTATCTGAA CACAGTGACT GTCTCTCCAG ATGGATCCCT CTGTGCTTCT    60

GGAGGCAAGG ATGGCCAGGC TATGCTGTGG GAT                                 93
```

(2) INFORMATION FOR SEQ ID NO:25:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: RACK1 rVI DNA Sequence, Fig. 1A (xi) SEQUENCE DESCRIPTION: SEQ ID NO:25:

```
TTAGATGGTG GAGACATCAT CAATGCCTTG TGCTTCAGCC CCAACCGCTA CTGGCTCTGT    60

GCTGCCACTG GCCCCAGTAT CAAGATCTGG GAC                                 93
```

(2) INFORMATION FOR SEQ ID NO:26:

(i) SEQUENCE CHARACTERISTICS:
        (A) LENGTH: 99 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: RACK1 rVII DNA Sequence, Fig. 1A (xi) SEQUENCE DESCRIPTION: SEQ ID NO:26:

```
AGCAAGGCAG AGCCACCCCA GTGTACCTCT TTGGCTTGGT CTGCTGATGG CCAGACTCTG          60

TTTGCTGGCT ATACCGACAA CTTGGTGCGT GTATGGCAG                                99
```

(2) INFORMATION FOR SEQ ID NO:27:

(i) SEQUENCE CHARACTERISTICS:
      (A) LENGTH: 317 amino acids
      (B) TYPE: amino acid
      (D) TOPOLOGY: unknown (ii) MOLECULE TYPE: protein (iii) HYPOTHETICAL: NO (iv) ANTI-SENSE: NO (vi) ORIGINAL SOURCE:
      (C) INDIVIDUAL ISOLATE: RACK1 Amino Acid Sequence, Fig. 1C (xi) SEQUENCE DESCRIPTION: SEQ ID NO:27:

```
Met Thr Glu Gln Met Thr Leu Arg Gly Thr Leu Lys Gly His Asn Gly
1               5                   10                  15

Trp Val Thr Gln Ile Ala Thr Thr Pro Gln Phe Pro Asp Met Ile Leu
            20                  25                  30

Ser Ala Ser Arg Asp Lys Thr Ile Ile Met Trp Lys Leu Thr Arg Asp
        35                  40                  45

Glu Thr Asn Tyr Gly Ile Pro Gln Arg Ala Leu Arg Gly His Ser His
    50                  55                  60

Phe Val Ser Asp Val Val Ile Ser Ser Asp Gly Gln Phe Ala Leu Ser
65                  70                  75                  80

Gly Ser Trp Asp Gly Thr Leu Arg Leu Trp Asp Leu Thr Thr Gly Thr
                85                  90                  95

Thr Thr Arg Arg Phe Val Gly His Thr Lys Asp Val Leu Ser Val Ala
            100                 105                 110

Phe Ser Ser Asp Asn Arg Gln Ile Val Ser Gly Ser Arg Asp Lys Thr
        115                 120                 125

Ile Lys Leu Trp Asn Thr Leu Gly Val Cys Lys Tyr Thr Val Gln Asp
    130                 135                 140

Glu Ser His Ser Glu Trp Val Ser Cys Val Arg Phe Ser Pro Asn Ser
145                 150                 155                 160

Ser Asn Pro Ile Ile Val Ser Cys Gly Trp Asp Lys Leu Val Lys Val
                165                 170                 175

Trp Asn Leu Ala Asn Cys Lys Leu Lys Thr Asn His Ile Gly His Thr
            180                 185                 190

Gly Tyr Leu Asn Thr Val Thr Val Ser Pro Asp Gly Ser Leu Cys Ala
        195                 200                 205

Ser Gly Gly Lys Asp Gly Gln Ala Met Leu Trp Asp Leu Asn Glu Gly
    210                 215                 220

Lys His Leu Tyr Thr Leu Asp Gly Gly Asp Ile Ile Asn Ala Leu Cys
225                 230                 235                 240

Phe Ser Pro Asn Arg Tyr Trp Leu Cys Ala Ala Thr Gly Pro Ser Ile
                245                 250                 255

Lys Ile Trp Asp Leu Glu Gly Lys Ile Ile Val Asp Glu Leu Lys Gln
            260                 265                 270

Glu Val Ile Ser Thr Ser Ser Lys Ala Glu Pro Pro Gln Cys Thr Ser
        275                 280                 285

Leu Ala Trp Ser Ala Asp Gly Gln Thr Leu Phe Ala Gly Tyr Thr Asp
```

```
                290                 295                 300
Asn Leu Val Arg Val Trp Gln Val Thr Ile Gly Thr Arg
305                 310                 315
```

(2) INFORMATION FOR SEQ ID NO:28:

(i) SEQUENCE CHARACTERISTICS:
        (A) LENGTH: 501 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: Human 55 kDa protein (PWP homolog),
            Fig. 11

(xi) SEQUENCE DESCRIPTION: SEQ ID NO:28:

```
Met Asn Arg Ser Arg Gln Val Thr Cys Val Ala Trp Val Arg Cys Gly
1               5                   10                  15

Val Ala Lys Glu Thr Pro Asp Lys Val Glu Leu Ser Lys Glu Glu Val
                20                  25                  30

Lys Arg Leu Ile Ala Glu Ala Lys Glu Lys Leu Gln Glu Glu Gly Gly
                35                  40                  45

Gly Ser Asp Glu Glu Thr Gly Ser Pro Ser Glu Asp Gly Met Gln
    50                  55                  60

Ser Ala Arg Thr Gln Ala Arg Pro Arg Glu Pro Leu Glu Asp Gly Asp
65                  70                  75                  80

Pro Glu Asp Asp Arg Thr Leu Asp Asp Glu Leu Ala Glu Tyr Asp
                    85                  90                  95

Leu Asp Lys Tyr Asp Glu Glu Gly Asp Pro Asp Ala Glu Thr Leu Gly
                100                 105                 110

Glu Ser Leu Leu Gly Leu Thr Val Tyr Gly Ser Asn Asp Gln Asp Pro
                115                 120                 125

Tyr Val Thr Leu Lys Asp Thr Glu Gln Tyr Glu Arg Glu Asp Phe Leu
                130                 135                 140

Ile Lys Pro Ser Asp Asn Leu Ile Val Cys Gly Arg Ala Glu Gln Asp
145                 150                 155                 160

Gln Cys Asn Leu Glu Val His Val Tyr Asn Gln Glu Glu Asp Ser Phe
                165                 170                 175

Tyr Val His His Asp Ile Leu Leu Ser Ala Tyr Pro Leu Ser Val Glu
                180                 185                 190

Trp Leu Asn Phe Asp Pro Ser Pro Asp Asp Ser Thr Gly Asn Tyr Ile
                195                 200                 205

Ala Val Gly Asn Met Thr Pro Val Ile Glu Val Trp Asp Leu Asp Ile
                210                 215                 220

Val Asp Ser Leu Glu Pro Val Phe Thr Leu Gly Ser Lys Leu Ser Lys
225                 230                 235                 240

Lys Lys Lys Lys Gly Lys Lys Ser Ser Ala Glu Gly His Thr
                245                 250                 255

Asp Ala Val Leu Asp Leu Ser Trp Asn Lys Leu Ile Arg Asn Val Leu
                260                 265                 270

Ala Ser Ala Ser Ala Asp Asn Thr Val Ile Leu Trp Asp Met Ser Leu
                275                 280                 285
```

```
Gly Lys Pro Ala Ala Ser Leu Ala Val His Thr Asp Lys Val Gln Thr
    290                 295                 300
Leu Gln Phe His Pro Phe Glu Ala Gln Thr Leu Ile Ser Gly Ser Tyr
305                 310                 315                 320
Asp Lys Ser Val Ala Leu Tyr Asp Cys Arg Ser Pro Asp Glu Ser His
                325                 330                 335
Arg Met Trp Arg Phe Ser Gly Gln Ile Glu Arg Val Thr Trp Asn His
            340                 345                 350
Phe Ser Pro Cys His Phe Leu Ala Ser Thr Asp Gly Phe Val Tyr
            355                 360                 365
Asn Leu Asp Ala Arg Ser Asp Lys Pro Ile Phe Thr Leu Asn Ala His
370                 375                 380
Asn Asp Glu Ile Ser Gly Leu Asp Leu Ser Ser Gln Ile Lys Gly Cys
385                 390                 395                 400
Leu Val Thr Ala Ser Ala Asp Lys Tyr Val Lys Ile Trp Asp Ile Leu
                405                 410                 415
Gly Asp Arg Pro Ser Leu Val His Ser Arg Asp Met Lys Met Gly Val
            420                 425                 430
Leu Phe Cys Ser Ser Cys Cys Pro Asp Leu Pro Phe Ile Tyr Ala Phe
            435                 440                 445
Gly Gly Gln Lys Glu Gly Leu Arg Val Trp Asp Ile Ser Thr Val Ser
        450                 455                 460
Ser Val Asn Glu Ala Phe Gly Arg Arg Glu Arg Leu Val Leu Gly Ser
465                 470                 475                 480
Ala Arg Asn Ser Ser Ile Ser Gly Pro Phe Gly Ser Arg Ser Ser Asp
                485                 490                 495
Thr Pro Met Glu Ser
            500

(2) INFORMATION FOR SEQ ID NO:29:

(i) SEQUENCE CHARACTERISTICS:
        (A) LENGTH: 428 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
         (C) INDIVIDUAL ISOLATE: AAC-RICH protein, Fig. 12

(xi) SEQUENCE DESCRIPTION: SEQ ID NO:29:

Pro Gly Gly Phe Gln His Leu Gln Gln Gln Gln Gln Gln Gln Gln Gln
1               5                   10                  15
Gln Gln Gln Gln Gln Gln Gln Gln Gln Gln Gln Gln Thr Gln Val Gln
                20                  25                  30
Gln Leu His Asn Gln Leu His Gln Gln His Asn Gln Gln Ile Gln Gln
            35                  40                  45
Gln Ala Gln Ala Thr Gln Gln His Leu Gln Thr Gln Gln Tyr Leu Gln
        50                  55                  60
Ser Gln Ile His Gln Gln Ser Gln Gln Ser Gln Leu Ser Asn Asn Leu
65                  70                  75                  80
Asn Ser Asn Ser Lys Glu Ser Thr Asn Ile Pro Lys Thr Asn Thr Gln
                85                  90                  95
```

Tyr Thr Asn Phe Asp Ser Lys Asn Leu Asp Leu Ala Ser Arg Tyr Phe
            100                 105                 110

Ser Glu Cys Ser Thr Lys Asp Phe Ile Gly Asn Lys Lys Ser Thr
        115                 120                 125

Ser Val Ala Trp Asn Ala Asn Gly Thr Lys Ile Ala Ser Ser Gly Ser
130                 135                 140

Asp Gly Ile Val Arg Val Trp Asn Phe Asp Pro Leu Gly Asn Ser Asn
145                 150                 155                 160

Asn Asn Asn Asn Ser Asn Asn Thr Ser Ser Asn Ser Lys Asn Asn Asn
                165                 170                 175

Ile Lys Glu Thr Ile Glu Leu Lys Gly His Asp Gly Ser Ile Glu Lys
            180                 185                 190

Ile Ser Trp Ser Pro Lys Asn Asn Asp Leu Leu Ala Ser Ala Gly Thr
        195                 200                 205

Asp Lys Val Ile Lys Ile Trp Asp Val Lys Ile Gly Lys Cys Ile Gly
210                 215                 220

Thr Val Ser Thr Asn Ser Glu Asn Ile Asp Val Arg Trp Ser Pro Asp
225                 230                 235                 240

Gly Asp His Leu Ala Leu Ile Asp Leu Pro Thr Ile Lys Thr Leu Lys
                245                 250                 255

Ile Tyr Lys Phe Asn Gly Glu Glu Leu Asn Gln Val Gly Trp Asp Asn
            260                 265                 270

Asn Gly Asp Leu Ile Leu Met Ala Asn Ser Met Gly Asn Ile Glu Ala
        275                 280                 285

Tyr Lys Phe Leu Pro Lys Ser Thr Thr His Val Lys His Leu Lys Thr
290                 295                 300

Leu Tyr Gly His Thr Ala Ser Ile Tyr Cys Met Glu Phe Asp Pro Thr
305                 310                 315                 320

Gly Lys Tyr Leu Ala Ala Gly Ser Ala Asp Ser Ile Val Ser Leu Trp
                325                 330                 335

Asp Ile Glu Asp Met Met Cys Val Lys Thr Phe Ile Lys Ser Thr Phe
            340                 345                 350

Pro Cys Arg Ser Val Ser Phe Ser Phe Asp Gly Gln Phe Ile Ala Ala
        355                 360                 365

Ser Ser Phe Glu Ser Thr Ile Glu Ile Phe His Ile Glu Ser Ser Gln
370                 375                 380

Pro Ile His Thr Ile Glu Cys Gly Val Ser Ser Leu Met Trp His Pro
385                 390                 395                 400

Thr Leu Pro Leu Leu Ala Tyr Ala Pro Glu Ser Ile Asn Glu Asn Asn
                405                 410                 415

Lys Asp Pro Ser Ile Arg Val Phe Gly Tyr His Ser
            420                 425

(2) INFORMATION FOR SEQ ID NO:30:

(i) SEQUENCE CHARACTERISTICS:
        (A) LENGTH: 517 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: BETA TRCP, Fig. 13

(xi) SEQUENCE DESCRIPTION: SEQ ID NO:30:

Met Glu Gly Phe Ser Cys Ser Leu Gln Pro Thr Ala Ser Glu Arg
1               5                   10                  15

Glu Asp Cys Asn Arg Asp Glu Pro Pro Arg Lys Ile Ile Thr Glu Lys
            20                  25                  30

Asn Thr Leu Arg Gln Thr Lys Leu Ala Asn Gly Thr Ser Ser Met Ile
        35                  40                  45

Val Pro Lys Gln Arg Lys Leu Ser Ala Asn Tyr Glu Lys Glu Lys Glu
    50                  55                  60

Leu Cys Val Lys Tyr Phe Glu Gln Trp Ser Glu Cys Asp Gln Val Glu
65                  70                  75                  80

Phe Val Glu His Leu Ile Ser Arg Met Cys Tyr Gln His Gly His
                85                  90                  95

Ile Asn Thr Tyr Leu Lys Pro Met Leu Gln Arg Asp Phe Ile Thr Ala
                100                 105                 110

Leu Pro Ala Arg Gly Leu Asp His Ile Ala Glu Asn Ile Leu Ser Tyr
            115                 120                 125

Leu Asp Ala Lys Ser Leu Cys Ser Ala Glu Leu Val Cys Lys Glu Trp
130                 135                 140

Tyr Arg Val Thr Ser Asp Gly Met Leu Trp Lys Lys Leu Ile Glu Arg
145                 150                 155                 160

Met Val Arg Thr Asp Ser Leu Trp Arg Gly Leu Ala Glu Arg Arg Gly
                165                 170                 175

Trp Gly Gln Tyr Leu Phe Lys Asn Lys Pro Pro Asp Gly Lys Thr Pro
                180                 185                 190

Pro Asn Ser Phe Tyr Arg Ala Leu Tyr Pro Lys Ile Ile Gln Asp Ile
            195                 200                 205

Glu Thr Ile Glu Ser Asn Trp Arg Cys Gly Arg His Ser Leu Gln Arg
            210                 215                 220

Ile His Cys Arg Ser Glu Thr Ser Lys Gly Val Tyr Cys Leu Gln Tyr
225                 230                 235                 240

Asp Asp Gln Lys Ile Val Ser Gly Leu Arg Asp Asn Thr Ile Lys Ile
                245                 250                 255

Trp Asp Lys Asn Thr Leu Glu Cys Lys Arg Val Leu Met Gly His Thr
                260                 265                 270

Gly Ser Val Leu Cys Leu Gln Tyr Asp Glu Arg Val Ile Ile Thr Gly
            275                 280                 285

Ser Asp Ser Thr Val Arg Val Trp Asp Val Asn Thr Gly Glu Met Leu
290                 295                 300

Asn Thr Leu Ile His His Cys Glu Ala Val Leu His Leu Arg Phe Asn
305                 310                 315                 320

Asn Gly Met Met Val Thr Cys Ser Lys Asp Arg Ser Ile Ala Val Trp
                325                 330                 335

Asp Met Ala Ser Ala Thr Asp Ile Thr Leu Arg Arg Val Leu Val Gly
            340                 345                 350

His Arg Ala Ala Val Asn Val Val Asp Phe Asp Asp Lys Tyr Ile Val
            355                 360                 365

Ser Ala Ser Gly Asp Arg Thr Ile Lys Val Trp Asn Thr Ser Thr Cys
            370                 375                 380

Glu Phe Val Arg Thr Leu Asn Gly His Lys Arg Gly Ile Ala Cys Leu
385                 390                 395                 400

Gln Tyr Arg Asp Arg Leu Val Val Ser Gly Ser Ser Asp Asn Thr Ile

```
                        405                 410                 415
Arg Leu Trp Asp Ile Glu Cys Gly Ala Cys Leu Arg Val Leu Glu Gly
                420                 425                 430

His Glu Leu Val Arg Cys Ile Arg Phe Asp Asn Lys Arg Ile Val
        435                 440                 445

Ser Gly Ala Tyr Asp Gly Lys Ile Lys Val Trp Asp Leu Val Ala Ala
    450                 455                 460

Leu Asp Pro Arg Ala Pro Ala Gly Thr Leu Cys Leu Arg Thr Leu Val
465                 470                 475                 480

Glu His Ser Gly Arg Val Phe Arg Leu Gln Phe Asp Glu Phe Gln Ile
                485                 490                 495

Val Ser Ser His Asp Asp Thr Ile Leu Ile Trp Asp Phe Leu Asn
        500                 505                 510

Asp Pro Gly Leu Ala
        515

(2) INFORMATION FOR SEQ ID NO:31:

(i) SEQUENCE CHARACTERISTICS:
        (A) LENGTH: 906 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: beta-prime-cop, Fig. 14

(xi) SEQUENCE DESCRIPTION: SEQ ID NO:31:

Met Pro Leu Arg Leu Asp Ile Lys Arg Lys Leu Thr Ala Arg Ser Asp
1               5                   10                  15

Arg Val Lys Ser Val Asp Leu His Pro Thr Glu Pro Trp Met Leu Ala
                20                  25                  30

Ser Leu Tyr Asn Gly Ser Val Cys Val Trp Asn His Glu Thr Gln Thr
            35                  40                  45

Leu Val Lys Thr Phe Glu Val Cys Asp Leu Pro Val Arg Ala Ala Lys
        50                  55                  60

Phe Val Ala Arg Lys Asn Trp Val Val Thr Gly Ala Asp Asp Met Gln
65                  70                  75                  80

Ile Arg Val Phe Asn Tyr Asn Thr Leu Glu Arg Val His Met Phe Glu
                85                  90                  95

Ala His Ser Asp Tyr Ile Arg Cys Ile Ala Val His Pro Thr Gln Pro
            100                 105                 110

Phe Ile Leu Thr Ser Ser Asp Asp Met Leu Ile Lys Leu Trp Asp Trp
        115                 120                 125

Asp Lys Lys Trp Ser Cys Ser Gln Val Phe Glu Gly His Thr His Tyr
    130                 135                 140

Val Met Gln Ile Val Ile Asn Pro Lys Asp Asn Asn Gln Phe Ala Ser
145                 150                 155                 160

Ala Ser Leu Asp Arg Thr Ile Lys Val Trp Gln Leu Gly Ser Ser Ser
                165                 170                 175

Pro Asn Phe Thr Leu Glu Gly His Glu Lys Gly Val Asn Cys Ile Asp
            180                 185                 190

Tyr Tyr Ser Gly Gly Asp Lys Pro Tyr Leu Ile Ser Gly Ala Asp Asp
```

-continued

```
            195                 200                 205
Arg Leu Val Lys Ile Trp Asp Tyr Gln Asn Lys Thr Cys Val Gln Thr
            210                 215                 220
Leu Glu Gly His Ala Gln Asn Val Ser Cys Ala Ser Phe His Pro Glu
225                 230                 235                 240
Leu Pro Ile Ile Ile Thr Gly Ser Glu Asp Gly Thr Val Arg Ile Trp
                245                 250                 255
His Ser Ser Thr Tyr Arg Leu Glu Ser Thr Leu Asn Tyr Gly Met Glu
                260                 265                 270
Arg Val Trp Cys Val Ala Ser Leu Arg Gly Ser Asn Asn Val Ala Leu
                275                 280                 285
Gly Tyr Asp Glu Gly Ser Ile Ile Val Lys Leu Gly Arg Glu Glu Pro
290                 295                 300
Ala Met Ser Met Asp Ala Asn Gly Lys Ile Ile Trp Ala Lys His Ser
305                 310                 315                 320
Glu Val Gln Gln Ala Asn Leu Lys Ala Met Gly Asp Ala Glu Ile Lys
                325                 330                 335
Asp Gly Glu Arg Leu Pro Leu Ala Val Lys Asp Met Gly Ser Cys Glu
                340                 345                 350
Ile Tyr Pro Gln Thr Ile Gln His Asn Pro Asn Gly Arg Phe Val Val
                355                 360                 365
Val Cys Gly Asp Gly Glu Tyr Ile Ile Tyr Thr Ala Met Ala Leu Arg
370                 375                 380
Asn Lys Ser Phe Gly Ser Ala Gln Glu Phe Ala Trp Ala His Asp Ser
385                 390                 395                 400
Ser Glu Tyr Ala Ile Arg Glu Ser Asn Ser Val Val Lys Ile Phe Lys
                405                 410                 415
Asn Phe Lys Glu Lys Lys Ser Phe Lys Pro Asp Phe Gly Ala Glu Ser
                420                 425                 430
Ile Tyr Gly Gly Phe Leu Leu Gly Val Arg Ser Val Asn Gly Leu Ala
                435                 440                 445
Phe Tyr Asp Trp Glu Asn Thr Glu Leu Ile Arg Arg Ile Glu Ile Gln
                450                 455                 460
Pro Lys His Ile Phe Trp Ser Asp Ser Gly Glu Leu Val Cys Ile Ala
465                 470                 475                 480
Thr Glu Glu Ser Phe Phe Ile Leu Lys Tyr Leu Ser Glu Lys Val Leu
                485                 490                 495
Ala Ala Gln Glu Thr His Glu Gly Val Thr Glu Asp Gly Ile Glu Asp
                500                 505                 510
Gly Phe Glu Val Leu Gly Glu Ile Gln Glu Ile Val Lys Thr Gly Leu
                515                 520                 525
Trp Val Gly Asp Cys Phe Ile Tyr Thr Ser Ser Val Asn Arg Leu Asn
530                 535                 540
Tyr Tyr Val Gly Gly Glu Ile Val Thr Ile Ala His Leu Asp Arg Thr
545                 550                 555                 560
Met Tyr Leu Leu Gly Tyr Ile Pro Lys Asp Asn Arg Leu Tyr Leu Gly
                565                 570                 575
Asp Lys Glu Leu Asn Ile Val Ser Tyr Ser Leu Leu Val Ser Val Leu
                580                 585                 590
Glu Tyr Gln Thr Ala Val Met Arg Arg Asp Phe Ser Met Ala Asp Lys
                595                 600                 605
Val Leu Pro Thr Ile Pro Lys Glu Gln Arg Thr Arg Val Ala His Phe
610                 615                 620
```

```
Leu Glu Lys Gln Gly Phe Lys Gln Gln Ala Leu Thr Val Ser Thr Asp
625                 630                 635                 640

Pro Glu His Arg Phe Glu Leu Ala Leu Gln Leu Gly Glu Leu Lys Ile
            645                 650                 655

Ala Tyr Gln Leu Ala Val Glu Ala Ser Glu Gln Lys Trp Lys Gln
        660                 665                 670

Leu Ala Glu Leu Ala Ile Ser Lys Cys Pro Phe Gly Leu Ala Gln Glu
        675                 680                 685

Cys Leu His His Ala Gln Asp Tyr Gly Gly Leu Leu Leu Ala Thr
        690                 695                 700

Ala Ser Gly Asn Ala Ser Met Val Asn Lys Leu Ala Glu Gly Ala Glu
705                 710                 715                 720

Arg Asp Gly Lys Asn Asn Val Ala Phe Met Ser Tyr Phe Leu Gln Gly
            725                 730                 735

Lys Leu Asp Ala Cys Leu Glu Leu Leu Ile Arg Thr Gly Arg Leu Pro
            740                 745                 750

Glu Ala Ala Phe Leu Ala Arg Thr Tyr Leu Pro Ser Gln Val Ser Arg
        755                 760                 765

Val Val Lys Leu Trp Arg Glu Asn Leu Ser Lys Val Asn Gln Lys Ala
770                 775                 780

Ala Glu Ser Leu Ala Asp Pro Thr Glu Tyr Glu Asn Leu Phe Pro Gly
785                 790                 795                 800

Leu Lys Glu Ala Phe Val Val Glu Glu Trp Val Lys Glu Thr His Ala
            805                 810                 815

Asp Leu Trp Pro Ala Lys Gln Tyr Pro Leu Val Thr Pro Asn Glu Glu
            820                 825                 830

Arg Asn Val Met Glu Glu Ala Lys Gly Phe Gln Pro Ser Arg Ser Ala
835                 840                 845

Ala Gln Gln Glu Leu Asp Gly Lys Pro Ala Ser Pro Thr Pro Val Ile
        850                 855                 860

Val Thr Ser Gln Thr Ala Asn Lys Glu Glu Lys Ser Leu Leu Glu Leu
865                 870                 875                 880

Glu Val Asp Leu Asp Asn Leu Glu Ile Glu Asp Ile Asp Thr Thr Asp
            885                 890                 895

Ile Asn Leu Asp Glu Asp Ile Leu Asp Asp
            900                 905

(2) INFORMATION FOR SEQ ID NO:32:

(i) SEQUENCE CHARACTERISTICS:
        (A) LENGTH: 779 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
         (C) INDIVIDUAL ISOLATE: CDC4 / CDC20 protein, Fig. 15

(xi) SEQUENCE DESCRIPTION: SEQ ID NO:32:

Met Gly Ser Phe Pro Leu Ala Glu Phe Pro Leu Arg Asp Ile Pro Val
1               5                   10                  15

Pro Tyr Ser Tyr Arg Val Ser Gly Gly Ile Ala Ser Ser Gly Ser Val
            20                  25                  30
```

-continued

```
Thr Ala Leu Val Thr Ala Ala Gly Thr His Arg Asn Ser Ser Thr Ala
         35                  40                  45
Lys Thr Val Glu Thr Glu Asp Gly Glu Asp Ile Asp Glu Tyr Gln
 50                  55                  60
Arg Lys Arg Ala Ala Gly Ser Gly Glu Ser Thr Pro Glu Arg Ser Asp
 65                  70                  75                  80
Phe Lys Arg Val Lys His Asp Asn His Lys Thr Leu His Pro Val Asn
                 85                  90                  95
Leu Gln Asn Thr Gly Ala Ala Ser Val Asp Asn Asp Gly Leu His Asn
            100                 105                 110
Leu Thr Asp Ile Ser Asn Asp Ala Glu Lys Leu Leu Met Ser Val Asp
            115                 120                 125
Asp Gly Ser Ala Ala Pro Ser Thr Leu Ser Val Asn Met Gly Val Ala
130                 135                 140
Ser His Asn Val Ala Ala Pro Thr Thr Val Asn Ala Ala Thr Ile Thr
145                 150                 155                 160
Gly Ser Asp Val Ser Asn Asn Val Asn Ser Ala Thr Ile Asn Asn Pro
                165                 170                 175
Met Glu Glu Gly Ala Leu Pro Leu Ser Pro Thr Ala Ser Ser Pro Gly
            180                 185                 190
Thr Thr Thr Pro Leu Ala Lys Thr Thr Lys Thr Ile Asn Asn Asn Asn
            195                 200                 205
Asn Ile Ala Asp Leu Ile Glu Ser Lys Asp Ser Ile Ile Ser Pro Glu
210                 215                 220
Tyr Leu Ser Asp Glu Ile Phe Ser Ala Ile Asn Asn Asn Leu Pro His
225                 230                 235                 240
Ala Tyr Phe Lys Asn Leu Leu Phe Arg Leu Val Ala Asn Met Asp Arg
                245                 250                 255
Ser Glu Leu Ser Asp Leu Gly Thr Leu Ile Lys Asp Asn Leu Lys Arg
            260                 265                 270
Asp Leu Ile Thr Ser Leu Pro Phe Glu Ile Ser Leu Lys Ile Phe Asn
            275                 280                 285
Tyr Leu Gln Phe Glu Asp Ile Ile Asn Ser Leu Gly Val Ser Gln Asn
            290                 295                 300
Trp Asn Lys Ile Ile Arg Lys Ser Thr Ser Leu Trp Lys Lys Leu Leu
305                 310                 315                 320
Ile Ser Glu Asn Phe Val Ser Pro Lys Gly Phe Asn Ser Leu Asn Leu
                325                 330                 335
Lys Leu Ser Gln Lys Tyr Pro Leu Ser Gln Gln Asp Arg Leu Arg
            340                 345                 350
Leu Ser Phe Leu Glu Asn Ile Phe Ile Leu Lys Asn Trp Tyr Asn Pro
            355                 360                 365
Lys Phe Val Pro Gln Arg Thr Thr Leu Arg Gly His Met Thr Ser Val
            370                 375                 380
Ile Thr Cys Leu Gln Phe Glu Asp Asn Tyr Val Ile Thr Gly Ala Asp
385                 390                 395                 400
Asp Lys Met Ile Arg Val Tyr Asp Ser Ile Asn Lys Lys Phe Leu Leu
                405                 410                 415
Gln Leu Ser Gly His Asp Gly Val Trp Ala Leu Lys Tyr Ala His
            420                 425                 430
Gly Gly Ile Leu Val Ser Gly Ser Asp Arg Thr Val Arg Val Trp
            435                 440                 445
```

```
Asp Ile Lys Lys Gly Cys Cys Thr His Val Phe Glu Gly His Asn Ser
    450                 455                 460
Thr Val Arg Cys Leu Asp Ile Val Glu Tyr Lys Asn Ile Lys Tyr Ile
465                 470                 475                 480
Val Thr Gly Ser Arg Asp Asn Thr Leu His Val Trp Lys Leu Pro Lys
                    485                 490                 495
Glu Ser Ser Val Pro Asp His Gly Glu Glu His Asp Tyr Pro Leu Val
            500                 505                 510
Phe His Thr Pro Glu Glu Asn Pro Tyr Phe Val Gly Val Leu Arg Gly
                515                 520                 525
His Met Ala Ser Val Arg Thr Val Ser Gly His Gly Asn Ile Val Val
    530                 535                 540
Ser Gly Ser Tyr Asp Asn Thr Leu Ile Val Trp Asp Val Ala Gln Met
545                 550                 555                 560
Lys Cys Leu Tyr Ile Leu Ser Gly His Thr Asp Arg Ile Tyr Ser Thr
                565                 570                 575
Ile Tyr Asp His Glu Arg Lys Arg Cys Ile Ser Ala Ser Met Asp Thr
                580                 585                 590
Thr Ile Arg Ile Trp Asp Leu Glu Asn Ile Trp Asn Asn Gly Glu Cys
            595                 600                 605
Ser Tyr Ala Thr Asn Ser Ala Ser Pro Cys Ala Lys Ile Leu Gly Ala
        610                 615                 620
Met Tyr Thr Leu Gln Gly His Thr Ala Leu Val Gly Leu Leu Arg Leu
625                 630                 635                 640
Ser Asp Lys Phe Leu Val Ser Ala Ala Ala Asp Gly Ser Ile Arg Gly
                645                 650                 655
Trp Asp Ala Asn Asp Tyr Ser Arg Lys Phe Ser Tyr His His Thr Asn
                660                 665                 670
Leu Ser Ala Ile Thr Thr Phe Tyr Val Ser Asp Asn Ile Leu Val Ser
            675                 680                 685
Gly Ser Glu Asn Gln Phe Asn Ile Tyr Asn Leu Arg Ser Gly Lys Leu
        690                 695                 700
Val His Ala Asn Ile Leu Lys Asp Ala Asp Gln Ile Trp Ser Val Asn
705                 710                 715                 720
Phe Lys Gly Lys Thr Leu Val Ala Ala Val Glu Lys Asp Gly Gln Ser
                725                 730                 735
Phe Leu Glu Ile Leu Asp Phe Ser Lys Ala Ser Lys Ile Asn Tyr Val
                740                 745                 750
Ser Asn Pro Val Asn Ser Ser Ser Ser Leu Glu Ser Ile Ser Thr
            755                 760                 765
Ser Leu Gly Leu Thr Arg Thr Thr Ile Ile Pro
770                 775
```

(2) INFORMATION FOR SEQ ID NO:33:

(i) SEQUENCE CHARACTERISTICS:
        (A) LENGTH: 318 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: GBLP -CHLAMIDOMONAS HOMOLOG, Fig. 16

(xi) SEQUENCE DESCRIPTION: SEQ ID NO:33:

```
Met Ala Glu Thr Leu Thr Leu Arg Ala Thr Leu Lys Gly His Thr Asn
1               5                   10                  15

Trp Val Thr Ala Ile Ala Thr Pro Leu Asp Pro Ser Ser Asn Thr Leu
                20                  25                  30

Leu Ser Ala Ser Arg Asp Lys Ser Val Leu Val Trp Glu Leu Glu Arg
            35                  40                  45

Ser Glu Ser Asn Tyr Gly Tyr Ala Arg Lys Ala Leu Arg Gly His Ser
        50                  55                  60

His Phe Val Gln Asp Val Val Ile Ser Ser Asp Gly Gln Phe Cys Leu
65                  70                  75                  80

Thr Gly Ser Trp Asp Gly Thr Leu Arg Leu Trp Asp Leu Asn Thr Gly
                85                  90                  95

Thr Thr Thr Arg Arg Phe Val Gly His Thr Lys Asp Val Leu Ser Val
                100                 105                 110

Ala Phe Ser Val Asp Asn Arg Gln Ile Val Ser Gly Ser Arg Asp Lys
            115                 120                 125

Thr Ile Lys Leu Trp Asn Thr Leu Gly Glu Cys Lys Tyr Thr Ile Gly
130                 135                 140

Glu Pro Glu Gly His Thr Glu Trp Val Ser Cys Val Arg Phe Ser Pro
145                 150                 155                 160

Met Thr Thr Asn Pro Ile Ile Val Ser Gly Gly Trp Asp Lys Met Val
                165                 170                 175

Lys Val Trp Asn Leu Thr Asn Cys Lys Leu Lys Asn Asn Leu Val Gly
            180                 185                 190

His His Gly Tyr Val Asn Thr Val Thr Val Ser Pro Asp Gly Ser Leu
        195                 200                 205

Cys Ala Ser Gly Gly Lys Asp Gly Ile Ala Met Leu Trp Asp Leu Ala
210                 215                 220

Glu Gly Lys Arg Leu Tyr Ser Leu Asp Ala Gly Asp Val Ile His Cys
225                 230                 235                 240

Leu Cys Phe Ser Pro Asn Arg Tyr Trp Leu Cys Ala Ala Thr Gln Ser
                245                 250                 255

Ser Ile Lys Ile Trp Asp Leu Glu Ser Lys Ser Ile Val Asp Asp Leu
            260                 265                 270

Arg Pro Glu Phe Asn Ile Thr Ser Lys Lys Ala Gln Val Pro Tyr Cys
        275                 280                 285

Val Ser Leu Ala Trp Ser Ala Asp Gly Ser Thr Leu Tyr Ser Gly Tyr
290                 295                 300

Thr Asp Gly Gln Ile Arg Val Trp Ala Val Gly His Ser Leu
305                 310                 315
```

(2) INFORMATION FOR SEQ ID NO:34:

(i) SEQUENCE CHARACTERISTICS:
        (A) LENGTH: 658 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: cop-1 protein, Fig. 17

(xi) SEQUENCE DESCRIPTION: SEQ ID NO:34:

```
Met Glu Glu Ile Ser Thr Asp Pro Val Val Pro Ala Val Lys Pro Asp
1               5                   10                  15

Pro Arg Thr Ser Ser Val Gly Glu Gly Ala Asn Arg His Glu Asn Asp
            20                  25                  30

Asp Gly Gly Ser Gly Ser Glu Ile Gly Ala Pro Asp Leu Asp Lys
        35                  40                  45

Asp Leu Leu Cys Pro Ile Cys Met Gln Ile Ile Lys Asp Ala Phe Leu
50                  55                  60

Thr Ala Cys Gly His Ser Phe Cys Tyr Met Cys Ile Ile Thr His Leu
65                  70                  75                  80

Arg Asn Lys Ser Asp Cys Pro Cys Ser Gln His Leu Thr Asn Asn
                85                  90                  95

Gln Leu Tyr Pro Asn Phe Leu Leu Asp Lys Leu Leu Lys Thr Ser
            100                 105                 110

Ala Arg His Val Ser Lys Thr Ala Ser Pro Leu Asp Gln Phe Arg Glu
            115                 120                 125

Ala Leu Gln Arg Gly Cys Asp Val Ser Ile Lys Glu Val Asp Asn Leu
130                 135                 140

Leu Thr Leu Leu Ala Glu Arg Lys Arg Lys Met Glu Gln Glu Glu Ala
145                 150                 155                 160

Glu Arg Asn Met Gln Ile Leu Leu Asp Phe Leu His Cys Leu Arg Lys
                165                 170                 175

Gln Lys Val Asp Glu Leu Asn Glu Val Gln Thr Asp Leu Gln Tyr Ile
            180                 185                 190

Lys Glu Asp Ile Asn Ala Val Glu Arg His Arg Ile Asp Leu Tyr Arg
            195                 200                 205

Ala Arg Asp Arg Tyr Ser Val Lys Leu Arg Met Leu Gly Asp Pro
210                 215                 220

Ser Thr Arg Asn Ala Trp Pro His Glu Lys Asn Gln Ile Gly Phe Asn
225                 230                 235                 240

Ser Asn Ser Leu Ser Ile Arg Gly Gly Asn Phe Val Gly Asn Tyr Gln
            245                 250                 255

Asn Lys Lys Val Glu Gly Lys Ala Gln Gly Ser Ser His Gly Leu Pro
            260                 265                 270

Lys Lys Asp Ala Leu Ser Gly Ser Asp Ser Gln Ser Leu Asn Gln Ser
            275                 280                 285

Thr Val Ser Met Ala Arg Lys Lys Arg Ile His Ala Gln Phe Asn Asp
            290                 295                 300

Leu Gln Glu Cys Tyr Leu Gln Lys Arg Arg Gln Leu Ala Asp Gln Pro
305                 310                 315                 320

Asn Ser Lys Gln Glu Asn Asp Lys Ser Val Val Arg Arg Glu Gly Tyr
                325                 330                 335

Ser Asn Gly Leu Ala Asp Phe Gln Ser Val Leu Thr Thr Phe Thr Arg
            340                 345                 350

Tyr Ser Arg Leu Arg Val Ile Ala Glu Ile Arg His Gly Asp Ile Phe
            355                 360                 365

His Ser Ala Asn Ile Val Ser Ser Ile Glu Phe Asp Arg Asp Asp Glu
            370                 375                 380

Leu Phe Ala Thr Ala Gly Val Ser Arg Cys Ile Lys Val Phe Asp Phe
385                 390                 395                 400

Ser Ser Val Val Asn Glu Pro Ala Asp Met Gln Cys Pro Ile Val Glu
```

-continued

```
                        405                 410                 415
Met Ser Thr Arg Ser Lys Leu Ser Cys Leu Ser Trp Asn Lys His Glu
                420                 425                 430

Lys Asn His Ile Ala Ser Ser Asp Tyr Glu Gly Ile Val Thr Val Trp
            435                 440                 445

Asp Val Thr Thr Arg Gln Ser Leu Met Glu Thr Glu Asn Glu Lys
450                 455                 460

Arg Ala Trp Ser Val Asp Phe Ser Arg Thr Glu Pro Ser Met Leu Val
465                 470                 475                 480

Ser Gly Ser Asp Asp Cys Lys Val Lys Val Trp Cys Thr Arg Gln Glu
                485                 490                 495

Ala Ser Val Ile Asn Ile Asp Met Lys Ala Asn Ile Cys Cys Val Lys
                500                 505                 510

Tyr Asn Pro Gly Ser Ser Asn Tyr Ile Ala Val Gly Ser Ala Asp His
            515                 520                 525

His Ile His Tyr Tyr Asp Leu Arg Asn Ile Ser Gln Pro Leu His Val
530                 535                 540

Phe Ser Gly His Lys Lys Ala Val Ser Tyr Met Lys Phe Leu Ser Asn
545                 550                 555                 560

Asn Glu Leu Ala Ser Ala Ser Thr Asp Ser Thr Leu Arg Leu Trp Asp
                565                 570                 575

Val Lys Asp Asn Leu Pro Val Arg Thr Phe Arg Gly His Thr Asn Glu
                580                 585                 590

Lys Asn Phe Val Gly Leu Thr Val Asn Ser Glu Tyr Leu Ala Cys Gly
            595                 600                 605

Ser Glu Thr Thr Arg Tyr Val Tyr His Lys Glu Ile Thr Arg Pro Val
        610                 615                 620

Thr Ser His Arg Phe Gly Ser Pro Asp Met Asp Asp Ala Glu Lys Arg
625                 630                 635                 640

Gln Val Pro Thr Leu Leu Val Arg Phe Ala Gly Arg Val Ile Val Pro
                645                 650                 655

Arg Cys
```

(2) INFORMATION FOR SEQ ID NO:35:

(i) SEQUENCE CHARACTERISTICS:
        (A) LENGTH: 440 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: CORO PROTEIN, Fig. 18

(xi) SEQUENCE DESCRIPTION: SEQ ID NO:35:

```
Met Ser Lys Val Val Arg Ser Ser Lys Tyr Arg His Val Phe Ala Ala
1               5                   10                  15

Gln Pro Lys Lys Glu Glu Cys Tyr Gln Asn Leu Lys Thr Lys Ser Ala
            20                  25                  30

Val Trp Asp Ser Asn Tyr Val Ala Ala Asn Thr Arg Tyr Ile Trp Asp
        35                  40                  45

Ala Ala Gly Gly Gly Ser Phe Ala Val Glu Ala Ile Pro His Ser Gly
    50                  55                  60
```

-continued

```
Lys Thr Thr Ser Val Pro Leu Phe Asn Gly His Lys Ser Ala Val Leu
 65                  70                  75                  80

Asp Ile Ala Phe His Pro Phe Asn Glu Asn Leu Val Gly Ser Val Ser
                 85                  90                  95

Glu Asp Cys Asn Ile Cys Ile Trp Gly Ile Pro Glu Gly Gly Leu Thr
            100                 105                 110

Asp Ser Ile Ser Thr Pro Leu Gln Thr Leu Ser Gly His Lys Arg Lys
        115                 120                 125

Val Gly Thr Ile Ser Phe Gly Pro Val Ala Asp Asn Val Ala Val Thr
130                 135                 140

Ser Ser Gly Asp Phe Leu Val Lys Thr Trp Asp Val Glu Gln Gly Lys
145                 150                 155                 160

Asn Leu Thr Thr Val Glu Gly His Ser Asp Met Ile Thr Ser Cys Glu
                165                 170                 175

His Asn Gly Ser Gln Ile Val Thr Thr Cys Lys Asp Lys Lys Ala Arg
            180                 185                 190

Val Phe Asp Pro Arg Thr Asn Ser Ile Val Asn Glu Val Val Cys His
        195                 200                 205

Gln Gly Val Lys Asn Ser Arg Ala Ile Phe Ala Lys Asp Lys Val Ile
210                 215                 220

Thr Val Gly Phe Ser Lys Thr Ser Glu Arg Glu Leu His Ile Tyr Asp
225                 230                 235                 240

Pro Arg Ala Phe Thr Thr Pro Leu Ser Ala Gln Val Val Asp Ser Ala
                245                 250                 255

Ser Gly Leu Leu Met Pro Phe Tyr Asp Ala Asp Asn Ser Ile Leu Tyr
            260                 265                 270

Leu Ala Gly Lys Gly Asp Gly Asn Ile Arg Tyr Tyr Glu Leu Val Asp
        275                 280                 285

Glu Ser Pro Tyr Ile His Phe Leu Ser Glu Phe Lys Ser Ala Thr Pro
290                 295                 300

Gln Arg Gly Leu Cys Phe Leu Pro Lys Arg Cys Leu Asn Thr Ser Glu
305                 310                 315                 320

Cys Glu Ile Ala Arg Gly Leu Lys Val Thr Pro Phe Thr Val Glu Pro
                325                 330                 335

Ile Ser Phe Arg Val Pro Arg Lys Ser Asp Ile Phe Gln Gly Asp Ile
            340                 345                 350

Tyr Pro Asp Thr Tyr Ala Gly Glu Pro Ser Leu Thr Ala Glu Gln Trp
        355                 360                 365

Val Ser Gly Thr Asn Ala Glu Pro Lys Thr Val Ser Leu Ala Gly Gly
370                 375                 380

Phe Val Lys Lys Ala Ser Ala Val Glu Phe Lys Pro Val Val Gln Val
385                 390                 395                 400

Gln Glu Gly Pro Lys Asn Glu Lys Glu Leu Arg Glu Glu Tyr Glu Lys
                405                 410                 415

Leu Lys Ile Arg Val Ala Tyr Leu Glu Ser Glu Ile Val Lys Lys Asp
            420                 425                 430

Ala Lys Ile Lys Glu Leu Thr Asn
        435                 440
```

(2) INFORMATION FOR SEQ ID NO:36:

(i) SEQUENCE CHARACTERISTICS:
        (A) LENGTH: 445 amino acids
        (B) TYPE: amino acid -continued

```
        (D) TOPOLOGY: unknown (ii) MOLECULE TYPE: protein (iii) HYPOTHETICAL: NO (iv) ANTI-SENSE: NO (vi) ORIGINAL SOURCE:
            (C) INDIVIDUAL ISOLATE: Coronin (p55), Fig. 19

(xi) SEQUENCE DESCRIPTION: SEQ ID NO:36:

Met Ser Lys Val Val Arg Ser Ser Lys Tyr Arg His Val Phe Ala Ala
1               5                  10                  15

Gln Pro Lys Lys Glu Glu Cys Tyr Gln Asn Leu Lys Val Thr Lys Ser
                20                  25                  30

Ala Trp Asp Ser Asn Tyr Val Ala Ala Asn Thr Arg Tyr Phe Gly Val
            35                  40                  45

Ile Trp Asp Ala Ala Gly Gly Gly Ser Phe Ala Val Ile Pro His Glu
50                  55                  60

Ala Ser Gly Lys Thr Thr Ser Val Pro Leu Phe Asn Gly His Lys Ser
65                  70                  75                  80

Ala Val Leu Asp Ile Ala Phe His Pro Phe Asn Glu Asn Leu Val Gly
                85                  90                  95

Ser Val Ser Glu Asp Cys Asn Ile Cys Ile Trp Gly Ile Pro Glu Gly
                100                 105                 110

Gly Leu Thr Asp Ser Ile Ser Thr Pro Leu Gln Thr Leu Ser Gly His
            115                 120                 125

Lys Arg Lys Val Gly Thr Ile Ser Phe Gly Pro Val Ala Asp Asn Val
130                 135                 140

Ala Val Thr Ser Ser Gly Asp Phe Leu Val Lys Thr Trp Asp Val Glu
145                 150                 155                 160

Gln Gly Lys Asn Leu Thr Thr Val Glu Gly His Ser Asp Met Ile Thr
                165                 170                 175

Ser Cys Glu Trp Asn His Asn Gly Ser Gln Ile Val Thr Thr Cys Lys
            180                 185                 190

Asp Lys Lys Ala Arg Val Phe Asp Pro Arg Thr Asn Ser Ile Val Asn
            195                 200                 205

Glu Val Val Cys His Gln Gly Val Lys Asn Ser Arg Ala Ile Phe Ala
210                 215                 220

Lys Asp Lys Val Ile Thr Val Gly Phe Ser Lys Thr Ser Glu Arg Glu
225                 230                 235                 240

Leu His Ile Tyr Asp Pro Arg Ala Phe Thr Thr Pro Leu Ser Ala Gln
                245                 250                 255

Val Val Asp Ser Ala Ser Gly Leu Leu Met Pro Phe Tyr Asp Ala Asp
                260                 265                 270

Asn Ser Ile Leu Tyr Leu Ala Gly Lys Gly Asp Gly Asn Ile Arg Tyr
            275                 280                 285

Tyr Glu Leu Val Asp Glu Ser Pro Tyr Ile His Phe Leu Ser Glu Phe
        290                 295                 300

Lys Ser Ala Thr Pro Gln Arg Gly Leu Cys Phe Leu Pro Lys Arg Cys
305                 310                 315                 320

Leu Asn Thr Ser Glu Cys Glu Ile Ala Arg Gly Leu Lys Val Thr Pro
                325                 330                 335

Phe Thr Val Glu Pro Ile Ser Phe Arg Val Pro Arg Lys Ser Asp Ile
            340                 345                 350
```

-continued

```
Phe Gln Gly Asp Ile Tyr Pro Asp Thr Tyr Ala Gly Glu Pro Ser Leu
        355                 360                 365

Thr Ala Glu Gln Trp Val Ser Gly Thr Asn Ala Glu Pro Lys Thr Val
    370                 375                 380

Ser Leu Ala Gly Gly Phe Val Lys Lys Ala Ser Ala Val Glu Phe Lys
385                 390                 395                 400

Pro Val Val Gln Val Gln Glu Gly Pro Lys Asn Glu Lys Glu Leu Arg
                405                 410                 415

Glu Glu Tyr Glu Lys Leu Lys Ile Arg Val Ala Tyr Leu Glu Ser Glu
            420                 425                 430

Ile Val Lys Lys Asp Ala Lys Ile Lys Glu Leu Thr Asn
            435                 440                 445
```

(2) INFORMATION FOR SEQ ID NO:37:

(i) SEQUENCE CHARACTERISTICS:
        (A) LENGTH: 431 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: CSTF 50kDa, Fig. 20

(xi) SEQUENCE DESCRIPTION: SEQ ID NO:37:

```
Met Tyr Arg Thr Lys Val Gly Leu Lys Asp Arg Gln Gln Leu Tyr Lys
1               5                   10                  15

Leu Ile Ile Ser Gln Leu Leu Tyr Asp Gly Tyr Ile Ser Ile Ala Asn
            20                  25                  30

Gly Leu Ile Asn Glu Ile Lys Pro Gln Ser Val Cys Ala Pro Ser Glu
        35                  40                  45

Gln Leu Leu His Leu Ile Lys Leu Gly Met Glu Asn Asp Asp Thr Ala
    50                  55                  60

Val Gln Tyr Ala Ile Gly Arg Ser Asp Thr Val Ala Pro Gly Thr Gly
65                  70                  75                  80

Ile Asp Leu Glu Phe Asp Ala Asp Val Gln Thr Met Ser Pro Glu Ala
                85                  90                  95

Ser Glu Tyr Glu Thr Cys Tyr Val Thr Ser His Lys Gly Pro Cys Arg
            100                 105                 110

Val Ala Thr Tyr Ser Arg Asp Gly Gln Leu Ile Ala Thr Gly Ser Ala
        115                 120                 125

Asp Ala Ser Ile Lys Ile Leu Asp Thr Glu Arg Met Leu Ala Lys Ser
    130                 135                 140

Ala Met Pro Ile Glu Val Met Met Asn Glu Thr Ala Gln Gln Asn Met
145                 150                 155                 160

Glu Asn His Pro Val Ile Arg Thr Leu Tyr Asp His Val Asp Glu Val
                165                 170                 175

Thr Cys Leu Ala Phe His Pro Thr Glu Gln Ile Leu Ala Ser Gly Ser
            180                 185                 190

Arg Asp Tyr Thr Leu Lys Leu Phe Asp Tyr Ser Lys Pro Ser Ala Lys
        195                 200                 205

Arg Ala Phe Lys Tyr Ile Gln Glu Ala Glu Met Leu Arg Ser Ile Ser
    210                 215                 220
```

```
Phe His Pro Ser Gly Asp Phe Ile Leu Val Gly Thr Gln His Pro Thr
225                 230                 235                 240

Leu Arg Leu Tyr Asp Ile Asn Thr Phe Gln Cys Phe Val Ser Cys Asn
            245                 250                 255

Pro Gln Asp Gln His Thr Asp Ala Ile Cys Ser Val Asn Tyr Asn Ser
            260                 265                 270

Ser Ala Asn Met Tyr Val Thr Gly Ser Lys Asp Gly Cys Ile Lys Leu
            275                 280                 285

Trp Asp Gly Val Ser Asn Arg Cys Ile Thr Thr Phe Glu Lys Ala His
        290                 295                 300

Asp Gly Ala Glu Val Cys Ser Ala Ile Phe Ser Lys Asn Ser Lys Tyr
305                 310                 315                 320

Ile Leu Ser Ser Gly Lys Asp Ser Val Ala Lys Leu Trp Glu Ile Ser
                325                 330                 335

Thr Gly Arg Thr Leu Val Arg Tyr Thr Gly Ala Gly Leu Ser Gly Arg
            340                 345                 350

Gln Val His Arg Thr Gln Ala Val Phe Asn His Thr Glu Asp Tyr Val
            355                 360                 365

Leu Leu Pro Asp Glu Arg Thr Ile Ser Leu Cys Cys Trp Asp Ser Arg
370                 375                 380

Thr Ala Glu Arg Arg Asn Leu Leu Ser Leu Gly His Asn Asn Ile Val
385                 390                 395                 400

Arg Cys Ile Val His Ser Pro Thr Asn Pro Gly Phe Met Thr Cys Ser
            405                 410                 415

Asp Asp Phe Arg Ala Arg Phe Trp Tyr Arg Arg Ser Thr Thr Asp
            420                 425                 430

(2) INFORMATION FOR SEQ ID NO:38:

(i) SEQUENCE CHARACTERISTICS:
        (A) LENGTH: 340 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: G-Beta 1 bovine, Fig. 21

(xi) SEQUENCE DESCRIPTION: SEQ ID NO:38:

Met Ser Glu Leu Asp Gln Leu Arg Gln Glu Ala Glu Gln Leu Lys Asn
1               5                   10                  15

Gln Ile Arg Asp Ala Arg Lys Ala Cys Ala Asp Ala Thr Leu Ser Gln
            20                  25                  30

Ile Thr Asn Asn Ile Asp Pro Val Gly Arg Ile Gln Met Arg Thr Arg
            35                  40                  45

Arg Thr Leu Arg Gly His Leu Ala Lys Ile Tyr Ala Met His Trp Gly
            50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
            100                 105                 110
```

-continued

```
Ala Cys Gly Gly Leu Asp Asn Ile Cys Ser Ile Tyr Asn Leu Lys Thr
            115                 120                 125

Arg Glu Gly Asn Val Arg Val Ser Arg Glu Leu Ala Gly His Thr Gly
        130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
            180                 185                 190

Ala Pro Asp Thr Arg Leu Phe Val Ser Gly Ala Cys Asp Ala Ser Ala
            195                 200                 205

Lys Leu Trp Asp Val Arg Glu Gly Met Cys Arg Gln Thr Phe Thr Gly
            210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255

Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
            275                 280                 285

Tyr Asp Asp Phe Asn Cys Asn Val Trp Asp Ala Leu Lys Ala Asp Arg
            290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340
```

(2) INFORMATION FOR SEQ ID NO:39:

(i) SEQUENCE CHARACTERISTICS:
        (A) LENGTH: 326 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: G-Beta- bovine (2), Fig. 22

(xi) SEQUENCE DESCRIPTION: SEQ ID NO:39:

```
Arg Asn Gln Ile Arg Asp Ala Arg Lys Ala Cys Gly Asp Ser Thr Leu
1               5                   10                  15

Thr Gln Ile Thr Ala Gly Leu Asp Pro Val Gly Arg Ile Gln Met Arg
            20                  25                  30

Thr Arg Arg Thr Leu Arg Gly His Leu Ala Lys Ile Tyr Ala Met His
            35                  40                  45

Trp Gly Thr Asp Ser Arg Leu Leu Val Ser Ala Ser Gln Asp Gly Lys
        50                  55                  60

Leu Ile Ile Trp Asp Ser Glu Gly Asn Val Arg Tyr Thr Thr Asn Lys
65                  70                  75                  80
```

```
Val His Ala Ile Pro Leu Arg Ser Ser Trp Val Met Thr Cys Ala Tyr
                85                  90                  95

Ala Pro Ser Gly Asn Phe Val Ala Cys Gly Gly Leu Asp Asn Ile Cys
            100                 105                 110

Ser Ile Tyr Ser Leu Lys Thr Arg Val Ser Arg Glu Leu Pro Gly His
            115                 120                 125

Thr Gly Tyr Leu Ser Cys Cys Arg Phe Leu Asp Asp Asn Gln Ile Ile
            130                 135                 140

Thr Ser Ser Gly Asp Thr Thr Cys Ala Leu Trp Asp Ile Glu Thr Gly
145                 150                 155                 160

Gln Gln Thr Val Gly Phe Ala Gly His Ser Gly Asp Val Met Ser Leu
                165                 170                 175

Ser Leu Ala Pro Asp Gly Arg Thr Phe Val Ser Gly Ala Cys Asp Ala
                180                 185                 190

Ser Ile Lys Leu Trp Asp Val Arg Asp Ser Met Cys Arg Gln Thr Phe
            195                 200                 205

Ile Gly His Glu Ser Asp Ile Asn Ala Val Ala Phe Phe Pro Asn Gly
            210                 215                 220

Tyr Ala Phe Thr Thr Gly Ser Asp Asp Ala Thr Cys Arg Leu Phe Asp
225                 230                 235                 240

Leu Arg Ala Asp Gln Glu Leu Leu Met Tyr Ser His Asp Asn Ile Ile
                245                 250                 255

Cys Gly Ile Thr Ser Val Ala Phe Ser Arg Ser Gly Arg Leu Leu Leu
                260                 265                 270

Ala Gly Tyr Asp Asp Phe Asn Cys Asn Ile Trp Asp Ala Met Lys Gly
            275                 280                 285

Asp Arg Ala Gly Val Leu Ala Gly His Asp Asn Arg Val Ser Cys Leu
            290                 295                 300

Gly Val Thr Asp Asp Gly Met Ala Val Ala Thr Gly Ser Trp Asp Ser
305                 310                 315                 320

Phe Leu Lys Ile Trp Asn
                325

(2) INFORMATION FOR SEQ ID NO:40:

(i) SEQUENCE CHARACTERISTICS:
        (A) LENGTH: 340 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: G- BETA DROSOPH, Fig. 23

(xi) SEQUENCE DESCRIPTION: SEQ ID NO:40:

Met Asn Glu Leu Asp Ser Leu Arg Gln Glu Ala Glu Ser Leu Lys Asn
1               5                   10                  15

Ala Ile Arg Asp Ala Arg Lys Ala Ala Cys Asp Thr Ser Leu Leu Gln
            20                  25                  30

Ala Ala Thr Ser Leu Glu Pro Ile Gly Arg Ile Gln Met Arg Thr Arg
        35                  40                  45

Arg Thr Leu Arg Gly His Leu Ala Lys Ile Tyr Ala Met His Trp Gly
    50                  55                  60
```

```
Asn Asp Ser Arg Asn Leu Val Ser Ala Ser Gln Asp Gly Lys Leu Ile
65                  70                  75                  80

Val Trp Asp Ser His Thr Thr Asn Lys Val His Ala Ile Pro Leu Arg
                85                  90                  95

Ser Ser Trp Val Met Thr Cys Ala Tyr Ala Pro Ser Gly Ser Tyr Val
            100                 105                 110

Ala Cys Gly Gly Leu Asp Asn Met Cys Ser Ile Tyr Asn Leu Lys Thr
            115                 120                 125

Arg Glu Gly Asn Val Arg Val Ser Arg Glu Leu Pro Gly His Gly Gly
            130                 135                 140

Tyr Leu Ser Cys Cys Arg Phe Leu Asp Asp Asn Gln Ile Val Thr Ser
145                 150                 155                 160

Ser Gly Asp Met Ser Cys Gly Leu Trp Asp Ile Glu Thr Gly Leu Gln
                165                 170                 175

Val Thr Ser Phe Leu Gly His Thr Gly Asp Val Met Ala Leu Ser Leu
                180                 185                 190

Ala Pro Gln Cys Lys Thr Phe Val Ser Gly Ala Cys Asp Ala Ser Ala
                195                 200                 205

Lys Leu Trp Asp Ile Arg Glu Gly Val Cys Lys Gln Thr Phe Pro Gly
210                 215                 220

His Glu Ser Asp Ile Asn Ala Val Thr Phe Phe Pro Asn Gly Gln Ala
225                 230                 235                 240

Phe Ala Thr Gly Ser Asp Asp Ala Thr Cys Arg Leu Phe Asp Ile Arg
                245                 250                 255

Ala Asp Gln Glu Leu Ala Met Tyr Ser His Asp Asn Ile Ile Cys Gly
                260                 265                 270

Ile Thr Ser Val Ala Phe Ser Lys Ser Gly Arg Leu Leu Leu Ala Gly
                275                 280                 285

Tyr Asp Asp Phe Asn Cys Asn Val Trp Asp Thr Met Lys Ala Glu Arg
                290                 295                 300

Ser Gly Ile Leu Ala Gly His Asp Asn Arg Val Ser Cys Leu Gly Val
305                 310                 315                 320

Thr Glu Asn Gly Met Ala Val Ala Thr Gly Ser Trp Asp Ser Phe Leu
                325                 330                 335

Arg Val Trp Asn
            340

(2) INFORMATION FOR SEQ ID NO:41:

(i) SEQUENCE CHARACTERISTICS:
        (A) LENGTH: 317 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
         (C) INDIVIDUAL ISOLATE: G-BETA HUMAN, Fig. 24

(xi) SEQUENCE DESCRIPTION: SEQ ID NO:41:

Met Thr Glu Gln Met Thr Leu Arg Gly Thr Leu Lys Gly His Asn Gly
1               5                   10                  15

Trp Val Thr Gln Ile Ala Thr Thr Pro Gln Phe Pro Asp Met Ile Leu
                20                  25                  30
```

```
Ser Ala Ser Arg Asp Lys Thr Ile Ile Met Trp Lys Leu Thr Arg Asp
            35                  40                  45

Glu Thr Asn Tyr Gly Ile Pro Gln Arg Ala Leu Arg Gly His Ser His
     50                  55                  60

Phe Val Ser Asp Val Val Ile Ser Ser Asp Gly Gln Phe Ala Leu Ser
65                   70                  75                  80

Gly Ser Trp Asp Gly Thr Leu Arg Leu Trp Asp Leu Thr Gly Thr
                85                  90                  95

Thr Thr Arg Arg Phe Val Gly His Thr Lys Asp Val Leu Ser Val Ala
            100                 105                 110

Phe Ser Ser Asp Asn Arg Gln Ile Val Ser Gly Ser Arg Asp Lys Thr
            115                 120                 125

Ile Lys Leu Trp Asn Thr Leu Gly Val Cys Lys Tyr Thr Val Gln Asp
     130                 135                 140

Glu Ser His Ser Glu Trp Val Ser Cys Val Arg Phe Ser Pro Asn Ser
145                 150                 155                 160

Ser Asn Pro Ile Ile Val Ser Cys Gly Trp Asp Lys Leu Val Lys Val
                165                 170                 175

Trp Asn Leu Ala Asn Cys Lys Leu Lys Thr Asn His Ile Gly His Thr
            180                 185                 190

Gly Tyr Leu Asn Thr Val Thr Val Ser Pro Asp Gly Ser Leu Cys Ala
     195                 200                 205

Ser Gly Gly Lys Asp Gly Gln Ala Met Leu Trp Asp Leu Asn Glu Gly
210                 215                 220

Lys His Leu Tyr Thr Leu Asp Gly Gly Asp Ile Ile Asn Ala Leu Cys
225                 230                 235                 240

Phe Ser Pro Asn Arg Tyr Trp Leu Cys Ala Ala Thr Gly Pro Ser Ile
                245                 250                 255

Lys Ile Trp Asp Leu Glu Gly Lys Ile Ile Val Asp Glu Leu Lys Gln
            260                 265                 270

Glu Val Ile Ser Thr Ser Ser Lys Ala Glu Pro Pro Gln Cys Thr Ser
     275                 280                 285

Leu Ala Trp Ser Ala Asp Gly Gln Thr Leu Phe Ala Gly Tyr Thr Asp
     290                 295                 300

Asn Leu Val Arg Val Trp Gln Val Thr Ile Gly Thr Arg
305                 310                 315

(2) INFORMATION FOR SEQ ID NO:42:

(i) SEQUENCE CHARACTERISTICS:
        (A) LENGTH: 340 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
         (C) INDIVIDUAL ISOLATE: G-Beta 2 (Human), Fig. 25

(xi) SEQUENCE DESCRIPTION: SEQ ID NO:42:

Met Ser Glu Leu Glu Gln Leu Arg Gln Glu Ala Glu Gln Leu Arg Asn
1               5                   10                  15

Gln Ile Arg Asp Ala Arg Lys Ala Cys Gly Asp Ser Thr Leu Thr Gln
            20                  25                  30
```

```
Ile Thr Ala Gly Leu Asp Pro Val Gly Arg Ile Gln Met Arg Thr Arg
         35                  40                  45

Arg Thr Leu Arg Gly His Leu Ala Lys Ile Tyr Ala Met His Trp Gly
     50                  55                  60

Thr Asp Ser Arg Leu Leu Val Ser Ala Ser Gln Asp Gly Lys Leu Ile
 65                  70                  75                  80

Ile Trp Asp Ser Tyr Thr Thr Asn Lys Val His Ala Ile Pro Leu Arg
                 85                  90                  95

Ser Ser Trp Val Met Thr Cys Ala Tyr Ala Pro Ser Gly Asn Phe Val
             100                 105                 110

Ala Cys Gly Gly Leu Asp Asn Ile Cys Ser Ile Tyr Ser Leu Lys Thr
         115                 120                 125

Arg Glu Gly Asn Val Arg Val Ser Arg Glu Leu Pro Gly His Thr Gly
     130                 135                 140

Tyr Leu Ser Cys Cys Arg Phe Leu Asp Asp Asn Gln Ile Ile Thr Ser
145                 150                 155                 160

Ser Gly Asp Thr Thr Cys Ala Leu Trp Asp Ile Glu Thr Gly Gln Gln
                 165                 170                 175

Thr Val Gly Phe Ala Gly His Ser Gly Asp Val Met Ser Leu Ser Leu
             180                 185                 190

Ala Pro Asp Gly Arg Thr Phe Val Ser Gly Ala Cys Asp Ala Ser Ile
         195                 200                 205

Lys Leu Trp Asp Val Arg Asp Ser Met Cys Arg Gln Thr Phe Ile Gly
     210                 215                 220

His Glu Ser Asp Ile Asn Ala Val Ala Phe Phe Pro Asn Gly Tyr Ala
225                 230                 235                 240

Phe Thr Thr Gly Ser Asp Asp Ala Thr Cys Arg Leu Phe Asp Leu Arg
                 245                 250                 255

Ala Asp Gln Glu Leu Leu Met Tyr Ser His Asp Asn Ile Ile Cys Gly
             260                 265                 270

Ile Thr Ser Val Ala Phe Ser Arg Ser Gly Arg Leu Leu Leu Ala Gly
         275                 280                 285

Tyr Asp Asp Phe Asn Cys Asn Ile Trp Asp Ala Met Lys Gly Asp Arg
     290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                 325                 330                 335

Lys Ile Trp Asn
         340

(2) INFORMATION FOR SEQ ID NO:43:

(i) SEQUENCE CHARACTERISTICS:
        (A) LENGTH: 29 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: G-Beta 4 (mouse), Fig. 26

(xi) SEQUENCE DESCRIPTION: SEQ ID NO:43:
```

```
Lys Lys Asx Glu Thr Asx Val Asn Met Gly Arg Tyr Thr Pro Arg Ile
 1               5                  10                  15

Lys His Ile Lys Arg Pro Arg Thr Asp Xaa Xaa Gly
             20                  25
```

(2) INFORMATION FOR SEQ ID NO:44:

(i) SEQUENCE CHARACTERISTICS:
        (A) LENGTH: 718 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: GROUCHO PROTEIN DROSOPH, Fig. 27

(xi) SEQUENCE DESCRIPTION: SEQ ID NO:44:

```
Met Tyr Pro Ser Pro Val Arg His Pro Ala Ala Gly Gly Pro Pro Pro
 1               5                  10                  15

Gln Gly Pro Ile Lys Phe Thr Ile Ala Asp Thr Leu Glu Arg Ile Lys
             20                  25                  30

Glu Glu Phe Asn Phe Leu Gln Ala His Tyr His Ser Ile Lys Leu Glu
         35                  40                  45

Cys Glu Lys Leu Ser Asn Glu Lys Thr Glu Met Gln Arg His Tyr Val
 50                  55                  60

Met Tyr Tyr Glu Met Ser Tyr Gly Leu Asn Val Glu Met His Lys Gln
65                  70                  75                  80

Thr Glu Ile Ala Lys Arg Leu Asn Thr Leu Ile Asn Gln Leu Leu Pro
             85                  90                  95

Phe Leu Gln Ala Asp His Gln Gln Val Leu Gln Ala Val Glu Arg
                100                 105                 110

Ala Lys Gln Val Thr Met Gln Glu Leu Asn Leu Ile Ile Gly Gln Gln
             115                 120                 125

Ile His Ala Gln Gln Val Pro Gly Gly Pro Pro Gln Pro Met Gly Ala
         130                 135                 140

Leu Asn Pro Phe Gly Ala Leu Gly Ala Thr Met Gly Leu Pro His Gly
145                 150                 155                 160

Pro Gln Gly Leu Leu Asn Lys Pro Pro Glu His His Arg Pro Asp Ile
                165                 170                 175

Lys Pro Thr Gly Leu Glu Gly Pro Ala Ala Ala Glu Glu Arg Leu Arg
             180                 185                 190

Asn Ser Val Ser Pro Ala Asp Arg Glu Lys Tyr Arg Thr Arg Ser Pro
         195                 200                 205

Leu Asp Ile Glu Asn Asp Ser Lys Arg Arg Lys Asp Glu Lys Leu Gln
210                 215                 220

Glu Asp Glu Gly Glu Lys Ser Asp Gln Asp Leu Val Val Asp Val Ala
225                 230                 235                 240

Asn Glu Met Glu Ser His Ser Pro Arg Pro Asn Gly Glu His Val Ser
                245                 250                 255

Met Glu Val Arg Asp Arg Glu Ser Leu Asn Gly Glu Arg Leu Glu Lys
             260                 265                 270

Pro Ser Ser Ser Gly Ile Lys Gln Glu Arg Pro Pro Ser Arg Ser Gly
         275                 280                 285
```

-continued

```
Ser Ser Ser Ser Arg Ser Thr Pro Ser Leu Lys Thr Lys Asp Met Glu
    290                 295                 300

Lys Pro Gly Thr Pro Gly Ala Lys Ala Arg Thr Pro Thr Pro Asn Ala
305                 310                 315                 320

Ala Ala Pro Ala Pro Gly Val Asn Pro Lys Gln Met Met Pro Gln Gly
                325                 330                 335

Pro Pro Pro Ala Gly Tyr Pro Gly Ala Pro Tyr Gln Arg Pro Ala Asp
            340                 345                 350

Pro Tyr Gln Arg Pro Pro Ser Asp Pro Ala Tyr Gly Arg Pro Pro Pro
        355                 360                 365

Met Pro Tyr Asp Pro His Ala His Val Arg Thr Asn Gly Ile Pro His
    370                 375                 380

Pro Ser Ala Leu Thr Gly Gly Lys Pro Ala Tyr Ser Phe His Met Asn
385                 390                 395                 400

Gly Glu Gly Ser Leu Gln Pro Val Pro Phe Pro Pro Asp Ala Leu Val
                405                 410                 415

Gly Val Gly Ile Pro Arg His Ala Arg Gln Ile Asn Thr Leu Ser His
            420                 425                 430

Gly Glu Val Val Cys Ala Val Thr Ile Ser Asn Pro Thr Lys Tyr Val
        435                 440                 445

Tyr Thr Gly Gly Lys Gly Cys Val Lys Val Trp Asp Ile Ser Gln Pro
    450                 455                 460

Gly Asn Lys Asn Pro Val Ser Gln Leu Asp Cys Leu Gln Arg Asp Asn
465                 470                 475                 480

Tyr Ile Arg Ser Val Lys Leu Leu Pro Asp Gly Arg Thr Leu Ile Val
                485                 490                 495

Gly Gly Glu Ala Ser Asn Leu Ser Ile Trp Asp Leu Ala Ser Pro Thr
            500                 505                 510

Pro Arg Ile Lys Ala Glu Leu Thr Ser Ala Ala Pro Ala Cys Tyr Ala
        515                 520                 525

Leu Ala Ser Pro Asp Ser Lys Val Cys Phe Ser Cys Cys Ser Asp Gly
    530                 535                 540

Asn Ile Ala Val Trp Asp Leu His Asn Glu Ile Leu Val Arg Gln Phe
545                 550                 555                 560

Gln Gly His Thr Asp Gly Ala Ser Cys Ile Asp Ile Ser Pro Asp Gly
                565                 570                 575

Ser Arg Leu Trp Thr Gly Gly Leu Asp Asn Thr Val Arg Ser Trp Asp
            580                 585                 590

Leu Arg Glu Gly Arg Gln Leu Gln Gln His Asp Phe Ser Ser Gln Ile
        595                 600                 605

Phe Ser Leu Gly Tyr Cys Pro Thr Gly Asp Trp Leu Ala Val Gly Met
    610                 615                 620

Glu Asn Ser His Val Glu Val Leu His Ala Ser Lys Pro Asp Lys Tyr
625                 630                 635                 640

Gln Leu His Leu His Glu Ser Cys Val Leu Ser Leu Arg Phe Ala Ala
                645                 650                 655

Cys Gly Lys Trp Phe Val Ser Thr Gly Lys Asp Asn Leu Leu Asn Ala
            660                 665                 670

Trp Arg Thr Pro Tyr Gly Ala Ser Ile Phe Gln Ser Lys Glu Thr Ser
        675                 680                 685

Ser Val Leu Ser Cys Asp Ile Ser Thr Asp Asp Lys Tyr Ile Val Thr
    690                 695                 700

Gly Ser Gly Asp Lys Lys Ala Thr Val Tyr Glu Val Ile Tyr
```

```
705              710           715
```

(2) INFORMATION FOR SEQ ID NO:45:

(i) SEQUENCE CHARACTERISTICS:
        (A) LENGTH: 341 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: GTP binding protein (squid), Fig. 28

(xi) SEQUENCE DESCRIPTION: SEQ ID NO:45:

```
Met Thr Ser Glu Leu Glu Ala Leu Arg Gln Glu Thr Glu Gln Leu Lys
1               5                   10                  15

Asn Gln Ile Arg Glu Ala Arg Lys Ala Ala Asp Thr Thr Leu Ala
            20                  25                  30

Met Ala Thr Ala Asn Val Glu Pro Val Gly Arg Ile Gln Met Arg Thr
            35                  40                  45

Arg Arg Thr Leu Arg Gly His Leu Ala Lys Ile Tyr Ala Met His Trp
50                      55                  60

Ala Ser Asp Ser Arg Asn Leu Val Ser Ala Ser Gln Asp Gly Lys Leu
65                      70                  75                  80

Ile Val Trp Asp Gly Tyr Thr Thr Asn Lys Val His Ala Ile Pro Leu
                85                  90                  95

Arg Ser Ser Trp Val Met Thr Cys Ala Tyr Ala Pro Ser Gly Asn Tyr
            100                 105                 110

Val Ala Cys Gly Gly Leu Asp Asn Ile Cys Ser Ile Tyr Ser Leu Lys
            115                 120                 125

Thr Arg Glu Gly Asn Val Arg Val Ser Arg Glu Leu Pro Gly His Thr
        130                 135                 140

Gly Tyr Leu Ser Cys Cys Arg Phe Ile Asp Asp Asn Gln Ile Val Thr
145                 150                 155                 160

Ser Ser Gly Asp Met Thr Cys Ala Leu Trp Asn Ile Glu Thr Gly Asn
                165                 170                 175

Gln Ile Thr Ser Phe Gly Gly His Thr Gly Asp Val Met Ser Leu Ser
            180                 185                 190

Leu Ala Pro Asp Met Arg Thr Phe Val Ser Gly Ala Cys Asp Ala Ser
            195                 200                 205

Ala Lys Leu Phe Asp Ile Arg Asp Gly Ile Cys Lys Gln Thr Phe Thr
210                 215                 220

Gly His Glu Ser Asp Ile Asn Ala Ile Thr Tyr Phe Pro Asn Gly Phe
225                 230                 235                 240

Ala Phe Ala Thr Gly Ser Asp Asp Ala Thr Cys Arg Leu Phe Asp Ile
            245                 250                 255

Arg Ala Asp Gln Glu Ile Gly Met Tyr Ser His Asp Asn Ile Ile Cys
            260                 265                 270

Gly Ile Thr Ser Val Ala Phe Ser Lys Ser Gly Arg Leu Leu Leu Gly
        275                 280                 285

Gly Tyr Asp Asp Phe Asn Cys Asn Val Trp Asp Val Leu Lys Gln Glu
    290                 295                 300

Arg Ala Gly Val Leu Ala Gly His Asp Asn Arg Val Ser Cys Leu Gly
```

```
305                 310                 315                 320
Val Thr Glu Asp Gly Met Ala Val Ala Thr Gly Ser Trp Asp Ser Phe
                325                 330                 335

Leu Lys Ile Trp Asn
            340
```

(2) INFORMATION FOR SEQ ID NO:46:

(i) SEQUENCE CHARACTERISTICS:
        (A) LENGTH: 410 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: IEF SSP 9306, Fig. 29

(xi) SEQUENCE DESCRIPTION: SEQ ID NO:46:

```
Met Ala Asp Lys Glu Ala Ala Phe Asp Asp Ala Val Glu Glu Arg Val
1               5                   10                  15

Ile Asn Glu Glu Tyr Lys Ile Trp Lys Lys Asn Thr Pro Phe Leu Tyr
                20                  25                  30

Asp Leu Val Met Thr His Ala Leu Glu Trp Pro Ser Leu Thr Ala Gln
            35                  40                  45

Trp Leu Pro Asp Val Thr Arg Pro Glu Gly Lys Asp Phe Ser Ile His
        50                  55                  60

Arg Leu Val Leu Gly Thr His Thr Ser Asp Glu Gln Asn His Leu Val
65                  70                  75                  80

Ile Ala Ser Val Gln Leu Pro Asn Asp Asp Ala Gln Phe Asp Ala Ser
                85                  90                  95

His Tyr Asp Ser Glu Lys Gly Glu Phe Gly Gly Phe Gly Ser Val Ser
                100                 105                 110

Gly Lys Ile Glu Ile Glu Ile Lys Ile Asn His Glu Gly Glu Val Asn
            115                 120                 125

Arg Ala Arg Tyr Met Pro Gln Asn Pro Cys Ile Ile Ala Thr Lys Thr
        130                 135                 140

Pro Ser Ser Asp Val Leu Val Phe Asp Tyr Thr Lys His Pro Ser Lys
145                 150                 155                 160

Pro Asp Pro Ser Gly Glu Cys Asn Pro Asp Leu Arg Leu Arg Gly His
                165                 170                 175

Gln Lys Glu Gly Tyr Gly Leu Ser Trp Asn Pro Asn Leu Ser Gly His
            180                 185                 190

Leu Leu Ser Ala Ser Asp Asp His Thr Ile Cys Leu Trp Asp Ile Ser
        195                 200                 205

Ala Val Pro Lys Glu Gly Lys Val Val Asp Ala Lys Thr Ile Phe Thr
        210                 215                 220

Gly His Thr Ala Val Val Glu Asp Val Ser Trp His Leu Leu His Glu
225                 230                 235                 240

Ser Leu Phe Gly Ser Val Ala Asp Asp Gln Lys Leu Met Ile Trp Asp
                245                 250                 255

Thr Arg Ser Asn Asn Thr Ser Lys Pro Ser His Ser Val Asp Ala His
            260                 265                 270

Thr Ala Glu Val Asn Cys Leu Ser Phe Asn Pro Tyr Ser Glu Phe Ile
```

```
                    275                 280                 285
Leu Ala Thr Gly Ser Ala Asp Lys Thr Val Ala Leu Trp Asp Leu Arg
    290                 295                 300

Asn Leu Lys Leu Lys Leu His Ser Phe Glu Ser His Lys Asp Glu Ile
305                 310                 315                 320

Phe Gln Val Gln Trp Ser Pro His Asn Glu Thr Ile Leu Ala Ser Ser
                325                 330                 335

Gly Thr Asp Arg Arg Leu Asn Val Trp Asp Leu Ser Lys Ile Gly Glu
            340                 345                 350

Glu Gln Ser Pro Glu Asp Ala Glu Asp Gly Pro Pro Glu Leu Leu Phe
                355                 360                 365

Ile His Gly Gly His Thr Ala Lys Ile Ser Asp Phe Ser Trp Asn Pro
    370                 375                 380

Asn Glu Pro Trp Val Ile Cys Ser Val Ser Glu Asp Asn Ile Met Gln
385                 390                 395                 400

Val Trp Gln Met Glu Leu Val Leu Asp His
                405                 410

(2) INFORMATION FOR SEQ ID NO:47:

(i) SEQUENCE CHARACTERISTICS:
        (A) LENGTH: 317 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: HUMAN 12.3, Fig. 30

(xi) SEQUENCE DESCRIPTION: SEQ ID NO:47:

Met Thr Glu Gln Met Thr Leu Arg Gly Thr Leu Lys Gly His Asn Gly
1               5                   10                  15

Trp Val Thr Gln Ile Ala Thr Thr Pro Gln Phe Pro Asp Met Ile Leu
                20                  25                  30

Ser Ala Ser Arg Asp Lys Thr Ile Ile Met Trp Lys Leu Thr Arg Asp
            35                  40                  45

Glu Thr Asn Tyr Gly Ile Pro Gln Arg Ala Leu Arg Gly His Ser His
        50                  55                  60

Phe Val Ser Asp Val Val Ile Ser Ser Asp Gly Gln Phe Ala Leu Ser
65                  70                  75                  80

Gly Ser Trp Asp Gly Thr Leu Arg Leu Trp Asp Leu Thr Thr Gly Thr
                85                  90                  95

Thr Thr Arg Arg Phe Val Gly His Thr Lys Asp Val Leu Ser Val Ala
                100                 105                 110

Phe Ser Ser Asp Asn Arg Gln Ile Val Ser Gly Ser Arg Asp Lys Thr
            115                 120                 125

Ile Lys Leu Trp Asn Thr Leu Gly Val Cys Lys Tyr Thr Val Gln Asp
        130                 135                 140

Glu Ser His Ser Glu Trp Val Ser Cys Val Arg Phe Ser Pro Asn Ser
145                 150                 155                 160

Ser Asn Pro Ile Ile Val Ser Cys Gly Trp Asp Lys Leu Val Lys Val
                165                 170                 175

Trp Asn Leu Ala Asn Cys Lys Leu Lys Thr Asn His Ile Gly His Thr
```

```
                    180                 185                 190
Gly Tyr Leu Asn Thr Val Thr Val Ser Pro Asp Gly Ser Leu Cys Ala
            195                 200                 205

Ser Gly Gly Lys Asp Gly Gln Ala Met Leu Trp Asp Leu Asn Glu Gly
    210                 215                 220

Lys His Leu Tyr Thr Leu Asp Gly Asp Ile Ile Asn Ala Leu Cys
225                 230                 235                 240

Phe Ser Pro Asn Arg Tyr Trp Leu Cys Ala Ala Thr Gly Pro Ser Ile
                245                 250                 255

Lys Ile Trp Asp Leu Glu Gly Lys Ile Ile Val Asp Glu Leu Lys Gln
                260                 265                 270

Glu Val Ile Ser Thr Ser Ser Lys Ala Glu Pro Pro Gln Cys Thr Ser
            275                 280                 285

Leu Ala Trp Ser Ala Asp Gly Gln Thr Leu Phe Ala Gly Tyr Thr Asp
    290                 295                 300

Asn Leu Val Arg Val Trp Gln Val Thr Ile Gly Thr Arg
305                 310                 315

(2) INFORMATION FOR SEQ ID NO:48:

(i) SEQUENCE CHARACTERISTICS:
        (A) LENGTH: 425 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
         (C) INDIVIDUAL ISOLATE: IEF -7442 - human, Fig. 31

(xi) SEQUENCE DESCRIPTION: SEQ ID NO:48:

Met Ala Ser Lys Glu Met Phe Glu Asp Thr Val Glu Glu Arg Val Ile
1               5                   10                  15

Asn Glu Glu Tyr Lys Ile Trp Lys Lys Asn Thr Pro Phe Leu Tyr Asp
                20                  25                  30

Leu Val Met Thr His Ala Leu Gln Trp Pro Ser Leu Thr Val Gln Trp
            35                  40                  45

Leu Pro Glu Val Thr Lys Pro Glu Gly Lys Asp Tyr Ala Leu His Trp
    50                  55                  60

Leu Val Leu Gly Thr His Thr Ser Asp Glu Gln Asn His Leu Val Val
65                  70                  75                  80

Ala Arg Val His Ile Pro Asn Asp Asp Ala Gln Phe Asp Ala Ser His
                85                  90                  95

Cys Asp Ser Asp Lys Gly Glu Phe Gly Gly Phe Gly Ser Val Thr Gly
            100                 105                 110

Lys Ile Glu Cys Glu Ile Lys Ile Asn His Glu Gly Glu Val Asn Arg
        115                 120                 125

Ala Arg Tyr Met Pro Gln Asn Pro His Ile Ile Ala Thr Lys Thr Pro
    130                 135                 140

Ser Ser Asp Val Leu Val Phe Asp Tyr Thr Lys His Pro Ala Lys Pro
145                 150                 155                 160

Asp Pro Ser Gly Glu Cys Asn Pro Asp Leu Arg Leu Arg Gly His Gln
                165                 170                 175

Lys Glu Gly Tyr Gly Leu Ser Trp Asn Ser Asn Leu Ser Gly His Leu
```

```
                    180               185               190
Leu Ser Ala Ser Asp Asp His Thr Val Cys Leu Trp Asp Ile Asn Ala
        195               200               205

Gly Pro Lys Glu Gly Lys Ile Val Asp Ala Lys Ala Ile Phe Thr Gly
    210               215               220

His Ser Ala Val Val Glu Asp Val Ala Trp His Leu Leu His Glu Ser
225               230               235               240

Leu Phe Gly Ser Val Ala Asp Asp Gln Lys Leu Met Ile Trp Asp Thr
                245               250               255

Arg Ser Asn Thr Thr Ser Lys Pro Ser His Leu Val Asp Ala His Thr
                260               265               270

Ala Glu Val Asn Cys Leu Ser Phe Asn Pro Tyr Ser Glu Phe Ile Leu
            275               280               285

Ala Thr Gly Ser Ala Asp Lys Thr Val Ala Leu Trp Asp Leu Arg Asn
        290               295               300

Leu Lys Leu Lys Leu His Thr Phe Glu Ser His Lys Asp Glu Ile Phe
305               310               315               320

Gln Val His Trp Ser Pro His Asn Glu Thr Ile Leu Ala Ser Ser Gly
                325               330               335

Thr Asp Arg Arg Leu Asn Val Trp Asp Leu Ser Lys Ile Gly Glu Glu
                340               345               350

Gln Ser Ala Glu Asp Ala Glu Asp Gly Pro Pro Glu Leu Leu Phe Ile
            355               360               365

His Gly Gly His Thr Ala Lys Ile Ser Asp Phe Ser Trp Asn Pro Asn
        370               375               380

Glu Pro Trp Val Ile Cys Ser Val Ser Glu Asp Asn Ile Met Gln Ile
385               390               395               400

Trp Gln Met Ala Glu Asn Ile Tyr Asn Asp Glu Glu Ser Asp Val Thr
                405               410               415

Thr Ser Glu Leu Glu Gly Gln Gly Ser
            420               425

(2) INFORMATION FOR SEQ ID NO:49:

(i) SEQUENCE CHARACTERISTICS:
        (A) LENGTH: 605 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: Insulin-like growth factor binding
            protein complex, Fig. 32

(xi) SEQUENCE DESCRIPTION: SEQ ID NO:49:

Met Ala Leu Arg Lys Gly Gly Leu Ala Leu Ala Leu Leu Leu Leu Ser
1               5                  10                  15

Trp Val Ala Leu Gly Pro Arg Ser Leu Glu Gly Ala Asp Pro Gly Thr
                20                  25                  30

Pro Gly Glu Ala Glu Gly Pro Ala Cys Pro Ala Ala Cys Val Cys Ser
            35                  40                  45

Tyr Asp Asp Asp Ala Asp Glu Leu Ser Val Phe Cys Ser Ser Arg Asn
        50                  55                  60
```

-continued

```
Leu Thr Arg Leu Pro Asp Gly Val Pro Gly Thr Gln Ala Leu Trp
 65                  70                  75                  80

Leu Asp Gly Asn Asn Leu Ser Ser Val Pro Pro Ala Ala Phe Gln Asn
                 85                  90                  95

Leu Ser Ser Leu Gly Phe Leu Asn Leu Gln Gly Gly Gln Leu Gly Ser
                100                 105                 110

Leu Glu Pro Gln Ala Leu Leu Gly Leu Glu Asn Leu Cys His Leu His
            115                 120                 125

Leu Glu Arg Asn Gln Leu Arg Ser Leu Ala Leu Gly Thr Phe Ala His
            130                 135                 140

Thr Pro Ala Leu Ala Ser Leu Gly Leu Ser Asn Asn Arg Leu Ser Arg
145                 150                 155                 160

Leu Glu Asp Gly Leu Phe Glu Gly Leu Gly Ser Leu Trp Asp Leu Asn
                165                 170                 175

Leu Gly Trp Asn Ser Leu Ala Val Leu Pro Asp Ala Ala Phe Arg Gly
                180                 185                 190

Leu Gly Ser Leu Arg Glu Leu Val Leu Ala Gly Asn Arg Leu Ala Tyr
                195                 200                 205

Leu Gln Pro Ala Leu Phe Ser Gly Leu Ala Glu Leu Arg Glu Leu Asp
            210                 215                 220

Leu Ser Arg Asn Ala Leu Arg Ala Ile Lys Ala Asn Val Phe Val Gln
225                 230                 235                 240

Leu Pro Arg Leu Gln Lys Leu Tyr Leu Asp Arg Asn Leu Ile Ala Ala
                245                 250                 255

Val Ala Pro Gly Ala Phe Leu Gly Leu Lys Ala Leu Arg Trp Leu Asp
                260                 265                 270

Leu Ser His Asn Arg Val Ala Gly Leu Leu Glu Asp Thr Phe Pro Gly
                275                 280                 285

Leu Leu Gly Leu Arg Val Leu Arg Leu Ser His Asn Ala Ile Ala Ser
            290                 295                 300

Leu Arg Pro Arg Thr Phe Lys Asp Leu His Phe Leu Glu Glu Leu Gln
305                 310                 315                 320

Leu Gly His Asn Arg Ile Arg Gln Leu Ala Glu Arg Ser Phe Glu Gly
                325                 330                 335

Leu Gly Gln Leu Glu Val Leu Thr Leu Asp His Asn Gln Leu Gln Glu
            340                 345                 350

Val Lys Ala Gly Ala Phe Leu Gly Leu Thr Asn Val Ala Val Met Asn
            355                 360                 365

Leu Ser Gly Asn Cys Leu Arg Asn Leu Pro Glu Gln Val Phe Arg Gly
            370                 375                 380

Leu Gly Lys Leu His Ser Leu His Leu Glu Gly Ser Cys Leu Gly Arg
385                 390                 395                 400

Ile Arg Pro His Thr Phe Thr Gly Leu Ser Gly Leu Arg Arg Leu Phe
                405                 410                 415

Leu Lys Asp Asn Gly Leu Val Gly Ile Glu Glu Gln Ser Leu Trp Gly
                420                 425                 430

Leu Ala Glu Leu Leu Glu Leu Asp Leu Thr Ser Asn Gln Leu Thr His
            435                 440                 445

Leu Pro His Arg Leu Phe Gln Gly Leu Gly Lys Leu Glu Tyr Leu Leu
            450                 455                 460

Leu Ser Arg Asn Arg Leu Ala Glu Leu Pro Ala Asp Ala Leu Gly Pro
465                 470                 475                 480

Leu Gln Arg Ala Phe Trp Leu Asp Val Ser His Asn Arg Leu Glu Ala
```

-continued

```
                    485                 490                     495
Leu Pro Asn Ser Leu Leu Ala Pro Leu Gly Arg Leu Arg Tyr Leu Ser
                500                 505                 510

Leu Arg Asn Asn Ser Leu Arg Thr Phe Thr Pro Gln Pro Pro Gly Leu
            515                 520                 525

Glu Arg Leu Trp Leu Glu Gly Asn Pro Trp Asp Cys Gly Cys Pro Leu
    530                 535                 540

Lys Ala Leu Arg Asp Phe Ala Leu Gln Asn Pro Ser Ala Val Pro Arg
545                 550                 555                 560

Phe Val Gln Ala Ile Cys Glu Gly Asp Asp Cys Gln Pro Pro Ala Tyr
                565                 570                 575

Thr Tyr Asn Asn Ile Thr Cys Ala Ser Pro Pro Glu Val Val Gly Leu
            580                 585                 590

Asp Leu Arg Asp Leu Ser Glu Ala His Phe Ala Pro Cys
        595                 600                 605
```

(2) INFORMATION FOR SEQ ID NO:50:

(i) SEQUENCE CHARACTERISTICS:
        (A) LENGTH: 603 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: Insulin-like growth factor bind.
            pro. complex-rat, Fig. 33

(xi) SEQUENCE DESCRIPTION: SEQ ID NO:50:

```
Met Ala Leu Arg Thr Gly Gly Pro Ala Leu Val Val Leu Leu Ala Phe
1               5                   10                  15

Trp Val Ala Leu Gly Pro Cys His Leu Gln Gly Thr Asp Pro Gly Ala
            20                  25                  30

Ser Ala Asp Ala Glu Gly Pro Gln Cys Pro Val Ala Cys Thr Cys Ser
        35                  40                  45

His Asp Asp Tyr Thr Asp Glu Leu Ser Val Phe Cys Ser Ser Lys Asn
    50                  55                  60

Leu Thr His Leu Pro Asp Asp Ile Pro Val Ser Thr Arg Ala Leu Trp
65                  70                  75                  80

Leu Asp Gly Asn Asn Leu Ser Ser Ile Pro Ser Ala Ala Phe Gln Asn
                85                  90                  95

Leu Ser Ser Leu Asp Phe Leu Asn Leu Gln Gly Ser Trp Leu Arg Ser
                100                 105                 110

Leu Glu Pro Gln Ala Leu Leu Gly Leu Gln Asn Leu Tyr Tyr Leu His
            115                 120                 125

Leu Glu Arg Asn Arg Leu Arg Asn Leu Ala Val Gly Leu Phe Thr His
        130                 135                 140

Thr Pro Ser Leu Ala Ser Leu Ser Leu Ser Asn Leu Leu Gly Arg
145                 150                 155                 160

Leu Glu Glu Gly Leu Phe Gln Gly Leu Ser His Leu Trp Asp Leu Asn
                165                 170                 175

Leu Gly Trp Asn Ser Leu Val Val Leu Pro Asp Thr Val Phe Gln Gly
            180                 185                 190
```

-continued

```
Leu Gly Asn Leu His Glu Leu Val Leu Ala Gly Asn Lys Leu Thr Tyr
        195                 200                 205

Leu Gln Pro Ala Leu Phe Cys Gly Leu Gly Glu Leu Arg Glu Leu Asp
    210                 215                 220

Leu Ser Arg Asn Ala Leu Arg Ser Val Lys Ala Asn Val Phe Val His
225                 230                 235                 240

Leu Pro Arg Leu Gln Lys Leu Tyr Leu Asp Arg Asn Leu Ile Thr Ala
                245                 250                 255

Val Ala Pro Gly Ala Phe Leu Gly Met Lys Ala Leu Arg Trp Leu Asp
            260                 265                 270

Leu Ser His Asn Arg Val Ala Gly Leu Met Glu Asp Thr Phe Pro Gly
        275                 280                 285

Leu Leu Gly Leu His Val Leu Arg Leu Ala His Asn Ala Ile Ala Ser
    290                 295                 300

Leu Arg Pro Arg Thr Phe Lys Asp Leu His Phe Leu Glu Glu Leu Gln
305                 310                 315                 320

Leu Gly His Asn Arg Ile Arg Gln Leu Gly Glu Arg Thr Phe Glu Gly
                325                 330                 335

Leu Gly Gln Leu Glu Val Leu Thr Leu Asn Asp Asn Gln Ile Thr Glu
            340                 345                 350

Val Arg Val Gly Ala Phe Ser Gly Leu Phe Asn Val Ala Val Met Asn
        355                 360                 365

Leu Ser Gly Asn Cys Leu Arg Ser Leu Pro Glu Arg Val Phe Gln Gly
    370                 375                 380

Leu Asp Lys Leu His Ser Leu His Leu Glu His Ser Cys Leu Gly His
385                 390                 395                 400

Val Arg Leu His Thr Phe Ala Gly Leu Ser Gly Leu Arg Arg Leu Phe
                405                 410                 415

Leu Arg Asp Asn Ser Ile Ser Ser Ile Glu Glu Gln Ser Leu Ala Gly
            420                 425                 430

Leu Ser Glu Leu Leu Glu Leu Asp Leu Thr Thr Asn Arg Leu Thr His
        435                 440                 445

Leu Pro Arg Gln Leu Phe Gln Gly Leu Gly His Leu Glu Tyr Leu Leu
    450                 455                 460

Leu Ser Tyr Asn Gln Leu Thr Thr Leu Ser Ala Glu Val Leu Gly Pro
465                 470                 475                 480

Leu Gln Arg Ala Phe Trp Leu Asp Ile Ser His Asn His Leu Glu Thr
                485                 490                 495

Leu Ala Glu Gly Leu Phe Ser Ser Leu Gly Arg Val Arg Tyr Leu Ser
            500                 505                 510

Leu Arg Asn Asn Ser Leu Gln Thr Phe Ser Pro Gln Pro Gly Leu Glu
        515                 520                 525

Arg Leu Trp Leu Asp Ala Asn Pro Trp Asp Cys Ser Cys Pro Leu Lys
    530                 535                 540

Ala Leu Arg Asp Phe Ala Leu Gln Asn Pro Gly Val Pro Arg Phe
545                 550                 555                 560

Val Gln Thr Val Cys Glu Gly Asp Asp Cys Gln Pro Val Tyr Thr Tyr
                565                 570                 575

Asn Asn Ile Thr Cys Ala Gly Pro Ala Asn Val Ser Gly Leu Asp Leu
            580                 585                 590

Arg Asp Val Ser Glu Thr His Phe Val His Cys
        595                 600
```

-continued (2) INFORMATION FOR SEQ ID NO:51:

(i) SEQUENCE CHARACTERISTICS:
        (A) LENGTH: 409 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: LIS1 (human), Fig. 34

(xi) SEQUENCE DESCRIPTION: SEQ ID NO:51:

```
Met Val Leu Ser Gln Arg Gln Arg Asp Glu Leu Asn Arg Ala Ile Ala
1               5                   10                  15

Asp Tyr Leu Arg Ser Asn Gly Tyr Glu Glu Ala Tyr Ser Val Phe Lys
            20                  25                  30

Lys Glu Ala Glu Leu Asp Val Asn Glu Glu Leu Asp Lys Lys Tyr Ala
        35                  40                  45

Gly Leu Leu Glu Lys Lys Trp Thr Ser Val Ile Arg Leu Gln Lys Lys
50                  55                  60

Val Met Glu Leu Glu Ser Lys Leu Asn Glu Ala Lys Glu Glu Phe Thr
65                  70                  75                  80

Ser Gly Gly Pro Leu Gly Gln Lys Arg Asp Pro Lys Glu Trp Ile Pro
                85                  90                  95

Arg Pro Pro Glu Lys Tyr Ala Leu Ser Gly His Arg Ser Pro Val Thr
                100                 105                 110

Arg Val Ile Phe His Pro Val Phe Ser Val Met Val Ser Ala Ser Glu
            115                 120                 125

Asp Ala Thr Ile Lys Val Trp Asp Tyr Glu Thr Gly Asp Phe Glu Arg
        130                 135                 140

Thr Leu Lys Gly His Thr Asp Ser Val Gln Asp Ile Ser Phe Asp His
145                 150                 155                 160

Ser Gly Lys Leu Leu Ala Ser Cys Ser Ala Asp Met Thr Ile Lys Leu
                165                 170                 175

Trp Asp Phe Gln Gly Phe Glu Cys Ile Arg Thr Met His Gly His Asp
                180                 185                 190

His Asn Val Ser Ser Val Ala Ile Met Pro Asn Gly Asp His Ile Val
            195                 200                 205

Ser Ala Ser Arg Asp Lys Thr Ile Lys Met Trp Glu Val Gln Thr Gly
        210                 215                 220

Tyr Cys Val Lys Thr Phe Thr Gly His Arg Glu Trp Val Arg Met Val
225                 230                 235                 240

Arg Pro Asn Gln Asp Gly Thr Leu Ile Ala Ser Cys Ser Asn Asp Gln
                245                 250                 255

Thr Val Arg Val Trp Val Val Ala Thr Lys Glu Cys Lys Ala Glu Leu
            260                 265                 270

Arg Glu His Glu His Val Val Glu Cys Ile Ser Trp Ala Pro Glu Ser
        275                 280                 285

Ser Tyr Ser Ser Ile Ser Glu Ala Thr Gly Ser Glu Thr Lys Lys Ser
    290                 295                 300

Gly Lys Pro Gly Pro Phe Leu Leu Ser Gly Ser Arg Asp Lys Thr Lys
305                 310                 315                 320

Met Trp Asp Val Ser Thr Gly Met Cys Leu Met Thr Leu Val Gly His
```

```
                    325                 330                 335
Asp Asn Trp Val Arg Gly Val Leu Phe His Ser Gly Lys Phe Ile
            340                 345                 350

Leu Ser Cys Ala Asp Asp Lys Thr Leu Arg Val Trp Asp Tyr Lys Asn
            355                 360                 365

Lys Arg Cys Met Lys Thr Leu Asn Ala His Glu His Phe Val Thr Ser
    370                 375                 380

Leu Asp Phe His Lys Thr Ala Pro Tyr Val Val Thr Gly Ser Val Asp
385                 390                 395                 400

Gln Thr Val Lys Val Trp Glu Cys Arg
                405

(2) INFORMATION FOR SEQ ID NO:52:

(i) SEQUENCE CHARACTERISTICS:
        (A) LENGTH: 422 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: MD6, Fig. 35

(xi) SEQUENCE DESCRIPTION: SEQ ID NO:52:

Met Glu Arg Lys Asp Phe Glu Thr Trp Leu Asp Asn Ile Ser Val Thr
1               5                   10                  15

Phe Leu Ser Leu Met Asp Leu Gln Lys Asn Glu Thr Leu Asp His Leu
            20                  25                  30

Ile Ser Leu Ser Gly Ala Val Gln Leu Arg His Leu Ser Asn Asn Leu
        35                  40                  45

Glu Thr Leu Leu Lys Arg Asp Phe Leu Lys Leu Leu Pro Leu Glu Leu
    50                  55                  60

Ser Phe Tyr Leu Leu Lys Trp Leu Asp Pro Gln Thr Leu Leu Thr Cys
65                  70                  75                  80

Cys Leu Val Ser Lys Gln Arg Asn Lys Val Ile Ser Ala Cys Thr Glu
                85                  90                  95

Val Trp Gln Thr Ala Cys Lys Asn Leu Gly Trp Gln Ile Asp Asp Ser
            100                 105                 110

Val Gln Asp Ser Leu His Trp Lys Lys Val Tyr Leu Lys Ala Ile Leu
            115                 120                 125

Arg Met Lys Gln Leu Glu Asp His Glu Ala Phe Glu Thr Ser Ser Leu
    130                 135                 140

Ile Gly His Ser Ala Arg Val Tyr Ala Leu Tyr Tyr Lys Asp Gly Leu
145                 150                 155                 160

Leu Cys Thr Gly Ser Asp Asp Leu Ser Ala Lys Leu Trp Asp Val Ser
                165                 170                 175

Thr Gly Gln Cys Val Tyr Gly Ile Gln Thr His Thr Cys Ala Ala Val
            180                 185                 190

Lys Phe Asp Glu Gln Lys Leu Val Thr Gly Ser Phe Asp Asn Thr Val
    195                 200                 205

Ala Cys Trp Glu Trp Ser Ser Gly Ala Arg Thr Gln His Phe Arg Gly
    210                 215                 220

His Thr Gly Ala Val Phe Ser Val Asp Tyr Ser Asp Glu Leu Asp Ile
```

-continued

```
                225                 230                 235                 240
Leu Val Ser Gly Ser Ala Asp Phe Ala Val Lys Val Trp Ala Leu Ser
                    245                 250                 255
Ala Gly Thr Cys Leu Asn Thr Leu Thr Gly His Thr Glu Trp Val Thr
                    260                 265                 270
Lys Val Val Leu Gln Lys Cys Lys Val Lys Ser Leu Leu His Ser Pro
                    275                 280                 285
Gly Asp Tyr Ile Leu Leu Ser Ala Asp Lys Tyr Glu Ile Lys Ile Trp
                    290                 295                 300
Pro Ile Gly Arg Glu Ile Asn Cys Lys Cys Leu Lys Thr Leu Ser Val
305                 310                 315                 320
Ser Glu Asp Arg Ser Ile Cys Leu Gln Pro Arg Leu His Phe Asp Gly
                    325                 330                 335
Lys Tyr Ile Val Cys Ser Ser Ala Leu Gly Leu Tyr Gln Trp Asp Phe
                    340                 345                 350
Ala Ser Tyr Asp Ile Leu Arg Val Ile Lys Thr Pro Glu Val Ala Asn
                    355                 360                 365
Leu Ala Leu Leu Gly Phe Gly Asp Val Phe Ala Leu Leu Phe Asp Asn
                    370                 375                 380
His Tyr Leu Tyr Ile Met Asp Leu Arg Thr Glu Ser Leu Ile Ser Arg
385                 390                 395                 400
Trp Pro Leu Pro Glu Tyr Arg Lys Ser Lys Arg Gly Thr Ser Phe Leu
                    405                 410                 415
Ala Gly Glu Arg Pro Gly
                    420
```

(2) INFORMATION FOR SEQ ID NO:53:

(i) SEQUENCE CHARACTERISTICS:
        (A) LENGTH: 422 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: MSL1, Fig. 36

(xi) SEQUENCE DESCRIPTION: SEQ ID NO:53:

```
Met Asn Gln Cys Ala Lys Asp Ile Thr His Glu Ala Ser Ser Ile Pro
1               5                   10                  15
Ile Asp Leu Gln Glu Arg Tyr Ser His Trp Lys Lys Asn Thr Lys Leu
                    20                  25                  30
Leu Tyr Asp Tyr Leu Asn Thr Asn Ser Thr Lys Trp Pro Ser Leu Thr
                    35                  40                  45
Cys Gln Phe Phe Pro Asp Leu Asp Thr Thr Ser Asp Glu His Arg Ile
                    50                  55                  60
Leu Leu Ser Ser Phe Thr Ser Ser Gln Lys Pro Glu Asp Glu Thr Ile
65                  70                  75                  80
Tyr Ile Ser Lys Ile Ser Thr Leu Gly His Ile Lys Trp Ser Ser Leu
                    85                  90                  95
Asn Asn Phe Asp Met Asp Glu Met Glu Phe Lys Pro Glu Asn Ser Thr
                    100                 105                 110
Arg Phe Pro Ser Lys His Leu Val Asn Asp Ile Ser Ile Phe Phe Pro
```

```
                115                 120                 125
Asn Gly Glu Cys Asn Arg Ala Arg Tyr Leu Pro Gln Asn Pro Asp Ile
    130                 135                 140

Ile Ala Gly Ala Ser Ser Asp Gly Ala Ile Tyr Ile Phe Asp Arg Thr
145                 150                 155                 160

Lys His Gly Ser Thr Arg Ile Arg Gln Ser Lys Ile Ser His Pro Phe
                165                 170                 175

Glu Thr Lys Leu Phe Gly Ser His Gly Val Ile Gln Asp Val Glu Ala
            180                 185                 190

Met Asp Thr Ser Ser Ala Asp Ile Asn Glu Ala Thr Ser Leu Ala Trp
        195                 200                 205

Asn Leu Gln Gln Glu Ala Leu Leu Ser Ser His Ser Asn Gly Gln
210                 215                 220

Val Gln Val Trp Asp Ile Lys Gln Tyr Ser His Glu Asn Pro Ile Ile
225                 230                 235                 240

Asp Leu Pro Leu Val Ser Ile Asn Ser Asp Gly Thr Ala Val Asn Asp
                245                 250                 255

Val Thr Trp Met Pro Thr His Asp Ser Leu Phe Ala Ala Cys Thr Glu
            260                 265                 270

Gly Asn Ala Val Ser Leu Leu Asp Leu Arg Thr Lys Lys Glu Lys Leu
        275                 280                 285

Gln Ser Asn Arg Glu Lys His Asp Gly Gly Val Asn Ser Cys Arg Phe
290                 295                 300

Asn Tyr Lys Asn Ser Leu Ile Leu Ala Ser Ala Asp Ser Asn Gly Arg
305                 310                 315                 320

Leu Asn Leu Trp Asp Ile Arg Asn Met Asn Lys Ser Pro Ile Ala Thr
                325                 330                 335

Met Glu His Gly Thr Ser Val Ser Thr Leu Glu Trp Ser Pro Asn Phe
            340                 345                 350

Asp Thr Val Leu Ala Thr Ala Gly Gln Glu Asp Gly Leu Val Lys Leu
        355                 360                 365

Trp Asp Thr Ser Cys Glu Glu Thr Ile Phe Thr His Gly Gly His Met
    370                 375                 380

Leu Gly Val Asn Asp Ile Ser Trp Asp Ala His Asp Pro Trp Leu Met
385                 390                 395                 400

Cys Ser Val Ala Asn Asp Asn Ser Val His Ile Trp Lys Pro Ala Gly
                405                 410                 415

Asn Leu Val Gly His Ser
            420

(2) INFORMATION FOR SEQ ID NO:54:

(i) SEQUENCE CHARACTERISTICS:
        (A) LENGTH: 816 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: MUS MUSCULUS PROTEIN, Fig. 37

(xi) SEQUENCE DESCRIPTION: SEQ ID NO:54:

Phe Arg Met Asp Asn Ala Ser Thr Arg Ile Asp Glu Arg Phe Arg Ile
```

-continued

```
1               5                   10                  15
Asp Ala Tyr Ala Asn Ala Arg Tyr Pro Met Pro Arg Thr Glu Ile Asn
                20                  25              30
Ser Glu Gln Glu Asn Cys Glu Asn Thr Ile Thr Leu Glu Asp Ser Glu
            35              40                  45
Gln Glu Asn Cys Glu Ala Ala Cys Met Pro Leu Glu Thr Glu Ser Glu
        50              55                  60
Gln Glu Asn Cys Glu Met Ser Ser His Glu Ser Tyr Thr Asn Ala Ala
65              70                  75                      80
Glu Thr Pro Glu Asn Ile Ser Ile Leu Ser Cys Leu Gly Glu Thr Ser
                85                  90                  95
Gly Ala Leu Val Asp Thr Lys Thr Ile Ser Asp Ile Lys Thr Met Asp
                100                 105                 110
Pro Arg Val Ser Leu Thr Pro Ser Ser Asp Val Thr Gly Thr Glu Asp
                115                 120                 125
Ser Ser Val Leu Thr Pro Gln Ser Thr Asp Val Asn Ser Val Asp Ser
        130                 135                 140
Tyr Gln Gly Tyr Glu Gly Asp Asp Asp Glu Glu Asp Asp Glu Asp
145                 150                 155                 160
Asp Lys Asp Gly Asp Ser Asn Leu Pro Ser Leu Glu Asp Ser Asp Asn
                165                 170                 175
Phe Ile Ser Cys Leu Glu Asn Ser Tyr Ile Pro Gln Asn Val Glu Asn
                180                 185                 190
Gly Glu Val Val Glu Glu Gln Ser Leu Gly Arg Arg Phe His Pro Tyr
            195                 200                 205
Glu Leu Glu Ala Gly Glu Val Val Glu Gly Gln Gly Gly Ser Leu
    210                 215                 220
Phe Tyr Pro Tyr Glu Leu Glu Ala Gly Glu Val Val Glu Ala Gln Asn
225                 230                 235                 240
Val Gln Asn Leu Phe His Arg Tyr Glu Leu Glu Glu Gly Glu Val Val
                245                 250                 255
Glu Ala Gln Val Gln Ser Met Phe Pro Tyr Tyr Glu Leu Glu Ala
                260                 265                 270
Gly Glu Val Val Glu Ala Glu Val Gln Gly Phe Phe Gln Arg Tyr
            275                 280                 285
Glu Leu Glu Ala Arg Glu Val Ile Gly Ala Gln Gly Gly Gln Gly Leu
    290                 295                 300
Ser Arg His Tyr Gly Leu Gly Gly Glu Val Val Glu Ala Thr Ala
305                 310                 315                 320
Val Arg Arg Leu Ile Gln His His Glu Leu Glu Glu Gly Glu Asp Val
                325                 330                 335
Asp Asp Gln Glu Glu Ser Ser Glu Met His Glu Glu Thr Ser Glu Asp
                340                 345                 350
Ser Ser Glu Gln Tyr Asp Ile Glu Asp Asp Ser Leu Ile Asp Glu Trp
            355                 360                 365
Ile Ala Leu Glu Thr Ser Pro Leu Pro Arg Pro Arg Trp Asn Val Leu
        370                 375                 380
Ser Ala Leu Arg Asp Arg Gln Leu Gly Ser Ser Gly Arg Phe Val Tyr
385                 390                 395                 400
Glu Ala Cys Gly Ala Arg Leu Phe Val Gln Arg Phe Ser Leu Glu His
                405                 410                 415
Val Phe Glu Gly His Ser Gly Cys Val Asn Thr Val His Phe Asn Gln
                420                 425                 430
```

```
His Gly Thr Leu Leu Ala Ser Gly Ser Asp Asp Leu Lys Val Ile Val
            435                 440                 445

Trp Asp Trp Leu Lys Lys Arg Ser Val Leu Asn Phe Asp Ser Gly His
450                 455                 460

Lys Asn Asn Ile Leu Gln Ala Lys Phe Leu Pro Asn Cys Asn Asp Ala
465                 470                 475                 480

Ile Leu Ala Met Cys Gly Arg Asp Gly Gln Val Arg Val Ala Gln Leu
                485                 490                 495

Ser Ala Val Ala Gly Thr His Met Thr Lys Arg Leu Val Lys His Gly
            500                 505                 510

Gly Ala Ser His Arg Leu Gly Leu Glu Pro Asp Ser Pro Phe Arg Phe
            515                 520                 525

Leu Thr Ser Gly Glu Asp Ala Val Phe Asn Ile Asp Leu Arg Gln
530                 535                 540

Ala His Pro Ala Ser Lys Leu Leu Val Ile Lys Asp Gly Asp Lys Lys
545                 550                 555                 560

Val Gly Leu Tyr Thr Val Phe Val Asn Pro Ala Asn Val Tyr Gln Phe
                565                 570                 575

Ala Val Gly Gly Gln Asp Gln Phe Met Arg Ile Tyr Asp Gln Arg Lys
            580                 585                 590

Ile Asp Glu Asn Val Asn Asn Gly Val Leu Lys Lys Phe Cys Pro His
            595                 600                 605

His Leu Leu Ser Ser Asp Tyr Pro Ala His Ile Thr Ser Leu Met Tyr
            610                 615                 620

Ser Tyr Asp Gly Thr Glu Ile Leu Ala Ser Tyr Asn Asp Glu Asp Ile
625                 630                 635                 640

Tyr Ile Phe Asn Ser Ser Asp Ser Asp Gly Ala Gln Tyr Ala Lys Arg
                645                 650                 655

Tyr Lys Gly His Arg Asn Asn Ser Thr Val Lys Gly Val Tyr Phe Tyr
            660                 665                 670

Gly Pro Arg Ser Glu Phe Val Met Ser Gly Ser Asp Cys Gly His Ile
            675                 680                 685

Phe Ile Trp Glu Lys Ser Ser Cys Gln Ile Val Gln Phe Leu Glu Ala
            690                 695                 700

Asp Glu Gly Gly Thr Ile Asn Cys Ile Asp Ser His Pro Tyr Leu Pro
705                 710                 715                 720

Val Leu Ala Ser Ser Gly Leu Asp His Glu Val Lys Ile Trp Ser Pro
                725                 730                 735

Ile Ala Glu Pro Ser Lys Lys Leu Ala Gly Leu Lys Asn Val Ile Lys
            740                 745                 750

Ile Asn Lys Leu Lys Arg Asp Asn Phe Thr Leu Arg His Thr Ser Leu
            755                 760                 765

Phe Asn Asn Ser Met Leu Cys Phe Leu Met Ser His Val Thr Gln Ser
            770                 775                 780

Asn Tyr Gly Arg Ser Trp Arg Gly Ile Arg Ile Asn Ala Gly Gly Gly
785                 790                 795                 800

Asp Phe Ser Asp Ser Ser Ser Ser Glu Glu Thr Asn Gln Glu Ser
                805                 810                 815

(2) INFORMATION FOR SEQ ID NO:55:

(i) SEQUENCE CHARACTERISTICS:
        (A) LENGTH: 422 amino acids
        (B) TYPE: amino acid
```

(D) TOPOLOGY: unknown (ii) MOLECULE TYPE: protein (iii) HYPOTHETICAL: NO (iv) ANTI-SENSE: NO (vi) ORIGINAL SOURCE:
         (C) INDIVIDUAL ISOLATE: ORF RB1, Fig. 38

(xi) SEQUENCE DESCRIPTION: SEQ ID NO:55:

```
Met Asn Gln Cys Ala Lys Asp Ile Thr His Glu Ala Ser Ser Ile Pro
1               5                  10                  15

Ile Asp Leu Gln Glu Arg Tyr Ser His Trp Lys Lys Asn Thr Lys Leu
            20                  25                  30

Leu Tyr Asp Tyr Leu Asn Thr Asn Ser Thr Lys Trp Pro Ser Leu Thr
        35                  40                  45

Cys Gln Phe Phe Pro Asp Leu Asp Thr Thr Ser Asp Glu His Arg Ile
50                  55                  60

Leu Leu Ser Ser Phe Thr Ser Ser Gln Lys Pro Glu Asp Glu Thr Ile
65                  70                  75                  80

Tyr Ile Ser Lys Ile Ser Thr Leu Gly His Ile Lys Trp Ser Ser Leu
                85                  90                  95

Asn Asn Phe Asp Met Asp Glu Met Glu Phe Lys Pro Glu Asn Ser Thr
            100                 105                 110

Arg Phe Pro Ser Lys His Leu Val Asn Asp Ile Ser Ile Phe Phe Pro
        115                 120                 125

Asn Gly Glu Cys Asn Arg Ala Arg Tyr Leu Pro Gln Asn Pro Asp Ile
130                 135                 140

Ile Ala Gly Ala Ser Ser Asp Gly Ala Ile Tyr Ile Phe Asp Arg Thr
145                 150                 155                 160

Lys His Gly Ser Thr Arg Ile Arg Gln Ser Lys Ile Ser His Pro Phe
                165                 170                 175

Glu Thr Lys Leu Phe Gly Ser His Gly Val Ile Gln Asp Val Glu Ala
            180                 185                 190

Met Asp Thr Ser Ser Ala Asp Ile Asn Glu Ala Thr Ser Leu Ala Trp
        195                 200                 205

Asn Leu Gln Gln Glu Ala Leu Leu Leu Ser Ser His Ser Asn Gly Gln
210                 215                 220

Val Gln Val Trp Asp Ile Lys Gln Tyr Ser His Glu Asn Pro Ile Ile
225                 230                 235                 240

Asp Leu Pro Leu Val Ser Ile Asn Ser Asp Gly Thr Ala Val Asn Asp
                245                 250                 255

Val Thr Trp Met Pro Thr His Asp Ser Leu Phe Ala Ala Cys Thr Glu
            260                 265                 270

Gly Asn Ala Val Ser Leu Leu Asp Leu Arg Thr Lys Lys Glu Lys Leu
        275                 280                 285

Gln Ser Asn Arg Glu Lys His Asp Gly Gly Val Asn Ser Cys Arg Phe
290                 295                 300

Asn Tyr Lys Asn Ser Leu Ile Leu Ala Ser Ala Asp Ser Asn Gly Arg
305                 310                 315                 320

Leu Asn Leu Trp Asp Ile Arg Asn Met Asn Lys Ser Pro Ile Ala Thr
                325                 330                 335

Met Glu His Gly Thr Ser Val Ser Thr Leu Glu Trp Ser Pro Asn Phe
            340                 345                 350
```

```
Asp Thr Val Leu Ala Thr Ala Gly Gln Glu Asp Gly Leu Val Lys Leu
        355                 360                 365

Trp Asp Thr Ser Cys Glu Glu Thr Ile Phe Thr His Gly Gly His Met
370                 375                 380

Leu Gly Val Asn Asp Ile Ser Trp Asp Ala His Asp Pro Trp Leu Met
385                 390                 395                 400

Cys Ser Val Ala Asn Asp Asn Ser Val His Ile Trp Lys Pro Ala Gly
                405                 410                 415

Asn Leu Val Gly His Ser
            420

(2) INFORMATION FOR SEQ ID NO:56:

(i) SEQUENCE CHARACTERISTICS:
        (A) LENGTH: 576 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
         (C) INDIVIDUAL ISOLATE: Periodic Trp protein, Fig. 39

(xi) SEQUENCE DESCRIPTION: SEQ ID NO:56:

Met Ile Ser Ala Thr Asn Trp Val Pro Arg Gly Phe Ser Ser Glu Phe
1               5                   10                  15

Pro Glu Lys Tyr Val Leu Asp Asp Glu Glu Val Glu Arg Ile Asn Gln
            20                  25                  30

Leu Ala Gln Leu Asn Leu Asp Asp Ala Lys Ala Thr Leu Glu Glu Ala
        35                  40                  45

Glu Gly Glu Ser Gly Val Glu Asp Ala Ala Thr Gly Ser Ser Asn
    50                  55                  60

Lys Leu Lys Asp Gln Leu Asp Ile Asp Asp Leu Lys Glu Tyr Asn
65                  70                  75                  80

Leu Glu Glu Tyr Asp Asp Glu Ile Ala Asp Asn Glu Gly Gly Lys
                85                  90                  95

Asp Val Ser Met Phe Pro Gly Leu Ser Asn Asp Ser Asp Val Lys Phe
                100                 105                 110

His Glu Gly Glu Lys Gly Glu Asp Pro Tyr Ile Ser Leu Pro Asn Gln
            115                 120                 125

Glu Asp Ser Gln Glu Glu Lys Gln Glu Leu Gln Val Tyr Pro Ser Asp
130                 135                 140

Asn Leu Val Leu Ala Ala Arg Thr Glu Asp Asp Val Ser Tyr Leu Asp
145                 150                 155                 160

Ile Tyr Val Tyr Asp Asp Gly Ala Gly Phe His Ser Ser Asp Ile Pro
                165                 170                 175

Val Glu Glu Gly Asp Glu Ala Asp Pro Asp Val Ala Arg Gly Leu Val
                180                 185                 190

Arg Asp Pro Ala Leu Tyr Val His His Asp Leu Met Leu Pro Ala Phe
            195                 200                 205

Pro Leu Cys Val Glu Trp Leu Asp Tyr Lys Val Gly Ser Asn Ser Glu
        210                 215                 220

Glu Ala Ala Asn Tyr Ala Ala Ile Gly Thr Phe Asp Pro Gln Ile Glu
225                 230                 235                 240
```

```
Ile Trp Asn Leu Asp Cys Val Asp Lys Ala Phe Pro Asp Met Ile Leu
            245                 250                 255
Gly Glu Pro Leu Asp Asn Ser Met Val Ser Leu Lys Ser Lys Lys Lys
            260                 265                 270
Lys Lys Lys Ser Lys Thr Gly His Ile Thr Thr His His Thr Asp Ala
            275                 280                 285
Val Leu Ser Met Ala His Asn Lys Tyr Phe Arg Ser Val Leu Ala Ser
            290                 295                 300
Thr Ser Ala Asp His Thr Val Lys Leu Trp Asp Leu Asn Ser Gly Asn
305                 310                 315                 320
Ala Ala Arg Ser Leu Ala Ser Ile His Ser Asn Lys Asn Val Ser Ser
            325                 330                 335
Ser Glu Trp His Met Leu Asn Gly Ser Ile Leu Leu Thr Gly Gly Tyr
            340                 345                 350
Asp Ser Arg Val Ala Leu Thr Asp Val Arg Ile Ser Asp Glu Ser Gln
            355                 360                 365
Met Ser Lys Tyr Trp Ser Ala Met Ala Gly Glu Glu Ile Glu Thr Val
            370                 375                 380
Thr Phe Ala Ser Glu Asn Ile Ile Leu Cys Gly Thr Asp Ser Gly Asn
385                 390                 395                 400
Val Tyr Ser Phe Asp Ile Arg Asn Asn Glu Asn Arg Lys Pro Val Trp
            405                 410                 415
Thr Leu Lys Ala His Asp Ala Gly Ile Ser Thr Leu Cys Ser Asn Lys
            420                 425                 430
Phe Ile Pro Gly Met Met Ser Thr Gly Ala Met Gly Glu Lys Thr Val
            435                 440                 445
Lys Leu Trp Lys Phe Pro Leu Asp Ala Thr Asn Thr Lys Gly Pro
    450                 455                 460
Ser Met Val Leu Ser Arg Asp Phe Asp Val Gly Asn Val Leu Thr Ser
465                 470                 475                 480
Ser Phe Ala Pro Asp Ile Glu Val Ala Gly Thr Met Val Ile Gly Gly
            485                 490                 495
Val Asn Lys Val Leu Lys Leu Trp Asp Val Phe Thr Asn Arg Ser Val
            500                 505                 510
Arg Lys Ser Phe Lys Ser Glu Leu Glu Asn Val Gln Ala Arg Ala Lys
            515                 520                 525
Glu Glu Ala Gln Lys Ile Gly Lys Ser Ser Arg Ile Ala Arg Lys Tyr
            530                 535                 540
Thr Ser Asn Asp Asn Pro Asp Thr Val Ile Thr Ile Asp Asp Gln Gly
545                 550                 555                 560
Glu Asp Glu Glu Glu Arg Glu Gly Gly Asp Glu His Asp Asp Met Ala
            565                 570                 575
```

(2) INFORMATION FOR SEQ ID NO:57:

(i) SEQUENCE CHARACTERISTICS:
        (A) LENGTH: 325 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: PLAP, Fig. 40

(xi) SEQUENCE DESCRIPTION: SEQ ID NO:57:

```
Met His Tyr Met Ser Gly His Ser Asn Phe Val Ser Tyr Val Cys Ile
1               5                   10                  15

Ile Pro Ser Ser Asp Ile Tyr Pro His Gly Leu Ile Ala Thr Gly Gly
                20                  25                  30

Asn Asp His Asn Ile Cys Ile Phe Ser Leu Asp Ser Pro Met Pro Leu
            35                  40                  45

Tyr Ile Leu Lys Gly His Lys Asp Thr Val Cys Ser Leu Ser Ser Gly
        50                  55                  60

Lys Phe Gly Thr Leu Leu Ser Gly Ser Trp Asp Thr Thr Ala Lys Val
65                  70                  75                  80

Trp Leu Asn Asp Lys Cys Met Met Thr Leu Gln Gly His Thr Ala Ala
                85                  90                  95

Val Trp Ala Val Lys Ile Leu Pro Glu Gln Gly Leu Met Leu Thr Gly
                100                 105                 110

Ser Ala Asp Lys Thr Ile Lys Leu Trp Lys Ala Gly Arg Cys Glu Arg
            115                 120                 125

Thr Phe Leu Gly His Glu Asp Cys Val Arg Gly Leu Ala Ile Leu Ser
        130                 135                 140

Glu Thr Glu Phe Leu Ser Cys Ala Asn Asp Ala Ser Ile Arg Arg Trp
145                 150                 155                 160

Gln Ile Thr Gly Glu Cys Leu Glu Val Tyr Phe Gly His Thr Asn Tyr
                165                 170                 175

Ile Tyr Ser Ile Ser Val Phe Pro Asn Ser Lys Asp Phe Val Thr Thr
            180                 185                 190

Ala Glu Asp Arg Ser Leu Arg Ile Trp Lys His Gly Glu Cys Ala Gln
        195                 200                 205

Thr Ile Arg Leu Pro Ala Gln Ser Ile Trp Cys Cys Cys Val Leu Glu
210                 215                 220

Asn Gly Asp Ile Val Gly Ala Ser Asp Gly Ile Ile Arg Val Phe
225                 230                 235                 240

Thr Glu Ser Glu Glu Arg Thr Ala Ser Ala Glu Glu Ile Lys Ala Ser
                245                 250                 255

Leu Ser Arg Glu Ser Pro Leu Ile Ala Lys Val Leu Thr Thr Glu Pro
            260                 265                 270

Pro Ile Ile Thr Pro Val Arg Arg Thr Leu Pro Cys Arg Val Thr Arg
        275                 280                 285

Ser Met Ile Ser Ser Cys Leu Ser Arg Leu Val Ser Thr Ser Leu Ser
290                 295                 300

Thr Ser Asp Ser His Leu Thr Ile Thr Ala Leu His Leu Phe Leu Thr
305                 310                 315                 320

Thr Thr Thr Thr Glu
                325
```

(2) INFORMATION FOR SEQ ID NO:58:

(i) SEQUENCE CHARACTERISTICS:
        (A) LENGTH: 425 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
    (C) INDIVIDUAL ISOLATE: RETINOBLASTOMA BINDING PROTEIN -
        HUMAN, Fig. 41

(xi) SEQUENCE DESCRIPTION: SEQ ID NO:58:

```
Met Ala Asp Lys Glu Ala Ala Phe Asp Asp Ala Val Glu Glu Arg Val
 1               5                  10                  15

Ile Asn Glu Glu Tyr Lys Ile Trp Lys Lys Asn Thr Pro Phe Leu Tyr
             20                  25                  30

Asp Leu Val Met Thr His Ala Leu Glu Trp Pro Ser Leu Thr Ala Gln
             35                  40                  45

Trp Leu Pro Asp Val Thr Arg Pro Glu Gly Lys Asp Phe Ser Ile His
 50                  55                  60

Arg Leu Val Leu Gly Thr His Thr Ser Asp Glu Gln Asn His Leu Val
 65                  70                  75                  80

Ile Ala Ser Val Gln Leu Pro Asn Asp Ala Gln Phe Asp Ala Ser
             85                  90                  95

His Tyr Asp Ser Glu Lys Gly Glu Phe Gly Gly Phe Gly Ser Val Ser
                100                 105                 110

Gly Lys Ile Glu Ile Glu Ile Lys Ile Asn His Glu Gly Glu Val Asn
            115                 120                 125

Arg Ala Arg Tyr Met Pro Gln Asn Pro Cys Ile Ile Ala Thr Lys Thr
130                 135                 140

Pro Ser Ser Asp Val Leu Val Phe Asp Tyr Thr Lys His Pro Ser Lys
145                 150                 155                 160

Pro Asp Pro Ser Gly Glu Cys Asn Pro Asp Leu Arg Leu Arg Gly His
                165                 170                 175

Gln Lys Glu Gly Tyr Gly Leu Ser Trp Asn Pro Asn Leu Ser Gly His
            180                 185                 190

Leu Leu Ser Ala Ser Asp Asp His Thr Ile Cys Leu Trp Asp Ile Ser
            195                 200                 205

Ala Val Pro Lys Glu Gly Lys Val Val Asp Ala Lys Thr Ile Phe Thr
210                 215                 220

Gly His Thr Ala Val Val Glu Asp Val Ser Trp His Leu Leu His Glu
225                 230                 235                 240

Ser Leu Phe Gly Ser Val Ala Asp Asp Gln Lys Leu Met Ile Trp Asp
                245                 250                 255

Thr Arg Ser Asn Asn Thr Ser Lys Pro Ser His Ser Val Asp Ala His
            260                 265                 270

Thr Ala Glu Val Asn Cys Leu Ser Phe Asn Pro Tyr Ser Glu Phe Ile
            275                 280                 285

Leu Ala Thr Gly Ser Ala Asp Lys Thr Val Ala Leu Trp Asp Leu Arg
290                 295                 300

Asn Leu Lys Leu Lys Leu His Ser Phe Glu Ser His Lys Asp Glu Ile
305                 310                 315                 320

Phe Gln Val Gln Trp Ser Pro His Asn Glu Thr Ile Leu Ala Ser Ser
                325                 330                 335

Gly Thr Asp Arg Arg Leu Asn Val Trp Asp Leu Ser Lys Ile Gly Glu
            340                 345                 350

Glu Gln Ser Pro Glu Asp Ala Glu Asp Gly Pro Pro Glu Leu Leu Phe
            355                 360                 365

Ile His Gly Gly His Thr Ala Lys Ile Ser Asp Phe Ser Trp Asn Pro
370                 375                 380
```

```
Asn Glu Pro Trp Val Ile Cys Ser Val Ser Glu Asp Asn Ile Met Gln
385                 390                 395                 400

Val Trp Gln Met Ala Glu Asn Ile Tyr Asn Asp Glu Asp Pro Glu Gly
                405                 410                 415

Ser Val Asp Pro Glu Gly Gln Gly Ser
                420             425
```

(2) INFORMATION FOR SEQ ID NO:59:

(i) SEQUENCE CHARACTERISTICS:
        (A) LENGTH: 852 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: S253 PROTEIN, Fig. 42

(xi) SEQUENCE DESCRIPTION: SEQ ID NO:59:

```
Met Phe Lys Ser Lys Thr Ser Thr Leu Ser Tyr Asp Glu Thr Pro Asn
1               5                   10                  15

Ser Asn Glu Gly Asp Arg Asn Ala Thr Pro Val Asn Pro Lys Glu Lys
                20                  25                  30

Ser Gln Thr Lys His Leu Asn Ile Pro Gly Asp Arg Ser Arg His Ser
                35                  40                  45

Ser Ile Ala Asp Ser Lys Arg Ser Ser Ser Arg Tyr Asp Gly Gly Tyr
50                  55                  60

Ser Ala Asp Ile Ile Pro Ala Gln Leu Arg Phe Ile Asp Asn Ile Asp
65                  70                  75                  80

Tyr Gly Thr Arg Leu Arg Lys Thr Leu His Arg Asn Ser Val Val Ser
                85                  90                  95

Asn Gly Tyr Asn Lys Leu Ser Glu Asn Asp Arg Trp Tyr Phe Asp Leu
                100                 105                 110

Phe Asp Arg Lys Tyr Phe Glu Asn Tyr Leu Glu Glu Pro Thr Tyr Ile
            115                 120                 125

Lys Ile Phe Lys Lys Lys Glu Gly Leu Glu Gln Phe Asp Arg Met Phe
130                 135                 140

Leu Ala Gln Glu Leu Lys Ile Pro Asp Val Tyr Lys Ser Thr Thr Tyr
145                 150                 155                 160

Gln Gly Glu Pro Ala Val Ala Asn Ser Glu Leu Phe Lys Asn Ser Ile
                165                 170                 175

Cys Cys Cys Thr Phe Ser His Asp Gly Lys Tyr Met Val Ile Gly Cys
                180                 185                 190

Lys Asp Gly Ser Leu His Leu Trp Lys Val Ile Asn Ser Pro Val Lys
                195                 200                 205

Arg Ser Glu Met Gly Arg Ser Gly Lys Ser Val Ser Ala Ser Arg Ala
                210                 215                 220

Asn Ser Leu Lys Ile Gln Arg His Leu Ala Ser Ile Ser Ser His Asn
225                 230                 235                 240

Gly Ser Ile Ser Ser Asn Asp Leu Lys Pro Ser Asp Gln Phe Glu Gly
                245                 250                 255

Pro Ser Lys Gln Leu His Leu Tyr Ala Pro Val Phe Tyr Ser Asp Val
                260                 265                 270
```

-continued

```
Phe Arg Val Phe Met Glu His Ala Leu Asp Ile Leu Asp Ala Asn Trp
        275                 280                 285

Ser Lys Asn Gly Phe Leu Ile Thr Ala Ser Met Asp Lys Thr Ala Lys
        290                 295                 300

Leu Trp His Pro Glu Arg Lys Tyr Ser Leu Lys Thr Phe Val His Pro
305                 310                 315                 320

Asp Phe Val Thr Ser Ala Ile Phe Phe Pro Asn Asp Asp Arg Phe Ile
                325                 330                 335

Ile Thr Gly Cys Leu Asp His Arg Cys Arg Leu Trp Ser Ile Leu Asp
            340                 345                 350

Asn Glu Val Ser Tyr Ala Phe Asp Cys Lys Asp Leu Ile Thr Ser Leu
        355                 360                 365

Thr Leu Ser Pro Pro Gly Gly Glu Tyr Thr Ile Ile Gly Thr Phe Asn
        370                 375                 380

Gly Tyr Ile Tyr Val Leu Leu Thr His Gly Leu Lys Phe Val Ser Ser
385                 390                 395                 400

Phe His Val Ser Asp Lys Ser Thr Gln Gly Thr Thr Lys Asn Ser Phe
                405                 410                 415

His Pro Ser Ser Glu Tyr Gly Lys Val Gln His Gly Pro Arg Ile Thr
            420                 425                 430

Gly Leu Gln Cys Phe Phe Ser Lys Val Asp Lys Asn Leu Arg Leu Ile
        435                 440                 445

Val Thr Thr Asn Asp Ser Lys Ile Gln Ile Phe Asp Leu Asn Glu Lys
    450                 455                 460

Lys Pro Leu Glu Leu Phe Lys Gly Phe Gln Ser Gly Ser Ser Arg His
465                 470                 475                 480

Arg Gly Gln Phe Leu Met Met Lys Asn Glu Pro Val Val Phe Thr Gly
                485                 490                 495

Ser Asp Asp His Trp Phe Tyr Thr Trp Lys Met Gln Ser Phe Asn Leu
            500                 505                 510

Ser Ala Glu Met Asn Cys Thr Ala Pro His Arg Lys Lys Arg Leu Ser
        515                 520                 525

Gly Ser Met Ser Leu Lys Gly Leu Leu Arg Ile Val Ser Asn Lys Ser
        530                 535                 540

Thr Asn Asp Glu Cys Leu Thr Glu Thr Ser Asn Gln Ser Ser Ser His
545                 550                 555                 560

Thr Phe Thr Asn Ser Ser Lys Asn Val Leu Gln Thr Gln Thr Val Gly
                565                 570                 575

Ser Gln Ala Ile Lys Asn Asn His Tyr Ile Ser Phe His Ala His Asn
            580                 585                 590

Ser Pro Val Thr Cys Ala Ser Ile Ala Pro Asp Val Ala Ile Lys Asn
        595                 600                 605

Leu Ser Leu Ser Asn Asp Leu Ile Phe Glu Leu Thr Ser Gln Tyr Phe
        610                 615                 620

Lys Glu Met Gly Gln Asn Tyr Ser Glu Ser Lys Glu Thr Cys Asp Asn
625                 630                 635                 640

Lys Pro Asn His Pro Val Thr Glu Thr Gly Gly Phe Ser Ser Asn Leu
                645                 650                 655

Ser Asn Val Val Asn Asn Val Gly Thr Ile Leu Ile Thr Thr Asp Ser
            660                 665                 670

Gln Gly Leu Ile Arg Val Phe Arg Thr Asp Ile Leu Pro Glu Ile Arg
        675                 680                 685

Lys Lys Ile Ile Glu Lys Phe His Glu Tyr Asn Leu Phe His Leu Glu
```

```
                690                 695                 700
Ala Ala Gly Lys Ile Asn Asn His Asn Asn Asp Ser Ile Leu Glu Asn
705                 710                 715                 720

Arg Met Asp Glu Arg Ser Ser Thr Glu Asp Asn Glu Phe Ser Thr Thr
                725                 730                 735

Pro Pro Ser Asn Thr His Asn Ser Arg Pro Ser His Asp Phe Cys Glu
                740                 745                 750

Leu His Pro Asn Asn Ser Pro Val Ile Ser Gly Met Pro Ser Arg Ala
                755                 760                 765

Ser Ala Ile Phe Lys Asn Ser Ile Phe Asn Lys Ser Asn Gly Ser Phe
770                 775                 780

Ile Ser Leu Lys Ser Arg Ser Glu Ser Thr Ser Ser Thr Val Phe Gly
785                 790                 795                 800

Pro His Asp Ile Pro Arg Val Ser Thr Thr Tyr Pro Lys Leu Lys Cys
                805                 810                 815

Asp Val Cys Asn Gly Ser Asn Phe Glu Cys Ala Ser Lys Asn Pro Ile
                820                 825                 830

Ala Gly Gly Asp Ser Gly Phe Thr Cys Ala Asp Cys Gly Thr Ile Leu
                835                 840                 845

Asn Asn Phe Arg
    850
```

(2) INFORMATION FOR SEQ ID NO:60:

(i) SEQUENCE CHARACTERISTICS:
        (A) LENGTH: 488 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: SOF1, Fig. 43

(xi) SEQUENCE DESCRIPTION: SEQ ID NO:60:

```
Met Lys Ile Lys Thr Ile Lys Arg Ser Ala Asp Asp Tyr Val Pro Val
1               5                   10                  15

Lys Ser Thr Gln Glu Ser Gln Met Pro Arg Asn Leu Asn Pro Glu Leu
                20                  25                  30

His Pro Phe Glu Arg Ala Arg Glu Tyr Thr Lys Ala Leu Asn Ala Thr
                35                  40                  45

Lys Leu Glu Arg Met Phe Ala Lys Pro Phe Val Gly Gln Leu Gly Tyr
50                  55                  60

Gly His Arg Asp Gly Val Tyr Ala Ile Ala Lys Asn Tyr Gly Ser Leu
65                  70                  75                  80

Asn Lys Leu Ala Thr Gly Ser Ala Asp Gly Val Ile Lys Tyr Trp Asn
                85                  90                  95

Met Ser Thr Arg Glu Glu Phe Val Ser Phe Lys Ala His Tyr Gly Leu
                100                 105                 110

Val Thr Gly Leu Cys Val Thr Gln Pro Arg Phe His Asp Lys Lys Pro
                115                 120                 125

Asp Leu Lys Ser Gln Asn Phe Met Leu Ser Cys Ser Asp Asp Lys Thr
                130                 135                 140

Val Lys Leu Trp Ser Ile Asn Val Asp Asp Tyr Ser Asn Lys Asn Ser
```

```
                    145                 150                 155                 160
              Ser Asp Asn Asp Ser Val Thr Asn Glu Glu Gly Leu Ile Arg Thr Phe
                              165                 170                 175
              Asp Gly Glu Ser Ala Phe Gln Gly Ile Asp Ser His Arg Glu Asn Ser
                              180                 185                 190
              Thr Phe Ala Thr Gly Gly Ala Lys Ile His Leu Trp Asp Val Asn Arg
                              195                 200                 205
              Leu Lys Pro Val Ser Asp Leu Ser Trp Gly Ala Asp Asn Ile Thr Ser
                              210                 215                 220
              Leu Lys Phe Asn Gln Asn Glu Thr Asp Ile Leu Ala Ser Thr Gly Ser
              225                 230                 235                 240
              Asp Asn Ser Ile Val Leu Tyr Asp Leu Arg Thr Asn Ser Pro Thr Gln
                              245                 250                 255
              Lys Ile Val Gln Thr Met Arg Thr Asn Ala Ile Cys Trp Asn Pro Met
                              260                 265                 270
              Glu Ala Phe Asn Phe Val Thr Ala Asn Glu Asp His Asn Ala Tyr Tyr
                              275                 280                 285
              Tyr Asp Met Arg Asn Leu Ser Arg Ser Leu Asn Val Phe Lys Asp His
                              290                 295                 300
              Val Ser Ala Val Met Asp Val Asp Phe Ser Pro Thr Gly Asp Glu Ile
              305                 310                 315                 320
              Val Thr Gly Ser Tyr Asp Lys Ser Ile Arg Ile Tyr Lys Thr Asn His
                              325                 330                 335
              Gly His Ser Arg Glu Ile Tyr His Thr Lys Arg Met Gln His Val Phe
                              340                 345                 350
              Val Lys Tyr Ser Met Asp Ser Lys Tyr Ile Ile Ser Gly Ser Asp Asp
                              355                 360                 365
              Gly Asn Val Arg Leu Trp Arg Ser Lys Ala Trp Glu Arg Ser Asn Val
                              370                 375                 380
              Lys Thr Thr Arg Glu Lys Asn Lys Leu Glu Tyr Asp Glu Lys Leu Lys
              385                 390                 395                 400
              Glu Arg Phe Arg His Met Pro Glu Ile Lys Arg Ile Ser Arg His Arg
                              405                 410                 415
              His Val Pro Gln Val Ile Lys Lys Ala Gln Glu Ile Lys Asn Ile Glu
                              420                 425                 430
              Leu Ser Ser Ile Lys Arg Arg Glu Ala Asn Glu Arg Arg Thr Arg Lys
                              435                 440                 445
              Asp Met Pro Tyr Ile Ser Glu Arg Lys Lys Gln Ile Val Gly Thr Val
                              450                 455                 460
              His Lys Tyr Glu Asp Ser Gly Arg Asp Arg Lys Arg Arg Lys Glu Asp
              465                 470                 475                 480
              Asp Lys Arg Asp Thr Gln Glu Lys
                              485

(2) INFORMATION FOR SEQ ID NO:61:

(i) SEQUENCE CHARACTERISTICS:
         (A) LENGTH: 423 amino acids
         (B) TYPE: amino acid
         (D) TOPOLOGY: unknown (ii) MOLECULE TYPE: protein (iii) HYPOTHETICAL: NO (iv) ANTI-SENSE: NO
```

-continued (vi) ORIGINAL SOURCE:
   (C) INDIVIDUAL ISOLATE: STE4 - YEAST, Fig. 44

(xi) SEQUENCE DESCRIPTION: SEQ ID NO:61:

```
Met Ala Ala His Gln Met Asp Ser Ile Thr Tyr Ser Asn Asn Val Thr
1               5                   10                  15

Gln Gln Tyr Ile Gln Pro Gln Ser Leu Gln Asp Ile Ser Ala Val Glu
            20                  25                  30

Asp Glu Ile Gln Asn Lys Ile Glu Ala Ala Arg Gln Glu Ser Lys Gln
        35                  40                  45

Leu His Ala Gln Ile Asn Lys Ala Lys His Lys Ile Gln Asp Ala Ser
    50                  55                  60

Leu Phe Gln Met Ala Asn Lys Val Thr Ser Leu Thr Lys Asn Lys Ile
65                  70                  75                  80

Asn Leu Lys Pro Asn Ile Val Leu Lys Gly His Asn Asn Lys Ile Ser
                85                  90                  95

Asp Phe Arg Trp Ser Arg Asp Ser Lys Arg Ile Leu Ser Ala Ser Gln
            100                 105                 110

Asp Gly Phe Met Leu Ile Trp Asp Ser Ala Ser Gly Leu Lys Gln Asn
        115                 120                 125

Ala Ile Pro Leu Asp Ser Gln Trp Val Leu Ser Cys Ala Ile Ser Pro
    130                 135                 140

Ser Ser Thr Leu Val Ala Ser Ala Gly Leu Asn Asn Asn Cys Thr Ile
145                 150                 155                 160

Tyr Arg Val Ser Lys Glu Asn Arg Val Ala Gln Asn Val Ala Ser Ile
                165                 170                 175

Phe Lys Gly His Thr Cys Tyr Ile Ser Asp Ile Glu Phe Thr Asp Asn
            180                 185                 190

Ala His Ile Leu Thr Ala Ser Gly Asp Met Thr Cys Ala Leu Trp Asp
        195                 200                 205

Ile Pro Lys Ala Lys Arg Val Arg Glu Tyr Ser Asp His Leu Gly Asp
    210                 215                 220

Val Leu Ala Leu Ala Ile Pro Glu Glu Pro Asn Leu Glu Asn Ser Ser
225                 230                 235                 240

Asn Thr Phe Ala Ser Cys Gly Ser Asp Gly Tyr Thr Tyr Ile Trp Asp
                245                 250                 255

Ser Arg Ser Pro Ser Ala Val Gln Ser Phe Tyr Val Asn Asp Ser Asp
            260                 265                 270

Ile Asn Ala Leu Arg Phe Phe Lys Asp Gly Met Ser Ile Val Ala Gly
        275                 280                 285

Ser Asp Asn Gly Ala Ile Asn Met Tyr Asp Leu Arg Ser Asp Cys Ser
    290                 295                 300

Ile Ala Thr Phe Ser Leu Phe Arg Gly Tyr Glu Glu Arg Thr Pro Thr
305                 310                 315                 320

Pro Thr Tyr Met Ala Ala Asn Met Glu Tyr Asn Thr Ala Gln Ser Pro
                325                 330                 335

Gln Thr Leu Lys Ser Thr Ser Ser Tyr Leu Asp Asn Gln Gly Val
            340                 345                 350

Val Ser Leu Asp Phe Ser Ala Ser Gly Arg Leu Met Tyr Ser Cys Tyr
    355                 360                 365

Thr Asp Ile Gly Cys Val Val Trp Asp Val Leu Lys Gly Glu Ile Val
370                 375                 380

Gly Lys Leu Glu Gly His Gly Gly Arg Val Thr Gly Val Arg Ser Ser
385                 390                 395                 400
```

```
Pro Asp Gly Leu Ala Val Cys Thr Gly Ser Trp Asp Ser Thr Met Lys
            405                 410                 415

Ile Trp Ser Pro Gly Tyr Gln
            420
```

(2) INFORMATION FOR SEQ ID NO:62:

(i) SEQUENCE CHARACTERISTICS:
        (A) LENGTH: 704 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: TRANSCRIPTION FACTOR TIIF, Fig. 45

(xi) SEQUENCE DESCRIPTION: SEQ ID NO:62:

```
Met Ser Leu Glu Val Ser Asn Ile Asn Gly Gly Asn Gly Thr Gln Leu
1               5                   10                  15

Ser His Asp Lys Arg Glu Leu Leu Cys Leu Leu Lys Leu Ile Lys Lys
            20                  25                  30

Tyr Gln Leu Lys Ser Thr Glu Glu Leu Leu Cys Gln Glu Ala Asn Val
            35                  40                  45

Ser Ser Val Glu Leu Ser Glu Ile Ser Glu Ser Asp Val Gln Gln Val
        50                  55                  60

Leu Gly Ala Val Leu Gly Ala Gly Asp Ala Asn Arg Glu Arg Lys His
65                  70                  75                  80

Val Gln Ser Pro Ala Gln Gly His Lys Gln Ser Ala Val Thr Glu Ala
            85                  90                  95

Asn Ala Ala Glu Glu Leu Ala Lys Phe Ile Asp Asp Ser Phe Asp
            100                 105                 110

Ala Gln His Tyr Glu Gln Ala Tyr Lys Glu Leu Arg Thr Phe Val Glu
            115                 120                 125

Asp Ser Leu Asp Ile Tyr Lys His Glu Leu Ser Met Val Leu Tyr Pro
            130                 135                 140

Ile Leu Val Gln Ile Tyr Phe Lys Ile Leu Ala Ser Gly Leu Arg Glu
145                 150                 155                 160

Lys Ala Lys Glu Phe Ile Glu Lys Tyr Lys Cys Asp Leu Asp Gly Tyr
            165                 170                 175

Tyr Ile Glu Gly Leu Phe Asn Leu Leu Leu Ser Lys Pro Glu Glu
            180                 185                 190

Leu Leu Glu Asn Asp Leu Val Val Ala Met Glu Gln Asp Lys Phe Val
            195                 200                 205

Ile Arg Met Ser Arg Asp Ser His Ser Leu Phe Lys Arg His Ile Gln
            210                 215                 220

Asp Arg Arg Gln Glu Val Val Ala Asp Ile Val Ser Lys Tyr Leu His
225                 230                 235                 240

Phe Asp Thr Tyr Glu Gly Met Ala Arg Asn Lys Leu Gln Cys Val Ala
            245                 250                 255

Thr Ala Gly Ser His Leu Gly Glu Ala Lys Arg Gln Asp Asn Lys Met
            260                 265                 270

Arg Val Tyr Tyr Gly Leu Leu Lys Glu Val Asp Phe Gln Thr Leu Thr
            275                 280                 285
```

```
Thr Pro Ala Pro Ala Pro Glu Glu Asp Asp Pro Asp Ala Pro
    290                 295                 300
Asp Arg Pro Lys Lys Lys Pro Lys Asp Pro Leu Leu Ser Lys
305                 310                 315                 320
Lys Ser Lys Ser Asp Pro Asn Ala Pro Ser Ile Asp Arg Ile Pro Leu
                325                 330                 335
Pro Glu Leu Lys Asp Ser Asp Lys Leu Leu Lys Leu Lys Ala Leu Arg
            340                 345                 350
Glu Ala Ser Lys Arg Leu Ala Leu Ser Lys Asp Gln Leu Pro Ser Ala
            355                 360                 365
Val Phe Tyr Thr Val Leu Asn Ser His Gln Gly Val Thr Cys Ala Glu
    370                 375                 380
Ile Ser Asp Asp Ser Thr Met Leu Ala Cys Gly Phe Gly Asp Ser Ser
385                 390                 395                 400
Val Arg Ile Trp Ser Leu Thr Pro Ala Asn Val Arg Thr Leu Lys Asp
                405                 410                 415
Ala Asp Ser Leu Arg Glu Leu Asp Lys Glu Ser Ala Asp Ile Asn Val
            420                 425                 430
Arg Met Leu Asp Asp Arg Ser Gly Glu Val Thr Arg Ser Leu Met Gly
    435                 440                 445
His Thr Gly Pro Val Tyr Arg Cys Ala Phe Ala Pro Glu Met Asn Leu
    450                 455                 460
Leu Leu Ser Cys Ser Glu Asp Ser Thr Ile Arg Leu Trp Ser Leu Leu
465                 470                 475                 480
Thr Trp Ser Cys Val Val Thr Tyr Arg Gly His Val Tyr Pro Val Trp
                485                 490                 495
Asp Val Arg Phe Ala Pro His Gly Tyr Tyr Phe Val Ser Cys Ser Tyr
            500                 505                 510
Asp Lys Thr Ala Arg Leu Trp Ala Thr Asp Ser Asn Gln Ala Leu Arg
    515                 520                 525
Val Phe Val Gly His Leu Ser Asp Val Asp Cys Val Gln Phe His Pro
    530                 535                 540
Asn Ser Asn Tyr Val Ala Thr Gly Ser Ser Asp Arg Thr Val Arg Leu
545                 550                 555                 560
Trp Asp Asn Met Thr Gly Gln Ser Val Arg Leu Met Thr Gly His Lys
                565                 570                 575
Gly Ser Val Ser Ser Leu Ala Phe Ser Ala Cys Gly Arg Tyr Leu Ala
            580                 585                 590
Ser Gly Ser Val Asp His Asn Ile Ile Ile Trp Asp Leu Ser Asn Gly
            595                 600                 605
Ser Leu Val Thr Thr Leu Leu Arg His Thr Ser Thr Val Thr Thr Ile
    610                 615                 620
Thr Phe Ser Arg Asp Gly Thr Val Leu Ala Ala Gly Leu Asp Asn
625                 630                 635                 640
Asn Leu Thr Leu Trp Asp Phe His Lys Val Thr Glu Asp Tyr Ile Ser
                645                 650                 655
Asn His Ile Thr Val Ser His His Gln Asp Glu Asn Asp Glu Asp Val
            660                 665                 670
Tyr Leu Met Arg Thr Phe Pro Ser Lys Asn Ser Pro Phe Val Ser Leu
    675                 680                 685
His Phe Thr Arg Arg Asn Leu Leu Met Cys Val Gly Leu Phe Lys Ser
    690                 695                 700
```

(2) INFORMATION FOR SEQ ID NO:63:

(i) SEQUENCE CHARACTERISTICS:
        (A) LENGTH: 713 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: TUP1, Fig. 46

(xi) SEQUENCE DESCRIPTION: SEQ ID NO:63:

```
Met Thr Ala Ser Val Ser Asn Thr Gln Asn Lys Leu Asn Glu Leu Leu
1               5                   10                  15

Asp Ala Ile Arg Gln Glu Phe Leu Gln Val Ser Gln Glu Ala Asn Thr
            20                  25                  30

Tyr Arg Leu Gln Asn Gln Lys Asp Tyr Asp Phe Lys Met Asn Gln Gln
        35                  40                  45

Leu Ala Glu Met Gln Gln Ile Arg Asn Thr Val Tyr Glu Leu Glu Leu
    50                  55                  60

Thr His Arg Lys Met Lys Asp Ala Tyr Glu Ala Glu Ile Lys His Leu
65                  70                  75                  80

Lys Leu Gly Leu Glu Gln Arg Asp His Gln Ile Ala Ser Leu Thr Val
                85                  90                  95

Gln Gln Gln Gln Gln Gln Gln Gln Gln Val Gln Gln His Leu
            100                 105                 110

Gln Gln Gln Gln Gln Gln Leu Ala Ala Ala Ser Ala Ser Val Pro Val
        115                 120                 125

Ala Gln Gln Pro Pro Ala Thr Thr Ser Ala Thr Ala Thr Pro Ala Ala
    130                 135                 140

Asn Thr Thr Thr Gly Ser Pro Ser Ala Phe Pro Val Gln Ala Ser Arg
145                 150                 155                 160

Pro Asn Leu Val Gly Ser Gln Leu Pro Thr Thr Thr Leu Pro Val Val
                165                 170                 175

Ser Ser Asn Ala Gln Gln Gln Leu Pro Gln Gln Gln Leu Gln Gln Gln
            180                 185                 190

Gln Leu Gln Gln Gln Gln Pro Pro Gln Val Ser Val Ala Pro Leu
        195                 200                 205

Ser Asn Thr Ala Ile Asn Gly Ser Pro Thr Ser Lys Glu Thr Thr Thr
    210                 215                 220

Leu Pro Ser Val Lys Ala Pro Glu Ser Thr Leu Lys Glu Thr Glu Pro
225                 230                 235                 240

Glu Asn Asn Asn Thr Ser Lys Ile Asn Asp Thr Gly Ser Ala Thr Thr
                245                 250                 255

Ala Thr Thr Thr Thr Ala Thr Gln Thr Glu Ile Lys Pro Lys Glu Glu
            260                 265                 270

Asp Ala Thr Pro Ala Ser Leu His Gln Asp His Tyr Leu Val Pro Tyr
        275                 280                 285

Asn Gln Arg Ala Asn His Ser Lys Pro Ile Pro Pro Phe Leu Leu Asp
    290                 295                 300

Leu Asp Ser Gln Ser Val Pro Asp Ala Leu Lys Lys Gln Thr Asn Asp
305                 310                 315                 320
```

Tyr Tyr Ile Leu Tyr Asn Pro Ala Leu Pro Arg Glu Ile Asp Val Glu
            325                 330                 335

Leu His Lys Ser Leu Asp His Thr Ser Val Val Cys Val Lys Phe
            340                 345                 350

Ser Asn Asp Gly Glu Tyr Leu Ala Thr Gly Cys Asn Lys Thr Thr Gln
            355                 360                 365

Val Tyr Arg Val Ser Asp Gly Ser Leu Val Ala Arg Leu Ser Asp Asp
            370                 375                 380

Ser Ala Ala Asn Asn His Arg Asn Ser Ile Thr Glu Asn Asn Thr Thr
385                 390                 395                 400

Thr Ser Thr Asp Asn Asn Thr Met Thr Thr Thr Thr Thr Thr Thr Ile
            405                 410                 415

Thr Thr Thr Ala Met Thr Ser Ala Ala Glu Leu Ala Lys Asp Val Glu
            420                 425                 430

Asn Leu Asn Thr Ser Ser Ser Pro Ser Ser Asp Leu Tyr Ile Arg Ser
            435                 440                 445

Val Cys Phe Ser Pro Asp Gly Lys Phe Leu Ala Thr Gly Ala Glu Asp
            450                 455                 460

Arg Leu Ile Arg Ile Trp Asp Ile Glu Asn Arg Lys Ile Val Met Ile
465                 470                 475                 480

Leu Gln Gly His Glu Gln Asp Ile Tyr Ser Leu Asp Tyr Phe Pro Ser
            485                 490                 495

Gly Asp Lys Leu Val Ser Gly Ser Gly Asp Arg Thr Val Arg Ile Trp
            500                 505                 510

Asp Leu Arg Thr Gly Gln Cys Ser Leu Thr Leu Ser Ile Glu Asp Gly
            515                 520                 525

Val Thr Thr Val Ala Val Ser Pro Gly Asp Gly Lys Tyr Ile Ala Ala
            530                 535                 540

Gly Ser Leu Asp Arg Ala Val Arg Val Trp Asp Ser Glu Thr Gly Phe
545                 550                 555                 560

Leu Val Glu Arg Leu Asp Ser Glu Asn Glu Ser Gly Thr Gly His Lys
            565                 570                 575

Asp Ser Val Tyr Ser Val Val Phe Thr Arg Asp Gly Gln Ser Val Val
            580                 585                 590

Ser Gly Ser Leu Asp Arg Ser Val Lys Leu Trp Asn Leu Gln Asn Ala
            595                 600                 605

Asn Asn Lys Ser Asp Ser Lys Thr Pro Asn Ser Gly Thr Cys Glu Val
            610                 615                 620

Thr Tyr Ile Gly His Lys Asp Phe Val Leu Ser Val Ala Thr Thr Gln
625                 630                 635                 640

Asn Asp Glu Tyr Ile Leu Ser Gly Ser Lys Asp Arg Gly Val Leu Phe
            645                 650                 655

Trp Asp Lys Lys Ser Gly Asn Pro Leu Leu Met Leu Gln Gly His Arg
            660                 665                 670

Asn Ser Val Ile Ser Val Ala Val Ala Asn Gly Ser Ser Leu Gly Pro
            675                 680                 685

Glu Tyr Asn Val Phe Ala Thr Gly Ser Gly Asp Cys Lys Ala Arg Ile
            690                 695                 700

Trp Lys Tyr Lys Lys Ile Ala Pro Asn
705                 710

(2) INFORMATION FOR SEQ ID NO:64:

(i) SEQUENCE CHARACTERISTICS:

(A) LENGTH: 798 amino acids
(B) TYPE: amino acid
(D) TOPOLOGY: unknown (ii) MOLECULE TYPE: protein (iii) HYPOTHETICAL: NO (iv) ANTI-SENSE: NO (vi) ORIGINAL SOURCE:
(C) INDIVIDUAL ISOLATE: TUP1 HOMOLOG, Fig. 47

(xi) SEQUENCE DESCRIPTION: SEQ ID NO:64:

```
Met Ser Gln Lys Gln Ser Thr Asn Gln Asn Gln Asn Gly Thr His Gln
  1               5                  10                  15

Pro Gln Pro Val Lys Asn Gln Arg Thr Asn Asn Ala Ala Gly Ala Asn
                 20                  25                  30

Ser Gly Gln Gln Pro Gln Gln Ser Gln Gly Gln Ser Gln Gln Gln
             35                  40                  45

Gly Arg Ser Asn Gly Pro Phe Ser Ala Ser Asp Leu Asn Arg Ile Val
 50                  55                  60

Leu Glu Tyr Leu Asn Lys Lys Gly Tyr His Arg Thr Glu Ala Met Leu
 65                  70                  75                  80

Arg Ala Glu Ser Gly Arg Thr Leu Thr Pro Gln Asn Lys Gln Ser Pro
                 85                  90                  95

Ala Asn Thr Lys Thr Gly Lys Phe Pro Glu Gln Ser Ser Ile Pro Pro
                100                 105                 110

Asn Pro Gly Lys Thr Ala Lys Pro Ile Ser Asn Pro Thr Asn Leu Ser
                115                 120                 125

Ser Lys Arg Asp Ala Glu Gly Gly Ile Val Ser Ser Gly Arg Leu Glu
                130                 135                 140

Gly Leu Asn Ala Pro Glu Asn Tyr Ile Arg Ala Tyr Ser Met Leu Lys
145                 150                 155                 160

Asn Trp Val Asp Ser Ser Leu Glu Ile Tyr Lys Pro Glu Leu Ser Tyr
                165                 170                 175

Ile Met Tyr Pro Ile Phe Ile Tyr Leu Phe Leu Asn Leu Val Ala Lys
                180                 185                 190

Asn Pro Val Tyr Ala Arg Arg Phe Phe Asp Arg Phe Ser Pro Asp Phe
                195                 200                 205

Lys Asp Phe His Gly Ser Glu Ile Asn Arg Leu Phe Ser Val Asn Ser
210                 215                 220

Ile Asp His Ile Lys Glu Asn Glu Val Ala Ser Ala Phe Gln Ser His
225                 230                 235                 240

Lys Tyr Arg Ile Thr Met Ser Lys Thr Thr Leu Asn Leu Leu Leu Tyr
                245                 250                 255

Phe Leu Asn Glu Asn Glu Ser Ile Gly Gly Ser Leu Ile Ile Ser Val
                260                 265                 270

Ile Asn Gln His Leu Asp Pro Asn Ile Val Glu Ser Val Thr Ala Arg
                275                 280                 285

Glu Lys Leu Ala Asp Gly Ile Lys Val Leu Ser Asp Ser Glu Asn Gly
                290                 295                 300

Asn Gly Lys Gln Asn Leu Glu Met Asn Ser Val Pro Val Lys Leu Gly
305                 310                 315                 320

Pro Phe Pro Lys Asp Glu Glu Phe Val Lys Glu Ile Glu Thr Glu Leu
                325                 330                 335

Lys Ile Lys Asp Asp Gln Glu Lys Gln Leu Asn Gln Gln Thr Ala Gly
```

-continued

```
                340                 345                 350
Asp Asn Tyr Ser Gly Ala Asn Asn Arg Thr Leu Leu Gln Glu Tyr Lys
            355                 360                 365

Ala Met Asn Asn Glu Lys Phe Lys Asp Asn Thr Gly Asp Asp Asp Lys
        370                 375                 380

Asp Lys Ile Lys Asp Lys Ile Ala Lys Asp Glu Glu Lys Lys Glu Ser
385                 390                 395                 400

Glu Leu Lys Val Asp Gly Lys Lys Asp Ser Asn Leu Ser Ser Pro
                405                 410                 415

Ala Arg Asp Ile Leu Pro Leu Pro Pro Lys Thr Ala Leu Asp Leu Lys
                420                 425                 430

Leu Glu Ile Gln Lys Val Lys Glu Ser Arg Asp Ala Ile Lys Leu Asp
            435                 440                 445

Asn Leu Gln Leu Ala Leu Pro Ser Val Cys Met Tyr Thr Phe Gln Asn
        450                 455                 460

Thr Asn Lys Asp Met Ser Cys Leu Asp Phe Ser Asp Asp Cys Arg Ile
465                 470                 475                 480

Ala Ala Ala Gly Phe Gln Asp Ser Tyr Ile Lys Ile Trp Ser Leu Asp
                485                 490                 495

Gly Ser Ser Leu Asn Asn Pro Asn Ile Ala Leu Asn Asn Asn Asp Lys
                500                 505                 510

Asp Glu Asp Pro Thr Cys Lys Thr Leu Val Gly His Ser Gly Thr Val
            515                 520                 525

Tyr Ser Thr Ser Phe Ser Pro Asp Asn Lys Tyr Leu Leu Ser Gly Ser
        530                 535                 540

Glu Asp Lys Thr Val Arg Leu Trp Ser Met Asp Thr His Thr Ala Leu
545                 550                 555                 560

Val Ser Tyr Lys Gly His Asn His Pro Val Trp Asp Val Ser Phe Ser
                565                 570                 575

Pro Leu Gly His Tyr Phe Ala Thr Ala Ser His Asp Gln Thr Ala Arg
                580                 585                 590

Leu Trp Ser Cys Asp His Ile Tyr Pro Leu Arg Ile Phe Ala Gly His
            595                 600                 605

Leu Asn Asp Val Asp Cys Val Ser Phe His Pro Asn Gly Cys Tyr Val
        610                 615                 620

Phe Thr Gly Ser Ser Asp Lys Thr Cys Arg Met Trp Asp Val Ser Thr
625                 630                 635                 640

Gly Asp Ser Val Arg Leu Phe Leu Gly His Thr Ala Pro Val Ile Ser
                645                 650                 655

Ile Ala Val Cys Pro Asp Gly Arg Trp Leu Ser Thr Gly Ser Glu Asp
                660                 665                 670

Gly Ile Ile Asn Val Trp Asp Ile Gly Thr Gly Lys Arg Leu Lys Gln
            675                 680                 685

Met Arg Gly His Gly Lys Asn Ala Ile Tyr Ser Leu Ser Tyr Ser Lys
        690                 695                 700

Glu Gly Asn Val Leu Ile Ser Gly Gly Ala Asp His Thr Val Arg Val
705                 710                 715                 720

Trp Asp Leu Lys Lys Ala Thr Thr Glu Pro Ser Ala Glu Pro Asp Glu
                725                 730                 735

Pro Phe Ile Gly Tyr Leu Gly Asp Val Thr Ala Ser Ile Asn Gln Asp
                740                 745                 750

Ile Lys Glu Tyr Gly Arg Arg Thr Val Ile Pro Thr Ser Asp Leu
            755                 760                 765
```

```
Val Ala Ser Phe Tyr Thr Lys Lys Thr Pro Val Phe Lys Val Lys Phe
    770                 775                 780

Ser Arg Ser Asn Leu Ala Leu Ala Gly Gly Ala Phe Arg Pro
785                 790                 795
```

(2) INFORMATION FOR SEQ ID NO:65:

(i) SEQUENCE CHARACTERISTICS:
        (A) LENGTH: 439 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: YCU7, Fig. 48

(xi) SEQUENCE DESCRIPTION: SEQ ID NO:65:

```
Met Val Arg Arg Phe Arg Gly Lys Glu Leu Ala Ala Thr Thr Phe Asn
1               5                   10                  15

Gly His Arg Asp Tyr Val Met Gly Ala Phe Phe Ser His Asp Gln Glu
                20                  25                  30

Lys Ile Tyr Thr Val Ser Lys Asp Gly Ala Val Phe Val Trp Glu Phe
            35                  40                  45

Thr Lys Arg Pro Ser Asp Asp Asp Asn Glu Ser Glu Asp Asp Asp
        50                  55                  60

Lys Gln Glu Glu Val Asp Ile Ser Lys Tyr Ser Trp Arg Ile Thr Lys
65                  70                  75                  80

Lys His Phe Phe Tyr Ala Asn Gln Ala Lys Val Lys Cys Val Thr Phe
                85                  90                  95

His Pro Ala Thr Arg Leu Leu Ala Val Gly Phe Thr Ser Gly Glu Phe
                100                 105                 110

Arg Leu Tyr Asp Leu Pro Asp Phe Thr Leu Ile Gln Gln Leu Ser Met
                115                 120                 125

Gly Gln Asn Pro Val Asn Thr Val Ser Val Asn Gln Thr Gly Glu Trp
130                 135                 140

Leu Ala Phe Gly Ser Ser Lys Leu Gly Gln Leu Leu Val Tyr Glu Trp
145                 150                 155                 160

Gln Ser Glu Ser Tyr Ile Leu Lys Gln Gln Gly His Phe Asp Ser Thr
                165                 170                 175

Asn Ser Leu Ala Tyr Ser Pro Asp Gly Ser Arg Val Val Thr Ala Ser
                180                 185                 190

Glu Asp Gly Lys Ile Lys Val Trp Asp Ile Thr Ser Gly Phe Cys Leu
                195                 200                 205

Ala Thr Phe Glu Glu His Thr Ser Ser Val Thr Ala Val Gln Phe Ala
                210                 215                 220

Lys Arg Gly Gln Val Met Phe Ser Ser Ser Leu Asp Gly Thr Val Arg
225                 230                 235                 240

Ala Trp Asp Leu Ile Arg Tyr Arg Asn Phe Arg Thr Phe Thr Gly Thr
                245                 250                 255

Glu Arg Ile Gln Phe Asn Cys Leu Ala Val Asp Pro Ser Gly Glu Val
                260                 265                 270

Val Cys Ala Gly Ser Leu Asp Asn Phe Asp Ile His Val Trp Ser Val
                275                 280                 285
```

```
Gln Thr Gly Gln Leu Leu Asp Ala Leu Ser Gly His Glu Gly Pro Val
    290                 295                 300

Ser Cys Leu Ser Phe Ser Gln Glu Asn Ser Val Leu Ala Ser Ala Ser
305                 310                 315                 320

Trp Asp Lys Thr Ile Arg Ile Trp Ser Ile Phe Gly Arg Ser Gln Gln
                325                 330                 335

Val Glu Pro Ile Glu Val Tyr Ser Asp Val Leu Ala Leu Ser Met Arg
                340                 345                 350

Pro Asp Gly Lys Glu Val Ala Val Ser Thr Leu Lys Gly Gln Ile Ser
            355                 360                 365

Ile Phe Asn Ile Glu Asp Ala Lys Gln Val Gly Asn Ile Asp Cys Arg
    370                 375                 380

Lys Asp Ile Ile Ser Gly Arg Phe Asn Gln Asp Arg Phe Thr Ala Lys
385                 390                 395                 400

Ile Leu Asn Asp Pro Asn Phe Leu Leu Gln Tyr Ile Thr Val Leu Met
                405                 410                 415

Val Trp Leu Leu Trp Leu Val Val Ile Ile Thr Pro Phe Val Tyr Met
            420                 425                 430

Met Phe Gln Met Lys Ser Cys
        435

(2) INFORMATION FOR SEQ ID NO:66:

(i) SEQUENCE CHARACTERISTICS:
        (A) LENGTH: 514 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
         (C) INDIVIDUAL ISOLATE: YCW2 PROTEIN, Fig. 49

(xi) SEQUENCE DESCRIPTION: SEQ ID NO:66:

Met Ser Thr Leu Ile Pro Pro Ser Lys Lys Gln Lys Lys Glu Ala
1                5                   10                  15

Gln Leu Pro Arg Glu Val Ala Ile Ile Pro Lys Asp Leu Pro Asn Val
                20                  25                  30

Ser Ile Lys Phe Gln Ala Leu Asp Thr Gly Asp Asn Val Gly Gly Ala
                35                  40                  45

Leu Arg Val Pro Gly Ala Ile Ser Glu Lys Gln Leu Glu Glu Leu Leu
    50                  55                  60

Asn Gln Leu Asn Gly Thr Ser Asp Asp Pro Val Pro Tyr Thr Phe Ser
65                  70                  75                  80

Cys Thr Ile Gln Gly Lys Lys Ala Ser Asp Pro Val Lys Thr Ile Asp
                85                  90                  95

Ile Thr Asp Asn Leu Tyr Ser Ser Leu Ile Lys Pro Gly Tyr Asn Ser
                100                 105                 110

Thr Glu Asp Gln Ile Thr Leu Leu Tyr Thr Pro Arg Ala Val Phe Lys
                115                 120                 125

Val Lys Pro Val Thr Arg Ser Ser Ser Ala Ile Ala Gly His Gly Ser
            130                 135                 140

Thr Ile Leu Cys Ser Ala Phe Ala Pro His Thr Ser Ser Arg Met Val
145                 150                 155                 160
```

```
Thr Gly Ala Gly Asp Asn Thr Ala Arg Ile Trp Asp Cys Asp Thr Gln
            165                 170                 175
Thr Pro Met His Thr Leu Lys Gly His Tyr Asn Trp Val Leu Cys Val
            180                 185                 190
Ser Trp Ser Pro Asp Gly Glu Val Ile Ala Thr Gly Ser Met Asp Asn
            195                 200                 205
Thr Ile Arg Leu Trp Asp Pro Lys Ser Gly Gln Cys Leu Gly Asp Ala
            210                 215                 220
Leu Arg Gly His Ser Lys Trp Ile Thr Ser Leu Ser Trp Glu Pro Ile
225                 230                 235                 240
His Leu Val Lys Pro Gly Ser Lys Pro Arg Leu Ala Ser Ser Ser Lys
            245                 250                 255
Asp Gly Thr Ile Lys Ile Trp Asp Thr Val Ser Arg Val Cys Gln Tyr
            260                 265                 270
Thr Met Ser Gly His Thr Asn Ser Val Ser Cys Val Lys Trp Gly Gly
            275                 280                 285
Gln Gly Leu Leu Tyr Ser Gly Ser His Asp Arg Thr Val Arg Val Trp
            290                 295                 300
Asp Ile Asn Ser Gln Gly Arg Cys Ile Asn Ile Leu Lys Ser His Ala
305                 310                 315                 320
His Trp Val Asn His Leu Ser Leu Ser Thr Asp Tyr Ala Leu Arg Ile
            325                 330                 335
Gly Ala Phe Asp His Thr Gly Lys Lys Pro Ser Thr Pro Glu Glu Ala
            340                 345                 350
Gln Lys Lys Ala Leu Glu Asn Tyr Glu Lys Ile Cys Lys Lys Asn Gly
            355                 360                 365
Asn Ser Glu Glu Met Met Val Thr Ala Ser Asp Asp Tyr Thr Met Phe
370                 375                 380
Leu Trp Asn Pro Leu Lys Ser Thr Lys Pro Ile Ala Arg Met Thr Gly
385                 390                 395                 400
His Gln Lys Leu Val Asn His Val Ala Phe Ser Pro Asp Gly Arg Tyr
            405                 410                 415
Ile Val Ser Ala Ser Phe Asp Asn Ser Ile Lys Leu Trp Asp Gly Arg
            420                 425                 430
Asp Gly Lys Phe Ile Ser Thr Phe Arg Gly His Ile Ala Ser Val Tyr
            435                 440                 445
Gln Val Ala Trp Ser Ser Asp Cys Arg Leu Leu Val Ser Cys Ser Lys
            450                 455                 460
Asp Thr Thr Leu Lys Val Trp Asp Val Arg Thr Arg Lys Leu Ser Val
465                 470                 475                 480
Asp Leu Pro Gly Ile Lys Thr Lys Leu Tyr Val Asp Trp Ser Val Asp
            485                 490                 495
Gly Lys Arg Val Cys Ser Gly Gly Lys Asp Lys Met Val Arg Leu Trp
            500                 505                 510
Thr His (2) INFORMATION FOR SEQ ID NO:67:

(i) SEQUENCE CHARACTERISTICS:
        (A) LENGTH: 852 amino acids
        (B) TYPE: amino acid
        (D) TOPOLOGY: unknown (ii) MOLECULE TYPE: protein
```

(iii) HYPOTHETICAL: NO (iv) ANTI-SENSE: NO (vi) ORIGINAL SOURCE:
    (C) INDIVIDUAL ISOLATE: YKL525, Fig. 50

(xi) SEQUENCE DESCRIPTION: SEQ ID NO:67:

```
Met Phe Lys Ser Lys Thr Ser Thr Leu Ser Tyr Asp Glu Thr Pro Asn
 1               5                  10                  15

Ser Asn Glu Gly Asp Arg Asn Ala Thr Pro Val Asn Pro Lys Glu Lys
                20                  25                  30

Ser Gln Thr Lys His Leu Asn Ile Pro Gly Asp Arg Ser Arg His Ser
                35                  40                  45

Ser Ile Ala Asp Ser Lys Arg Ser Ser Arg Tyr Asp Gly Gly Tyr
50                  55                  60

Ser Ala Asp Ile Ile Pro Ala Gln Leu Arg Phe Ile Asp Asn Ile Asp
65                  70                  75                  80

Tyr Gly Thr Arg Leu Arg Lys Thr Leu His Arg Asn Ser Val Val Ser
                85                  90                  95

Asn Gly Tyr Asn Lys Leu Ser Glu Asn Asp Arg Trp Tyr Phe Asp Leu
                100                 105                 110

Phe Asp Arg Lys Tyr Phe Glu Asn Tyr Leu Glu Glu Pro Thr Tyr Ile
                115                 120                 125

Lys Ile Phe Lys Lys Lys Glu Gly Leu Glu Gln Phe Asp Arg Met Phe
130                 135                 140

Leu Ala Gln Glu Leu Lys Ile Pro Asp Val Tyr Lys Ser Thr Thr Tyr
145                 150                 155                 160

Gln Gly Glu Pro Ala Val Ala Asn Ser Glu Leu Phe Lys Asn Ser Ile
                165                 170                 175

Cys Cys Cys Thr Phe Ser His Asp Gly Lys Tyr Met Val Ile Gly Cys
                180                 185                 190

Lys Asp Gly Ser Leu His Leu Trp Lys Val Ile Asn Ser Pro Val Lys
                195                 200                 205

Arg Ser Glu Met Gly Arg Ser Glu Lys Ser Val Ser Ala Ser Arg Ala
                210                 215                 220

Asn Ser Leu Lys Ile Gln Arg His Leu Ala Ser Ile Ser Ser His Asn
225                 230                 235                 240

Gly Ser Ile Ser Ser Asn Asp Leu Lys Pro Ser Asp Gln Phe Glu Gly
                245                 250                 255

Pro Ser Lys Gln Leu His Leu Tyr Ala Pro Val Phe Tyr Ser Asp Val
                260                 265                 270

Phe Arg Val Phe Met Glu His Ala Leu Asp Ile Leu Asp Ala Asn Trp
                275                 280                 285

Ser Lys Asn Gly Phe Leu Ile Thr Ala Ser Met Asp Lys Thr Ala Lys
                290                 295                 300

Leu Trp His Pro Glu Arg Lys Tyr Ser Leu Lys Thr Phe Val His Pro
305                 310                 315                 320

Asp Phe Val Thr Ser Ala Ile Phe Phe Pro Asn Asp Arg Phe Ile
                325                 330                 335

Ile Thr Gly Cys Leu Asp His Arg Cys Arg Leu Trp Ser Ile Leu Asp
                340                 345                 350

Asn Glu Val Ser Tyr Ala Phe Asp Cys Lys Asp Leu Ile Thr Ser Leu
                355                 360                 365

Thr Leu Ser Pro Pro Gly Gly Glu Tyr Thr Ile Ile Gly Thr Phe Asn
```

-continued

```
            370                 375                 380
Gly Tyr Ile Tyr Val Leu Leu Thr His Gly Leu Lys Phe Val Ser Ser
385                 390                 395                 400

Phe His Val Ser Asp Lys Ser Thr Gln Gly Thr Thr Lys Asn Ser Phe
                405                 410                 415

His Pro Ser Ser Glu Tyr Gly Lys Val Gln His Gly Pro Arg Ile Thr
                420                 425                 430

Gly Leu Gln Cys Phe Phe Ser Lys Val Asp Lys Asn Leu Arg Leu Ile
                435                 440                 445

Val Thr Thr Asn Asp Ser Lys Ile Gln Ile Phe Asp Leu Asn Glu Lys
                450                 455                 460

Lys Pro Leu Glu Leu Phe Lys Gly Phe Gln Ser Gly Ser Ser Arg His
465                 470                 475                 480

Arg Gly Gln Phe Leu Met Met Lys Asn Glu Pro Val Val Phe Thr Gly
                485                 490                 495

Ser Asp Asp His Trp Phe Tyr Thr Trp Lys Met Gln Ser Phe Asn Leu
                500                 505                 510

Ser Ala Glu Met Asn Cys Thr Ala Pro His Arg Lys Lys Arg Leu Ser
                515                 520                 525

Gly Ser Met Ser Leu Lys Gly Leu Leu Arg Ile Val Ser Asn Lys Ser
                530                 535                 540

Thr Asn Asp Glu Cys Leu Thr Glu Thr Ser Asn Gln Ser Ser Ser His
545                 550                 555                 560

Thr Phe Thr Asn Ser Ser Lys Asn Val Leu Gln Thr Gln Thr Val Gly
                565                 570                 575

Ser Gln Ala Ile Lys Asn Asn His Tyr Ile Ser Phe His Ala His Asn
                580                 585                 590

Ser Pro Val Thr Cys Ala Ser Ile Ala Pro Asp Val Ala Ile Lys Asn
                595                 600                 605

Leu Ser Leu Ser Asn Asp Leu Ile Phe Glu Leu Thr Ser Gln Tyr Phe
                610                 615                 620

Lys Glu Met Gly Gln Asn Tyr Ser Glu Ser Lys Glu Thr Cys Asp Asn
625                 630                 635                 640

Lys Pro Asn His Pro Val Thr Glu Thr Gly Gly Phe Ser Ser Asn Leu
                645                 650                 655

Ser Asn Val Val Asn Asn Val Gly Thr Ile Leu Ile Thr Thr Asp Ser
                660                 665                 670

Gln Gly Leu Ile Arg Val Phe Arg Thr Asp Ile Leu Pro Glu Ile Arg
                675                 680                 685

Lys Lys Ile Ile Glu Lys Phe His Glu Tyr Asn Leu Phe His Leu Glu
                690                 695                 700

Ala Ala Gly Lys Ile Asn Asn His Asn Asn Asp Ser Ile Leu Glu Asn
705                 710                 715                 720

Arg Met Asp Glu Arg Ser Ser Thr Glu Asp Asn Glu Phe Ser Thr Thr
                725                 730                 735

Pro Pro Ser Asn Thr His Asn Ser Arg Pro Ser His Asp Phe Cys Glu
                740                 745                 750

Leu His Pro Asn Asn Ser Pro Val Ile Ser Gly Met Pro Ser Arg Ala
                755                 760                 765

Ser Ala Ile Phe Lys Asn Ser Ile Phe Asn Lys Ser Asn Gly Ser Phe
                770                 775                 780

Ile Ser Leu Lys Ser Arg Ser Glu Ser Thr Ser Ser Thr Val Phe Gly
785                 790                 795                 800
```

```
Pro His Asp Ile Pro Arg Val Ser Thr Thr Tyr Pro Lys Leu Lys Cys
                805                 810                 815

Asp Val Cys Asn Gly Ser Asn Phe Glu Cys Ala Ser Lys Asn Pro Ile
            820                 825                 830

Ala Gly Gly Asp Ser Gly Phe Thr Cys Ala Asp Cys Gly Thr Ile Leu
        835                 840                 845

Asn Asn Phe Arg
    850

(2) INFORMATION FOR SEQ ID NO:68:

(i) SEQUENCE CHARACTERISTICS:
        (A) LENGTH: 798 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: yrb 1410 yeast, Fig. 51

(xi) SEQUENCE DESCRIPTION: SEQ ID NO:68:

Met Ser Gln Lys Gln Ser Thr Asn Gln Asn Gln Asn Gly Thr His Gln
1               5                   10                  15

Pro Gln Pro Val Lys Asn Gln Arg Thr Asn Asn Ala Ala Gly Ala Asn
                20                  25                  30

Ser Gly Gln Gln Pro Gln Gln Ser Gln Gly Gln Ser Gln Gln Gln
            35                  40                  45

Gly Arg Ser Asn Gly Pro Phe Ser Ala Ser Asp Leu Asn Arg Ile Val
    50                  55                  60

Leu Glu Tyr Leu Asn Lys Lys Gly Tyr His Arg Thr Glu Ala Met Leu
65                  70                  75                  80

Arg Ala Glu Ser Gly Arg Thr Leu Thr Pro Gln Asn Lys Gln Ser Pro
                85                  90                  95

Ala Asn Thr Lys Thr Gly Lys Phe Pro Glu Gln Ser Ser Ile Pro Pro
            100                 105                 110

Asn Pro Gly Lys Thr Ala Lys Pro Ile Ser Asn Pro Thr Asn Leu Ser
        115                 120                 125

Ser Lys Arg Asp Ala Glu Gly Gly Ile Val Ser Ser Gly Arg Leu Glu
    130                 135                 140

Gly Leu Asn Ala Pro Glu Asn Tyr Ile Arg Ala Tyr Ser Met Leu Lys
145                 150                 155                 160

Asn Trp Val Asp Ser Ser Leu Glu Ile Tyr Lys Pro Glu Leu Ser Tyr
                165                 170                 175

Ile Met Tyr Pro Ile Phe Ile Tyr Leu Phe Leu Asn Leu Val Ala Lys
            180                 185                 190

Asn Pro Val Tyr Ala Arg Arg Phe Phe Asp Arg Phe Ser Pro Asp Phe
        195                 200                 205

Lys Asp Phe His Gly Ser Glu Ile Asn Arg Leu Phe Ser Val Asn Ser
    210                 215                 220

Ile Asp His Ile Lys Glu Asn Glu Val Ala Ser Ala Phe Gln Ser His
225                 230                 235                 240

Lys Tyr Arg Ile Thr Met Ser Lys Thr Thr Leu Asn Leu Leu Leu Tyr
                245                 250                 255
```

```
Phe Leu Asn Glu Asn Glu Ser Ile Gly Gly Ser Leu Ile Ile Ser Val
                260                 265                 270
Ile Asn Gln His Leu Asp Pro Asn Ile Val Glu Ser Val Thr Ala Arg
                275                 280                 285
Glu Lys Leu Ala Asp Gly Ile Lys Val Leu Ser Asp Ser Glu Asn Gly
                290                 295                 300
Asn Gly Lys Gln Asn Leu Glu Met Asn Ser Val Pro Val Lys Leu Gly
305                 310                 315                 320
Pro Phe Pro Lys Asp Glu Phe Val Lys Glu Ile Glu Thr Glu Leu
                325                 330                 335
Lys Ile Lys Asp Asp Gln Glu Lys Gln Leu Asn Gln Gln Thr Ala Gly
                340                 345                 350
Asp Asn Tyr Ser Gly Ala Asn Asn Arg Thr Leu Leu Gln Glu Tyr Lys
                355                 360                 365
Ala Met Asn Asn Glu Lys Phe Lys Asp Asn Thr Gly Asp Asp Asp Lys
                370                 375                 380
Asp Lys Ile Lys Asp Lys Ile Ala Lys Asp Glu Glu Lys Lys Glu Ser
385                 390                 395                 400
Glu Leu Lys Val Asp Gly Glu Lys Lys Asp Ser Asn Leu Ser Ser Pro
                405                 410                 415
Ala Arg Asp Ile Leu Pro Leu Pro Pro Lys Thr Ala Leu Asp Leu Lys
                420                 425                 430
Leu Glu Ile Gln Lys Val Lys Glu Ser Arg Asp Ala Ile Lys Leu Asp
                435                 440                 445
Asn Leu Gln Leu Ala Leu Pro Ser Val Cys Met Tyr Thr Phe Gln Asn
                450                 455                 460
Thr Asn Lys Asp Met Ser Cys Leu Asp Phe Ser Asp Cys Arg Ile
465                 470                 475                 480
Ala Ala Ala Gly Phe Gln Asp Ser Tyr Ile Lys Ile Trp Ser Leu Asp
                485                 490                 495
Gly Ser Ser Leu Asn Asn Pro Asn Ile Ala Leu Asn Asn Asn Asp Lys
                500                 505                 510
Asp Glu Asp Pro Thr Cys Lys Thr Leu Val Gly His Ser Gly Thr Val
                515                 520                 525
Tyr Ser Thr Ser Phe Ser Pro Asp Asn Lys Tyr Leu Leu Ser Gly Ser
                530                 535                 540
Glu Asp Lys Thr Val Arg Leu Trp Ser Met Asp Thr His Thr Ala Leu
545                 550                 555                 560
Val Ser Tyr Lys Gly His Asn His Pro Val Trp Asp Val Ser Phe Ser
                565                 570                 575
Pro Leu Gly His Tyr Phe Ala Thr Ala Ser His Asp Gln Thr Ala Arg
                580                 585                 590
Leu Trp Ser Cys Asp His Ile Tyr Pro Leu Arg Ile Phe Ala Gly His
                595                 600                 605
Leu Asn Asp Val Asp Cys Val Ser Phe His Pro Asn Gly Cys Tyr Val
                610                 615                 620
Phe Thr Gly Ser Ser Asp Lys Thr Cys Arg Met Trp Asp Val Ser Thr
625                 630                 635                 640
Gly Asp Ser Val Arg Leu Phe Leu Gly His Thr Ala Pro Val Ile Ser
                645                 650                 655
Ile Ala Val Cys Pro Asp Gly Arg Trp Leu Ser Thr Gly Ser Glu Asp
                660                 665                 670
```

```
Gly Ile Ile Asn Val Trp Asp Ile Gly Thr Gly Lys Arg Leu Lys Gln
            675                 680                 685

Met Arg Gly His Gly Lys Asn Ala Ile Tyr Ser Leu Ser Tyr Ser Lys
        690                 695                 700

Glu Gly Asn Val Leu Ile Ser Gly Gly Ala Asp His Thr Val Arg Val
705                 710                 715                 720

Trp Asp Leu Lys Lys Ala Thr Thr Glu Pro Ser Ala Glu Pro Asp Glu
                725                 730                 735

Pro Phe Ile Gly Tyr Leu Gly Asp Val Thr Ala Ser Ile Asn Gln Asp
            740                 745                 750

Ile Lys Glu Tyr Gly Arg Arg Thr Val Ile Pro Thr Ser Asp Leu
            755                 760                 765

Val Ala Ser Phe Tyr Thr Lys Lys Thr Pro Val Phe Lys Val Lys Phe
    770                 775                 780

Ser Arg Ser Asn Leu Ala Leu Ala Gly Gly Ala Phe Arg Pro
785                 790                 795
```

(2) INFORMATION FOR SEQ ID NO:69:

(i) SEQUENCE CHARACTERISTICS:
      (A) LENGTH: 32 amino acids
      (B) TYPE: amino acid
      (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: RACK1 protein rI, Fig. 1C (xi) SEQUENCE DESCRIPTION: SEQ ID NO:69:

```
Gly His Asn Gly Trp Val Thr Gln Ile Ala Thr Thr Pro Gln Phe Pro
1               5                   10                  15

Asp Met Ile Leu Ser Ala Ser Arg Asp Lys Thr Ile Ile Met Trp Lys
            20                  25                  30
```

(2) INFORMATION FOR SEQ ID NO:70:

(i) SEQUENCE CHARACTERISTICS:
      (A) LENGTH: 31 amino acids
      (B) TYPE: amino acid
      (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: RACK1 protein rII, Fig. 1C (xi) SEQUENCE DESCRIPTION: SEQ ID NO:70:

```
Gly His Ser His Phe Val Ser Asp Val Val Ile Ser Ser Asp Gly Gln
1               5                   10                  15

Phe Ala Leu Ser Gly Ser Trp Asp Gly Thr Leu Arg Leu Trp Asp
            20                  25                  30
```

(2) INFORMATION FOR SEQ ID NO:71:

(i) SEQUENCE CHARACTERISTICS:
      (A) LENGTH: 31 amino acids (B) TYPE: amino acid
              (D) TOPOLOGY: unknown (ii) MOLECULE TYPE: peptide (iii) HYPOTHETICAL: NO (iv) ANTI-SENSE: NO (vi) ORIGINAL SOURCE:
              (C) INDIVIDUAL ISOLATE: RACK1 protein rIII, Fig. 1C (xi) SEQUENCE DESCRIPTION: SEQ ID NO:71:

Gly His Thr Lys Asp Val Leu Ser Val Ala Phe Ser Ser Asp Asn Arg
1               5                   10                  15

Gln Ile Val Ser Gly Ser Arg Asp Lys Thr Ile Lys Leu Trp Asn
            20                  25                  30

(2) INFORMATION FOR SEQ ID NO:72:

(i) SEQUENCE CHARACTERISTICS:
              (A) LENGTH: 33 amino acids
              (B) TYPE: amino acid
              (D) TOPOLOGY: unknown (ii) MOLECULE TYPE: peptide (iii) HYPOTHETICAL: NO (iv) ANTI-SENSE: NO (vi) ORIGINAL SOURCE:
              (C) INDIVIDUAL ISOLATE: RACK1 protein rIV, Fig. 1C (xi) SEQUENCE DESCRIPTION: SEQ ID NO:72:

Ser His Ser Glu Trp Val Ser Cys Val Arg Phe Ser Pro Asn Ser Ser
1               5                   10                  15

Asn Pro Ile Ile Val Ser Cys Gly Trp Asp Lys Leu Val Lys Val Trp
            20                  25                  30

Asn (2) INFORMATION FOR SEQ ID NO:73:

(i) SEQUENCE CHARACTERISTICS:
              (A) LENGTH: 31 amino acids
              (B) TYPE: amino acid
              (D) TOPOLOGY: unknown (ii) MOLECULE TYPE: peptide (iii) HYPOTHETICAL: NO (iv) ANTI-SENSE: NO (vi) ORIGINAL SOURCE:
              (C) INDIVIDUAL ISOLATE: RACK1 protein rV, Fig. 1C (xi) SEQUENCE DESCRIPTION: SEQ ID NO:73:

Gly His Thr Gly Tyr Leu Asn Thr Val Thr Val Ser Pro Asp Gly Ser
1               5                   10                  15

Leu Cys Ala Ser Gly Gly Lys Asp Gly Gln Ala Met Leu Trp Asp
            20                  25                  30

(2) INFORMATION FOR SEQ ID NO:74:

(i) SEQUENCE CHARACTERISTICS:
              (A) LENGTH: 31 amino acids
              (B) TYPE: amino acid
              (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: RACK1 protein rVI, Fig. 1C (xi) SEQUENCE DESCRIPTION: SEQ ID NO:74:

Leu Asp Gly Gly Asp Ile Ile Asn Ala Leu Cys Phe Ser Pro Asn Arg
1               5                   10                  15

Tyr Trp Leu Cys Ala Ala Thr Gly Pro Ser Ile Lys Ile Trp Asp
            20                  25                  30

(2) INFORMATION FOR SEQ ID NO:75:

(i) SEQUENCE CHARACTERISTICS:
            (A) LENGTH: 33 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: RACK1 protein rVII, Fig. 1C (xi) SEQUENCE DESCRIPTION: SEQ ID NO:75:

Ser Lys Ala Glu Pro Pro Gln Cys Thr Ser Leu Ala Trp Ser Ala Asp
1               5                   10                  15

Gly Gln Thr Leu Phe Ala Gly Tyr Thr Asp Asn Leu Val Arg Val Trp
            20                  25                  30

Gln (2) INFORMATION FOR SEQ ID NO:76:

(i) SEQUENCE CHARACTERISTICS:
            (A) LENGTH: 32 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: Human 55 kDa protein rI, Fig. 11

(xi) SEQUENCE DESCRIPTION: SEQ ID NO:76:

Gly His Thr Asp Ala Val Leu Asp Leu Ser Trp Asn Lys Leu Ile Arg
1               5                   10                  15

Asn Val Leu Ala Ser Ala Ser Ala Asp Asn Thr Val Ile Leu Trp Asp
            20                  25                  30

(2) INFORMATION FOR SEQ ID NO:77:

(i) SEQUENCE CHARACTERISTICS:
            (A) LENGTH: 32 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: Human 55 kDa protein rII, Fig. 11

(xi) SEQUENCE DESCRIPTION: SEQ ID NO:77:

Ala His Asn Asp Glu Ile Ser Gly Leu Asp Leu Ser Ser Gln Ile Lys
1               5                   10                  15
Gly Cys Leu Val Thr Ala Ser Ala Asp Lys Tyr Val Lys Ile Trp Asp
            20                  25                  30

(2) INFORMATION FOR SEQ ID NO:78:

(i) SEQUENCE CHARACTERISTICS:
             (A) LENGTH: 37 amino acids
             (B) TYPE: amino acid
             (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: Human 55 kDa protein rIII, Fig. 11

(xi) SEQUENCE DESCRIPTION: SEQ ID NO:78:

Val His Ser Arg Asp Met Lys Met Gly Val Leu Phe Cys Ser Ser Cys
1               5                   10                  15
Cys Pro Asp Leu Pro Phe Ile Tyr Ala Phe Gly Gly Gln Lys Glu Gly
            20                  25                  30
Leu Arg Val Trp Asp
        35

(2) INFORMATION FOR SEQ ID NO:79:

(i) SEQUENCE CHARACTERISTICS:
             (A) LENGTH: 31 amino acids
             (B) TYPE: amino acid
             (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: AAC-RICH protein rI, Fig. 12

(xi) SEQUENCE DESCRIPTION: SEQ ID NO:79:

Gly Asn Lys Lys Lys Ser Thr Ser Val Ala Trp Asn Ala Asn Gly Thr
1               5                   10                  15
Lys Ile Ala Ser Ser Gly Ser Asp Gly Ile Val Arg Val Trp Asn
            20                  25                  30

(2) INFORMATION FOR SEQ ID NO:80:

(i) SEQUENCE CHARACTERISTICS:
             (A) LENGTH: 32 amino acids
             (B) TYPE: amino acid
             (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: AAC-RICH protein rII, Fig. 12

(xi) SEQUENCE DESCRIPTION: SEQ ID NO:80:

```
Gly His Asp Gly Ser Ile Glu Lys Ile Ser Trp Ser Pro Lys Asn Asn
1               5                   10                  15

Asp Leu Leu Ala Ser Ala Gly Thr Asp Lys Val Ile Lys Ile Trp Asp
            20                  25                  30
```

(2) INFORMATION FOR SEQ ID NO:81:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: AAC-RICH protein rIII, Fig. 12

(xi) SEQUENCE DESCRIPTION: SEQ ID NO:81:

```
Asp His Leu Ala Leu Ile Asp Leu Pro Thr Ile Lys Thr Leu Lys Ile
1               5                   10                  15

Tyr Lys Phe Asn Gly Glu Glu Leu Asn Gln Val Gly Trp Asp
            20                  25                  30
```

(2) INFORMATION FOR SEQ ID NO:82:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: AAC-RICH protein rIV, Fig. 12

(xi) SEQUENCE DESCRIPTION: SEQ ID NO:82:

```
Gly His Thr Ala Ser Ile Tyr Cys Met Glu Phe Asp Pro Thr Gly Lys
1               5                   10                  15

Tyr Leu Ala Ala Gly Ser Ala Asp Ser Ile Val Ser Leu Trp Asp
            20                  25                  30
```

(2) INFORMATION FOR SEQ ID NO:83:

(i) SEQUENCE CHARACTERISTICS:
        (A) LENGTH: 34 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: BETA TRCP rI, Fig. 13

(xi) SEQUENCE DESCRIPTION: SEQ ID NO:83:

Ile His Cys Arg Ser Glu Thr Ser Lys Gly Val Tyr Cys Leu Gln Tyr
1               5                   10                  15

Asp Asp Gln Lys Ile Val Ser Gly Leu Arg Asp Asn Thr Ile Lys Ile
            20                  25                  30

Trp Asp (2) INFORMATION FOR SEQ ID NO:84:

(i) SEQUENCE CHARACTERISTICS:
        (A) LENGTH: 28 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: BETA TRCP rII, Fig. 13

(xi) SEQUENCE DESCRIPTION: SEQ ID NO:84:

Gly His Thr Gly Ser Val Leu Cys Leu Gln Tyr Asp Glu Arg Val Ile
1               5                   10                  15

Ile Thr Gly Ser Asp Ser Thr Val Arg Val Trp Asp
            20                  25

(2) INFORMATION FOR SEQ ID NO:85:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: BETA TRCP rIII, Fig. 13

(xi) SEQUENCE DESCRIPTION: SEQ ID NO:85:

Ile His His Cys Glu Ala Val Leu His Leu Arg Phe Asn Asn Gly Met
1               5                   10                  15

Met Val Thr Cys Ser Lys Asp Arg Ser Ile Ala Val Trp Asp
            20                  25                  30

(2) INFORMATION FOR SEQ ID NO:86:

(i) SEQUENCE CHARACTERISTICS:
        (A) LENGTH: 29 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: BETA TRCP rIV, Fig. 13

(xi) SEQUENCE DESCRIPTION: SEQ ID NO:86:

Gly His Arg Ala Ala Val Asn Val Val Asp Phe Asp Asp Lys Tyr Ile
1               5                   10                  15
Val Ser Ala Ser Gly Asp Arg Thr Ile Lys Val Trp Asn
                20                  25

(2) INFORMATION FOR SEQ ID NO:87:

(i) SEQUENCE CHARACTERISTICS:
        (A) LENGTH: 29 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: BETA TRCP rV, Fig. 13

(xi) SEQUENCE DESCRIPTION: SEQ ID NO:87:

Gly His Lys Arg Gly Ile Ala Cys Leu Gln Tyr Arg Asp Arg Leu Val
1               5                   10                  15
Val Ser Gly Ser Ser Asp Asn Thr Ile Arg Leu Trp Asp
                20                  25

(2) INFORMATION FOR SEQ ID NO:88:

(i) SEQUENCE CHARACTERISTICS:
        (A) LENGTH: 29 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: BETA TRCP rVI, Fig. 13

(xi) SEQUENCE DESCRIPTION: SEQ ID NO:88:

Gly His Glu Glu Leu Val Arg Cys Ile Arg Phe Asp Asn Lys Arg Ile
1               5                   10                  15
Val Ser Gly Ala Tyr Asp Gly Lys Ile Lys Val Trp Asp
                20                  25

(2) INFORMATION FOR SEQ ID NO:89:

(i) SEQUENCE CHARACTERISTICS:
        (A) LENGTH: 29 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: BETA TRCP rVII, Fig. 13

(xi) SEQUENCE DESCRIPTION: SEQ ID NO:89:

Glu His Ser Gly Arg Val Phe Arg Leu Gln Phe Asp Glu Phe Gln Ile

```
                 1               5              10              15
Val Ser Ser Ser His Asp Asp Thr Ile Leu Ile Trp Asp
                          20              25

(2) INFORMATION FOR SEQ ID NO:90:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: beta-prime-cop rI, Fig. 14

(xi) SEQUENCE DESCRIPTION: SEQ ID NO:90:

Ala His Ser Asp Tyr Ile Arg Cys Ile Ala Val His Pro Thr Gln Pro
1               5                  10                  15
Phe Ile Leu Thr Ser Ser Asp Asp Met Leu Ile Lys Leu Trp Asp
                20                  25                  30

(2) INFORMATION FOR SEQ ID NO:91:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: beta-prime-cop rII, Fig. 14

(xi) SEQUENCE DESCRIPTION: SEQ ID NO:91:

Gly His Thr His Tyr Val Met Gln Ile Val Ile Asn Pro Lys Asp Asn
1               5                  10                  15
Asn Gln Phe Ala Ser Ala Ser Leu Asp Arg Thr Ile Lys Val Trp Gln
                20                  25                  30

(2) INFORMATION FOR SEQ ID NO:92:

(i) SEQUENCE CHARACTERISTICS:
        (A) LENGTH: 33 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: beta-prime-cop rIII, Fig. 14

(xi) SEQUENCE DESCRIPTION: SEQ ID NO:92:

Gly His Glu Lys Gly Val Asn Cys Ile Asp Tyr Tyr Ser Gly Gly Asp
1               5                  10                  15
Lys Pro Tyr Leu Ile Ser Gly Ala Asp Asp Arg Leu Val Lys Ile Trp
                20                  25                  30
```

Asp (2) INFORMATION FOR SEQ ID NO:93:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: beta-prime-cop rIV, Fig. 14

(xi) SEQUENCE DESCRIPTION: SEQ ID NO:93:

```
Gly His Ala Gln Asn Val Ser Cys Ala Ser Phe His Pro Glu Leu Pro
1               5                   10                  15
Ile Ile Ile Thr Gly Ser Glu Asp Gly Thr Val Arg Ile Trp His
            20                  25                  30
```

(2) INFORMATION FOR SEQ ID NO:94:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: CDC4 / CDC20 protein rI, Fig. 15

(xi) SEQUENCE DESCRIPTION: SEQ ID NO:94:

```
Gly His Met Thr Ser Val Ile Thr Cys Leu Gln Phe Glu Asp Asn Tyr
1               5                   10                  15
Val Ile Thr Gly Ala Asp Asp Lys Met Ile Arg Val Tyr Asp
            20                  25                  30
```

(2) INFORMATION FOR SEQ ID NO:95:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: CDC4 / CDC20 protein rII, Fig. 15

(xi) SEQUENCE DESCRIPTION: SEQ ID NO:95:

```
Gly His Asp Gly Gly Val Trp Ala Leu Lys Tyr Ala His Gly Gly Ile
1               5                   10                  15
Leu Val Ser Gly Ser Thr Asp Arg Thr Val Arg Val Trp Asp
            20                  25                  30
```

(2) INFORMATION FOR SEQ ID NO:96:

(i) SEQUENCE CHARACTERISTICS:
        (A) LENGTH: 33 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: CDC4 / CDC20 protein rIII, Fig. 15

(xi) SEQUENCE DESCRIPTION: SEQ ID NO:96:

```
Gly His Asn Ser Thr Val Arg Cys Leu Asp Ile Val Glu Tyr Lys Asn
1               5                   10                  15
Ile Lys Tyr Ile Val Thr Gly Ser Arg Asp Asn Thr Leu His Val Trp
            20                  25                  30
Lys
```

(2) INFORMATION FOR SEQ ID NO:97:

(i) SEQUENCE CHARACTERISTICS:
        (A) LENGTH: 29 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: CDC4 / CDC20 protein rIV, Fig. 15

(xi) SEQUENCE DESCRIPTION: SEQ ID NO:97:

```
Gly His Met Ala Ser Val Arg Thr Val Ser Gly His Gly Asn Ile Val
1               5                   10                  15
Val Ser Gly Ser Tyr Asp Asn Thr Leu Ile Val Trp Asp
            20                  25
```

(2) INFORMATION FOR SEQ ID NO:98:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: CDC4 / CDC20 protein rV, Fig. 15

(xi) SEQUENCE DESCRIPTION: SEQ ID NO:98:

```
Gly His Thr Asp Arg Ile Tyr Ser Thr Ile Tyr Asp His Glu Arg Lys
1               5                   10                  15
Arg Cys Ile Ser Ala Ser Met Asp Thr Thr Ile Arg Ile Trp Asp
            20                  25                  30
```

(2) INFORMATION FOR SEQ ID NO:99:

```
        (i) SEQUENCE CHARACTERISTICS:
            (A) LENGTH: 29 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: CDC4 / CDC20 protein rVI, Fig. 15

(xi) SEQUENCE DESCRIPTION: SEQ ID NO:99:

Gly His Thr Ala Leu Val Gly Leu Leu Arg Leu Ser Asp Lys Phe Leu
1               5                  10                  15

Val Ser Ala Ala Ala Asp Gly Ser Ile Arg Gly Trp Asp
                20                  25

(2) INFORMATION FOR SEQ ID NO:100:

(i) SEQUENCE CHARACTERISTICS:
            (A) LENGTH: 33 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: GBLP-CHLAMIDOMONAS HOMOLOG rI, Fig. 16

(xi) SEQUENCE DESCRIPTION: SEQ ID NO:100:

Gly His Thr Asn Trp Val Thr Ala Ile Ala Thr Pro Leu Asp Pro Ser
1               5                  10                  15

Ser Asn Thr Leu Leu Ser Ala Ser Arg Asp Lys Ser Val Leu Val Trp
                20                  25                  30

Glu (2) INFORMATION FOR SEQ ID NO:101:

(i) SEQUENCE CHARACTERISTICS:
            (A) LENGTH: 31 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: GBLP -CHLAMIDOMONAS HOMOLOG rII, Fig.
                16

(xi) SEQUENCE DESCRIPTION: SEQ ID NO:101:

Gly His Ser His Phe Val Gln Asp Val Val Ile Ser Ser Asp Gly Gln
1               5                  10                  15

Phe Cys Leu Thr Gly Ser Trp Asp Gly Thr Leu Arg Leu Trp Asp
                20                  25                  30

(2) INFORMATION FOR SEQ ID NO:102:

(i) SEQUENCE CHARACTERISTICS:
```

(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: GBLP -CHLAMIDOMONAS HOMOLOG rIII, Fig. 16

(xi) SEQUENCE DESCRIPTION: SEQ ID NO:102:

Gly His Thr Lys Asp Val Leu Ser Val Ala Phe Ser Val Asp Asn Arg
1               5                   10                  15

Gln Ile Val Ser Gly Ser Arg Asp Lys Thr Ile Lys Leu Trp Asn
            20                  25                  30

(2) INFORMATION FOR SEQ ID NO:103:

(i) SEQUENCE CHARACTERISTICS:
(A) LENGTH: 33 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: GBLP -CHLAMIDOMONAS HOMOLOG rIV, Fig. 16

(xi) SEQUENCE DESCRIPTION: SEQ ID NO:103:

Gly His Thr Glu Trp Val Ser Cys Val Arg Phe Ser Pro Met Thr Thr
1               5                   10                  15

Asn Pro Ile Ile Val Ser Gly Gly Trp Asp Lys Met Val Lys Val Trp
            20                  25                  30

Asn (2) INFORMATION FOR SEQ ID NO:104:

(i) SEQUENCE CHARACTERISTICS:
(A) LENGTH: 31 amino acids
(B) TYPE: amino acid
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: GBLP -CHLAMIDOMONAS HOMOLOG rV, Fig. 16

(xi) SEQUENCE DESCRIPTION: SEQ ID NO:104:

Gly His His Gly Tyr Val Asn Thr Val Thr Val Ser Pro Asp Gly Ser
1               5                   10                  15

Leu Cys Ala Ser Gly Gly Lys Asp Gly Ile Ala Met Leu Trp Asp
            20                  25                  30

(2) INFORMATION FOR SEQ ID NO:105:

```
        (i) SEQUENCE CHARACTERISTICS:
            (A) LENGTH: 32 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: GBLP -CHLAMIDOMONAS HOMOLOG rVI, Fig.
                16

(xi) SEQUENCE DESCRIPTION: SEQ ID NO:105:

Ile His Cys Leu Cys Phe Ser Pro Asn Arg Tyr Trp Leu Cys Ala Ala
1               5                  10                  15

Thr Gln Ser Ser Ile Lys Ile Trp Asp Leu Glu Ser Lys Ser Ile Val
            20                  25                  30

(2) INFORMATION FOR SEQ ID NO:106:

(i) SEQUENCE CHARACTERISTICS:
            (A) LENGTH: 33 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: GBLP -CHLAMIDOMONAS HOMOLOG rVII, Fig.
                16

(xi) SEQUENCE DESCRIPTION: SEQ ID NO:106:

Lys Lys Ala Gln Val Pro Tyr Cys Val Ser Leu Ala Trp Ser Ala Asp
1               5                  10                  15

Gly Ser Thr Leu Tyr Ser Gly Tyr Thr Asp Gly Gln Ile Arg Val Trp
            20                  25                  30

Ala (2) INFORMATION FOR SEQ ID NO:107:

(i) SEQUENCE CHARACTERISTICS:
            (A) LENGTH: 33 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: cop-1 protein rI, Fig. 17

(xi) SEQUENCE DESCRIPTION: SEQ ID NO:107:

Met Ser Thr Arg Ser Lys Leu Ser Cys Leu Ser Trp Asn Lys His Glu
1               5                  10                  15

Lys Asn His Ile Ala Ser Ser Asp Tyr Glu Gly Ile Val Thr Val Trp
            20                  25                  30

Asp
```

(2) INFORMATION FOR SEQ ID NO:108:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: cop-1 protein rII, Fig. 17

(xi) SEQUENCE DESCRIPTION: SEQ ID NO:108:

```
Glu Lys Arg Ala Trp Ser Val Asp Phe Ser Arg Thr Glu Pro Ser Met
  1               5                  10                  15
Leu Val Ser Gly Ser Asp Asp Cys Lys Val Lys Val Trp Cys
                 20                  25                  30
```

(2) INFORMATION FOR SEQ ID NO:109:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: cop-1 protein rIII, Fig. 17

(xi) SEQUENCE DESCRIPTION: SEQ ID NO:109:

```
Gly His Lys Lys Ala Val Ser Tyr Met Lys Phe Leu Ser Asn Asn Glu
  1               5                  10                  15
Leu Ala Ser Ala Ser Thr Asp Ser Thr Leu Arg Leu Trp Asp
                 20                  25                  30
```

(2) INFORMATION FOR SEQ ID NO:110:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Coronin (p55) rI, Fig. 19

(xi) SEQUENCE DESCRIPTION: SEQ ID NO:110:

```
Gly His Lys Ser Ala Val Leu Asp Ile Ala Phe His Pro Phe Asn Glu
  1               5                  10                  15
Asn Leu Val Gly Ser Val Ser Glu Asp Cys Asn Ile Cys Ile Trp Gly
                 20                  25                  30
```

(2) INFORMATION FOR SEQ ID NO:111:

(i) SEQUENCE CHARACTERISTICS:
        (A) LENGTH: 32 amino acids (B) TYPE: amino acid
                (D) TOPOLOGY: unknown (ii) MOLECULE TYPE: peptide (iii) HYPOTHETICAL: NO (iv) ANTI-SENSE: NO (vi) ORIGINAL SOURCE:
                (C) INDIVIDUAL ISOLATE: Coronin (p55) rII, Fig. 19

(xi) SEQUENCE DESCRIPTION: SEQ ID NO:111:

Gly His Lys Arg Lys Val Gly Thr Ile Ser Phe Gly Pro Val Ala Asp
1               5                   10                  15

Asn Val Ala Val Thr Ser Ser Gly Asp Phe Leu Val Lys Thr Trp Asp
            20                  25                  30

(2) INFORMATION FOR SEQ ID NO:112:

(i) SEQUENCE CHARACTERISTICS:
                (A) LENGTH: 31 amino acids
                (B) TYPE: amino acid
                (D) TOPOLOGY: unknown (ii) MOLECULE TYPE: peptide (iii) HYPOTHETICAL: NO (iv) ANTI-SENSE: NO (vi) ORIGINAL SOURCE:
                (C) INDIVIDUAL ISOLATE: Coronin (p55) rIII, Fig. 19

(xi) SEQUENCE DESCRIPTION: SEQ ID NO:112:

Gly His Ser Asp Met Ile Thr Ser Cys Glu Trp Asn His Asn Gly Ser
1               5                   10                  15

Gln Ile Val Thr Thr Cys Lys Asp Lys Lys Ala Arg Val Phe Asp
            20                  25                  30

(2) INFORMATION FOR SEQ ID NO:113:

(i) SEQUENCE CHARACTERISTICS:
                (A) LENGTH: 38 amino acids
                (B) TYPE: amino acid
                (D) TOPOLOGY: unknown (ii) MOLECULE TYPE: peptide (iii) HYPOTHETICAL: NO (iv) ANTI-SENSE: NO (vi) ORIGINAL SOURCE:
                (C) INDIVIDUAL ISOLATE: CORO PROTEIN rI, Fig. 18

(xi) SEQUENCE DESCRIPTION: SEQ ID NO:113:

Arg His Val Phe Ala Ala Gln Pro Lys Lys Glu Glu Cys Tyr Gln Asn
1               5                   10                  15

Leu Lys Thr Lys Ser Ala Val Trp Asp Ser Asn Tyr Val Ala Ala Asn
            20                  25                  30

Thr Arg Tyr Ile Trp Asp
            35

(2) INFORMATION FOR SEQ ID NO:114:

(i) SEQUENCE CHARACTERISTICS:
                (A) LENGTH: 32 amino acids
                (B) TYPE: amino acid (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: CORO PROTEIN rII, Fig. 18

(xi) SEQUENCE DESCRIPTION: SEQ ID NO:114:

Gly His Lys Ser Ala Val Leu Asp Ile Ala Phe His Pro Phe Asn Glu
1               5                   10                  15

Asn Leu Val Gly Ser Val Ser Glu Asp Cys Asn Ile Cys Ile Trp Gly
            20                  25                  30

(2) INFORMATION FOR SEQ ID NO:115:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: CORO PROTEIN rIII, Fig. 18

(xi) SEQUENCE DESCRIPTION: SEQ ID NO:115:

Gly His Lys Arg Lys Val Gly Thr Ile Ser Phe Gly Pro Val Ala Asp
1               5                   10                  15

Asn Val Ala Val Thr Ser Ser Gly Asp Phe Leu Val Lys Thr Trp Asp
            20                  25                  30

(2) INFORMATION FOR SEQ ID NO:116:

(i) SEQUENCE CHARACTERISTICS:
        (A) LENGTH: 29 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: CORO PROTEIN rIV, Fig. 18

(xi) SEQUENCE DESCRIPTION: SEQ ID NO:116:

Gly His Ser Asp Met Ile Thr Ser Cys Glu His Asn Gly Ser Gln Ile
1               5                   10                  15

Val Thr Thr Cys Lys Asp Lys Lys Ala Arg Val Phe Asp
            20                  25

(2) INFORMATION FOR SEQ ID NO:117:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: CSTF 50kDa rI, Fig. 20

(xi) SEQUENCE DESCRIPTION: SEQ ID NO:117:

```
Asp His Val Asp Glu Val Thr Cys Leu Ala Phe His Pro Thr Glu Gln
1               5                   10                  15
Ile Leu Ala Ser Gly Ser Arg Asp Tyr Thr Leu Lys Leu Phe Asp
            20                  25                  30
```

(2) INFORMATION FOR SEQ ID NO:118:

(i) SEQUENCE CHARACTERISTICS:
    (A) LENGTH: 31 amino acids
    (B) TYPE: amino acid
    (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: CSTF 50kDa rII, Fig. 20

(xi) SEQUENCE DESCRIPTION: SEQ ID NO:118:

```
Asp His Val Asp Glu Val Thr Cys Leu Ala Phe His Pro Thr Glu Gln
1               5                   10                  15
Ile Leu Ala Ser Gly Ser Arg Asp Tyr Thr Leu Lys Leu Phe Asp
            20                  25                  30
```

(2) INFORMATION FOR SEQ ID NO:119:

(i) SEQUENCE CHARACTERISTICS:
    (A) LENGTH: 32 amino acids
    (B) TYPE: amino acid
    (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: CSTF 50kDa rIII, Fig. 20

(xi) SEQUENCE DESCRIPTION: SEQ ID NO:119:

```
Ala His Asp Gly Ala Glu Val Cys Ser Ala Ile Phe Ser Lys Asn Ser
1               5                   10                  15
Lys Tyr Ile Leu Ser Ser Gly Lys Asp Ser Val Ala Lys Leu Trp Glu
            20                  25                  30
```

(2) INFORMATION FOR SEQ ID NO:120:

(i) SEQUENCE CHARACTERISTICS:
    (A) LENGTH: 29 amino acids
    (B) TYPE: amino acid
    (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: CSTF 50kDa rIV, Fig. 20

(xi) SEQUENCE DESCRIPTION: SEQ ID NO:120:

Val His Arg Thr Gln Ala Val Phe Asn His Thr Glu Asp Tyr Val Leu
1               5                   10                  15

Leu Pro Asp Glu Arg Thr Ile Ser Leu Cys Cys Trp Asp
            20                  25

(2) INFORMATION FOR SEQ ID NO:121:

(i) SEQUENCE CHARACTERISTICS:
         (A) LENGTH: 31 amino acids
         (B) TYPE: amino acid
         (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: CSTF 50kDa rV, Fig. 20

(xi) SEQUENCE DESCRIPTION: SEQ ID NO:121:

Gly His Asn Asn Ile Val Arg Cys Ile Val His Ser Pro Thr Asn Pro
1               5                   10                  15

Gly Phe Met Thr Cys Ser Asp Asp Phe Arg Ala Arg Phe Trp Tyr
            20                  25                  30

(2) INFORMATION FOR SEQ ID NO:122:

(i) SEQUENCE CHARACTERISTICS:
         (A) LENGTH: 31 amino acids
         (B) TYPE: amino acid
         (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: G- BETA DROSOPH rI, Fig. 23

(xi) SEQUENCE DESCRIPTION: SEQ ID NO:122:

Gly His Leu Ala Lys Ile Tyr Ala Met His Trp Gly Asn Asp Ser Arg
1               5                   10                  15

Asn Leu Val Ser Ala Ser Gln Asp Gly Lys Leu Ile Val Trp Asp
            20                  25                  30

(2) INFORMATION FOR SEQ ID NO:123:

(i) SEQUENCE CHARACTERISTICS:
         (A) LENGTH: 30 amino acids
         (B) TYPE: amino acid
         (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: G- BETA DROSOPH rII, Fig. 23

(xi) SEQUENCE DESCRIPTION: SEQ ID NO:123:

```
Gly His Gly Gly Tyr Leu Ser Cys Cys Arg Phe Leu Asp Asp Asn Gln
1               5                   10                  15

Ile Val Thr Ser Ser Gly Asp Met Ser Cys Gly Leu Trp Asp
                20                  25                  30
```

(2) INFORMATION FOR SEQ ID NO:124:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G- BETA DROSOPH rIII, Fig. 23

(xi) SEQUENCE DESCRIPTION: SEQ ID NO:124:

```
Gly His Thr Gly Asp Val Met Ala Leu Ser Leu Ala Pro Gln Cys Lys
1               5                   10                  15

Thr Phe Val Ser Gly Ala Cys Asp Ala Ser Ala Lys Leu Trp Asp
                20                  25                  30
```

(2) INFORMATION FOR SEQ ID NO:125:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G- BETA DROSOPH rIV, Fig. 23

(xi) SEQUENCE DESCRIPTION: SEQ ID NO:125:

```
Gly His Glu Ser Asp Ile Asn Ala Val Thr Phe Phe Pro Asn Gly Gln
1               5                   10                  15

Ala Phe Ala Thr Gly Ser Asp Asp Ala Thr Cys Arg Leu Phe Asp
                20                  25                  30
```

(2) INFORMATION FOR SEQ ID NO:126:

(i) SEQUENCE CHARACTERISTICS:
        (A) LENGTH: 34 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G- BETA DROSOPH rV, Fig. 23

(xi) SEQUENCE DESCRIPTION: SEQ ID NO:126:

```
Ser His Asp Asn Ile Ile Cys Gly Ile Thr Ser Val Ala Phe Ser Lys
1               5                   10                  15
```

```
Ser Gly Arg Leu Leu Leu Ala Gly Tyr Asp Asp Phe Asn Cys Asn Val
        20                  25                  30

Trp Asp
```

(2) INFORMATION FOR SEQ ID NO:127:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G- BETA DROSOPH rVI, Fig. 23

(xi) SEQUENCE DESCRIPTION: SEQ ID NO:127:

```
Gly His Asp Asn Arg Val Ser Cys Leu Gly Val Thr Glu Asn Gly Met
1               5                   10                  15

Ala Val Ala Thr Gly Ser Trp Asp Ser Phe Leu Arg Val Trp Asn
        20                  25                  30
```

(2) INFORMATION FOR SEQ ID NO:128:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-BETA HUMAN rI, Fig. 24

(xi) SEQUENCE DESCRIPTION: SEQ ID NO:128:

```
Gly His Asn Gly Trp Val Thr Gln Ile Ala Thr Thr Pro Gln Phe Pro
1               5                   10                  15

Asp Met Ile Leu Ser Ala Ser Arg Asp Lys Thr Ile Ile Met Trp Lys
        20                  25                  30
```

(2) INFORMATION FOR SEQ ID NO:129:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-BETA HUMAN rII, Fig. 24

(xi) SEQUENCE DESCRIPTION: SEQ ID NO:129:

```
Gly His Ser His Phe Val Ser Asp Val Val Ile Ser Ser Asp Gly Gln
1               5                   10                  15

Phe Ala Leu Ser Gly Ser Trp Asp Gly Thr Leu Arg Leu Trp Asp
        20                  25                  30
```

(2) INFORMATION FOR SEQ ID NO:130:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-BETA HUMAN rIII, Fig. 24

(xi) SEQUENCE DESCRIPTION: SEQ ID NO:130:

```
Gly His Thr Lys Asp Val Leu Ser Val Ala Phe Ser Ser Asp Asn Arg
1               5                   10                  15

Gln Ile Val Ser Gly Ser Arg Asp Lys Thr Ile Lys Leu Trp Asn
                20                  25                  30
```

(2) INFORMATION FOR SEQ ID NO:131:

(i) SEQUENCE CHARACTERISTICS:
        (A) LENGTH: 33 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-BETA HUMAN rIV, Fig. 24

(xi) SEQUENCE DESCRIPTION: SEQ ID NO:131:

```
Ser His Ser Glu Trp Val Ser Cys Val Arg Phe Ser Pro Asn Ser Ser
1               5                   10                  15

Asn Pro Ile Ile Val Ser Cys Gly Trp Asp Lys Leu Val Lys Val Trp
                20                  25                  30

Asn
```

(2) INFORMATION FOR SEQ ID NO:132:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-BETA HUMAN rV, Fig. 24

(xi) SEQUENCE DESCRIPTION: SEQ ID NO:132:

```
Gly His Thr Gly Tyr Leu Asn Thr Val Thr Val Ser Pro Asp Gly Ser
1               5                   10                  15

Leu Cys Ala Ser Gly Gly Lys Asp Gly Gln Ala Met Leu Trp Asp
                20                  25                  30
```

(2) INFORMATION FOR SEQ ID NO:133:

(i) SEQUENCE CHARACTERISTICS:
       (A) LENGTH: 36 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-BETA HUMAN rVI, Fig. 24

(xi) SEQUENCE DESCRIPTION: SEQ ID NO:133:

Lys His Leu Tyr Thr Leu Asp Gly Gly Asp Ile Ile Asn Ala Leu Cys
1               5                   10                  15

Phe Ser Pro Asn Arg Tyr Trp Leu Cys Ala Ala Thr Gly Pro Ser Ile
                20                  25                  30

Lys Ile Trp Asp
            35

(2) INFORMATION FOR SEQ ID NO:134:

(i) SEQUENCE CHARACTERISTICS:
       (A) LENGTH: 31 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-BETA HUMAN rVII, Fig. 24

(xi) SEQUENCE DESCRIPTION: SEQ ID NO:134:

Ala Glu Pro Pro Gln Cys Thr Ser Leu Ala Trp Ser Ala Asp Gly Gln
1               5                   10                  15

Thr Leu Phe Ala Gly Tyr Thr Asp Asn Leu Val Arg Val Trp Gln
                20                  25                  30

(2) INFORMATION FOR SEQ ID NO:135:

(i) SEQUENCE CHARACTERISTICS:
       (A) LENGTH: 31 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-Beta 1 bovine rI, Fig. 21

(xi) SEQUENCE DESCRIPTION: SEQ ID NO:135:

Gly His Leu Ala Lys Ile Tyr Ala Met His Trp Gly Thr Asp Ser Arg
1               5                   10                  15

Leu Leu Val Ser Ala Ser Gln Asp Gly Lys Leu Ile Ile Trp Asp
                20                  25                  30

(2) INFORMATION FOR SEQ ID NO:136:

(i) SEQUENCE CHARACTERISTICS:
    (A) LENGTH: 30 amino acids
    (B) TYPE: amino acid
    (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: G-Beta 1 bovine rII, Fig. 21

(xi) SEQUENCE DESCRIPTION: SEQ ID NO:136:

Gly His Thr Gly Tyr Leu Ser Cys Cys Arg Phe Leu Asp Asp Asn Gln
1               5                   10                  15

Ile Val Thr Ser Ser Gly Asp Thr Thr Cys Ala Leu Trp Asp
                20                  25                  30

(2) INFORMATION FOR SEQ ID NO:137:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-Beta 1 bovine rIII, Fig. 21

(xi) SEQUENCE DESCRIPTION: SEQ ID NO:137:

Gly His Thr Gly Asp Val Met Ser Leu Ser Leu Ala Pro Asp Thr Arg
1               5                   10                  15

Leu Phe Val Ser Gly Ala Cys Asp Ala Ser Ala Lys Leu Trp Asp
                20                  25                  30

(2) INFORMATION FOR SEQ ID NO:138:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-Beta 1 bovine rIV, Fig. 21

(xi) SEQUENCE DESCRIPTION: SEQ ID NO:138:

Gly His Glu Ser Asp Ile Asn Ala Ile Cys Phe Phe Pro Asn Gly Asn
1               5                   10                  15

Ala Phe Ala Thr Gly Ser Asp Asp Ala Thr Cys Arg Leu Phe Asp
                20                  25                  30

(2) INFORMATION FOR SEQ ID NO:139:

(i) SEQUENCE CHARACTERISTICS:
        (A) LENGTH: 34 amino acids
        (B) TYPE: amino acid (D) TOPOLOGY: unknown (ii) MOLECULE TYPE: peptide (iii) HYPOTHETICAL: NO (iv) ANTI-SENSE: NO (vi) ORIGINAL SOURCE:
                (C) INDIVIDUAL ISOLATE: G-Beta 1 bovine rV, Fig. 21

(xi) SEQUENCE DESCRIPTION: SEQ ID NO:139:

Ser His Asp Asn Ile Ile Cys Gly Ile Thr Ser Val Ser Phe Ser Lys
1               5                  10                  15

Ser Gly Arg Leu Leu Leu Ala Gly Tyr Asp Asp Phe Asn Cys Asn Val
            20                  25                  30

Trp Asp (2) INFORMATION FOR SEQ ID NO:140:

(i) SEQUENCE CHARACTERISTICS:
                (A) LENGTH: 31 amino acids
                (B) TYPE: amino acid
                (D) TOPOLOGY: unknown (ii) MOLECULE TYPE: peptide (iii) HYPOTHETICAL: NO (iv) ANTI-SENSE: NO (vi) ORIGINAL SOURCE:
                (C) INDIVIDUAL ISOLATE: G-Beta 1 bovine rVI, Fig. 21

(xi) SEQUENCE DESCRIPTION: SEQ ID NO:140:

Gly His Asp Asn Arg Val Ser Cys Leu Gly Val Thr Asp Asp Gly Met
1               5                  10                  15

Ala Val Ala Thr Gly Ser Trp Asp Ser Phe Leu Lys Ile Trp Asn
            20                  25                  30

(2) INFORMATION FOR SEQ ID NO:141:

(i) SEQUENCE CHARACTERISTICS:
                (A) LENGTH: 31 amino acids
                (B) TYPE: amino acid
                (D) TOPOLOGY: unknown (ii) MOLECULE TYPE: peptide (iii) HYPOTHETICAL: NO (iv) ANTI-SENSE: NO (vi) ORIGINAL SOURCE:
                (C) INDIVIDUAL ISOLATE: G-Beta-bovine(2) rI, Fig. 22

(xi) SEQUENCE DESCRIPTION: SEQ ID NO:141:

Gly His Leu Ala Lys Ile Tyr Ala Met His Trp Gly Thr Asp Ser Arg
1               5                  10                  15

Leu Leu Val Ser Ala Ser Gln Asp Gly Lys Leu Ile Ile Trp Asp
            20                  25                  30

(2) INFORMATION FOR SEQ ID NO:142:

(i) SEQUENCE CHARACTERISTICS:
                (A) LENGTH: 30 amino acids
                (B) TYPE: amino acid
                (D) TOPOLOGY: unknown (ii) MOLECULE TYPE: peptide (iii) HYPOTHETICAL: NO (iv) ANTI-SENSE: NO (vi) ORIGINAL SOURCE:
          (C) INDIVIDUAL ISOLATE: G-Beta-bovine(2) rII, Fig. 22

(xi) SEQUENCE DESCRIPTION: SEQ ID NO:142:

Gly His Thr Gly Tyr Leu Ser Cys Cys Arg Phe Leu Asp Asp Asn Gln
1               5                  10                  15

Ile Ile Thr Ser Ser Gly Asp Thr Thr Cys Ala Leu Trp Asp
                20                  25                  30

(2) INFORMATION FOR SEQ ID NO:143:

(i) SEQUENCE CHARACTERISTICS:
          (A) LENGTH: 31 amino acids
          (B) TYPE: amino acid
          (D) TOPOLOGY: unknown (ii) MOLECULE TYPE: peptide (iii) HYPOTHETICAL: NO (iv) ANTI-SENSE: NO (vi) ORIGINAL SOURCE:
          (C) INDIVIDUAL ISOLATE: G-Beta-bovine(2) rIII, Fig. 22

(xi) SEQUENCE DESCRIPTION: SEQ ID NO:143:

Gly His Ser Gly Asp Val Met Ser Leu Ser Leu Ala Pro Asp Gly Arg
1               5                  10                  15

Thr Phe Val Ser Gly Ala Cys Asp Ala Ser Ile Lys Leu Trp Asp
                20                  25                  30

(2) INFORMATION FOR SEQ ID NO:144:

(i) SEQUENCE CHARACTERISTICS:
          (A) LENGTH: 31 amino acids
          (B) TYPE: amino acid
          (D) TOPOLOGY: unknown (ii) MOLECULE TYPE: peptide (iii) HYPOTHETICAL: NO (iv) ANTI-SENSE: NO (vi) ORIGINAL SOURCE:
          (C) INDIVIDUAL ISOLATE: G-Beta-bovine(2) rIV, Fig. 22

(xi) SEQUENCE DESCRIPTION: SEQ ID NO:144:

Gly His Glu Ser Asp Ile Asn Ala Val Ala Phe Phe Pro Asn Gly Tyr
1               5                  10                  15

Ala Phe Thr Thr Gly Ser Asp Asp Ala Thr Cys Arg Leu Phe Asp
                20                  25                  30

(2) INFORMATION FOR SEQ ID NO:145:

(i) SEQUENCE CHARACTERISTICS:
          (A) LENGTH: 34 amino acids
          (B) TYPE: amino acid
          (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: G-Beta-bovine(2) rV, Fig. 22

(xi) SEQUENCE DESCRIPTION: SEQ ID NO:145:

Ser His Asp Asn Ile Ile Cys Gly Ile Thr Ser Val Ala Phe Ser Arg
1               5                   10                  15

Ser Gly Arg Leu Leu Leu Ala Gly Tyr Asp Asp Phe Asn Cys Asn Ile
            20                  25                  30

Trp Asp (2) INFORMATION FOR SEQ ID NO:146:

(i) SEQUENCE CHARACTERISTICS:
         (A) LENGTH: 31 amino acids
         (B) TYPE: amino acid
         (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: G-Beta-bovine(2) rVI, Fig. 22

(xi) SEQUENCE DESCRIPTION: SEQ ID NO:146:

Gly His Asp Asn Arg Val Ser Cys Leu Gly Val Thr Asp Asp Gly Met
1               5                   10                  15

Ala Val Ala Thr Gly Ser Trp Asp Ser Phe Leu Lys Ile Trp Asn
            20                  25                  30

(2) INFORMATION FOR SEQ ID NO:147:

(i) SEQUENCE CHARACTERISTICS:
         (A) LENGTH: 31 amino acids
         (B) TYPE: amino acid
         (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: G-Beta2(Human) rI, Fig. 25

(xi) SEQUENCE DESCRIPTION: SEQ ID NO:147:

Gly His Leu Ala Lys Ile Tyr Ala Met His Trp Gly Thr Asp Ser Arg
1               5                   10                  15

Leu Leu Val Ser Ala Ser Gln Asp Gly Lys Leu Ile Ile Trp Asp
            20                  25                  30

(2) INFORMATION FOR SEQ ID NO:148:

(i) SEQUENCE CHARACTERISTICS:
         (A) LENGTH: 30 amino acids
         (B) TYPE: amino acid
         (D) TOPOLOGY: unknown (ii) MOLECULE TYPE: peptide (iii) HYPOTHETICAL: NO (iv) ANTI-SENSE: NO (vi) ORIGINAL SOURCE:
      (C) INDIVIDUAL ISOLATE: G-Beta2(Human) rII, Fig. 25

(xi) SEQUENCE DESCRIPTION: SEQ ID NO:148:

Gly His Thr Gly Tyr Leu Ser Cys Cys Arg Phe Leu Asp Asp Asn Gln
1               5                   10                  15
Ile Ile Thr Ser Ser Gly Asp Thr Thr Cys Ala Leu Trp Asp
            20                  25                  30

(2) INFORMATION FOR SEQ ID NO:149:

(i) SEQUENCE CHARACTERISTICS:
       (A) LENGTH: 31 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: G-Beta2(Human) rIII, Fig. 25

(xi) SEQUENCE DESCRIPTION: SEQ ID NO:149:

Gly His Ser Gly Asp Val Met Ser Leu Ser Leu Ala Pro Asp Gly Arg
1               5                   10                  15
Thr Phe Val Ser Gly Ala Cys Asp Ala Ser Ile Lys Leu Trp Asp
            20                  25                  30

(2) INFORMATION FOR SEQ ID NO:150:

(i) SEQUENCE CHARACTERISTICS:
       (A) LENGTH: 31 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: G-Beta2(Human) rIV, Fig. 25

(xi) SEQUENCE DESCRIPTION: SEQ ID NO:150:

Gly His Glu Ser Asp Ile Asn Ala Val Ala Phe Phe Pro Asn Gly Tyr
1               5                   10                  15
Ala Phe Thr Thr Gly Ser Asp Asp Ala Thr Cys Arg Leu Phe Asp
            20                  25                  30

(2) INFORMATION FOR SEQ ID NO:151:

(i) SEQUENCE CHARACTERISTICS:
       (A) LENGTH: 34 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: G-Beta2(Human) rV, Fig. 25

(xi) SEQUENCE DESCRIPTION: SEQ ID NO:151:

Ser His Asp Asn Ile Ile Cys Gly Ile Thr Ser Val Ala Phe Ser Arg
1               5                   10                  15

Ser Gly Arg Leu Leu Leu Ala Gly Tyr Asp Asp Phe Asn Cys Asn Ile
            20                  25                  30

Trp Asp (2) INFORMATION FOR SEQ ID NO:152:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-Beta2(Human) rVI, Fig. 25

(xi) SEQUENCE DESCRIPTION: SEQ ID NO:152:

Gly His Asp Asn Arg Val Ser Cys Leu Gly Val Thr Asp Asp Gly Met
1               5                   10                  15

Ala Val Ala Thr Gly Ser Trp Asp Ser Phe Leu Lys Ile Trp Asn
            20                  25                  30

(2) INFORMATION FOR SEQ ID NO:153:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-Beta4(mouse) rI, Fig. 26

(xi) SEQUENCE DESCRIPTION: SEQ ID NO:153:

Gly His Leu Ala Lys Ile Tyr Ala Met His Trp Gly Tyr Asp Ser Arg
1               5                   10                  15

Leu Leu Val Ser Ala Ser Gln Asp Gly Lys Leu Ile Ile Trp Asp
            20                  25                  30

(2) INFORMATION FOR SEQ ID NO:154:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: G-Beta4(mouse) rII, Fig. 26

(xi) SEQUENCE DESCRIPTION: SEQ ID NO:154:

Gly His Thr Gly Tyr Leu Ser Cys Cys Arg Phe Leu Asp Asp Gly Gln

```
1               5              10              15
Ile Ile Thr Ser Ser Gly Asp Thr Thr Cys Ala Leu Trp Asp
            20                  25              30
```

(2) INFORMATION FOR SEQ ID NO:155:

(i) SEQUENCE CHARACTERISTICS:
      (A) LENGTH: 31 amino acids
      (B) TYPE: amino acid
      (D) TOPOLOGY: unknown (ii) MOLECULE TYPE: peptide (iii) HYPOTHETICAL: NO (iv) ANTI-SENSE: NO (vi) ORIGINAL SOURCE:
      (C) INDIVIDUAL ISOLATE: G-Beta4(mouse) rIII, Fig. 26

(xi) SEQUENCE DESCRIPTION: SEQ ID NO:155:

```
Gly His Ser Gly Asp Val Met Ser Leu Ser Leu Ser Pro Asp Leu Lys
1               5                   10                  15
Thr Phe Val Ser Gly Ala Cys Asp Ala Ser Ser Lys Leu Trp Asp
            20                  25              30
```

(2) INFORMATION FOR SEQ ID NO:156:

(i) SEQUENCE CHARACTERISTICS:
      (A) LENGTH: 31 amino acids
      (B) TYPE: amino acid
      (D) TOPOLOGY: unknown (ii) MOLECULE TYPE: peptide (iii) HYPOTHETICAL: NO (iv) ANTI-SENSE: NO (vi) ORIGINAL SOURCE:
      (C) INDIVIDUAL ISOLATE: G-Beta4(mouse) rIV, Fig. 26

(xi) SEQUENCE DESCRIPTION: SEQ ID NO:156:

```
Gly His Ile Ser Asp Ile Asn Ala Val Ser Phe Phe Pro Ser Gly Tyr
1               5                   10                  15
Ala Phe Ala Thr Gly Ser Asp Asp Ala Thr Cys Arg Leu Phe Asp
            20                  25              30
```

(2) INFORMATION FOR SEQ ID NO:157:

(i) SEQUENCE CHARACTERISTICS:
      (A) LENGTH: 34 amino acids
      (B) TYPE: amino acid
      (D) TOPOLOGY: unknown (ii) MOLECULE TYPE: peptide (iii) HYPOTHETICAL: NO (iv) ANTI-SENSE: NO (vi) ORIGINAL SOURCE:
      (C) INDIVIDUAL ISOLATE: G-Beta4(mouse) rV, Fig. 26

(xi) SEQUENCE DESCRIPTION: SEQ ID NO:157:

```
Ser His Asp Asn Ile Ile Cys Gly Ile Thr Ser Val Ala Phe Ser Lys
1               5                   10                  15
Ser Gly Arg Leu Leu Leu Ala Gly Tyr Asp Asp Phe Asn Cys Ser Val
            20                  25                  30
```

Trp Asp (2) INFORMATION FOR SEQ ID NO:158:

(i) SEQUENCE CHARACTERISTICS:
       (A) LENGTH: 31 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: G-Beta4(mouse) rVI, Fig. 26

(xi) SEQUENCE DESCRIPTION: SEQ ID NO:158:

Gly His Asp Asn Arg Val Ser Cys Leu Gly Val Thr Asp Asp Gly Met
1               5                   10                  15

Ala Val Ala Thr Gly Ser Trp Asp Ser Phe Leu Arg Ile Trp Asn
            20                  25                  30

(2) INFORMATION FOR SEQ ID NO:159:

(i) SEQUENCE CHARACTERISTICS:
       (A) LENGTH: 31 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: GROUCHO PROT. DRSPH rI, Fig. 27

(xi) SEQUENCE DESCRIPTION: SEQ ID NO:159:

Thr Ser Ala Ala Pro Ala Cys Tyr Ala Leu Ala Ser Pro Asp Ser Lys
1               5                   10                  15

Val Cys Phe Ser Cys Cys Ser Asp Gly Asn Ile Ala Val Trp Asp
            20                  25                  30

(2) INFORMATION FOR SEQ ID NO:160:

(i) SEQUENCE CHARACTERISTICS:
       (A) LENGTH: 31 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: GROUCHO PROT. DRSPH rII, Fig. 27

(xi) SEQUENCE DESCRIPTION: SEQ ID NO:160:

Gly His Thr Asp Gly Ala Ser Cys Ile Asp Ile Ser Pro Asp Gly Ser
1               5                   10                  15

Arg Leu Trp Thr Gly Gly Leu Asp Asn Thr Val Arg Ser Trp Asp
            20                  25                  30

-continued

```
(2) INFORMATION FOR SEQ ID NO:161:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: GTP binding prt squid rI, Fig. 28

(xi) SEQUENCE DESCRIPTION: SEQ ID NO:161:

Gly His Leu Ala Lys Ile Tyr Ala Met His Trp Ala Ser Asp Ser Arg
1               5                   10                  15

Asn Leu Val Ser Ala Ser Gln Asp Gly Lys Leu Ile Val Trp Asp
            20                  25                  30

(2) INFORMATION FOR SEQ ID NO:162:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: GTP binding prt squid rII, Fig. 28

(xi) SEQUENCE DESCRIPTION: SEQ ID NO:162:

Gly His Thr Gly Tyr Leu Ser Cys Cys Arg Phe Ile Asp Asp Asn Gln
1               5                   10                  15

Ile Val Thr Ser Ser Gly Asp Met Thr Cys Ala Leu Trp Asn
            20                  25                  30

(2) INFORMATION FOR SEQ ID NO:163:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: GTP binding prt squid rIII, Fig. 28

(xi) SEQUENCE DESCRIPTION: SEQ ID NO:163:

Gly His Thr Gly Asp Val Met Ser Leu Ser Leu Ala Pro Asp Met Arg
1               5                   10                  15

Thr Phe Val Ser Gly Ala Cys Asp Ala Ser Ala Lys Leu Phe Asp
            20                  25                  30

(2) INFORMATION FOR SEQ ID NO:164:

(i) SEQUENCE CHARACTERISTICS:
        (A) LENGTH: 31 amino acids
```

(B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: GTP binding prt squid rIV, Fig. 28

(xi) SEQUENCE DESCRIPTION: SEQ ID NO:164:

Gly His Glu Ser Asp Ile Asn Ala Ile Thr Tyr Phe Pro Asn Gly Phe
1               5                   10                  15

Ala Phe Ala Thr Gly Ser Asp Asp Ala Thr Cys Arg Leu Phe Asp
                20                  25                  30

(2) INFORMATION FOR SEQ ID NO:165:

(i) SEQUENCE CHARACTERISTICS:
            (A) LENGTH: 34 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: GTP binding prt squid rV, Fig. 28

(xi) SEQUENCE DESCRIPTION: SEQ ID NO:165:

Ser His Asp Asn Ile Ile Cys Gly Ile Thr Ser Val Ala Phe Ser Lys
1               5                   10                  15

Ser Gly Arg Leu Leu Leu Gly Gly Tyr Asp Asp Phe Asn Cys Asn Val
                20                  25                  30

Trp Asp (2) INFORMATION FOR SEQ ID NO:166:

(i) SEQUENCE CHARACTERISTICS:
            (A) LENGTH: 24 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: GTP binding prt squid rVI, Fig. 28

(xi) SEQUENCE DESCRIPTION: SEQ ID NO:166:

Gly His Asp Asn Arg Val Ser Cys Leu Gly Val Thr Glu Asp Gly Met
1               5                   10                  15

Ala Val Ala Thr Gly Ser Trp Asp
                20

(2) INFORMATION FOR SEQ ID NO:167:

(i) SEQUENCE CHARACTERISTICS:
            (A) LENGTH: 32 amino acids
            (B) TYPE: amino acid
            (D) TOPOLOGY: unknown

```
    (ii) MOLECULE TYPE: peptide (iii) HYPOTHETICAL: NO (iv) ANTI-SENSE: NO (vi) ORIGINAL SOURCE:
         (C) INDIVIDUAL ISOLATE: IEF SSP 9306 rI, Fig. 29

(xi) SEQUENCE DESCRIPTION: SEQ ID NO:167:

Gly His Gln Lys Glu Gly Tyr Gly Leu Ser Trp Asn Pro Asn Leu Ser
1               5                  10                  15

Gly His Leu Leu Ser Ala Ser Asp Asp His Thr Ile Cys Leu Trp Asp
                20                  25                  30

(2) INFORMATION FOR SEQ ID NO:168:

(i) SEQUENCE CHARACTERISTICS:
         (A) LENGTH: 32 amino acids
         (B) TYPE: amino acid
         (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: IEF SSP 9306 rII, Fig. 29

(xi) SEQUENCE DESCRIPTION: SEQ ID NO:168:

Gly His Thr Ala Val Val Glu Asp Val Ser Trp His Leu Leu His Glu
1               5                  10                  15

Ser Leu Phe Gly Ser Val Ala Asp Asp Gln Lys Leu Met Ile Trp Asp
                20                  25                  30

(2) INFORMATION FOR SEQ ID NO:169:

(i) SEQUENCE CHARACTERISTICS:
         (A) LENGTH: 37 amino acids
         (B) TYPE: amino acid
         (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: IEF SSP 9306 rIII, Fig. 29

(xi) SEQUENCE DESCRIPTION: SEQ ID NO:169:

Ser His Ser Val Asp Ala His Thr Ala Glu Val Asn Cys Leu Ser Phe
1               5                  10                  15

Asn Pro Tyr Ser Glu Phe Ile Leu Ala Thr Gly Ser Ala Asp Lys Thr
                20                  25                  30

Val Ala Leu Trp Asp
            35

(2) INFORMATION FOR SEQ ID NO:170:

(i) SEQUENCE CHARACTERISTICS:
         (A) LENGTH: 37 amino acids
         (B) TYPE: amino acid
         (D) TOPOLOGY: unknown
```

(ii) MOLECULE TYPE: peptide (iii) HYPOTHETICAL: NO (iv) ANTI-SENSE: NO (vi) ORIGINAL SOURCE:
             (C) INDIVIDUAL ISOLATE: IEF SSP 9306 rIV, Fig. 29

(xi) SEQUENCE DESCRIPTION: SEQ ID NO:170:

Leu His Ser Phe Glu Ser His Lys Asp Glu Ile Phe Gln Val Gln Trp
1               5                   10                  15

Ser Pro His Asn Glu Thr Ile Leu Ala Ser Ser Gly Thr Asp Arg Arg
            20                  25                  30

Leu Asn Val Trp Asp
        35

(2) INFORMATION FOR SEQ ID NO:171:

(i) SEQUENCE CHARACTERISTICS:
            (A) LENGTH: 34 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: IEF SSP 9306 rV, Fig. 29

(xi) SEQUENCE DESCRIPTION: SEQ ID NO:171:

Ile Gly Glu Glu Gln Ser Pro Glu Asp Ala Glu Asp Gly Pro Pro Glu
1               5                   10                  15

Leu Leu Phe Ile His Gly Gly His Thr Ala Lys Ile Ser Asp Phe Ser
            20                  25                  30

Trp Asn (2) INFORMATION FOR SEQ ID NO:172:

(i) SEQUENCE CHARACTERISTICS:
            (A) LENGTH: 32 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: HUMAN 12.3 rI, Fig. 30

(xi) SEQUENCE DESCRIPTION: SEQ ID NO:172:

Gly His Asn Gly Trp Val Thr Gln Ile Ala Thr Thr Pro Gln Phe Pro
1               5                   10                  15

Asp Met Ile Leu Ser Ala Ser Arg Asp Lys Thr Ile Ile Met Trp Lys
            20                  25                  30

(2) INFORMATION FOR SEQ ID NO:173:

(i) SEQUENCE CHARACTERISTICS:
            (A) LENGTH: 31 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: HUMAN 12.3 rII, Fig. 30

(xi) SEQUENCE DESCRIPTION: SEQ ID NO:173:

Gly His Ser His Phe Val Ser Asp Val Val Ile Ser Ser Asp Gly Gln
 1               5                  10                  15

Phe Ala Leu Ser Gly Ser Trp Asp Gly Thr Leu Arg Leu Trp Asp
             20                  25                  30

(2) INFORMATION FOR SEQ ID NO:174:

(i) SEQUENCE CHARACTERISTICS:
            (A) LENGTH: 31 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: HUMAN 12.3 rIII, Fig. 30

(xi) SEQUENCE DESCRIPTION: SEQ ID NO:174:

Gly His Thr Lys Asp Val Leu Ser Val Ala Phe Ser Ser Asp Asn Arg
 1               5                  10                  15

Gln Ile Val Ser Gly Ser Arg Asp Lys Thr Ile Lys Leu Trp Asn
             20                  25                  30

(2) INFORMATION FOR SEQ ID NO:175:

(i) SEQUENCE CHARACTERISTICS:
            (A) LENGTH: 33 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: HUMAN 12.3 rIV, Fig. 30

(xi) SEQUENCE DESCRIPTION: SEQ ID NO:175:

Ser His Ser Glu Trp Val Ser Cys Val Arg Phe Ser Pro Asn Ser Ser
 1               5                  10                  15

Asn Pro Ile Ile Val Ser Cys Gly Trp Asp Lys Leu Val Lys Val Trp
             20                  25                  30

Asn (2) INFORMATION FOR SEQ ID NO:176:

(i) SEQUENCE CHARACTERISTICS:
            (A) LENGTH: 31 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: HUMAN 12.3 rV, Fig. 30

(xi) SEQUENCE DESCRIPTION: SEQ ID NO:176:

Gly His Thr Gly Tyr Leu Asn Thr Val Thr Val Ser Pro Asp Gly Ser
1               5                   10                  15

Leu Cys Ala Ser Gly Gly Lys Asp Gly Gln Ala Met Leu Trp Asp
            20                  25                  30

(2) INFORMATION FOR SEQ ID NO:177:

(i) SEQUENCE CHARACTERISTICS:
        (A) LENGTH: 36 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: HUMAN 12.3 rVI, Fig. 30

(xi) SEQUENCE DESCRIPTION: SEQ ID NO:177:

Lys His Leu Tyr Thr Leu Asp Gly Gly Asp Ile Ile Asn Ala Leu Cys
1               5                   10                  15

Phe Ser Pro Asn Arg Tyr Trp Leu Cys Ala Ala Thr Gly Pro Ser Ile
            20                  25                  30

Lys Ile Trp Asp
        35

(2) INFORMATION FOR SEQ ID NO:178:

(i) SEQUENCE CHARACTERISTICS:
        (A) LENGTH: 38 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: HUMAN 12.3 rVII, Fig. 30

(xi) SEQUENCE DESCRIPTION: SEQ ID NO:178:

Val Ile Ser Thr Ser Ser Lys Ala Glu Pro Pro Gln Cys Thr Ser Leu
1               5                   10                  15

Ala Trp Ser Ala Asp Gly Gln Thr Leu Phe Ala Gly Tyr Thr Asp Asn
            20                  25                  30

Leu Val Arg Val Trp Gln
        35

(2) INFORMATION FOR SEQ ID NO:179:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: IEF-7442-human rI, Fig. 31

(xi) SEQUENCE DESCRIPTION: SEQ ID NO:179:

Gly His Gln Lys Glu Gly Tyr Gly Leu Ser Trp Asn Ser Asn Leu Ser
1               5                  10                 15

Gly His Leu Leu Ser Ala Ser Asp Asp His Thr Val Cys Leu Trp Asp
            20                  25                 30

(2) INFORMATION FOR SEQ ID NO:180:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: IEF-7442-human rII, Fig. 31

(xi) SEQUENCE DESCRIPTION: SEQ ID NO:180:

Gly His Ser Ala Val Val Glu Asp Val Ala Trp His Leu Leu His Glu
1               5                  10                 15

Ser Leu Phe Gly Ser Val Ala Asp Asp Gln Lys Leu Met Ile Trp Asp
            20                  25                 30

(2) INFORMATION FOR SEQ ID NO:181:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
         (C) INDIVIDUAL ISOLATE: IEF-7442-human rIII, Fig. 31

(xi) SEQUENCE DESCRIPTION: SEQ ID NO:181:

Ala His Thr Ala Glu Val Asn Cys Leu Ser Phe Asn Pro Tyr Ser Glu
1               5                  10                 15

Phe Ile Leu Ala Thr Gly Ser Ala Asp Lys Thr Val Ala Leu Trp Asp
            20                  25                 30

(2) INFORMATION FOR SEQ ID NO:182:

(i) SEQUENCE CHARACTERISTICS:
        (A) LENGTH: 24 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: IEF-7442-human rIV, Fig. 31

(xi) SEQUENCE DESCRIPTION: SEQ ID NO:182:

Val His Trp Ser Pro His Asn Glu Thr Ile Leu Ala Ser Ser Gly Thr
1               5                   10                  15

Asp Arg Arg Leu Asn Val Trp Asp
            20

(2) INFORMATION FOR SEQ ID NO:183:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: IEF-7442-human rV, Fig. 31

(xi) SEQUENCE DESCRIPTION: SEQ ID NO:183:

Gly His Thr Ala Lys Ile Ser Asp Phe Ser Trp Asn Pro Asn Glu Pro
1               5                   10                  15

Trp Val Ile Cys Ser Val Ser Glu Asp Asn Ile Met Gln Ile Trp Gln
            20                  25                  30

(2) INFORMATION FOR SEQ ID NO:184:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Insulin-like GF binding
            protein complex rI, Fig. 32

(xi) SEQUENCE DESCRIPTION: SEQ ID NO:184:

Ala His Thr Pro Ala Leu Ala Ser Leu Gly Leu Ser Asn Asn Arg Leu
1               5                   10                  15

Ser Arg Leu Glu Asp Gly Leu Phe Glu Gly Leu Gly Ser Leu Trp Asp
            20                  25                  30

(2) INFORMATION FOR SEQ ID NO:185:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: Insulin-like growth factor bind.
        pro. complex-rat rI, Fig. 33

(xi) SEQUENCE DESCRIPTION: SEQ ID NO:185:

Thr His Thr Pro Ser Leu Ala Ser Leu Ser Leu Ser Ser Asn Leu Leu
 1               5                  10                  15
Gly Arg Leu Glu Glu Gly Leu Phe Gln Gly Leu Ser His Leu Trp Asp
                20                  25                  30

(2) INFORMATION FOR SEQ ID NO:186:

(i) SEQUENCE CHARACTERISTICS:
        (A) LENGTH: 47 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Insulin-like growth factor bind.
            pro. complex-rat rII, Fig. 33

(xi) SEQUENCE DESCRIPTION: SEQ ID NO:186:

Asn His Leu Glu Thr Leu Ala Glu Gly Leu Phe Ser Ser Leu Gly Arg
 1               5                  10                  15
Val Arg Tyr Leu Ser Leu Arg Asn Asn Ser Leu Gln Thr Phe Ser Pro
                20                  25                  30
Gln Pro Gly Leu Glu Arg Leu Trp Leu Asp Ala Asn Pro Trp Asp
                35                  40                  45

(2) INFORMATION FOR SEQ ID NO:187:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: LIS1 (human) rI, Fig. 34

(xi) SEQUENCE DESCRIPTION: SEQ ID NO:187:

Gly His Arg Ser Pro Val Thr Arg Val Ile Phe His Pro Val Phe Ser
 1               5                  10                  15
Val Met Val Ser Ala Ser Glu Asp Ala Thr Ile Lys Val Trp Asp
                20                  25                  30

(2) INFORMATION FOR SEQ ID NO:188:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: LIS1 (human) rII, Fig. 34

(xi) SEQUENCE DESCRIPTION: SEQ ID NO:188:

Gly His Thr Asp Ser Val Gln Asp Ile Ser Phe Asp His Ser Gly Lys
1               5                  10                  15
Leu Leu Ala Ser Cys Ser Ala Asp Met Thr Ile Lys Leu Trp Asp
            20                  25                  30

(2) INFORMATION FOR SEQ ID NO:189:

(i) SEQUENCE CHARACTERISTICS:
            (A) LENGTH: 31 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: LIS1 (human) rIII, Fig. 34

(xi) SEQUENCE DESCRIPTION: SEQ ID NO:189:

Gly His Asp His Asn Val Ser Ser Val Ala Ile Met Pro Asn Gly Asp
1               5                  10                  15
His Ile Val Ser Ala Ser Arg Asp Lys Thr Ile Lys Met Trp Glu
            20                  25                  30

(2) INFORMATION FOR SEQ ID NO:190:

(i) SEQUENCE CHARACTERISTICS:
            (A) LENGTH: 31 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: LIS1 (human) rIV, Fig. 34

(xi) SEQUENCE DESCRIPTION: SEQ ID NO:190:

Gly His Arg Glu Trp Val Arg Met Val Arg Pro Asn Gln Asp Gly Thr
1               5                  10                  15
Leu Ile Ala Ser Cys Ser Asn Asp Gln Thr Val Arg Val Trp Val
            20                  25                  30

(2) INFORMATION FOR SEQ ID NO:191:

(i) SEQUENCE CHARACTERISTICS:
            (A) LENGTH: 26 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: LIS1 (human) rV, Fig. 34

(xi) SEQUENCE DESCRIPTION: SEQ ID NO:191:

Gly Ser Glu Thr Lys Lys Ser Gly Lys Pro Gly Pro Phe Leu Leu Ser
1               5                   10                  15
Gly Ser Arg Asp Lys Thr Lys Met Trp Asp
            20                  25

(2) INFORMATION FOR SEQ ID NO:192:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: LIS1 (human) rVI, Fig. 34

(xi) SEQUENCE DESCRIPTION: SEQ ID NO:192:

Gly His Asp Asn Trp Val Arg Gly Val Leu Phe His Ser Gly Gly Lys
1               5                   10                  15
Phe Ile Leu Ser Cys Ala Asp Asp Lys Thr Leu Arg Val Trp Asp
            20                  25                  30

(2) INFORMATION FOR SEQ ID NO:193:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: LIS1 (human) rVII, Fig. 34

(xi) SEQUENCE DESCRIPTION: SEQ ID NO:193:

Ala His Glu His Phe Val Thr Ser Leu Asp Phe His Lys Thr Ala Pro
1               5                   10                  15
Tyr Val Val Thr Gly Ser Val Asp Gln Thr Val Lys Val Trp Glu
            20                  25                  30

(2) INFORMATION FOR SEQ ID NO:194:

(i) SEQUENCE CHARACTERISTICS:
        (A) LENGTH: 29 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: MD6 rI, Fig. 35

(xi) SEQUENCE DESCRIPTION: SEQ ID NO:194:

Gly His Ser Ala Arg Val Tyr Ala Leu Tyr Tyr Lys Asp Gly Leu Leu
1               5                   10                  15

```
Cys Thr Gly Ser Asp Asp Leu Ser Ala Lys Leu Trp Asp
            20                  25
```

(2) INFORMATION FOR SEQ ID NO:195:

(i) SEQUENCE CHARACTERISTICS:
        (A) LENGTH: 27 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: MD6 rII, Fig. 35

(xi) SEQUENCE DESCRIPTION: SEQ ID NO:195:

```
Thr His Thr Cys Ala Ala Val Lys Phe Asp Glu Gln Lys Leu Val Thr
1               5                   10                  15
Gly Ser Phe Asp Asn Thr Val Ala Cys Trp Glu
            20                  25
```

(2) INFORMATION FOR SEQ ID NO:196:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: MD6 rIII, Fig. 35

(xi) SEQUENCE DESCRIPTION: SEQ ID NO:196:

```
Gly His Thr Gly Ala Val Phe Ser Val Asp Tyr Ser Asp Glu Leu Asp
1               5                   10                  15
Ile Leu Val Ser Gly Ser Ala Asp Phe Ala Val Lys Val Trp Ala
            20                  25                  30
```

(2) INFORMATION FOR SEQ ID NO:197:

(i) SEQUENCE CHARACTERISTICS:
        (A) LENGTH: 40 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: MD6 rIV, Fig. 35

(xi) SEQUENCE DESCRIPTION: SEQ ID NO:197:

```
Gly His Thr Glu Trp Val Thr Lys Val Val Leu Gln Lys Cys Lys Val
1               5                   10                  15
Lys Ser Leu Leu His Ser Pro Gly Asp Tyr Ile Leu Leu Ser Ala Asp
            20                  25                  30
```

```
Lys Tyr Glu Ile Lys Ile Trp Pro
        35                  40
```

(2) INFORMATION FOR SEQ ID NO:198:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: MSL1 rI, Fig. 36

(xi) SEQUENCE DESCRIPTION: SEQ ID NO:198:

```
Lys His Asp Gly Gly Val Asn Ser Cys Arg Phe Asn Tyr Lys Asn Ser
1               5                   10                  15
Leu Ile Leu Ala Ser Ala Asp Ser Asn Gly Arg Leu Asn Leu Trp Asp
            20                  25                  30
```

(2) INFORMATION FOR SEQ ID NO:199:

(i) SEQUENCE CHARACTERISTICS:
        (A) LENGTH: 33 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: MSL1 rII, Fig. 36

(xi) SEQUENCE DESCRIPTION: SEQ ID NO:199:

```
Glu His Gly Thr Ser Val Ser Thr Leu Glu Trp Ser Pro Asn Phe Asp
1               5                   10                  15
Thr Val Leu Ala Thr Ala Gly Gln Glu Asp Gly Leu Val Lys Leu Trp
            20                  25                  30
Asp
```

(2) INFORMATION FOR SEQ ID NO:200:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: MSL1 rIII, Fig. 36

(xi) SEQUENCE DESCRIPTION: SEQ ID NO:200:

```
Gly His Met Leu Gly Val Asn Asp Ile Ser Trp Asp Ala His Asp Pro
1               5                   10                  15
Trp Leu Met Cys Ser Val Ala Asn Asp Asn Ser Val His Ile Trp Lys
            20                  25                  30
```

(2) INFORMATION FOR SEQ ID NO:201:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: MUS MUSCULUS PROTEIN rI, Fig. 37

(xi) SEQUENCE DESCRIPTION: SEQ ID NO:201:

```
Gly His Ser Gly Cys Val Asn Thr Val His Phe Asn Gln His Gly Thr
1               5                   10                  15

Leu Leu Ala Ser Gly Ser Asp Asp Leu Lys Val Ile Val Trp Asp
            20                  25                  30
```

(2) INFORMATION FOR SEQ ID NO:202:

(i) SEQUENCE CHARACTERISTICS:
        (A) LENGTH: 50 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: MUS MUSCULUS PROTEIN rII, Fig. 37

(xi) SEQUENCE DESCRIPTION: SEQ ID NO:202:

```
Gly His Ile Phe Ile Trp Glu Lys Ser Ser Cys Gln Ile Val Gln Phe
1               5                   10                  15

Leu Glu Ala Asp Glu Gly Gly Thr Ile Asn Cys Ile Asp Ser His Pro
            20                  25                  30

Tyr Leu Pro Val Leu Ala Ser Ser Gly Leu Asp His Glu Val Lys Ile
            35                  40                  45

Trp Ser
    50
```

(2) INFORMATION FOR SEQ ID NO:203:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: ORF RB1 rI, Fig. 38

(xi) SEQUENCE DESCRIPTION: SEQ ID NO:203:

```
Lys His Asp Gly Gly Val Asn Ser Cys Arg Phe Asn Tyr Lys Asn Ser
1               5                   10                  15
```

-continued

```
Leu Ile Leu Ala Ser Ala Asp Ser Asn Gly Arg Leu Asn Leu Trp Asp
            20                  25                  30
```

(2) INFORMATION FOR SEQ ID NO:204:

(i) SEQUENCE CHARACTERISTICS:
        (A) LENGTH: 33 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: ORF RB1 rII, Fig. 38

(xi) SEQUENCE DESCRIPTION: SEQ ID NO:204:

```
Glu His Gly Thr Ser Val Ser Thr Leu Glu Trp Ser Pro Asn Phe Asp
1               5                   10                  15
Thr Val Leu Ala Thr Ala Gly Gln Glu Asp Gly Leu Val Lys Leu Trp
            20                  25                  30
Asp
```

(2) INFORMATION FOR SEQ ID NO:205:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: ORF RB1 rIII, Fig. 38

(xi) SEQUENCE DESCRIPTION: SEQ ID NO:205:

```
Gly His Met Leu Gly Val Asn Asp Ile Ser Trp Asp Ala His Asp Pro
1               5                   10                  15
Trp Leu Met Cys Ser Val Ala Asn Asp Asn Ser Val His Ile Trp Lys
            20                  25                  30
```

(2) INFORMATION FOR SEQ ID NO:206:

(i) SEQUENCE CHARACTERISTICS:
        (A) LENGTH: 37 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Periodic Trp prt rI, Fig. 39

(xi) SEQUENCE DESCRIPTION: SEQ ID NO:206:

```
Gly His Ile Thr Thr His His Thr Asp Ala Val Leu Ser Met Ala His
1               5                   10                  15
Asn Lys Tyr Phe Arg Ser Val Leu Ala Ser Thr Ser Ala Asp His Thr
            20                  25                  30
```

Val Lys Leu Trp Asp
        35

(2) INFORMATION FOR SEQ ID NO:207:

(i) SEQUENCE CHARACTERISTICS:
        (A) LENGTH: 47 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Periodic Trp prt rII, Fig. 39

(xi) SEQUENCE DESCRIPTION: SEQ ID NO:207:

Ile His Ser Asn Lys Asn Val Ser Ser Ser Glu Trp His Met Leu Asn
1               5                   10                  15

Gly Ser Ile Leu Leu Thr Gly Gly Tyr Asp Ser Arg Val Ala Leu Thr
            20                  25                  30

Asp Val Arg Ile Ser Asp Glu Ser Gln Met Ser Lys Tyr Trp Ser
        35                  40                  45

(2) INFORMATION FOR SEQ ID NO:208:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: PLAP rI, Fig. 40

(xi) SEQUENCE DESCRIPTION: SEQ ID NO:208:

Gly His Lys Asp Thr Val Cys Ser Leu Ser Ser Gly Lys Phe Gly Thr
1               5                   10                  15

Leu Leu Ser Gly Ser Trp Asp Thr Thr Ala Lys Val Trp Leu
            20                  25                  30

(2) INFORMATION FOR SEQ ID NO:209:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: PLAP rII, Fig. 40

(xi) SEQUENCE DESCRIPTION: SEQ ID NO:209:

Gly His Thr Ala Ala Val Trp Ala Val Lys Ile Leu Pro Glu Gln Gly
1               5                   10                  15

```
Leu Met Leu Thr Gly Ser Ala Asp Lys Thr Ile Lys Leu Trp Lys
            20                  25                  30
```

(2) INFORMATION FOR SEQ ID NO:210:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: PLAP rIII, Fig. 40

(xi) SEQUENCE DESCRIPTION: SEQ ID NO:210:

```
Gly His Glu Asp Cys Val Arg Gly Leu Ala Ile Leu Ser Glu Thr Glu
1               5                   10                  15

Phe Leu Ser Cys Ala Asn Asp Ala Ser Ile Arg Arg Trp Gln
            20                  25                  30
```

(2) INFORMATION FOR SEQ ID NO:211:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: PLAP rIV, Fig. 40

(xi) SEQUENCE DESCRIPTION: SEQ ID NO:211:

```
Gly His Thr Asn Tyr Ile Tyr Ser Ile Ser Val Phe Pro Asn Ser Lys
1               5                   10                  15

Asp Phe Val Thr Thr Ala Glu Asp Arg Ser Leu Arg Ile Trp Lys
            20                  25                  30
```

(2) INFORMATION FOR SEQ ID NO:212:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: RETINOBLASTOMA BINDING PROTEIN -
           HUMAN. rI, Fig. 41

(xi) SEQUENCE DESCRIPTION: SEQ ID NO:212:

```
Gly His Gln Lys Glu Gly Tyr Gly Leu Ser Trp Asn Pro Asn Leu Ser
1               5                   10                  15

Gly His Leu Leu Ser Ala Ser Asp Asp His Thr Ile Cys Leu Trp Asp
            20                  25                  30
```

(2) INFORMATION FOR SEQ ID NO:213:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: RETINOBLASTOMA BINDING PROTEIN -
           HUMAN rII, Fig. 41

(xi) SEQUENCE DESCRIPTION: SEQ ID NO:213:

```
Gly His Thr Ala Val Val Glu Asp Val Ser Trp His Leu Leu His Glu
1               5                   10                  15

Ser Leu Phe Gly Ser Val Ala Asp Asp Gln Lys Leu Met Ile Trp Asp
            20                  25                  30
```

(2) INFORMATION FOR SEQ ID NO:214:

(i) SEQUENCE CHARACTERISTICS:
        (A) LENGTH: 37 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: RETINOBLASTOMA BINDING PROTEIN -
           HUMAN rIII, Fig. 41

(xi) SEQUENCE DESCRIPTION: SEQ ID NO:214:

```
Ser His Ser Val Asp Ala His Thr Ala Glu Val Asn Cys Leu Ser Phe
1               5                   10                  15

Asn Pro Tyr Ser Glu Phe Ile Leu Ala Thr Gly Ser Ala Asp Lys Thr
            20                  25                  30

Val Ala Leu Trp Asp
            35
```

(2) INFORMATION FOR SEQ ID NO:215:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: RETINOBLASTOMA BINDING PROTEIN -
           HUMAN rIV, Fig. 41

(xi) SEQUENCE DESCRIPTION: SEQ ID NO:215:

```
Ser His Lys Asp Glu Ile Phe Gln Val Gln Trp Ser Pro His Asn Glu
1               5                   10                  15

Thr Ile Leu Ala Ser Ser Gly Thr Asp Arg Arg Leu Asn Val Trp Asp
```

```
                    20                  25                  30
```

(2) INFORMATION FOR SEQ ID NO:216:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: RETINOBLASTOMA BINDING PROTEIN -
            HUMAN rV, Fig. 41

(xi) SEQUENCE DESCRIPTION: SEQ ID NO:216:

```
Gly His Thr Ala Lys Ile Ser Asp Phe Ser Trp Asn Pro Asn Glu Pro
1               5                  10                  15
Trp Val Ile Cys Ser Val Ser Glu Asp Asn Ile Met Gln Val Trp Gln
                20                  25                  30
```

(2) INFORMATION FOR SEQ ID NO:217:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: S253 PROTEIN rI, Fig. 42

(xi) SEQUENCE DESCRIPTION: SEQ ID NO:217:

```
Glu His Ala Leu Asp Ile Leu Asp Ala Asn Trp Ser Lys Asn Gly Phe
1               5                  10                  15
Leu Ile Thr Ala Ser Met Asp Lys Thr Ala Lys Leu Trp His
                20                  25                  30
```

(2) INFORMATION FOR SEQ ID NO:218:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: S253 PROTEIN rII, Fig. 42

(xi) SEQUENCE DESCRIPTION: SEQ ID NO:218:

```
Val His Pro Asp Phe Val Thr Ser Ala Ile Phe Phe Pro Asn Asp Asp
1               5                  10                  15
Arg Phe Ile Ile Thr Gly Cys Leu Asp His Arg Cys Arg Leu Trp Ser
                20                  25                  30
```

(2) INFORMATION FOR SEQ ID NO:219:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SOF1 rI, Fig. 43

(xi) SEQUENCE DESCRIPTION: SEQ ID NO:219:

```
Gly His Arg Asp Gly Val Tyr Ala Ile Ala Lys Asn Tyr Gly Ser Leu
1               5                   10                  15
Asn Lys Leu Ala Thr Gly Ser Ala Asp Gly Val Ile Lys Tyr Trp
            20                  25                  30
```

(2) INFORMATION FOR SEQ ID NO:220:

(i) SEQUENCE CHARACTERISTICS:
        (A) LENGTH: 35 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SOF1 rII, Fig. 43

(xi) SEQUENCE DESCRIPTION: SEQ ID NO:220:

```
Gly Leu Cys Val Thr Gln Pro Arg Phe His Asp Lys Lys Pro Asp Leu
1               5                   10                  15
Lys Ser Gln Asn Phe Met Leu Ser Cys Ser Asp Asp Lys Thr Val Lys
            20                  25                  30
Leu Trp Ser
    35
```

(2) INFORMATION FOR SEQ ID NO:221:

(i) SEQUENCE CHARACTERISTICS:
        (A) LENGTH: 35 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SOF1 rIII, Fig. 43

(xi) SEQUENCE DESCRIPTION: SEQ ID NO:221:

```
Gly Leu Ile Arg Thr Phe Asp Gly Glu Ser Ala Phe Gln Gly Ile Asp
1               5                   10                  15
Ser His Arg Glu Asn Ser Thr Phe Ala Thr Gly Gly Ala Lys Ile His
            20                  25                  30
Leu Trp Asp
    35
```

(2) INFORMATION FOR SEQ ID NO:222:

(i) SEQUENCE CHARACTERISTICS:
        (A) LENGTH: 39 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SOF1 rIV, Fig. 43

(xi) SEQUENCE DESCRIPTION: SEQ ID NO:222:

```
Gly His Ser Arg Glu Ile Tyr His Thr Lys Arg Met Gln His Val Phe
1               5                  10                  15

Val Lys Tyr Ser Met Asp Ser Lys Tyr Ile Ile Ser Gly Ser Asp Asp
                20                  25                  30

Gly Asn Val Arg Leu Trp Arg
            35
```

(2) INFORMATION FOR SEQ ID NO:223:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: STE4-YEAST rI, Fig. 44

(xi) SEQUENCE DESCRIPTION: SEQ ID NO:223:

```
Gly His Asn Asn Lys Ile Ser Asp Phe Arg Trp Ser Arg Asp Ser Lys
1               5                  10                  15

Arg Ile Leu Ser Ala Ser Gln Asp Gly Phe Met Leu Ile Trp Asp
                20                  25                  30
```

(2) INFORMATION FOR SEQ ID NO:224:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: STE4-YEAST rII, Fig. 44

(xi) SEQUENCE DESCRIPTION: SEQ ID NO:224:

```
Gly His Thr Cys Tyr Ile Ser Asp Ile Glu Phe Thr Asp Asn Ala His
1               5                  10                  15

Ile Leu Thr Ala Ser Gly Asp Met Thr Cys Ala Leu Trp Asp
                20                  25                  30
```

(2) INFORMATION FOR SEQ ID NO:225:

(i) SEQUENCE CHARACTERISTICS:
        (A) LENGTH: 37 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: STE4-YEAST rIII, Fig. 44

(xi) SEQUENCE DESCRIPTION: SEQ ID NO:225:

Asp His Leu Gly Asp Val Leu Ala Leu Ala Ile Pro Glu Glu Pro Asn
1               5                   10                  15

Leu Glu Asn Ser Ser Asn Thr Phe Ala Ser Cys Gly Ser Asp Gly Tyr
            20                  25                  30

Thr Tyr Ile Trp Asp
        35

(2) INFORMATION FOR SEQ ID NO:226:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: STE4-YEAST rIV, Fig. 44

(xi) SEQUENCE DESCRIPTION: SEQ ID NO:226:

Leu Asp Asn Gln Gly Val Val Ser Leu Asp Phe Ser Ala Ser Gly Arg
1               5                   10                  15

Leu Met Tyr Ser Cys Tyr Thr Asp Ile Gly Cys Val Val Trp Asp
            20                  25                  30

(2) INFORMATION FOR SEQ ID NO:227:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: STE4-YEAST rV, Fig. 44

(xi) SEQUENCE DESCRIPTION: SEQ ID NO:227:

Gly His Gly Gly Arg Val Thr Gly Val Arg Ser Ser Pro Asp Gly Leu
1               5                   10                  15

Ala Val Cys Thr Gly Ser Trp Asp Ser Thr Met Lys Ile Trp Ser
            20                  25                  30

```
(2) INFORMATION FOR SEQ ID NO:228:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: TRNSCRPTION FCTR TIIF rI, Fig. 45

(xi) SEQUENCE DESCRIPTION: SEQ ID NO:228:

Gly His Thr Gly Pro Val Tyr Arg Cys Ala Phe Ala Pro Glu Met Asn
1               5                   10                  15

Leu Leu Leu Ser Cys Ser Glu Asp Ser Thr Ile Arg Leu Trp Ser
            20                  25                  30

(2) INFORMATION FOR SEQ ID NO:229:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: TRNSCRPTION FCTR TIIF rII, Fig. 45

(xi) SEQUENCE DESCRIPTION: SEQ ID NO:229:

Gly His Val Tyr Pro Val Trp Asp Val Arg Phe Ala Pro His Gly Tyr
1               5                   10                  15

Tyr Phe Val Ser Cys Ser Tyr Asp Lys Thr Ala Arg Leu Trp Ala
            20                  25                  30

(2) INFORMATION FOR SEQ ID NO:230:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: TRNSCRPTION FCTR TIIF rIII, Fig. 45

(xi) SEQUENCE DESCRIPTION: SEQ ID NO:230:

Gly His Leu Ser Asp Val Asp Cys Val Gln Phe His Pro Asn Ser Asn
1               5                   10                  15

Tyr Val Ala Thr Gly Ser Ser Asp Arg Thr Val Arg Leu Trp Asp
            20                  25                  30

(2) INFORMATION FOR SEQ ID NO:231:

(i) SEQUENCE CHARACTERISTICS:
        (A) LENGTH: 31 amino acids
```

(B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: TRNSCRPTION FCTR TIIF rIV, Fig. 45

(xi) SEQUENCE DESCRIPTION: SEQ ID NO:231:

Gly His Lys Gly Ser Val Ser Ser Leu Ala Phe Ser Ala Cys Gly Arg
1               5                   10                  15

Tyr Leu Ala Ser Gly Ser Val Asp His Asn Ile Ile Ile Trp Asp
            20                  25                  30

(2) INFORMATION FOR SEQ ID NO:232:

(i) SEQUENCE CHARACTERISTICS:
            (A) LENGTH: 31 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: TRNSCRPTION FCTR TIIF rV, Fig. 45

(xi) SEQUENCE DESCRIPTION: SEQ ID NO:232:

Arg His Thr Ser Thr Val Thr Thr Ile Thr Phe Ser Arg Asp Gly Thr
1               5                   10                  15

Val Leu Ala Ala Ala Gly Leu Asp Asn Asn Leu Thr Leu Trp Asp
            20                  25                  30

(2) INFORMATION FOR SEQ ID NO:233:

(i) SEQUENCE CHARACTERISTICS:
            (A) LENGTH: 31 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: TUP1 rI, Fig. 46

(xi) SEQUENCE DESCRIPTION: SEQ ID NO:233:

Ser Ser Asp Leu Tyr Ile Arg Ser Val Cys Phe Ser Pro Asp Gly Lys
1               5                   10                  15

Phe Leu Ala Thr Gly Ala Glu Asp Arg Leu Ile Arg Ile Trp Asp
            20                  25                  30

(2) INFORMATION FOR SEQ ID NO:234:

(i) SEQUENCE CHARACTERISTICS:
            (A) LENGTH: 31 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: TUP1 rII, Fig. 46

(xi) SEQUENCE DESCRIPTION: SEQ ID NO:234:

Gly His Glu Gln Asp Ile Tyr Ser Leu Asp Tyr Phe Pro Ser Gly Asp
1               5                   10                  15

Lys Leu Val Ser Gly Ser Gly Asp Arg Thr Val Arg Ile Trp Asp
            20                  25                  30

(2) INFORMATION FOR SEQ ID NO:235:

(i) SEQUENCE CHARACTERISTICS:
             (A) LENGTH: 31 amino acids
             (B) TYPE: amino acid
             (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: TUP1 rIII, Fig. 46

(xi) SEQUENCE DESCRIPTION: SEQ ID NO:235:

Ile Glu Asp Gly Val Thr Thr Val Ala Val Ser Pro Gly Asp Gly Lys
1               5                   10                  15

Tyr Ile Ala Ala Gly Ser Leu Asp Arg Ala Val Arg Val Trp Asp
            20                  25                  30

(2) INFORMATION FOR SEQ ID NO:236:

(i) SEQUENCE CHARACTERISTICS:
             (A) LENGTH: 31 amino acids
             (B) TYPE: amino acid
             (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: TUP1 rIV, Fig. 46

(xi) SEQUENCE DESCRIPTION: SEQ ID NO:236:

Gly His Lys Asp Ser Val Tyr Ser Val Val Phe Thr Arg Asp Gly Gln
1               5                   10                  15

Ser Val Val Ser Gly Ser Leu Asp Arg Ser Val Lys Leu Trp Asn
            20                  25                  30

(2) INFORMATION FOR SEQ ID NO:237:

(i) SEQUENCE CHARACTERISTICS:
             (A) LENGTH: 31 amino acids
             (B) TYPE: amino acid
             (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: TUP1 rV, Fig. 46

(xi) SEQUENCE DESCRIPTION: SEQ ID NO:237:

Gly His Lys Asp Phe Val Leu Ser Val Ala Thr Thr Gln Asn Asp Glu
1               5                   10                  15
Tyr Ile Leu Ser Gly Ser Lys Asp Arg Gly Val Leu Phe Trp Asp
            20                  25                  30

(2) INFORMATION FOR SEQ ID NO:238:

(i) SEQUENCE CHARACTERISTICS:
        (A) LENGTH: 22 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: TUP1 HOMOLOG rI, Fig. 47

(xi) SEQUENCE DESCRIPTION: SEQ ID NO:238:

Asp Phe Ser Asp Asp Cys Arg Ile Ala Ala Ala Gly Phe Gln Asp Ser
1               5                   10                  15
Tyr Ile Lys Ile Trp Ser
            20

(2) INFORMATION FOR SEQ ID NO:239:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: TUP1 HOMOLOG rII, Fig. 47

(xi) SEQUENCE DESCRIPTION: SEQ ID NO:239:

Gly His Ser Gly Thr Val Tyr Ser Thr Ser Phe Ser Pro Asp Asn Lys
1               5                   10                  15
Tyr Leu Leu Ser Gly Ser Glu Asp Lys Thr Val Arg Leu Trp Ser
            20                  25                  30

(2) INFORMATION FOR SEQ ID NO:240:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: TUP1 HOMOLOG rIII, Fig. 47

(xi) SEQUENCE DESCRIPTION: SEQ ID NO:240:

Gly His Asn His Pro Val Trp Asp Val Ser Phe Ser Pro Leu Gly His
1               5                   10                  15

Tyr Phe Ala Thr Ala Ser His Asp Gln Thr Ala Arg Leu Trp Ser
                20                  25                  30

(2) INFORMATION FOR SEQ ID NO:241:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: TUP1 HOMOLOG rIV, Fig. 47

(xi) SEQUENCE DESCRIPTION: SEQ ID NO:241:

Gly His Leu Asn Asp Val Asp Cys Val Ser Phe His Pro Asn Gly Cys
1               5                   10                  15

Tyr Val Phe Thr Gly Ser Ser Asp Lys Thr Cys Arg Met Trp Asp
                20                  25                  30

(2) INFORMATION FOR SEQ ID NO:242:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: TUP1 HOMOLOG rV, Fig. 47

(xi) SEQUENCE DESCRIPTION: SEQ ID NO:242:

Gly His Thr Ala Pro Val Ile Ser Ile Ala Val Cys Pro Asp Gly Arg
1               5                   10                  15

Trp Leu Ser Thr Gly Ser Glu Asp Gly Ile Ile Asn Val Trp Asp
                20                  25                  30

(2) INFORMATION FOR SEQ ID NO:243:

(i) SEQUENCE CHARACTERISTICS:
        (A) LENGTH: 32 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: TUP1 HOMOLOG rVI, Fig. 47

(xi) SEQUENCE DESCRIPTION: SEQ ID NO:243:

Gly His Gly Lys Asn Ala Ile Tyr Ser Leu Ser Tyr Ser Lys Glu Gly
1               5                   10                  15

```
Asn Val Leu Ile Ser Gly Gly Ala Asp His Thr Val Arg Val Trp Asp
            20                  25                  30
```

(2) INFORMATION FOR SEQ ID NO:244:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: YCU7 rI, Fig. 48

(xi) SEQUENCE DESCRIPTION: SEQ ID NO:244:

```
Gly His Phe Asp Ser Thr Asn Ser Leu Ala Tyr Ser Pro Asp Gly Ser
1               5                   10                  15
Arg Val Val Thr Ala Ser Glu Asp Gly Lys Ile Lys Val Trp Asp
            20                  25                  30
```

(2) INFORMATION FOR SEQ ID NO:245:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: YCU7 rII, Fig. 48

(xi) SEQUENCE DESCRIPTION: SEQ ID NO:245:

```
Glu His Thr Ser Ser Val Thr Ala Val Gln Phe Ala Lys Arg Gly Gln
1               5                   10                  15
Val Met Phe Ser Ser Ser Leu Asp Gly Thr Val Arg Ala Trp Asp
            20                  25                  30
```

(2) INFORMATION FOR SEQ ID NO:246:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: YCU7 rIII, Fig. 48

(xi) SEQUENCE DESCRIPTION: SEQ ID NO:246:

```
Arg Ile Gln Phe Asn Cys Leu Ala Val Asp Pro Ser Gly Glu Val Val
1               5                   10                  15
Cys Ala Gly Ser Leu Asp Asn Phe Asp Ile His Val Trp Ser
            20                  25                  30
```

(2) INFORMATION FOR SEQ ID NO:247:

(i) SEQUENCE CHARACTERISTICS:
       (A) LENGTH: 31 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: YCU7 rIV, Fig. 48

(xi) SEQUENCE DESCRIPTION: SEQ ID NO:247:

```
Gly His Glu Gly Pro Val Ser Cys Leu Ser Phe Ser Gln Glu Asn Ser
1               5                  10                  15
Val Leu Ala Ser Ala Ser Trp Asp Lys Thr Ile Arg Ile Trp Ser
            20                  25                  30
```

(2) INFORMATION FOR SEQ ID NO:248:

(i) SEQUENCE CHARACTERISTICS:
       (A) LENGTH: 32 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: YCW2 PROTEIN rI, Fig. 49

(xi) SEQUENCE DESCRIPTION: SEQ ID NO:248:

```
Gly His Gly Ser Thr Ile Leu Cys Ser Ala Phe Ala Pro His Thr Ser
1               5                  10                  15
Ser Arg Met Val Thr Gly Ala Gly Asp Asn Thr Ala Arg Ile Trp Asp
            20                  25                  30
```

(2) INFORMATION FOR SEQ ID NO:249:

(i) SEQUENCE CHARACTERISTICS:
       (A) LENGTH: 31 amino acids
       (B) TYPE: amino acid
       (D) TOPOLOGY: unknown (ii) MOLECULE TYPE: peptide (iii) HYPOTHETICAL: NO (iv) ANTI-SENSE: NO (vi) ORIGINAL SOURCE:
       (C) INDIVIDUAL ISOLATE: YCW2 PROTEIN rII, Fig. 49

(xi) SEQUENCE DESCRIPTION: SEQ ID NO:249:

```
Gly His Tyr Asn Trp Val Leu Cys Val Ser Trp Ser Pro Asp Gly Glu
1               5                  10                  15
Val Ile Ala Thr Gly Ser Met Asp Asn Thr Ile Arg Leu Trp Asp
            20                  25                  30
```

(2) INFORMATION FOR SEQ ID NO:250:

(i) SEQUENCE CHARACTERISTICS:

(A) LENGTH: 38 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: YCW2 PROTEIN rIII, Fig. 49

(xi) SEQUENCE DESCRIPTION: SEQ ID NO:250:

Gly His Ser Lys Trp Ile Thr Ser Leu Ser Trp Glu Pro Ile His Leu
1               5                   10                  15

Val Lys Pro Gly Ser Lys Pro Arg Leu Ala Ser Ser Lys Asp Gly
            20                  25                  30

Thr Ile Lys Ile Trp Asp
        35

(2) INFORMATION FOR SEQ ID NO:251:

(i) SEQUENCE CHARACTERISTICS:
        (A) LENGTH: 30 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: YCW2 PROTEIN rIV, Fig. 49

(xi) SEQUENCE DESCRIPTION: SEQ ID NO:251:

Gly His Thr Asn Ser Val Ser Cys Val Lys Trp Gly Gly Gln Gly Leu
1               5                   10                  15

Leu Tyr Ser Gly Ser His Asp Arg Thr Val Arg Val Trp Asp
            20                  25                  30

(2) INFORMATION FOR SEQ ID NO:252:

(i) SEQUENCE CHARACTERISTICS:
        (A) LENGTH: 26 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: YCW2 PROTEIN rV, Fig. 49

(xi) SEQUENCE DESCRIPTION: SEQ ID NO:252:

Lys Ile Cys Lys Lys Asn Gly Asn Ser Glu Glu Met Met Val Thr Ala
1               5                   10                  15

Ser Asp Asp Tyr Thr Met Phe Leu Trp Asn
            20                  25

(2) INFORMATION FOR SEQ ID NO:253:

(i) SEQUENCE CHARACTERISTICS:
        (A) LENGTH: 25 amino acids (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: YCW2 PROTEIN rVI, Fig. 49

(xi) SEQUENCE DESCRIPTION: SEQ ID NO:253:

Asn His Val Ala Phe Ser Pro Asp Gly Arg Tyr Ile Val Ser Ala Ser
1               5                   10                  15

Phe Asp Asn Ser Ile Lys Leu Trp Asp
            20                  25

(2) INFORMATION FOR SEQ ID NO:254:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: YCW2 PROTEIN rVII, Fig. 49

(xi) SEQUENCE DESCRIPTION: SEQ ID NO:254:

Gly His Ile Ala Ser Val Tyr Gln Val Ala Trp Ser Ser Asp Cys Arg
1               5                   10                  15

Leu Leu Val Ser Cys Ser Lys Asp Thr Thr Leu Lys Val Trp Asp
            20                  25                  30

(2) INFORMATION FOR SEQ ID NO:255:

(i) SEQUENCE CHARACTERISTICS:
        (A) LENGTH: 35 amino acids
        (B) TYPE: amino acid
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: YCW2 PROTEIN rVIII, Fig. 49

(xi) SEQUENCE DESCRIPTION: SEQ ID NO:255:

Ser Val Asp Leu Pro Gly Ile Lys Thr Lys Leu Tyr Val Asp Trp Ser
1               5                   10                  15

Val Asp Gly Lys Arg Val Cys Ser Gly Gly Lys Asp Lys Met Val Arg
            20                  25                  30

Leu Trp Thr
        35

(2) INFORMATION FOR SEQ ID NO:256:

(i) SEQUENCE CHARACTERISTICS:
        (A) LENGTH: 29 amino acids
        (B) TYPE: amino acid (D) TOPOLOGY: unknown (ii) MOLECULE TYPE: peptide (iii) HYPOTHETICAL: NO (iv) ANTI-SENSE: NO (vi) ORIGINAL SOURCE:
          (C) INDIVIDUAL ISOLATE: YKL525 rI, Fig. 50

(xi) SEQUENCE DESCRIPTION: SEQ ID NO:256:

Leu His Leu Tyr Ala Pro Val Phe Tyr Ser Asp Val Phe Arg Val Phe
1               5                   10                  15

Met Glu His Ala Leu Asp Ile Leu Asp Ala Asn Trp Ser
            20                  25

(2) INFORMATION FOR SEQ ID NO:257:

(i) SEQUENCE CHARACTERISTICS:
          (A) LENGTH: 32 amino acids
          (B) TYPE: amino acid
          (D) TOPOLOGY: unknown (ii) MOLECULE TYPE: peptide (iii) HYPOTHETICAL: NO (iv) ANTI-SENSE: NO (vi) ORIGINAL SOURCE:
          (C) INDIVIDUAL ISOLATE: YKL525 rII, Fig. 50

(xi) SEQUENCE DESCRIPTION: SEQ ID NO:257:

Val His Pro Asp Phe Val Thr Ser Ala Ile Phe Phe Pro Asn Asp Asp
1               5                   10                  15

Arg Phe Ile Ile Thr Gly Cys Leu Asp His Arg Cys Arg Leu Trp Ser
            20                  25                  30

(2) INFORMATION FOR SEQ ID NO:258:

(i) SEQUENCE CHARACTERISTICS:
          (A) LENGTH: 31 amino acids
          (B) TYPE: amino acid
          (D) TOPOLOGY: unknown (ii) MOLECULE TYPE: peptide (iii) HYPOTHETICAL: NO (iv) ANTI-SENSE: NO (vi) ORIGINAL SOURCE:
          (C) INDIVIDUAL ISOLATE: yrb 1410 yeast rI, Fig. 51

(xi) SEQUENCE DESCRIPTION: SEQ ID NO:258:

Gly His Asn His Pro Val Trp Asp Val Ser Phe Ser Pro Leu Gly His
1               5                   10                  15

Tyr Phe Ala Thr Ala Ser His Asp Gln Thr Ala Arg Leu Trp Ser
            20                  25                  30

(2) INFORMATION FOR SEQ ID NO:259:

(i) SEQUENCE CHARACTERISTICS:
          (A) LENGTH: 31 amino acids
          (B) TYPE: amino acid
          (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: yrb 1410 yeast rII, Fig. 51

(xi) SEQUENCE DESCRIPTION: SEQ ID NO:259:

Gly His Leu Asn Asp Val Asp Cys Val Ser Phe His Pro Asn Gly Cys
1               5                   10                  15

Tyr Val Phe Thr Gly Ser Ser Asp Lys Thr Cys Arg Met Trp Asp
                20                  25                  30

(2) INFORMATION FOR SEQ ID NO:260:

(i) SEQUENCE CHARACTERISTICS:
            (A) LENGTH: 31 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: yrb 1410 yeast rIII, Fig. 51

(xi) SEQUENCE DESCRIPTION: SEQ ID NO:260:

Gly His Thr Ala Pro Val Ile Ser Ile Ala Val Cys Pro Asp Gly Arg
1               5                   10                  15

Trp Leu Ser Thr Gly Ser Glu Asp Gly Ile Ile Asn Val Trp Asp
                20                  25                  30

(2) INFORMATION FOR SEQ ID NO:261:

(i) SEQUENCE CHARACTERISTICS:
            (A) LENGTH: 32 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
             (C) INDIVIDUAL ISOLATE: yrb 1410 yeast rIV, Fig. 51

(xi) SEQUENCE DESCRIPTION: SEQ ID NO:261:

Gly His Gly Lys Asn Ala Ile Tyr Ser Leu Ser Tyr Ser Lys Glu Gly
1               5                   10                  15

Asn Val Leu Ile Ser Gly Gly Ala Asp His Thr Val Arg Val Trp Asp
                20                  25                  30

(2) INFORMATION FOR SEQ ID NO:262:

(i) SEQUENCE CHARACTERISTICS:
            (A) LENGTH: 34 amino acids
            (B) TYPE: amino acid
            (D) TOPOLOGY: unknown (ii) MOLECULE TYPE: peptide (iii) HYPOTHETICAL: NO (iv) ANTI-SENSE: NO (vi) ORIGINAL SOURCE:
            (C) INDIVIDUAL ISOLATE: WD40 Consensus Sequence (xi) SEQUENCE DESCRIPTION: SEQ ID NO:262:

Gly His Ser Ala Ala Leu Ala Ala Leu Ala Leu Ser Pro Asp Ala Ala
1               5                   10                  15

Ala Ala Ala Leu Ala Ser Gly Ala Arg Asp Ala Thr Leu Arg Leu Trp
                20                  25                  30

Asp Leu (2) INFORMATION FOR SEQ ID NO:263:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (vi) ORIGINAL SOURCE:
        (C) INDIVIDUAL ISOLATE: WRTAA peptide (xi) SEQUENCE DESCRIPTION: SEQ ID NO:263:

Trp Arg Thr Ala Ala
1               5

(2) INFORMATION FOR SEQ ID NO:264:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (vi) ORIGINAL SOURCE:
        (C) INDIVIDUAL ISOLATE: WRTAV peptide (xi) SEQUENCE DESCRIPTION: SEQ ID NO:264:

Trp Arg Thr Ala Val
1               5

(2) INFORMATION FOR SEQ ID NO:265:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO -continued

```
    (vi) ORIGINAL SOURCE:
        (C) INDIVIDUAL ISOLATE: WRTA peptide (xi) SEQUENCE DESCRIPTION: SEQ ID NO:265:

Trp Arg Thr Ala
1
```

US 6,423,684 B1

WD-40 DERIVED PEPTIDES AND USES THEREOF

This application is a continuation-in-part of the parent application Ser. No. 08/190,802 filed on Feb. 1, 1994 now U.S. Pat. No. 5,519,003.

FIELD OF THE INVENTION the present invention relates in general to composition and methods of modulating the function of proteins involved in protein-protein interactions. It relates more specifically to modulating the function of a first protein of a pair of interacting proteins wherein a second protein of the pair contains a "WD-40" or "β-transducin" amino acid repeat motif.

BACKGROUND ART

Many intracellular processes are carried out or regulated by multi-subunit protein complexes that become active or repressed by the association or dissociation of individual polypeptide subunits.

One such group or family of proteins is related to the subunit of transducin. Members of this group are all at least somewhat homologous to the β-subunit of transducin at the amino acid level, and contain a varying number of repeats of a particular motif identified in β-transducin. The repeats have been termed "β-transducin", or "WD-40" repeats (Fong, et al.).

Among the members of this protein family (Duronio, et al.) are the Gβ subunits that couple many receptors to their intracellular effector molecules, Gβ/γ subunits that anchor another protein kinase (the β-adrenergic receptor kinase, βARK), DNA binding proteins and yeast cell cycle proteins. All of these require a transient protein-protein interaction for their function. However, the sequences at the interface of these proteins and their partners have not been identified.

The following are the references cited above and throughout the specification:

U.S. PATENT DOCUMENTS

Crea, R., U.S. Pat. No. 4,888,286, issued Dec. 19, 1989.
Eaton, M. A. W., et al., U.S. Pat. No. 4,719,180, issued Jan. 12, 1988.
Yoshio, T., et al., U.S. Pat. No. 4,849,350, issued Jul. 18, 1989.

OTHER REFERENCES

Ausubel, F. M., et al., *Current Protocols in Molecular Biology*, John Wiley and Sons, Inc., Media Pa.
Bohinski, R. C., *Modern Concepts in Biochemistry*, Second Edition, Allyn and Bacon, Inc.
Dayhoff, M. O., in *Atlas of Protein Sequence and Structure* (1972) Vol. 5, National Biomedical Research Foundation, pp. 101–110, and Supplement 2 to this volume, pp. 1–10.
Duronio, R. J., et al., (1992) *Proteins: Structure, Function, and Genetics* 13:41–56.
Escobedo, J. A., et al., *Mol. Cell. Biol.*, 11:1125–1132 (1991).
Fong, et al., (1986) *Proc Natl Acad Sci USA* 83:2162–2166.
Hari, et al., *Endocrinology*, 120:829–831 (1987).
Kleuss, C., et al., *Science* 259:832–834 (1993).
Makowske, O. M. and Rosen, O. M. *J. Biol. Chem.* 264:16155–16159 (1989)
Maniatis, T., et al., *Molecular Cloning: A Laboratory Manual*, Cold Spring Harbor Laboratory (1982).
Miller, J. F., et al., *Nature* (London) 216:659–63 (1969).
Mochly-Rosen, D., and Koshland, D. E., Jr. *J. Biol. Chem.* 262:2291–2297 (1987).
Mochly-Rosen, et al., *Molec. Biol. Cell.* 1:693–706 (1990).
Mochly-Rosen, D., et al., *Proc. Natl. Acad. Sci. USA* 88:3997–4000 (1991).
Orr, J. W., et al., *J. Biol. Chem.* 267, 16155–16159 (1992)
Pitcher, J., et al., *Science* 257:1264–1267 (1992).
Reiner, et al., *Nature* 364:717–721 (1993).
Schulz, G. E. and R. H. Schirmer., *Principles of Protein Structure*, Springer-Verlag.
Smith, B. L. and Mochly-Rosen, D. *Biochem. Biophys. Res. Commun.* 188:1235–1240 (1992).
Smith, D. B., et al., *Gene* 67:31 (1988).
Stith, B. J. and J. L. Maller. *Exp. Cell. Res.* 169:514–523 (1987).
Wolf, M. and N. Sahyoun, *Chem.*, 261:13327–13332 (1986).

DISCLOSURE OF THE INVENTION

The invention includes, in one aspect, a polypeptide composition effective to alter the activity of a first protein, such as protein kinase C, or β-adrenergic receptor kinase (βARK). The polypeptide blocks or inhibits an interaction, such as a binding interaction, between the first protein and a second protein containing a WD-40 region.

The polypeptide contains between 4 and 50 amino acids whose sequence is the same as a sequence of the same length in the WD-40 region of the second protein.

The polypeptide may block the binding of the first to the second protein, or may be an agonist or antagonist of the first protein. The WD-40 region preferably has an amino acid sequence homologous or identical to the sequences defined by SEQ ID NO:76–261.

In a second embodiment, the invention includes a method of altering the activity of the first protein of the type defined above. The method includes selecting a polypeptide having between 4 and 50 amino acids whose sequence is the same as a sequence of the same length in the WD-40 region of the second protein, and contacting the polypeptide with the first protein under conditions which allow the formation of a complex between the polypeptide and the first protein, where this interaction alters the activity of the first protein.

In one embodiment, the contacting is effective to inhibit the interaction between the first and second proteins. In another embodiment, the contacting is effective to stimulate the activity of the first protein.

In still another embodiment, the contacting is effective to inhibit the activity of the first protein.

The polypeptide preferably has an amino acid sequence homologous or identical to the sequences defined by SEQ ID NO:76–261.

In a more specific aspect of the invention, the invention includes a polypeptide composition effective to alter the activity of protein kinase C, where the protein kinase C interacts with a second protein, and the second protein contains at least one WD-40 region. The polypeptide has between 4 and 50 amino acids whose sequence is the same as a sequence of the same length in the WD-40 region of the second protein.

In a preferred embodiment, the second protein is a receptor for activated protein kinase C, and has the sequence represented by SEQ ID NO:27.

In other specific embodiments, the polypeptide is (i) an agonist of protein kinase C, and the polypeptide has the sequence represented by SEQ ID NO:7; (ii) an antagonist of the activity of protein kinase C; and/or (iii) an inhibitor of the interaction between protein kinase C and the second protein. In the latter embodiment, the polypeptide has sequence corresponding to SEQ ID NO:4 or SEQ ID NO:7.

The WD-40 region preferably has an amino acid sequence homologous or identical to SEQ ID NO:69–75.

In a related embodiment, the invention includes a method of altering the activity of a protein kinase C that interacts with a second protein, where said second protein contains at least one WD-40 region.

The method includes selecting a polypeptide having between 4 and 50 amino acids whose sequence is the same as a sequence of the same length in the WD-40 region of the second protein, and contacting the polypeptide with the protein kinase C under conditions which allow the formation of a complex between the polypeptide and the protein kinase C, where said interaction alters the activity of said protein kinase C.

Other aspects of the invention include the polypeptide compositions of the invention wherein said polypeptide is coupled to a solid support, as well as a method to bind selectively said first protein which method comprises contacting a sample putatively containing said first protein with the polypeptide composition bound to solid support and removing any unbound components of the sample from said composition.

In still another aspect, the invention relates to a method to assess the interaction of a first protein with a polypeptide represented by an amino acid sequence contained in a second protein, wherein said second protein contains at least one WD-40 region, which method comprises contacting a sample containing said first protein with a polypeptide composition wherein the polypeptide has between 4 and 50 amino acids whose sequence is the same as the sequence of the same length in the WD-40 region of the second protein, and observing any interaction of the first protein with said polypeptide composition. The invention also concerns a method to assess the ability of a candidate compound to bind a first protein which method comprises contacting said first protein with a polypeptide composition which binds said first protein, wherein the polypeptide of said composition has between 4 and 50 amino acids whose sequence is the same as a sequence of the same length in a WD-40 region of a second protein which interacts with said first protein, in the presence and absence of said candidate compound; and measuring the binding of said polypeptide in the presence and in the absence of said candidate, wherein decreased binding of the polypeptide in the presence as opposed to the absence of said candidate indicates that said candidate binds to said first protein.

In still another aspect, the invention is directed to recombinant materials for the production of the polypeptides of the invention and methods for their production.

These and other objects and features of the invention will become more fully apparent when the following detailed description of the invention is read in conjunction with the accompanying drawings.

BRIEF DESCRIPTION OF THE FIGURES

FIG. 1A shows the cDNA sequence of rat brain RACK1.

FIG. 1C shows the amino acid sequence of RACK1, aligned to show the seven WD-40 repeats represented in the molecule.

FIG. 11 shows the amino acid sequence of the 56 kDa human protein with the WD-40 repeats aligned and putative binding peptide regions delineated by a box.

FIG. 12 shows the amino acid sequence of the AAC-rich protein with the WD-40 repeats aligned and putative binding peptide regions delineated by a box.

FIG. 13 shows the amino acid sequence of the B-TRCP protein with the WD-40 repeats aligned and putative binding peptide regions delineated by a box.

FIG. 14 shows the amino acid sequence of the Beta-prime-COP protein with the WD-40 repeats aligned and putative binding peptide regions delineated by a box.

FIG. 15 shows the amino acid sequence of the CDC4 protein with the WD-40 repeats aligned and putative binding peptide regions delineated by a box.

FIG. 16 shows the amino acid sequence of the Chlam-3 protein with the WD-40 repeats aligned and putative binding peptide regions delineated by a box.

FIG. 17 shows the amino acid sequence of the COP-1 protein with the WD-40 repeats aligned and putative binding peptide regions delineated by a box.

FIG. 18 shows the amino acid sequence of the CORO protein with the WD-40 repeats aligned and putative binding peptide regions delineated by a box.

FIG. 19 shows the amino acid sequence of the Coronin p55 protein with the WD-40 repeats aligned and putative binding peptide regions delineated by a box.

FIG. 20 shows the amino acid sequence of the Cstf 50 kDa protein with the WD-40 repeats aligned and putative binding peptide regions delineated by a box.

FIG. 21 shows the amino acid sequence of the bovine G-beta-1 protein with the WD-40 repeats aligned and putative binding peptide regions delineated by a box.

FIG. 22 shows the amino acid sequence of the bovine G-beta-2 protein with the WD-40 repeats aligned and putative binding peptide regions delineated by a box.

FIG. 23 shows the amino acid sequence of the drosophila G-beta protein with the WD-40 repeats aligned and putative binding peptide regions delineated by a box.

FIG. 24 shows the amino acid sequence of the human G-beta-1 protein with the WD-40 repeats aligned and putative binding peptide regions delineated by a box.

FIG. 25 shows the amino acid sequence of the human G-beta-2 protein with the WD-40 repeats aligned and putative binding peptide regions delineated by a box.

FIG. 26 shows the amino acid sequence of the mouse G-beta protein with the WD-40 repeats aligned and putative binding peptide regions delineated by a box.

FIG. 27 shows the amino acid sequence of the drosophila groucho protein with the WD-40 repeats aligned and putative binding peptide regions delineated by a box.

FIG. 28 shows the amino acid sequence of the squid GTP-binding protein with the WD-40 repeats aligned and putative binding peptide regions delineated by a box.

FIG. 29 shows the amino acid sequence of the HSIEF 930 protein with the WD-40 repeats aligned and putative binding peptide regions delineated by a box.

FIG. 30 shows the amino acid sequence of the human 12.3 protein with the WD-40 repeats aligned and putative binding peptide regions delineated by a box.

FIG. 31 shows the amino acid sequence of the human IEF-7442 protein with the WD-40 repeats aligned and putative binding peptide regions delineated by a box.

FIG. 32 shows the amino acid sequence of the insulin-like growth factor binding protein complex with the WD-40 repeats aligned and putative binding peptide regions delineated by a box.

FIG. 33 shows the amino acid sequence of the rat insulin-like growth factor binding protein with the WD-40 repeats aligned and putative binding peptide regions delineated by a box.

FIG. 34 shows the amino acid sequence of the human LIS1 protein with the WD-40 repeats aligned and putative binding peptide regions delineated by a box.

FIG. 35 shows the amino acid sequence of the MD6 protein with the WD-40 repeats aligned and putative binding peptide regions delineated by a box.

FIG. 36 shows the amino acid sequence of the yeast MSI1 protein with the WD-40 repeats aligned and putative binding peptide regions delineated by a box.

FIG. 37 shows the amino acid sequence of the mouse pc326 MUS protein with the WD-40 repeats aligned and putative binding peptide regions delineated by a box.

FIG. 38 shows the amino acid sequence of the ORD RB1 protein with the WD-40 repeats aligned and putative binding peptide regions delineated by a box.

FIG. 39 shows the amino acid sequence of the periodic trp protein with the WD-40 repeats aligned and putative binding peptide regions delineated by a box.

FIG. 40 shows the amino acid sequence of the PLAP protein with the WD-40 repeats aligned and putative binding peptide regions delineated by a box.

FIG. 41 shows the amino acid sequence of the retinoblastoma binding protein with the WD-40 repeats aligned and putative binding peptide regions delineated by a box.

FIG. 42 shows the amino acid sequence of the S253 protein with the WD-40 repeats aligned and putative binding peptide regions delineated by a box.

FIG. 43 shows the amino acid sequence of the SOF1 protein with the WD-40 repeats aligned and putative binding peptide regions delineated by a box.

FIG. 44 shows the amino acid sequence of the STE4 yeast protein with the WD-40 repeats aligned and putative binding peptide regions delineated by a box.

FIG. 45 shows the amino acid sequence of the TF1 transcription factor protein with the WD-40 repeats aligned and putative binding peptide regions delineated by a box.

FIG. 46 shows the amino acid sequence of the TUP1 protein with the WD-40 repeats aligned and putative binding peptide regions delineated by a box.

FIG. 47 shows the amino acid sequence of the TUP1 homolog protein with the WD-40 repeats aligned and putative binding peptide regions delineated by a box.

FIG. 48 shows the amino acid sequence of the YCU7 protein with the WD-40 repeats aligned and putative binding peptide regions delineated by a box.

FIG. 49 shows the amino acid sequence of the YCW2 protein with the WD-40 repeats aligned and putative binding peptide regions delineated by a box.

FIG. 50 shows the amino acid sequence of the YKL25 protein with the WD-40 repeats aligned and putative binding peptide regions delineated by a box.

FIG. 51 shows the amino acid sequence of the YRB140 protein with the WD-40 repeats aligned and putative binding peptide regions delineated by a box.

DETAILED DESCRIPTION OF THE INVENTION

I. Definitions

Figure 1B:
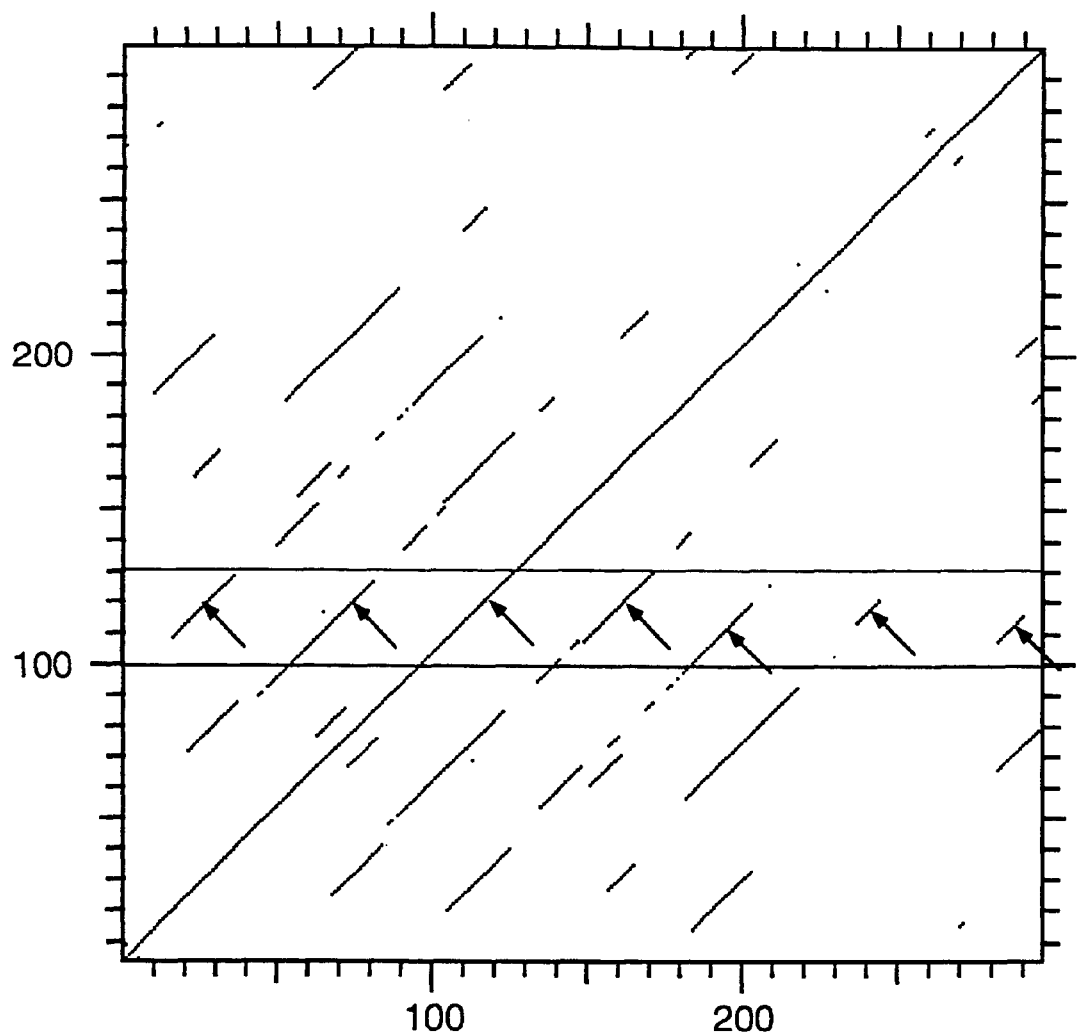
FIG. 1B shows an amino acid self-homology matrix analysis of RACK1.

Unless otherwise indicated, all terms used herein have the same meaning as they would to one skilled in the art of the present invention. Practitioners are particularly directed to *Current Protocols in Molecular Biology* (Ausubel) for definitions and terms of the art.

Abbreviations for amino acid residues are the standard 3-letter and/or 1-letter codes used in the art to refer to one of the 20 common L-amino acids. Likewise, abbreviations for nucleic acids are the standard codes used in the art.

An "amino acid group" refers to a group of amino acids where the group is based on common properties, such as hydrophobicity, charge, or size.

A "conserved set" of amino acids refers to a contiguous sequence of amino acids that is conserved between members of a group of proteins. A conserved set may be anywhere from two to over 50 amino acid residues in length. Typically, a conserved set is between two and ten contiguous residues in length. The individual positions within a conserved set each typically comprise one of several amino acids, selected from an amino acid group(s). In cases where a residue is 100% conserved at a particular position, the conserved set sequence will contain only that residue at that position. For example, for the two peptides WRTAA (SEQ ID NO:263) and WRTAV (SEQ ID NO:264), there are 4 identical positions (WRTA; SEQ ID NO:265) and one position where the residue is an "A" or a "V".

Proteins are typically long chains of amino acid based polyamides (polypeptides) capable of creating secondary and tertiary structure. Proteins may be composed of one, two or more polypeptide chains and may further contain some other type of substance in association with the polypeptide chain(s), such as metal ions or carbohydrates. The size of proteins covers a rather wide range from ~5,000 to several hundred thousand g/mole. The 5,000 figure corresponds to the presence or roughly 40–45 amino acids.

Unless otherwise indicated, the sequence for proteins and peptides is given in the order from the amino terminus to the carboxyl terminus. Similarly, the sequence for nucleic acids is given in the order from the 5' end to the 3' end.

The term "interacting proteins" refers to a pair of polypeptides that can form a stably-associated complex due to, for example, electrostatic, hydrophobic, ionic and/or hydrogen-bond interactions under physiological conditions.

Proteins smaller than about 5,000 g/mole are typically referred to as polypeptides or simply peptides (Bohinski).

Two amino acid sequences or two nucleotide sequences are considered homologous (as this term is preferably used in this specification) if they have an alignment score of >5 (in standard deviation units) using the program ALIGN with the mutation gap matrix and a gap penalty of 6 or greater (Dayhoff). The two sequences (or parts thereof) are more preferably homologous if their amino acids are greater than or equal to 50%, more preferably 70%, still more preferably 80%, identical when optimally aligned using the ALIGN program mentioned above.

A peptide or peptide fragment is "derived from" a parent peptide or polypeptide if it has an amino acid sequence that is identical or homologous to the amino acid sequence of the parent peptide or polypeptide. Homologous peptides are defined above. Exemplary derived peptides are peptide rIII (SEQ ID NO:4) and peptide rVI (SEQ ID NO:7), which are derived from the third and seventh WD-40 repeats of RACK1 (SEQ ID NO:27), respectively.

The term "expression vector" refers to vectors that have the ability to incorporate and express heterologous DNA fragments in a foreign cell. Many prokaryotic and eukaryotic expression vectors are commercially available. Selection of appropriate expression vectors is within the knowledge of those having skill in the art.

The term "PKC" refers to protein kinase C, or C-kinase.
The term "RACK" refers to receptor for activated C-kinase.
The term "PS" refers to phosphatidylserine.
The term "DG" refers to diacylglycerol.
The term "PL" refers to phospholipids. Phospholipids include both phosphatidylserine and diacylglycerol.
The term "GVBD" refers to germinal vesicle breakdown, a measure of insulin-induced maturation in Xenopus oocytes.
The term "PCR" refers to polymerase chain reaction.
The term "NMR" refers to nuclear magnetic resonance.
The term "βARK" refers to β-adrenergic receptor kinase.

II. General Overview of Invention

The invention relates to interacting proteins, at least one of which contains an amino acid sequence with one or more of the characteristic repeats termed WD-40 (Fong, et al.).

According to one aspect of the invention, the function of a first protein of a pair of interacting proteins may be modulated, altered or disrupted by the addition, to a solution or medium containing the protein, of a peptide having a sequence that is identical or homologous to a part of the sequence of a WD-40 motif-containing repeat present in a second protein of the pair of interacting proteins.

The modulation or disruption of function of the first protein is due to the binding or association of the WD-40-derived peptide, termed "binding peptide", with the first protein. The consequences of the binding or association of the binding peptide with the first protein depend on the sequence of the peptide.

Typically, the presence of the binding peptide will inhibit the binding of the first protein to the second protein. This binding may be assayed in vitro by, for example, an overlay assay, whereby the degree of binding of one protein to another may be assessed. Several adaptations of overlay assays applied to embodiments of the present invention are described herein.

Regardless of whether or not the WD-40-derived peptide affects the association of the first protein with the second protein, the peptide may alter or modulate defined activities of the first protein. These activities may be assayed by a variety of methods in vivo and/or in vitro. The method(s) employed depend on the protein whose activity is being measured.

An exemplary first protein of a pair of interacting proteins is protein kinase C (PKC). Upon activation, PKC interacts with receptors for activated C kinase (RACKs), at least one of which (RACK1) contains WD-40 repeats. Several assays for determining the activity of PKC in the presence and in the absence of peptides derived from the WD-40 region of RACK1 are detailed herein.

Certain "interacting proteins" interact only after one or more of them has been stimulated by an exogenous or endogenous factor(s). For instance, PKC, as shown herein, does not bind to RACK proteins until it has been activated by, for example, phosphatydilserine (PS), diacylglycerol (DG) and calcium. However, peptides derived from WD-40 repeats of a second protein of such a pair may be able to associate with or bind to the first protein even in the absence of activators of the first protein, and in so doing, affect the function of the first protein (e.g. activate, inactivate, potentiate, sensitize, desensitize, alter the specificity, etc.).

Binding peptides derived from WD-40 repeats of a second protein of a pair of interacting proteins, may be useful as specific agonists, antagonists, potentiators of function, and the like, of the first protein of the pair. These properties may make the peptides useful in a number of applications, for example, direct use in therapeutic applications or as lead compounds for the development of other therapeutic agents, e.g., small organic molecules.

III. Advantages of the Invention for the Inhibition of Activated PKC Binding to RACK1

Protein kinase C (PKC) is a family of at least 10 isozymes that share common structures and biochemical characteristics. It has been demonstrated that several isozymes are present within a single cell type, and it has been assumed that individual PKC isozymes are involved in different cellular functions. However, so far, the available activators and inhibitors of PKC do not appear to be isozyme-specific. Therefore, it is currently impossible to determine the role of individual PKC isozymes in normal cellular functions as well as in disease.

PKC activation by, for example, diacylglycerol and calcium, induces the translocation of PKC from a soluble (cytosolic) to a cell particulate (membrane-associated) fraction, as shown in experiments herein (Example 8). Activated PKC is stabilized in the cell particulate fraction by binding to membrane-associated receptors (receptors for activated C-Kinase, or RACKs).

In experiments done in support of the present invention and described herein, a clone (pRACK1) encoding a RACK has been isolated (Example 1). RACK1 belongs to a growing family of proteins that are homologous to the β-subunit of transducin and contain the WD-40 motif (Fong, et al.). It was demonstrated that peptide I (SEQ ID NO:1) binds to purified PKC (see Example 6 and FIG. 4), inhibits the binding of PKC to purified recombinant RACK1 protein (see Example 4 and FIG. 3), and inhibits PKC activity in several in vivo and in vitro assays (see Examples 7–11 and FIGS. 5–9).

Peptide I (SEQ ID NO:1) is homologous to a sequence identified in the sixth WD-40 repeats of RACK1 (see FIG. 1C). A synthetic peptide was prepared based on this sequence (peptide rVI; SEQ ID NO:7; underlined amino acids in repeat VI of FIG. 1C). Six more peptides were also prepared based on the corresponding regions in repeats I–V and VII (peptides rI–rV, rVII; SEQ ID NO:2–6, 8; underlined regions in corresponding repeats, FIG. 1C). Some of the peptides were also found to inhibit the binding of PKC to RACK1 (see Example 4 and FIG. 3). In addition, some of the peptides were found to bind to purified PKC (see Example 6, FIG. 4), partially activate PKC in the absence of other activators (peptide rVI; see Examples 7, 10, 11 and FIGS. 5, 8 and 9, and potentiate the effects of known PKC activators on the enzyme (see Examples 7–9 and FIGS. 5–7).

In Xenopus oocyte maturation studies (see, for instance, Example 7), peptide rVI (SEQ ID NO:7) is an agonist of βPKC. Peptide rIII, while less potent, is also an agonist of PKC; it enhances insulin-induced oocyte maturation at 50 and 500 µM.

In cardiac myocytes, norepinephrine (NE, 2 µM) causes translocation of δ and εPKC isozymes from the cytosolic to the particulate fraction. Introduction into cardiac myocytes of peptide rIII, and to a lesser extent peptide rVI, caused an immediate translocation of δ and εPKC isozymes in the absence of hormone stimulation. This peptide-induced translocation was followed by degradation of δ and εPKC isozymes. Moreover, NE-induced translocation is further enhanced in cells containing peptide rIII.

In contrast, introduction of peptide I to these cells does not affect PKC distribution in the absence of hormone stimulation, nor does it induce PKC degradation. Furthermore, NE-induced translocation is inhibited by peptide I. Similar concentrations of a number of control peptides did not affect PKC distribution or degradation in control or NE-treated cells.

In studies on rat cardiac myocytes, peptide rIII induced δPKC and εPKC activation that was followed by degradation of these activated isozymes.

Figure 6:
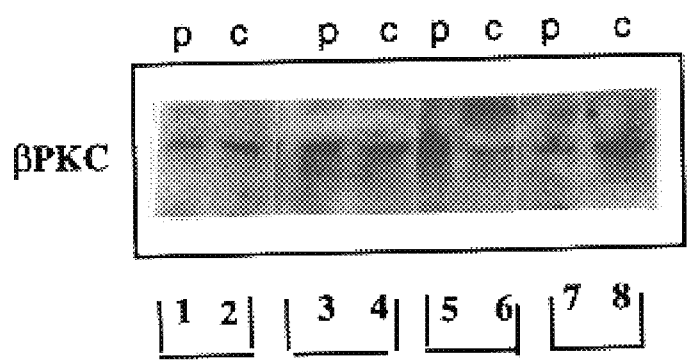
FIG. 6 shows the distribution of βPKC in Xenopus oocytes between the cytosolic and membrane-associated fractions following microinjection of either injection solution, peptide I (SEQ ID NO:1) or peptide rVI (SEQ ID NO:7) with or without insulin stimulation.

Peptide rVI also augments hormone-induced translocation of PKC isozymes (see, for example, Example 8 and FIG. 6). In contrast, peptide I (SEQ ID NO:1) inhibited hormone-induced translocation of PKC isozymes (Example 8, FIG. 6) and did not cause degradation.

The data summarized above demonstrate that peptides derived from WD-40 repeats of RACK1 can serve as PKC agonists and antagonists in vivo, and suggest that peptides derived from WD-40 regions of RACK1 contain at least part of the protein-protein interface between PKC and RACK1.

Furthermore, the results suggest that (i) WD-40 repeats present in other proteins, such as Gβ subunit, may also be located at or near a surface involved in protein-protein interactions, (ii) peptides derived from these repeats may be effective in disrupting the interactions of the proteins with their partners (e.g. β-adrenergic receptor kinase (βARK), (iii) the peptides may modulate or alter the activity of the proteins with which the WD-40 repeat-containing proteins interact, and (iv) the peptides may therefore have specific biological effects when administered in vivo.

IV. Identification of Pairs of Interacting Proteins

A. Biochemical Approaches

Novel interacting proteins may be identified and isolated by a number of methods known to those skilled in the art. For example, monoclonal antibodies raised to a mixture of antigens, such as a particular tissue homogenate, may be characterized and used to immunoprecipitate a single class of antigen molecules present in that tissue. The precipitated proteins may then be characterized further, and used to co-precipitate other proteins with which they normally interact (Hari, et al., Escobedo, et al.).

An alternate method to identify unknown polypeptides that interact with a known, isolated protein is by the use of, for example, an overlay assay (Wolf, et al., Mochly-Rosen, et al., 1991). A mixture (such as a fraction of a tissue homogenate, for example, a Triton-insoluble protein fraction) potentially containing proteins that bind to a known, isolated protein can be resolved using PAGE, blotted onto a nitrocellulose or nylon membrane, and contacted with a solution containing the known protein and any necessary co-factors or small molecules. After washing, the membrane can be contacted with a probe for the known protein, for example an antibody or a mixture of antibodies, and the signal visualized.

B. Molecular Approaches

Putative binding proteins of a known protein may be isolated from tissue homogenates, as described above. Alternatively, DNA clones encoding putative binding proteins may be identified by screening, for example, an appropriate cDNA expression library. Expression libraries made from a wide variety of tissues are commercially available (for example, from Clonetech, Palo Alto, Calif.). Expression libraries may also be made de novo from organisms and tissues of choice by practitioners skilled in the art.

The screening of expression libraries for clones expressing a protein or protein fragment of interest may be readily accomplished using techniques known in the art, for example, an overlay assay.

An overlay-assay screening method may be used to identify clones expressing a (known or unknown) protein or protein fragment that binds to a probe in hand. The probe may be a protein postulated to be involved in protein-protein interactions with a protein expected to be present in a cDNA library selected for screening (as was the case for the cloning of RACK1, detailed in Example 1).

Actual screening of a selected cDNA library may be accomplished by inducing plated clones to express cloned exogenous sequences, transferring replicas of the induced plaques or colonies to filter membranes, and screening the membranes with an appropriate probe. According to this method, lifts of filters (for example, nylon or nitrocellulose) from an appropriately-induced cDNA library plates (induced by, for example, IPTG) are washed, blocked, and incubated with a selected probe for a period of time sufficient to allow the selected probe(s) to bind specifically to polypeptide fragments present on the filters. The filters may then be washed and reacted with a reagent (for example, antibodies such as alkaline phosphatase-conjugated goat anti-rabbit or anti-mouse antibodies, available from Boehringer Mannheim Biochemicals, Indianapolis, Ind.). Additional reactions may be carried out as required to detect the presence of bound probe.

One such overlay assay, described in Example 1, was used to screen a rat brain cDNA expression library for proteins that bind purified PKC in the presence of PKC activators (phosphatydilserine, diacylglycerol and calcium). The filters were screened with a mixture of rat brain PKC isozymes (α, β, γ, δ, ε and ζ). Following a series of washes, bound PKC isozymes were detected with a mixture of anti-α, β, γ PKC mouse monoclonal antibodies, and anti-δ, ε and ζ PKC rabbit polyclonal antibodies. Bound antibodies were detected using alkaline phosphatase-conjugated goat anti-rabbit or anti-mouse antibodies and 5-bromo-4-chloro-3-indoyl phosphate p-toluidine salt as a substrate.

Once a clone is identified in a screen such as the one described above, it can be isolated or plaque purified and sequenced. The insert may then be used in other cloning reactions, for example, cloning into an expression vector that enables efficient production of recombinant fusion protein. Examples of appropriate expression vectors are pGEX (Smith, et al., 1988) and pMAL-c2 (New England BioLabs, Beverly, Mass.). An expression vector containing an insert of interest may be used to transform appropriate host cells, such as *E. coli*, and the transformed host cells can be used to produce the recombinant protein in large amounts.

Typically, a recombinant protein is expressed in tandem with a bacterial or viral gene product (endogenous polypeptide) as part of a fusion protein. The junction between the endogenous polypeptide and the recombinant protein typically includes a recognition site for a rare-cutting protease. The endogenous peptide may be designed to incorporate a unique affinity tag (a short peptide sequence) to facilitate the purification of the fusion protein with an affinity reagent, such an antibody directed against the affinity tag. The recombinant protein may then be purified from the fusion protein using the appropriate protease.

Purified recombinant protein may be used in a number of ways, including in an overlay binding assay to screen for peptides or substances that inhibit binding between the recombinant protein and an interacting protein.

An example of the use of a cDNA clone to express protein is detailed in Example 2. RACK1 cDNA, isolated as described above and in Example 1, was subcloned into an expression vector (pMAL-c2, New England BioLabs, Beverly, Mass.) capable of expressing a cloned insert in tandem with maltose-binding protein (MBP). The vector containing the RACK1 insert was used to transform TB1 *E. coli*, which were then induced with IPTG. The cells produced a 78 kDa fusion protein comprised of RACK1 fused to the MBP. The overexpressed fusion protein was purified on an amylose affinity column according to the manufacture's protocol (New England BioLabs, Beverly, Mass.) and incubated with protease Xa to separate the expressed insert from the MBP. Following the incubation, a 36 kDa RACK1 protein was obtained.

V. Identification of WD-40 Repeats

According to a method of the present invention, protein-protein interactions can be disrupted and/or the activity of an interacting protein can be altered, given at least one of the interacting proteins contains a WD-40 motif, or region, with a peptide(s) derived from a WD-40 repeat(s) of one of the proteins.

WD-40 repeats are typically found in a family of proteins having at least a limited homology with the β subunit of transducin. WD-40 repeats present in a selected member of this family can be identified by (A) performing a self-homology analysis on a selected protein using a homology matrix (performed by, for example, the computer program DNA Strider 1.2, available from Christian Marck, Service de Biochemie et de Genetique Moleculaire, Department de Biologie Cellulaire et Moleculaire, Direction des Sciences de la Vie-CEA-FRANCE), (B) aligning sequences comprising the repeating elements revealed by the homology matrix analysis, and (C) identifying conserved amino acid residues that typically serve to define a WD-40 repeat. The steps are discussed individually, below.

A. Homology Matrix Analysis

Determining whether a particular amino acid sequence contains repeated motifs may be accomplished by a number of methods known to those skilled in the art. They range from a simple visual inspection of the sequence to the use of computer programs which can identify repeated motifs. One widely-implemented computer-assisted method is to generate a self-homology matrix. A self-homology matrix computes the homology of each amino acid residue in a particular sequence with every other residue in that sequence. The homology scores are stored in a 2-dimensional matrix. Values higher than a selected criterion level are flagged and displayed as points on an x-y coordinate. The x- and y-axes correspond to consecutive amino acid positions in the sequence.

An example of a self-homology matrix analysis is shown in FIG. 1B. The matrix was generated using the computer program DNA Strider 1.2 (Christian Marck, Service de Biochemie et de Genetique Moleculaire, Department de Biologie Cellulaire et Moleculaire, Direction des Sciences de la Vie-CEA-FRANCE) with the amino acid sequence of RACK1 (SEQ ID NO:27) with a window setting of 21 and a stringency of 6. Some typical features of a self-homology matrix are evident in the figure. The graph shows a "primary" diagonal line extending from the origin with a slope of unity, corresponding to the fact that the sequence is identical to itself. If the sequence contains repeating elements, as RACK1 does, there will be other, shorter sets of contiguous points arranged in diagonal lines substantially parallel to the primary diagonal and offset from the primary diagonal in the x- or y-directions. These shorter lines identify the locations of repeating elements with the sequence. Each repeating element will result in two sets of displayed points, symmetrically distributed about the primary diagonal.

The data displayed in a homology matrix analysis can be used to locate and roughly align the sequences of repeating elements for a more detailed analysis. The horizontal band delineating the region between ~100 and ~130 on the y-axis in FIG. 1B highlights the fact that portions of that region of RACK1, that is, the amino acids between about amino acid 100 and amino acid 130, are repeated a total of seven times in the sequence of RACK1. Arrows point to the repeats in the homology matrix. For purposes of rough alignment, the short diagonal lines pointed out by the arrows can be extended to the horizontal line at amino acid ~100 on the y-axis, and the x-axis location corresponding to the intersection be noted. For example, the intersection corresponding to the second repeat (second arrow from the left) is at x=~50).

Values determined in this manner may then be used to align the amino acid sequence of the repeats with each consecutive repeat beneath the preceding one, the start of each repeat corresponding approximately to the amino acid position determined by the analysis in the preceding paragraph. The amino acid sequence of RACK1, aligned in this manner, is shown in FIG. 1C.

Most commercially-available DNA and protein sequence analysis programs have the capability to perform a self-homology matrix analysis. One example is the program DNA Strider 1.2 (Christian Marck, Service de Biochemie et de Genetique Moleculaire, Department de Biologie Cellulaire et Moleculaire, Direction des Sciences de la Vie-CEA-FRANCE).

Once the repeating elements are identified and the sequences corresponding to repeating elements are roughly aligned, one may proceed to define the degree of homology among the individual repeats at the specific positions within the repeats, as is described below.

B. Aligning Amino Acid Sequences

If a self-homology matrix was used to obtain a crude alignment, the sequences may aligned by eye on a personal computer or the like using, for example, a text editor, a drawing program or a sequence-analysis program. Examples of programs effective to accomplish an alignment include "MACDRAW PRO" (Claris Corp., Santa Clara, Calif.) and "WORD" (Microsoft Corp., Redmond, Wash.), both of which are available for "MACINTOSH" series computers (Apple Computer Corporation, Cupertino, Calif.), as well as IBM-compatible computers running "WINDOWS" (Microsoft Corp.).

Amino acid sequences corresponding to internal repeats can also be aligned automatically using a protein sequence analysis program, such as "MACVECTOR" (Eastman Kodak Co., New Haven, Conn.).

According to a method of the invention, aligned sequences are examined further to determine if they fulfil criteria to be defined as WD-40 repeats. These criteria are detailed in part C, below.

C. Amino Acid Residues that Define a WD-40 Repeat

Upon completion of steps outlined in parts A and B above, that is, determining whether a particular protein contains internal repeats, and if so, aligning those repeats, it is necessary to determine whether the aligned repeats contain WD-40 regions.

A WD-40 motif is roughly defined as a contiguous sequence of about 25 to 50 amino acids with relatively-well conserved sets of amino acids at the two ends (amino- and carboxyl-terminal) of the sequence. Conserved sets of at least one WD-40 repeat of a WD-40 repeat-containing protein typically contain conserved amino acids at certain positions. The amino-terminal set, comprised of two contiguous amino acids, often contains a Gly followed by a His. The carboxyl-terminal set, comprised of six to eight contiguous amino acids, typically contains an Asp at its first position, and a Trp followed by an Asp at its last two positions.

A more accurate definition of a WD-40 motif incorporates the observation that while specific residues, such as those identified above, are not always conserved within a WD-40 motif, conserved positions within the motif are typically occupied by residues selected from a restricted class of amino acids.

In order to better define the class of conserved residues at selected positions, it is necessary to group amino acids on the basis of certain common properties. A functional way to define common properties between individual amino acids is to analyze the normalized frequencies of amino acid changes between corresponding proteins of homologous organisms (Schulz). According to such analyses, groups of amino acids may be defined where amino acids within a group exchange preferentially with each other, and therefore resemble each other most in their impact on the overall protein structure (Schulz). Examples of amino acid groups defined in this manner, some of which are used in the definition of a WD-40 motif herein, include:

(i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art.

A "WD-40" motif is defined herein as a contiguous set of amino acids between (inclusive) two sets of relatively well conserved residues, termed herein as an "amino-terminal set" and a "carboxyl-terminal set".

The amino-terminal set contains two adjacent amino acids. The residue at the first position is typically selected from groups ii, vi or viii, while the residue at the second position is typically selected from groups i, x or Ile. The first and second positions will often consist of Gly and His, respectively. The Gly and His residues are typically present in at least one of the aligned repeats of a WD-40-containing protein.

The carboxyl-terminal conserved set typically includes eight residues, but may contain as few as six residues. The most well-conserved residue in WD-40 motifs identified thus far is an Asp residue, comprising the first amino acid of the carboxyl-terminal conserved set. It is present in virtually all WD-40 repeats illustrated herein. In those repeats where it is not present, the position is occupied by a residue from groups iii or Gly.

The last two amino acids in the carboxyl-terminal conserved set are typically selected from groups iv or Ile, and groups i or viii, respectively. The most commonly used residue at the first of these positions is Trp. It is typically present in at least one of the WD-40 repeats of any given protein. The second position is occupied less consistently by a single residue, but is often occupied by Asp. The Trp-Asp (WD) combination is part of the namesake of WD-40 repeats.

The amino acids present in the internal portion of the carboxyl-terminal conserved set are less well-conserved than the terminal residues, and their total number may differ by up to two residues in different WD-40 repeats. The third position in from the carboxyl-terminal end of the carboxyl-terminal conserved set is typically selected from groups viii or ix, more typically ix. The fifth position in from the carboxyl-terminal end of the carboxyl-terminal conserved set is also typically selected from groups viii or ix, more typically ix.

The length of a WD-40 repeat, including the amino-terminal and carboxyl-terminal conserved sets is typically between about 25 and about 50 residues, more typically between about 29 and 34 residues. The distribution arises primarily from differences in the number of residues present between the amino-terminal and carboxyl-terminal conserved sets.

The number of WD-40 repeats in a particular protein can range from two to more than eight. The average number is about 5.

A determination of whether or not a set of aligned internal repeats are WD-40 repeats can be facilitated by an examination of all of the repeats as a whole, rather than an examination of each repeat individually. This is in part because not all of the aligned repeats will necessarily contain all of the conserved sequences that serve to identify WD-40 repeats, although the conserved residues will typically appear in at least one of the repeats.

For example, FIG. 1C shows the RACK1 amino acid sequence aligned to illustrate the internal repeats present in the sequence. All of the repeats are WD-40 repeats, even though the amino-terminal conserved set of repeat VI, for instance, contains an "LD" as opposed to the more usual "GH", and the carboxyl-terminal conserved set contains a "G" at its first position, as opposed to the highly-conserved "D". Similarly, the carboxyl-conserved set of, for example, repeat I, contains a "WK" at the last to positions, as opposed to the more usual "WD".

It will be appreciated that certain residues or sets of residues will be well-conserved in the WD-40 repeats of a selected protein, even though they may not be conserved in WD-40 repeats in general. Such residues or sets of residues may be useful in several ways. For example, they may be used in performing an alignment of internal repeats in a selected protein, as described in part B, above. The residues may also be useful for identifying regions based on which effective binding peptides may be designed (see section VI., below).

D. Identification of WD-40 Repeats in RACK1

In experiments done in support of the present invention, a protein that binds to activated PKC was cloned and sequenced (see Example 1). Sequence analysis of the deduced amino acid sequence revealed the presence of repeats, which were aligned and are shown in FIG. 1C.

The aligned repeats were identified as WD-40 repeats by application of the criteria identified in parts A, B and C above. For example, the conserved amino-terminal set in repeats I, II, III and V consists of the typical "GH", whereas in repeats IV, VI and VII, the set consists of other residues. These other residues, however, are contained in at least one of the amino acid groups identified above as conserved at the appropriate position. The conserved carboxyl-terminal set contains the highly-conserved "D" at its first position in all repeats except repeat VI. The second-to-last position of this set contains the relatively-well conserved "W" in each repeat, while the last position contains the typical "D" in repeats II, V and VI, and other residues in the other repeats.

Taken together, these data indicate that the repeats contained in RACK1 are WD-40 repeats. The data also illustrate that not all repeats contain all of the elements typical of a WD-40 motif, but that when the repeats are aligned and viewed together as a whole, a WD-40 motif is apparent in all repeats.

E. Identification of WD-40 Repeats in Sequenced Proteins

Data were compiled in support of the present invention to illustrate how WD-40 repeats in various proteins may be identified, and to illustrate the diversity of amino acid sequences that may be properly identified as WD-40 repeats by those skilled in the art following the guidance set forth herein. Two methods that were used to identify WD-40-containing protein sequences are detailed in Example 7.

In the first method, proteins identified in their description as having a homology to β-transducin were examined as detailed in parts B–D, above, for WD-40 repeats. 30 proteins were identified in this manner. The amino acid sequences of these proteins, with the WD-40 regions aligned and delineated, are shown in FIGS. 12–18, 20–27, 29–30, 34–35, 37–38, 40 and 42–50. The sequences are represented in the Sequence Listing as SEQ ID NO:29–35, 37–44, 46–47, 51–52, 54–55, 57 and 59–67.

In the second method, proteins whose sequences were homologous to a consensus WD-40 motif (SEQ ID NO:262), were identified and examined for WD-40 repeats. Ten additional proteins containing WD-40 repeats were identified with this strategy. The amino acid sequences of those proteins, with the WD-40 repeats aligned and delineated, are shown in FIGS. 11, 19, 28, 31–33, 36, 39, 41 and 51. The sequences are represented in the Sequence Listing as SEQ ID NO:28, 36, 45, 48–50, 53, 56, 58 and 68.

Other types of searches may be equally effective at identifying proteins which may contain WD-40 repeats. For example, on-line databases such as GenBank or SwissProt can be searched, either with an entire sequence of a WD-40-containing protein, or with a consensus WD-40 repeat sequence. Various search algorithms and/or programs may be used, including FASTA, BLAST or ENTREZ. FASTA and BLAST are available as a part of the GCG sequence analysis package (University of Wisconsin, Madison, Wis.). ENTREZ is available through the National Center for Biotechnology Information, National Library of Medicine, National Institutes of Health, Bethesda, Md.

Sequences identified with a protein homology search are then analyzed as described in parts A, B and C, above, to identify potential WD-40 motifs. Once located, the motifs can be aligned, and effective binding peptides may be designed.

F. Identification of WD-40 Regions in Novel Polypeptides

WD-40 repeats may be identified in a novel polypeptide by, for example, the methods described in parts A–D above. It will be appreciated, however, that step A above (homology matrix) is not required in the identification of WD-40 repeats. Following the guidance of the present invention, one skilled in the art may, for instance, identify a WD-40 motif while scanning the sequence of some, perhaps novel, polypeptide merely through a recognition of one or more of the features characteristic of WD-40 repeats.

The precise methods by which one skilled in the art arrives at the conclusion that a particular motif is a WD-40 repeat is less relevant to the present invention than is the use of sequences derived from WD-40 motifs, regardless of how they are identified, to design peptides effective to alter or modulate the activity of one member of a pair of interacting proteins and/or to disrupt protein-protein interactions.

VI. Identification of Activity-altering Peptides

Upon the alignment and recognition of WD-40 repeats in a particular protein, one may proceed to design a peptide or a set of peptides that may be effective to associate with or bind to the protein with which the WD-40-containing protein normally associates. Such a binding or association may be expected to alter or modulate the activity of the protein and/or disrupt the association of the pair of interacting proteins.

The sequence of such a peptide will typically be homologous, if not identical to, a contiguous amino acid sequence contained within at least one of the WD-40 repeats. Examples of the selection of WD-40-derived peptides effective to disrupt protein-protein interactions are detailed in parts C and D below, for RACK-PKC and Gβ/γ-βARK interactions, respectively.

A. Choosing an Appropriate Region within a WD-40 Repeat

Putative binding peptides may be selected from any portion of a WD-40 repeat. If it is desired to obtain a degree of discrimination between the various WD-40-containing proteins, peptides should be chosen from the region between, and not including, the amino-terminal and carboxyl-terminal conserved sets. This "central region" typically shows greater sequence diversity between different WD-40-containing proteins than the terminal regions, and is roughly outlined by boxes in FIGS. 11–51, which show the amino acid sequences and aligned WD-40 repeats of various WD-40 repeat-containing proteins. Within the central region, peptides should be selected from sequences that have little or no homology to any other known sequences, save the sequence(s) of the protein(s) targeted for disruption.

For example, peptides rIII (SEQ ID NO:4, seven amino acids) and rVI (SEQ ID NO:7, eight amino acids), are identical to segments of RACK1 WD-40 repeats (III and VI, respectively) beginning five amino acids in from the amino termini of the WD-40 repeats from which they are derived (see FIG. 1C, underlined segments). The WD-40 repeat segments corresponding to the binding peptides comprise the left portion of the central region of the respective WD-40 repeats, and are not well-conserved in RACK1.

If it is desired to inhibit the interactions of, for example, all of the isoforms of a particular WD-40-containing protein family, a sequences is selected that includes a significant number of residues that are shared or highly homologous among at least one WD-40 repeat of each of the targeted isoforms.

If, on the other hand, an isoform-specific reagent is desired, a sequence is selected from a WD-40 repeat(s) of a specific isoform, where that sequence does not include a significant number of residues that are identical or highly homologous to residues in WD-40 sequences from related isoforms.

B. Choosing an Appropriate Length for a Peptide

Effective binding peptides may be designed that range in length from as few as about four residues to 40 or more residues. Preferably, binding peptides will have a length of at least about six residues, and less than about 20 residues. The length will be determined in part by the degree of desired homology to other WD-40 repeats, as described in part A above, and by the level of discrimination between proteins that is required.

For example, binding peptides selected from RACK1 sequences to inhibit RACK1/PKC interactions were seven and eight amino acids in length. The peptides are long enough to bind specifically to the targeted sequences, but short enough to not cross-react with other WD-40 repeat binding proteins. These properties enable the peptides to have very selective and specific effects, as is shown below in Examples 6–11.

C. Design of RACK1 WD-40-derived Peptides to Inhibit RACK1-PKC Interactions

Peptides rIII (SEQ ID NO:4, seven amino acids) and rVI (SEQ ID NO:7, eight amino acids) were designed in part following the guidance presented in parts A and B above. The peptides are identical to segments of RACK1 WD-40 repeat sequences beginning five amino acids in from the amino termini of the WD-40 repeats from which they are derived. The WD-40 repeat segments corresponding to the binding peptides comprise the left portion of the central region of the WD-40 repeats. The peptides were tested for their ability to disrupt protein-protein interactions in vitro and in vivo, as described in section VII and Examples 6–11 below.

D. Peptides Derived from WD-40 Repeats of Human G-Beta Inhibit Interactions of G-Beta Subunits with βARK Methods described in section V part E were used to identify WD-40 repeats (SEQ ID NO:128–134) in Human G-Beta (SEQ ID NO:41). Segments from the first six WD-40 repeats were selected for the design of G-beta binding peptides (SEQ ID NO:13–18). The segments were selected based on criteria detailed in parts A and B, above.

The G-beta binding peptides are used to disrupt the interactions of G-beta subunits with LARK. The disruption is assayed using a modification of the overlay assay described in Example 4.

VII. Testing of Putative Binding Peptides

Detailed below are several assays by which the efficacy of WD-40-derived peptides at binding to a target protein, inhibiting protein-protein interactions, and altering or modulating the activity of a target protein may be determined.

One class of assays, widely-used to assess the binding of two proteins to each other, are overlay assays. Overlay assays are generally applicable to most proteins. They can be used to, for example, assess the binding of WD-40-derived peptides to their targets, as shown in Example 6 and described in part B below. Overlay assays can also be used to assess the ability of WD-40-derived peptides to inhibit the binding of two interacting proteins, one of which contains a WD-40 motif from which the peptides were derived (see, for instance, Example 4 and part C below).

Other assays may be used to assess effects of WD-40-derived peptides on the activity of the target protein. These assays may be in vivo assays, in vitro assays, or a combination of in vivo and in vitro assays. The assay used will depend on the proteins involved and on the system(s) and/or process(es) that involve the interacting proteins against which the peptide was targeted. For instance, the assays described in parts D–I below are appropriate for characterizing PKC activity in vivo and in vitro.

While many of the assays below are particularly useful for characterizing the activity of PKC, they also illustrate a general framework of experiments by which the effects of WD-40 derived peptides on other proteins may be assessed.

A. Overlay Assays to Evaluate Efficacy of Putative Binding Peptides Derived from WD-40 Regions An overlay assay can be used to assess the disruption of the ability of a pair of proteins to associate. Methods for conducting overlay assays are well-known in the art (see, for example, Mochly-Rosen, et al., 1991).

Applications of overlay assays to evaluate putative binding peptides for PKC/RACK1 interactions are presented in Examples 4 and 5 herein. The assays can be generally described as follows.

One protein of a pair of interacting proteins ("immobilized" protein) can be resolved on an SDS/PAGE gel and blotted onto an appropriate membrane (for example, nitrocellulose or nylon) by methods known to those skilled in the art. The blots may then be contacted with a solution containing the other protein of the pair of interacting proteins ("overlay" protein) in the presence, and in the absence of putative binding peptides. Following appropriate wash steps, bound overlay protein can be detected by the use of an appropriate probe, such as an antibody directed against the overlay protein.

A variation on the above protocol may be performed to minimize a possible interference between unbound binding peptide and antibodies used to detect the presence of bound overlay protein. The modification consists of performing another SDS/PAGE electrophoresis between the steps of binding the overlay protein, and detecting the overlay protein with antibody or other probe. It is accomplished by cutting the blot into pieces sized to just encompass the area occupied by the blotted immobilized protein, after the overlay protein had been contacted (in the presence or in the absence of binding peptides) and allowed to bind to the blot. The pieces of membrane are then incubated in a sample buffer, placed in the wells of a second SDS polyacrylamide gel and subjected to electrophoresis.

Following electrophoresis, the gel is blotted as above, and contacted with a probe, for example antibodies, to detect bound overlay protein.

B. Binding of βPKC to Peptides Homologous to a WD-40 Region of RACK1

The binding of βPKC to peptide I (SEQ ID NO:1), peptide rVI (SEQ ID NO:7) and control peptide (SEQ ID NO:9) was assessed in Example 6 using a PKC overlay assay similar to that described in Example 3. Increasing amounts of peptides were applied onto nitrocellulose using a slot-blot apparatus. The membranes were incubated with PKC in the presence and absence of PS, DG, and calcium.

Figure 4:
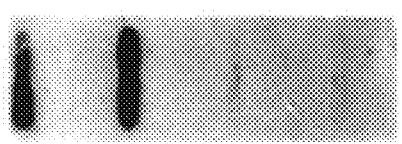
FIG. 4 shows the results of an overlay assay to detect binding of βPKC to either peptide I (SEQ ID NO:1) or peptide rVI (SEQ ID NO:7) immobilized on nitrocellulose membranes under various conditions.
Figure 4:
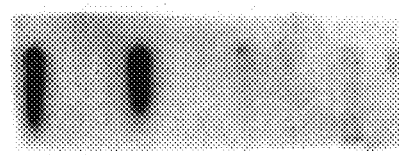
Figure 4:
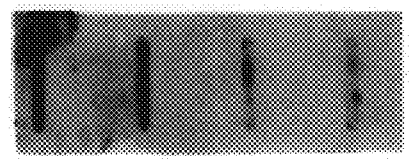
Figure 4:
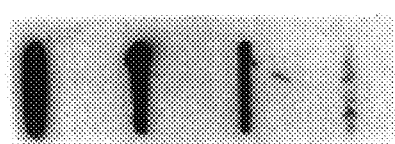
Figure 4:
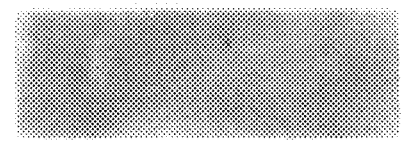

The data are shown in FIG. 4, and show that activated PKC bound to both peptides I and rVI at peptide amounts as low as 5 μmoles, but not to the control peptide. Unactivated PKC did not bind to peptide I, but did bind to peptide rVI at similar concentrations.

The results indicate that while the peptides were homologous to one another and were capable of binding to the same protein, they behaved differently. Peptide rVI (SEQ ID NO:7; 8 residues) was able to bind to both activated as well as unactivated forms of PKC, whereas peptide I (SEQ ID NO:1; 15 residues) could bind only to activated PKC. The differences between the binding properties may be due, for example, to charge differences and/or length differences between the two peptides.

C. Effects of Peptides Homologous to WD-40 Region of RACK1 on PKC Binding to RACK1

Figure 3:
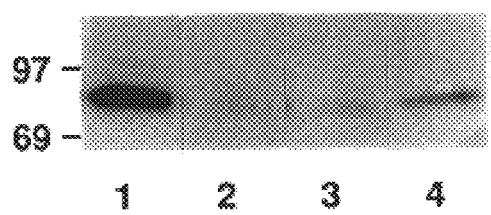
FIG. 3 shows the results of an overlay assay to detect PKC binding to immobilized RACK1 in the presence and absence of WD-40-derived peptides.

Two peptides (peptide rIII; SEQ ID NO:4 and peptide rVI; SEQ ID NO:7) identical to regions of RACK1 WD-40 repeats (underlined, FIG. 1C) were tested for their ability to inhibit PKC binding to recombinant RACK1 using a modification of the overlay procedure referred to above. The experiment is detailed in Example 4 and the results are shown in FIG. 3.

Peptide I caused an 81±6% inhibition of PKC binding to recombinant RACK1 as compared with binding in the absence of added peptide. Both peptides rIII and rVI inhibited the binding of PKC to RACK1. In addition, peptides rI and rII were also effective inhibitors of the interaction of PKC to RACK1. A lesser inhibitory effect was obtained with peptides rIV and rV and no inhibition was obtained with peptide rVII.

The difference in the peptide's ability to inhibit binding may reflect differences in the roles played by the corresponding WD-40 repeats in the protein-protein interactions between PKC and RACK1. The peptide's ability or inability to inhibit protein-protein interactions as assayed by an overlay assay, however, is not necessarily correlated with the effects those peptides may have on the activity of the targeted proteins, as measured by both in vivo and in vitro assays and described in parts D–I below.

D. Effects of Peptides Homologous to WD-40 Regions of RACK1 on PKC-mediated Oocyte Maturation Peptides I (SEQ ID NO:1), rIII (SEQ ID NO:4) and rVI (SEQ ID NO:7) were also tested for their ability to affect insulin-induced, PKC-mediated maturation in Xenopus oocytes, as detailed in Example 7 and shown in FIGS. 5A and 5C.

PKC is involved in the maturation of Xenopus oocytes. Phorbol esters, which activate PKC, or microinjection of a constitutively active mutant of PKC induce the first stage of oocyte maturation in the absence of hormones. Exposure to insulin causes an increase in diacylglycerol levels and microinjection of activated PKC enhances insulin-induced maturation (Stith, et al.). Microinjection of purified RACK proteins causes a significant decrease in the rate of oocyte maturation (Smith, et al., 1992). The insulin-induced oocyte maturation assay therefore provides an effective in vivo assay for compounds that interfere with the function of PKC.

The maturation response was quantified by monitoring the appearance of a white spot in the animal hemisphere of the oocyte, indicating germinal vesicle breakdown (GVBD) and maturation. The indicated peptides were microinjected into Xenopus oocytes and the percent of oocytes with GVBD following insulin exposure was plotted as a function of time in FIGS. 5A and C.

Figures 5A, 5B:
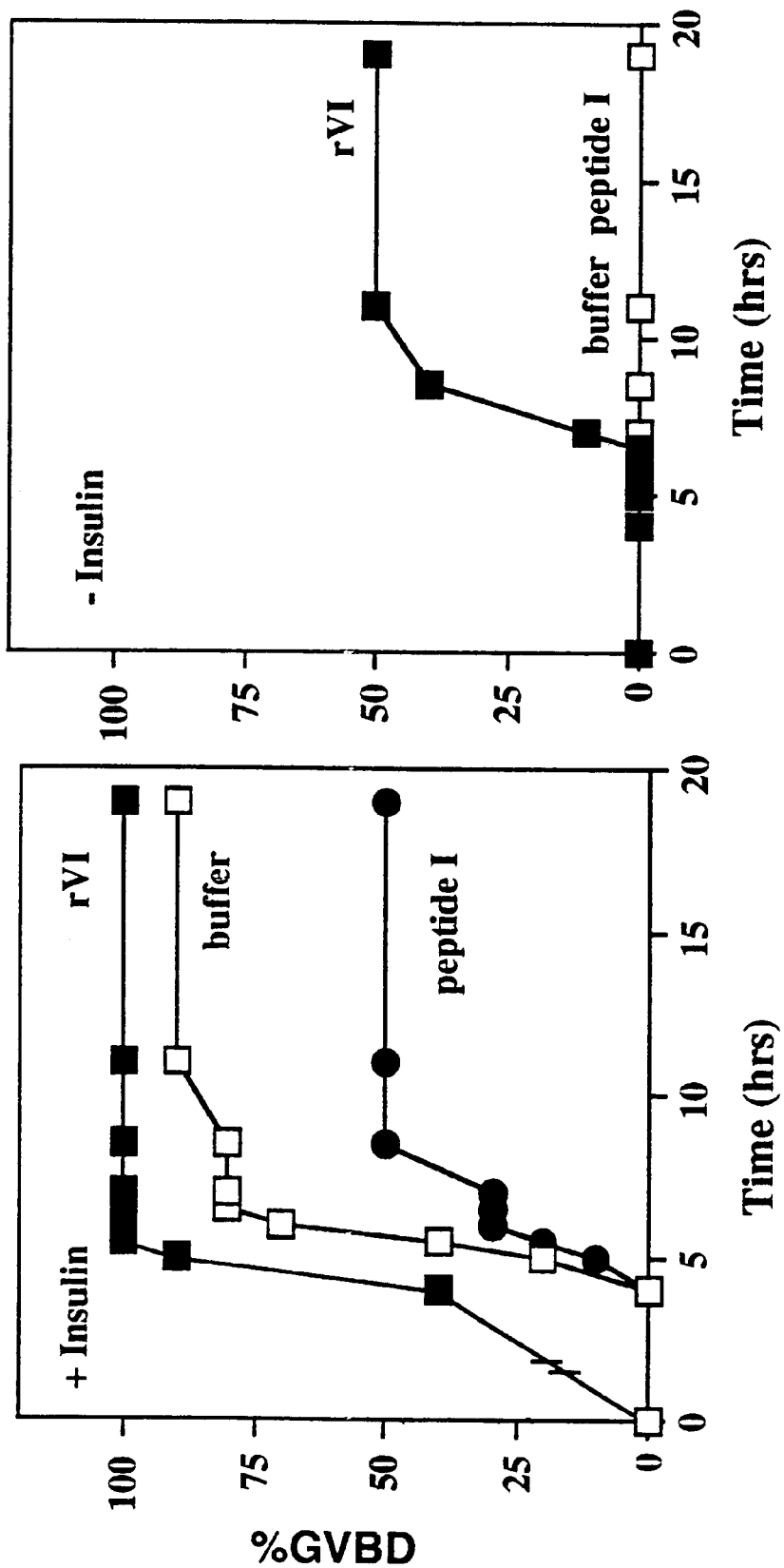
FIG. 5A shows the effects of injecting peptides I (SEQ ID NO:1) and rVI (SEQ ID NO:7) on PKC-mediated germinal vesicle breakdown (GVBD), a measure of insulin-induced oocyte maturation.
FIG. 5B shows the effects of injecting peptides I (SEQ ID NO:1) and rVI (SEQ ID NO:7) on PKC-mediated germinal vesicle breakdown (GVBD) in the absence of insulin induction.
Figure 5C:
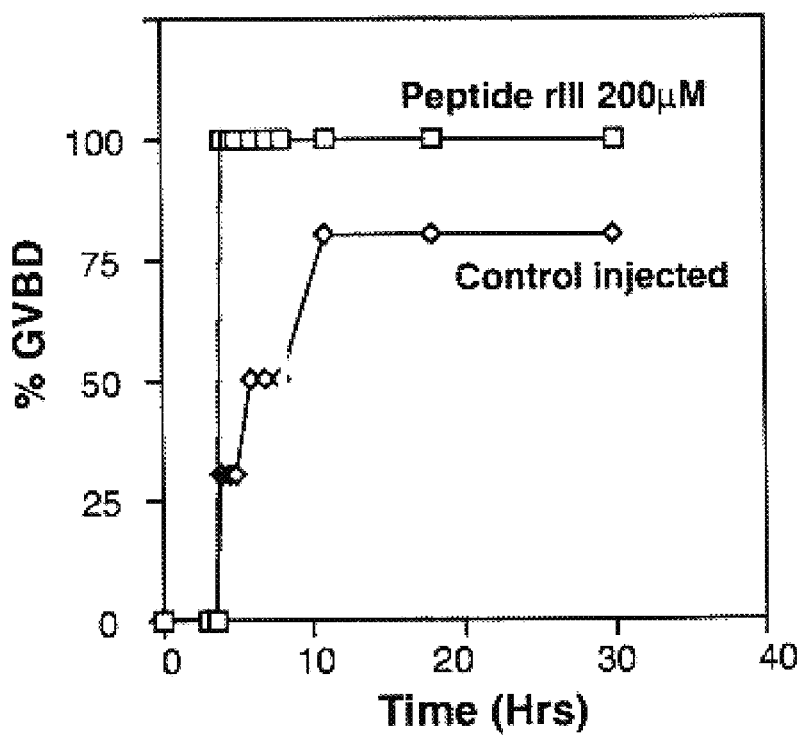
FIG. 5C shows the effects of injecting peptide rIII (SEQ ID NO:4) on PKC-mediated germinal vesicle breakdown (GVBD) in the absence of insulin induction.

Approximately 80–85% of sham-injected (control) oocytes exposed to insulin reach maturation, as compared with 45–50% of oocytes injected with peptide I. The rate of maturation of those oocytes that did mature was similar in the two cases. In contrast the effects of peptide I, both peptides rIII and rVI potentiated the effects of insulin on oocyte maturation, both in terms of the rate of maturation, and in the total fraction of oocytes that mature during the experiment. Injection of peptides rIII or rVI increases the fraction of maturing oocytes to essentially 100%. Furthermore, peptide rVI induced oocyte maturation in the absence of insulin stimulation (FIG. 5B).

Together, the data above indicate that peptides homologous to the WD-40 region of RACK1 can modulate the function of a protein with which RACK1 interacts (e.g. PKC), that the modulation can occur in vivo, and that it can have clear and profound physiological consequences. Furthermore, the results with peptide rVI suggest that under appropriate circumstances, the peptide alone may act to activate PKC, in the absence of other activating substances.

E. Effects of Peptides Homologous to WD-40 Regions of RACK1 on PKC Translocation in Xenopus oocytes Insulin causes the redistribution of βPKC, but not other PKC isozymes, from a cytosolic form to a membrane-associated form, as evidenced by the relative levels of PKC in the soluble vs. the particulate fraction of oocyte homogenate. To assess the effects of RACK1 WD-40-derived peptides on insulin-induced PKC translocation, 50 nl of a 20 mM NaCl solution containing the indicated peptides were microinjected into Xenopus oocytes. The oocytes were then homogenized, and the relative amount of PKC in the soluble and particulate fractions was assayed. The protocol followed was a modification of a method described by Smith, et al (1992). The results are shown in FIG. 6.

Peptide I (50 μM) did not affect βPKC distribution in untreated oocytes, but inhibited insulin-induced βPKC translocation (FIG. 3, lanes 7,8). In contrast, peptide rVI (50 μM) induced βPKC translocation in the absence of insulin treatment (FIG. 3, lanes 3,4). These results suggest that peptide I is an antagonist of hormone-induced PKC translocation, whereas peptide rVI is an agonist and an activator of PKC translocation. In light of the results presented in Example 7, the data also suggest that the inhibition of insulin-induced GVBD following microinjection of peptide I was due to an inhibition of βPKC translocation.

F. Effects of Peptides Homologous to WD-40 Regions of RACK1 on Sensitivity of βPKC to Arg-C Endopeptidase Upon activation of PKC, a pseudosubstrate autoinhibitory sequence at the N-terminus of PKC dissociates from the catalytic site and renders the molecule sensitive to endopeptidase Arg-C (Orr, et al.). Exposure of activated βPKC to Arg-C results in a limited proteolysis, or "nicking" of the enzyme. The nicking typically generates a 78 kDa fragment and several small fragments. Continued exposure to Arg-C typically results in the disappearance of βPKC (Orr, et al.).

Since peptides rIII (SEQ ID NO:4) and rVI (SEQ ID NO:7) exhibited PKC agonist activities in other assays (see, for instance Examples 7 and 8), experiments were performed to determine whether the peptides were capable of activating PKC in a manner to make it susceptible to endopeptidase Arg-C. The experiments are detailed in Example 9 and the results are shown in FIG. 7.

Figure 7:
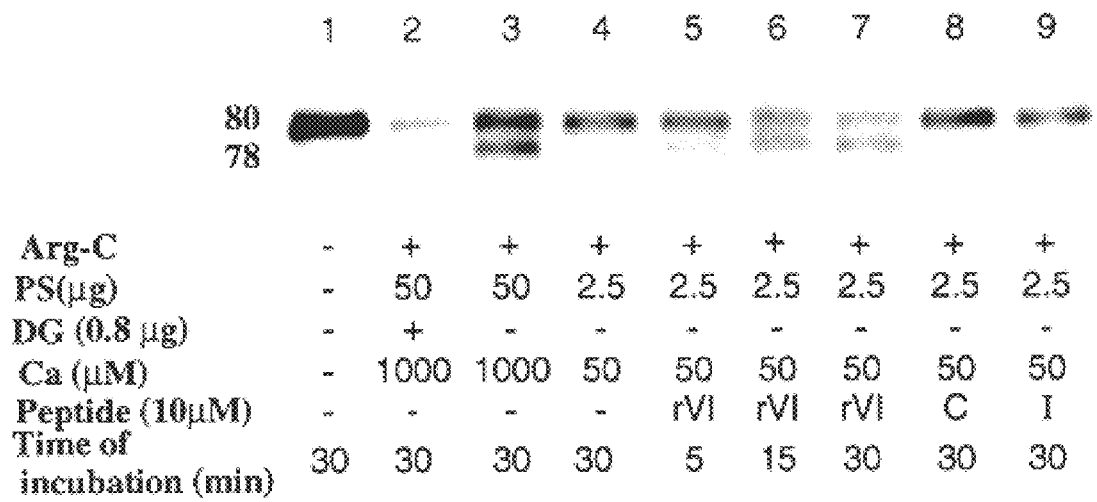
FIG. 7 shows the effects of peptides I and rVI on the sensitivity of βPKC to Arg-C endopeptidase.

In the presence of effective concentrations of PKC activators (0.8 µg/ml DG, 50 µg/ml PS and 1 mM $CaCl_2$), exposure of βPKC to Arg-C resulted in nicking, generating the 78 kDa fragment (FIG. 7, lane 2). In the absence of PKC activators, exposure of βPKC (80 kDa) to endopeptidase Arg-C had no effect on the enzyme (FIG. 7, lane 1).

Incubation of βPKC with Arg-C at low concentrations of activators (2.5 µg/ml PS and 50 µM $CaCl_2$) in the absence of added peptide, in the presence of control peptide (SEQ ID NO:9) and in the presence of peptide I (SEQ ID NO:1) did not result in appreciable nicking activity (FIG. 7, lanes 4, 8 and 9, respectively). However, incubation of βPKC with the same low concentration of activators in the presence of peptides rIII or rVI resulted in the appearance of the 78 kDa nicked PKC fragment (effects of peptide rVI in FIG. 4, lanes 5–7). Concentrations as low as 10 nM of peptide rVI were sufficient to result in nicking activity, indicative of βPKC activation.

The results indicate that peptides rIII and rVI, but not peptide I, are effective to stabilize PKC in an activated conformation that renders it susceptible to Arg-C under conditions of low PKC activators that would otherwise not render the enzyme susceptible to Arg-C.

Figure 8:
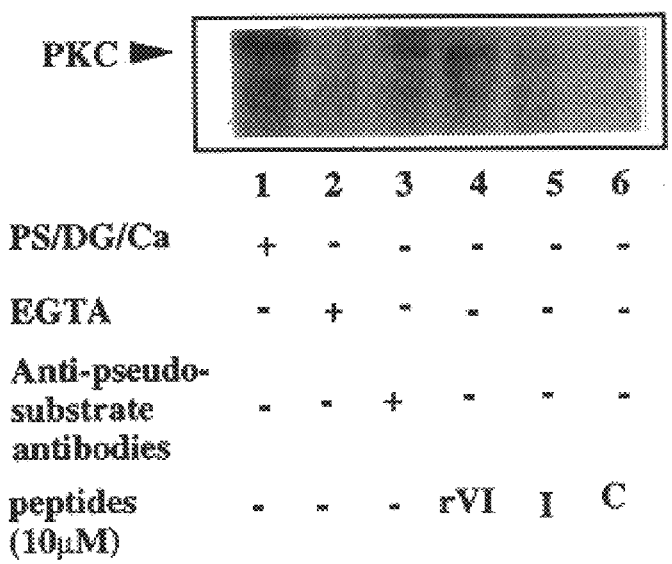
FIG. 8 shows the effects of peptides I and rVI on PKC autophosphorylation in the absence of PKC activators.

G. Effects of Peptides Homologous to WD-40 Regions of RACK1 on βPKC Autophosphorylation Activated PKC is capable of autophosphorylation, which can be assayed by incubation with [$\gamma$-$^{32}$P] ATP and visualized on an autoradiograph of a gel. Anti-pseudosubstrate antibodies were shown previously to induce autophosphorylation in the absence of PKC activators (Makowske, et al.). Since peptide rVI (SEQ ID NO:7) was effective to induce PKC translocation and GVBD in the absence of PKC activators, experiments were performed to determine if the peptide was also capable of inducing PKC autophosphorylation. The experiments are detailed in Example 10 and the data are shown in FIG. 8.

PKC activated with PS (50 µg/ml), DG (0.8 µg/ml) and $CaCl_2$ (1 mM) shows normal levels of autophosphorylation (lane 1). No autophosphorylation was seen in the absence of PKC activators (lane 2), or in the absence of PKC activators with peptide I (SEQ ID NO:1; lane 5) or control peptide (SEQ ID NO:9; lane 6). In contrast, peptide rVI in the absence of PKC activators induced PKC autophosphorylation to over 80% of the levels obtained for PKC alone in the presence of optimal concentration of PS, DG, and calcium (compare FIG. 8 lane 1 (control) with lane 4 (peptide rVI)).

H. Effects of Peptides Homologous to WD-40 Regions of RACK1 on Histone Phosphorylation by βPKC Another measure of PKC activity is the ability of activated PKC enzyme to phosphorylate histones. PKC phosphorylation of histone was carried out using a modification of the protocol described by Mochly-Rosen, et al., (1987). Phosphorylation was carried out in the presence or absence of PKC activators (PS, DG and calcium) and RACK1-derived peptides. Phosphorylated histone was detected by autoradiography, following SDS-PAGE on a 10% gel.

Figure 9:
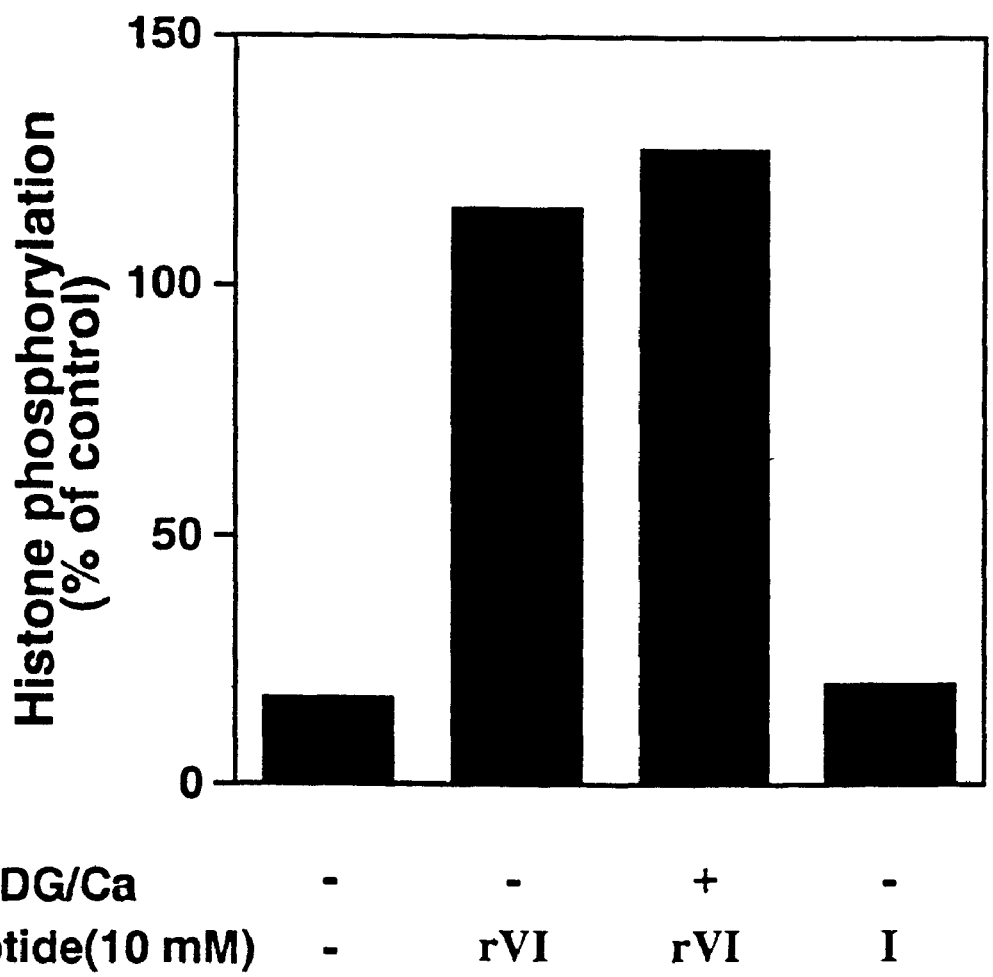
FIG. 9 shows the effects of peptides I and rVI on PKC phosphorylation of histones in the absence of PKC activators.
Figure 10:
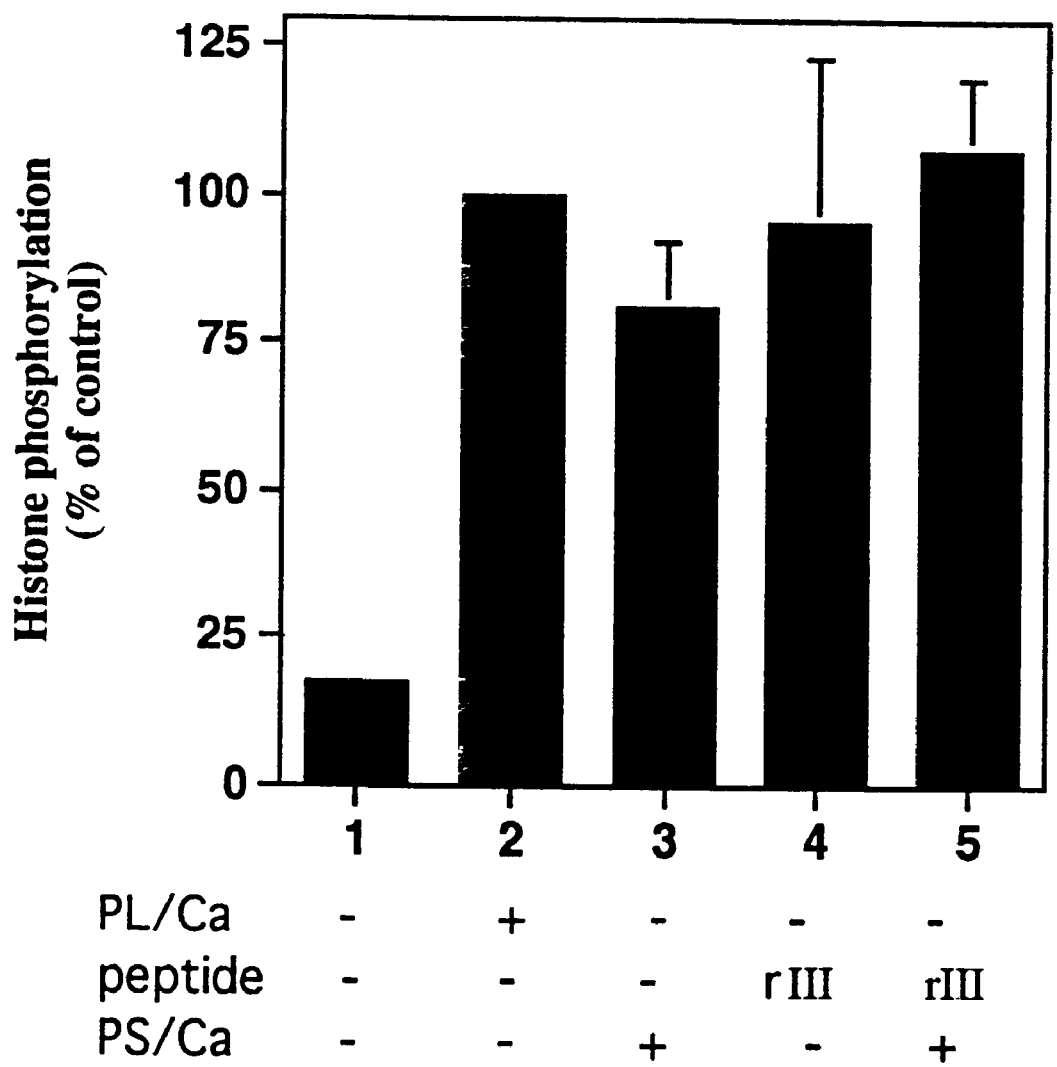
FIG. 10 shows the effects of peptide rIII on PKC phosphorylation of histones in the absence of PKC activators.

Since peptide rVI (SEQ ID NO:7) was effective to induce the autophosphorylation of PKC in the absence of PKC activators, and both peptides rIII (SEQ ID NO:4) and rVI rendered PKC susceptible to proteolysis by Arg-C, experiments were performed to characterize the effect of the peptides on histone type III phosphorylation by PKC. The experiments are detailed in Example 11 and the results are shown in FIGS. 9 and 10.

The results are similar to those obtained for the effects of peptide rVI on autophosphorylation of PKC, that is, peptide rVI was effective to induce PKC-mediated histone phosphorylation in the absence of the PKC activators PS, DG, and calcium, once again supporting that peptide rVI is an agonist of PKC activation. Peptide rIII similarly induced histone phosphorylation (FIG. 10).

VIII. Utility

A. Peptides as Probes for the Identification of Target Proteins

WD-40 derived peptides may be used, for example, to isolate clones encoding target proteins from an expression library. Variations on the cloning methods described herein can be used to identify clones expressing sequences capable of binding the peptides. For example, WD-40 derived peptides may be used to detect a target protein on a membrane using a standard binding assay. Positive clones may be detected, for example, by radiolabeling the peptides and exposing the membrane to film.

Target proteins isolated in this manner may be completely novel, or they may be partially characterized (in terms of a biological activity in a homogenate, or a band on a protein gel, for example).

Upon isolation of a cDNA encoding a binding protein, the cDNA may be expressed, for example, as detailed herein, and the protein may be characterized. Purified protein thus isolated may be used for a number of applications, including the production of antibodies.

Peptides designed according a method of the present invention may also be used, for example, as probes in a Western blot of a tissue homogenate to identify and determine the molecular weight of known or putative target proteins.

Screens such as those described above may be facilitated by the modification of peptides used for screening to incorporate any of a variety of reporter moieties. For example, the peptides can be radiolabeled with $^{125}$I. Alternatively, the peptides can be modified with a sequence-tag or a ligand for an affinity column by methods known to those skilled in the art.

The peptides may also be modified to covalently cross-link to their targets after binding, for example with any of various affinity reagent for cross linking known to those skilled in the art. This enables the isolation of target proteins that bind the peptides relatively weakly.

B. Peptides as Substitutes for Defective WD-40 Containing Proteins

In cases where a WD-40 containing protein is implicated in a disease (see, for example Reiner, et al.), peptides derived from WD-40 regions of the defective protein may be used as substitutes, for example, to activate a target enzyme. Such an approach may be more feasible than attempting therapy with intact proteins. The approach has an additional advantage in that it does not require knowledge of the chromosomal location of the affected gene.

The peptides can be introduced into affected cells by any of several methods known to those skilled in the art, including through the use of an appropriate expression vector or through in vitro synthesis and administration by an effective, expedient route. In vitro studies can be carried out using skinning or microinjection techniques.

C. Peptides as Pharmaceutical Agents

WD-40 derived peptides of the present invention may be used therapeutically, as described above. Such peptides may be designed so as to interact with endogenous target molecules to augment or correct their function. Alternatively, peptides may be designed to specifically interact with target molecules unique to a pathogenic organism.

D. Peptides as Modulators of Enzyme Activity of Proteins Involved in Protein-protein Interactions Peptides synthesized according to a method of the invention may be effective to modulate the function of a target molecule (e.g. serve as agonists or antagonists). As shown herein, for example, peptides rVIII and rVI can serve to activate or enhance the activation of PKC, whereas peptide I can inhibit PKC.

These activities may be used in screens to identify other compounds which may affect the function of target molecules such as PKC. In particular, because WD-40 derived peptides may interact with PKC in a manner that is more similar to in vivo interactions (i.e. protein binding), they may be useful for identifying molecules or compounds that may interfere with PKC function in vivo, but might not necessarily interfere with PKC in vitro.

For example, peptide rVI can be used to stimulate PKC in the absence of traditional PKC activators, and the rVI-stimulated enzyme may be used in a screen to identify, for example, novel PKC-inhibiting or PKC-potentiating compounds.

If constitutive activation or inactivation of a target enzyme is desired, peptides may be designed with integrated or derivatized cross-linking moieties. The peptides can be cross-linked to their targets upon binding such that the target molecule assumes the desired state of activity for the lifetime of the target molecule.

Conversely, as described herein for PKC, peptides may also be designed so as to accelerate the degradation of the target molecule. For example, peptide rIII accelerated the degradation of PKC in cardiac myocytes.

E. WD-40 Derived Peptides as Specific Modulators of Isozymes

Peptides designed according to a method of the present invention can also be used to provide target isozyme-specific modulator molecules. For example, most cells have several PKC isozymes, all of which are activated by the same cellular stimuli. Determining the function of the individual isozymes is therefore difficult.

WD-40 derived peptides that selectively stimulate or inhibit specific target isozymes or groups of isozymes may be useful, both in terms of therapeutic value, and in terms of determining the roles of different isozymes in cellular function and disease. Such information can be useful for the identification of new molecular targets for drug development, as is described in part F, below.

F. Compounds Designed Based on the Predicted Structure of Binding Peptides as Pharmaceutical Agents Peptides derived from WD-40 repeats may be useful for identifying lead compounds for drug development. Peptides as small as 7 residues have been shown herein to possess specific bioactivities upon interaction with their targets in vivo. The structure of such small peptides can be readily determined by a number of methods, such as NMR and X-ray crystallography. A comparison of the structures of peptides similar in sequence, but differing in the biological activities they elicit in the target molecules, can provide information about the structure-activity relationship (SAR) of the target enzyme.

For example, peptide I and RACK1-derived peptides rIII (SEQ ID NO:4) and rVI (SEQ ID NO:7) had opposite effect in vivo, although they are homologous in sequence.

Information gleaned from the examination of structure-activity relationships can be used to design either modified peptides, or other small molecules or lead compounds which can be tested for predicted properties (e.g. agonist or antagonist), as related to the target enzyme. The activity of the lead compounds can be evaluated using assays similar to those used in the evaluation of peptide-binding effects.

Information relating to a SAR of a target enzyme may also be obtained from co-crystallization studies. In such studies, a peptide with a desired activity is crystallized in association with a target protein, and the X-ray structure of the complex is determined. The structure can then be compared, for example, to the structure of the target protein in its native state, and information from such a comparison may be used to design compounds expected to possess specific activities. The compounds can be evaluated using assays similar to those used in the evaluation of peptide-binding effects.

G. PCR of cDNA Corresponding to WD-40 Repeats to Identify Mutations in WD-40 Containing Proteins Results presented herein suggest that the middle regions of WD-40 motifs are involved in the association of a WD-40 protein with its target protein. Because this association is likely to play a central role in the activity of a polypeptide complex comprised of interacting proteins, some genetic diseases may include mutations at these regions of WD-40 containing proteins. Therefore, if a WD-40 containing protein is implicated in a genetic disorder, it may be possible to use PCR to amplify DNA from the WD-40 regions to quickly check if a mutation is contained within one of the WD-40 motifs. Primers can be made corresponding to either (i) the flanking regions of each repeat or (ii) the flanking regions of a series of tandem repeats from the affected gene. Standard sequencing techniques can be used to determine whether a mutation is present. This method does not require prior chromosome mapping of the affected gene and can save time by obviating the need to sequence the entire gene encoding a defective WD-40 protein.

H. WD-40 Based Polypeptides as Affinity Ligands

Since the polypeptide compositions of the invention are able to bind proteins of interest, generically called a "first protein", the polypeptide compositions can also be used to retrieve the proteins of interest from samples and the peptides can be used as affinity ligands for chromatographic procedures to purify and analyze said proteins. Standard chromatographic techniques are employed. Typically, the polypeptide is coupled to a solid support and the sample putatively containing the first protein is contacted with the polypeptide composition of the invention; any unbound components of the sample are removed and, if desired, the first protein, bound to support, is eluted and recovered.

I. Use of Peptides in Screening Tests for Candidates

Various candidate compounds, not necessarily polypeptides, may be shown to bind to a first protein using the polypeptides of the invention as competitors. In these screening assays, the ability of a candidate compound to bind a first protein can be assessed by contacting the first protein with the polypeptide composition of the invention in the presence and absence of the candidate compound and evaluating the level of binding of the polypeptide in the presence as opposed to the absence of the candidate. Decreased binding of the polypeptide in the presence of the candidate indicates that the candidate binds to the first protein.

More broadly, the interaction of a protein with a polypeptide subsequence contained in the second protein can be assessed by contacting the first protein with a polypeptide representing the subsequence and observing any interaction with the polypeptide composition.

IX. Production of the Peptides of the Invention

The polypeptides of the invention can be prepared using standard techniques for the synthesis of peptides from amino acids. Such techniques, when conducted in solid phase chemistry are available commercially.

The polypeptides of the invention may also be produced using recombinant methods. These methods are by now well known in the art; DNA molecules containing nucleotide sequences encoding the desired polypeptides can readily be synthesized and ligated into expression systems for production of the peptides as is understood in the art. A wide variety of hosts is available, including procaryotic and eucuryatic hosts. The construction of expression vectors, means to modify these hosts, and culturing the modified hosts for recombinant production of polypeptides are conducted using standard techniques.

The following examples illustrate, but do not limit the present invention.

Materials and Methods

Nitrocellulose filters were obtained from Schleicher and Schuell (Keene, N.H.).

Synthetic peptides were prepared using commercially available automated peptide synthesizers. Alternatively, custom designed peptides may be purchased, for example, from Bachem Bioscience (King of Prussia, Pa.). Peptides may also be prepared recombinantly by expressing oligonucleotide sequences encoding the peptides. The oligonucleotide sequences may be either synthesized directly by standard methods of oligonucleotide synthesis, or, in the case of large coding sequences, synthesized by a series of cloning steps involving a tandem array of multiple oligonucleotide fragments corresponding to the coding sequence (Crea; Yoshio, et al.; Eaton, et al.). Oligonucleotide coding sequences can be expressed by standard recombinant procedures (Maniatis, et al.; Ausubel, et al.).

"Triton" refers to a nonionic detergent comprising a polyoxyethylene ether and other surface-active compounds. An exemplary Triton detergent is "TRITON X-100", available from Sigma Chemical Company, St. Louis, Mo.

"Tween" refers to a nonionic detergent comprising polyoxyethylenesorbitan monolaurate with a fatty acid composition of approximately 55% lauric acid, with a balance composed primarily of myristic, palmitic and stearic acids. An exemplary Tween detergent is "TWEEN 20", available from Sigma Chemical Company, St. Louis, Mo.

"SDS" refers to sodium dodecyl sulfate.

"PAGE" refers to polyacrylamide gel electrophoresis.

"IPTG" refers to isopropyl β-D-thiogalactopyranoside.

EXAMPLE 1

Expression Cloning of a PKC-binding Protein

A. Buffers

Overlay block buffer: 50 mM Tris-HCl (pH 7.5), 0.2 M NaCl, 3% bovine serum albumin (BSA) and 0.1% polyethylene glycol.

Overlay buffer: 50 mM Tris-HCl (pH 7.5), 0.2 M NaCl, 12 mM 2-mercaptoethanol, 0.1% BSA, 1% polyethylene glycol, 10 μg per ml soybean trypsin inhibitor and 10 μg per ml leupeptin.

B. Isolation of a PKC-binding cDNA Clone by an Overlay Assay

A rat brain (Sprague Dawley) cDNA expression library, constructed in the lambda phage cloning vector "UNI-ZAP XR" (Stratagene, La Jolla, Calif.), was screened by an overlay assay as follows.

Lifts of nitrocellulose filters from IPTG-induced cDNA library plates were incubated for 2 hours in overlay block buffer. The filters were then transferred to overlay buffer with or without 1 unit of a mixture of rat brain PKC isozymes (α, β, γ, δ, ε and ζ, ~10 nM final concentration each) and incubated for 20 minutes at room temperature with PKC activators (60 μg/ml phosphatidylserine (PS), 2 μg/ml diacylglycerol (DG), 1 mM $CaCl_2$)

Following three 15 minute washes in the overlay buffer, the filters were incubated in the overlay block buffer in the presence of a mixture of monoclonal anti-α, β and γ PKC antibodies (1:1000 dilution; Seikagaku Kogyo, Tokyo, Japan) and polyclonal anti-δ, ε and ζ PKC antibodies (1:500 dilution; Life Technologies, Gaithersburg, Md.). After a 16 hr incubation at room temperature, the filters were washed three times, 15 minutes per wash, in overlay buffer.

Binding of PKC was determined using alkaline phosphatase-conjugated goat anti-rabbit or goat anti-mouse antibodies (1:2000 dilution, Boehringer Mannheim Biochemicals, Indianapolis, Ind.). The alkaline phosphatase reaction used 5-bromo-4-chloro-3-indoyl phosphate p-toluidine salt as a substrate, and was performed following the manufacturer's protocol.

Library screening of $2.4 \times 10^6$ recombinant "UNI-ZAP" lambda phage plaques yielded one clone, pRACK1, that reacted with anti-PKC antibodies in the PKC overlay membrane, but not in the control overlay membrane. These results suggest that pRACK1 encodes a PKC binding protein.

C. Cloning and Sequencing cDNA from Positive Plaques

The clone pRACK1, identified as detailed in part B above, was plaque purified and cDNA inserts were isolated as phagemids by in vivo excision of the cloning vector, according to the manufacture's protocol (Stratagene, La Jolla, Calif.). DNA sequencing of pRACK1 was carried out using standard di-deoxy sequencing techniques (Maniatis, et al.) The DNA sequence of RACK1 is shown in FIG. 1A. The sequence is also contained in the Sequence Listing as SEQ ID NO:19.

EXAMPLE 2

Expression and Purification of Recombinant RACK1 Protein in *E. coli*

A PstI/XhoI DNA fragment containing an open reading frame of 317 amino acids from the putative translation start site of pRACK1 (see underlined ATG in FIG. 1A) and 8 additional nucleotides upstream of the initiating methionine was subcloned into *E. coli* expression vector pMAL-c2 (New England BioLabs, Beverly, Mass.). This vector contains the malE gene, which encodes maltose-binding protein (MBP). Induction of *E. coli* containing the vector results in the production of an MBP-fusion protein (Ausubel, et al.). The vector also includes a recognition site for the protease factor Xa, which allows the protein of interest to be cleaved from MBP after purification without adding any vector-derived residues to the protein.

A culture of TB1 *E. coli* transformed with RACK1-containing pMAL-c2 was induced by a 3 hr incubation with 1.8 mM IPTG. A protein fraction containing a 78 kDa fusion protein, comprised of RACK1 fused to MBP was isolated from the cultured *E. coli* by standard methods (Ausubel). The fusion protein was purified on an amylose affinity column according to the manufacture's protocol (New England BioLabs, Beverly, Mass.) and incubated with protease Xa (New England BioLabs) to yield a 36 kDa protein (RACK1) and a 34 kDa protein (possibly a RACK1 degradation product).

EXAMPLE 3

Binding of PKC to Recombinant RACK1

A. Buffers

PBS/Tween buffer: 140 mM NaCl, 8 mM $Na_2PO_4$, 1.5 mM $KH_2PO_4$, 3 mM KCl and 0.05% Tween at pH 7.0.

Overlay wash buffer: 50 mM Tris-HCl (pH 7.5), 0.2 M NaCl, 12 mM 2-mercaptoethanol, 0.1% polyethylene glycol and 0.1 mM $CaCl_2$.

B. Overlay Assay

Purified recombinant RACK1 protein (100–250 μg per lane, produced as detailed in Example 2) was subjected to SDS/PAGE and blotted onto nitrocellulose membranes (Ausubel). The nitrocellulose membranes were cut into strips, which were incubated for 0.5 hr in overlay buffer (Example 1) in the presence or absence of a mixture of PKC isozymes (α, β, γ, δ, ε and ζ, ~10 nM each final concentration) and PKC activators (60 μg/ml phosphatidylserine (PS), 2 μg/ml diacylglycerol (DG), and 1 mM $CaCl_2$). Unbound material was removed by five washes, 5-min each, in overlay wash buffer. Where indicated, PKC activators were present during the incubation of PKC with the nitrocellulose strips. The conditions for each sample and corresponding results are presented in part D below.

C. Detection of Bound PKC

PKC bound to RACK1 immobilized on nitrocellulose strips was detected as follows. The strips were incubated for 16 hours at room temperature with a mixture of anti-PKC antibodies as detailed in part B of Example 1, and then washed three times, 15 minutes per wash, with PBS/Tween buffer. The strips were incubated with anti-mouse and anti-rabbit horseradish peroxidase-linked secondary antibodies (Amersham Life Science, Arlington Heights, Ill.) diluted 1:1000 in PBS/Tween buffer supplements with 2% BSA, for 1 hour at room temperature. After washing three times, 15 minutes per wash with PBS/Tween buffer, the strips were subjected to a chemiluminescent reaction with luminol (diacylhydrazide) as detailed in the manufacturer's protocol (Amersham Life Science, Arlington Heights, Ill.), followed by an immediate exposure to autoradiography film (Eastman Kodak, Rochester, N.Y.) for 30 seconds to 5 minutes.

D. Effects of PKC Activation on PKC Binding to RACK1

Figure 2:
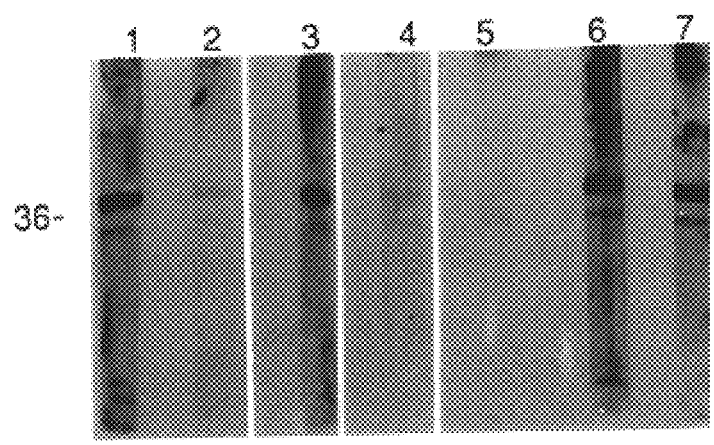
FIG. 2 shows the results of an overlay assay to detect PKC binding to immobilized RACK1 in the presence and absence of PKC activators.

The results presented in FIG. 2 show the influence of PKC activators on the binding of PKC to RACK1 immobilized on nitrocellulose membranes. The overlay assay was carried out as described in part B above. The test reagents contained in each sample and the corresponding lanes on the blot presented in FIG. 2 are as follows. Lane 1: PKC, 60 μg/ml PS, 2 μg/ml DG and 1 mM $CaCl_2$; lane 2: PKC and 1 mM EGTA; lane 3: PKC, 60 μg/ml PS and 2 μg/ml DG; lane 4: PKC and 1 mM $CaCl_2$; lane 5: No PKC added; lanes 6 and 7: PKC, 60 μg/ml PS 2 μg/ml DG, 1 mM $CaCl_2$, and 10 μM substrate peptide (SEQ ID NO:11; lane 6) or 10 μM pseudosubstrate peptide (SEQ ID NO:12; lane 7). The results are representative of three independent experiments.

It can be appreciated that the binding of PKC as detected by anti-PKC antibodies is minimal in the presence of EGTA or calcium alone (FIG. 2, lanes 2, 4, respectively), is greater in the presence of phosphatidylserine (PS) and diacylglycerol (DG; lane 3), and is maximal in the presence PS, DG and calcium (lane 1). Antibody binding was not observed in the absence of added PKC (lane 5). Furthermore, maltose binding protein alone, or an extract from non-transformed *E. coli* did not bind PKC.

The concentration dependence of PKC binding to RACK1 was characterized with βPKC, since this isozyme is a major component of the PKC mixture used for the overlay assay. The mean half maximal binding was ~0.375 nM, and maximal binding was ~4 nM (n=3; values reflect binding of βPKC isozyme in the presence of other PKC isozymes and was determined by scanning autoradiograms in the linear range of detection, as described in Mochly-Rosen, et al., (1991).

The results presented above indicate that in order for PKC to bind to RACK1 it must be activated. In vitro, activation may be accomplished, for example, by phosphatidylserine and diacylglycerol, or, more preferably, by phosphatidylserine, diacylglycerol and calcium.

EXAMPLE 4

Inhibition of PKC Binding to RACK1 by RACK1-specific WD-40-homologous Peptides Assays for the inhibition of PKC binding to RACK1 by putative binding peptides were carried out by combining a variation of the overlay protocol described in Example 3 part B above, with an overlay extraction assay described in part B below. The variation in the overlay protocol consisted of incubating the putative binding peptides with a mixture of PKC isozymes for 15 minutes at room temperature before the mixture was used to contact the nitrocellulose strips containing immobilized RACK1.

A. Buffers

Sample buffer: 0.3 M Tris HCl, 5% SDS, 50% glycerol, 0.01% bromophenol blue and 5% β-mercaptoethanol.

B. Overlay Extraction Protocol

Nitrocellulose strips containing immobilized RACK1, that had been contacted with a solution containing a mixture of PKC isozymes, were washed and the area corresponding to the 36 kDa (RACK1-containing) band was cut out. The pieces (containing PKC/RACK1 complexes) were incubated with sample buffer for 10 minutes at 80° C. The sample buffer and the nitrocellulose pieces were then placed in wells in the PAGE gel and subjected to SDS-PAGE to elute the bound proteins. The gel was blotted onto nitrocellulose and a Western blot analysis was carried out using the mixture of antibodies (specific for PKC α, β, γ, δ, ε and ζ isozymes) described in Example 1 part B. Bound antibodies were detected by $^{123}$I-protein A.

C. PKC Overlay in the Presence of Binding Peptides

Peptides derived from or homologous to WD-40 repeats of RACK1 were tested for their ability to inhibit PKC binding to recombinant RACK1. Binding of PKC to RACK1 was carried out using a variation of the overlay procedure described in Example 3 part B. In the experimental samples, peptides were incubated with a solution containing a mixture of rat brain PKC isozymes (~10 nM each) for 15 minutes at room temperature.

Following completion of the modified overlay protocol, the samples were subjected to the overlay-extraction protocol detailed in part B, above.

The results in FIG. 3 show the binding of PKC to RACK1, carried out without (lane 1) or with (lanes 2–4) a preincubation of peptides with PKC. Lane 2 shows PKC binding following a preincubation with 10 μM peptide I (SEQ ID NO:1). Peptide I caused an 81±6% inhibition of PKC binding to recombinant RACK1 as compared with binding in the absence of added peptide (n=3). Lanes 3 and 4 show PKC binding following a preincubation with 10 μM peptide rIII (SEQ ID NO:4) and 10 μM peptide rVI (SEQ ID NO:7), respectively. Both peptides inhibit the binding of PKC to RACK1. It can be seen that peptide rIII is somewhat more effective than peptide rVI. The results shown are representative of three independent experiments.

The overlay-extraction method (part B above) was used in experiments relating to the peptide inhibition of PKC binding in order to decrease the possibility that some part of the inhibition of PKC binding to RACK1 reflects an interference in the binding of anti-PKC antibodies to the PKC/RACK1 complexes. Free peptides are effectively removed from the PKC/RACK1 complexes during the second round of SDS/PAGE, prior to blotting and detection of immobilized PKC/RACK1 complexes by anti-PKC antibodies.

EXAMPLE 5

Identification of Sequenced Proteins Containing WD-40 Repeats

A search for WD-40 motif-containing proteins was done using the ENTREZ program, release 6.0 (National Center for Biotechnology Information, National Library of Medicine, National Institutes of Health, Bethesda, Md.). The ENTREZ database was searched for protein sequences related to the β subunit of transducin.

Protein sequences homologous to β-transducin were examined for the existence of WD-40 repeats, following the guidance for identification of WD-40 repeats presented in section V of the specification, above.

The proteins were also used to carry out additional searches of the database, in order to identify other proteins which may contain WD-40 repeats, but which might not be homologous to the β subunit of transducin. Sequences identified during the second round of searches were again examined for WD-40 repeats.

This search strategy identified 30 proteins containing WD-40 sequences. The amino acid sequences of these proteins, with the WD-40 regions aligned and delineated, are shown in FIGS. 12–18, 20–27, 29–30, 34–35, 37–38, 40 and 42–50. The sequences are represented in the Sequence Listing as SEQ ID NO:29–35, 37–44, 46–47, 51–52, 54–55, 57 and 59–67. An examination of the sequences in the figures reveals that although there can be divergence between the WD-40 motifs of different proteins, a consistent pattern can be inferred based on the teachings presented in part V of the specification above.

An additional search, using a consensus WD-40 sequence (SEQ ID NO:262), was conducted with the "MACVECTOR" program (Eastman Kodak Co., New Haven, Conn.) to search GenBank (December 1993 release). Default settings (matrix=250) were used for the search. The search identified the 250 proteins with the highest homology to the consensus sequence. These proteins were examined, as detailed in part V above, for WD-40 repeats. Ten additional proteins containing WD-40 repeats were identified with this strategy. The amino acid sequences of those proteins, with the WD-40 repeats aligned and delineated, are shown in FIGS. 11, 19, 28, 31–33, 36, 39, 41 and 51. The sequences are represented in the Sequence Listing as SEQ ID NO:28, 36, 45, 48–50, 53, 56, 58 and 68.

EXAMPLE 6

Binding of βPKC to RACK1 WD-40-derived Peptides

A. Buffers

Peptide overlay block buffer: 20 mM Tris-HCl (pH 7.5), 0.2 M NaCl, 3% bovine serum albumin (BSA) and 0.1% polyethylene glycol.

Overlay wash buffer: 50 mM Tris-HCl (pH 7.5), 0.2 M NaCl, 12 mM 2-mercaptoethanol, 0.1% polyethylene glycol and 0.1 mM $CaCl_2$.

B. PKC Overlay of Immobilized Peptides

The binding of βPKC to peptide I (SEQ ID NO:1), peptide rVI (SEQ ID NO:7) and control peptide (SEQ ID NO:9) was assessed using a PKC overlay assay similar to that described in Example 3. Increasing amounts of peptides (0.5 μmole, 1.0 μmole, 5.0 μmole and 10.0 μmole) suspended in 20 mM NaCl were applied individually onto nitrocellulose using a slot-blot apparatus (Schleicher and Schuell, Keene, N.H.). The nitrocellulose membrane was washed three times, 15 minutes per wash, in peptide overlay buffer and incubated for two hours in peptide overlay block buffer. The membrane was cut into sections and the sections were transferred to different PKC-containing solutions and incubated for 30 minutes at room temperature. All the solutions contained 5 nM rat brain PKC in peptide overlay buffer. Some solutions additionally contained PS, DG, and calcium. The membranes were then washed three times, 15 minutes per wash, in peptide overlay buffer and incubated in peptide overlay block buffer containing anti-βPKC monoclonal antibodies (1:1000 dilution; Seikagaku Kogyo, Tokyo, Japan). After a 16 hr incubation at room temperature, the filters were washed three times, 15 minutes per wash, in peptide overlay buffer.

Binding of PKC was determined using chemiluminescence as described in Example 3, part C. Quantitation of PKC binding was carried out using a "MICRO SCAN" 1000 gel analyzer (Galai Inc., Yokneam, Israel).

The data show that activated PKC bound to both peptides I and rVI, but not to the control peptide, at peptide amounts as low as 5 μmoles. Unactivated PKC did not bind to peptide I, but did bind to peptide rVI at similar concentrations.

The results indicate that peptide rVI is capable of binding both activated as well as unactivated forms of PKC, whereas peptide I binds only to activated PKC.

EXAMPLE 7

Effects of RACK1 WD-40-derived Peptides on PKC-mediated Oocyte Maturation

Exposure to insulin induces maturation in Xenopus oocytes via a PKC-dependent pathway (Smith, et al., 1992). The maturation response may be quantified by monitoring the appearance of a white spot in the animal hemisphere of the oocyte, indicating germinal vesicle breakdown (GVBD) and maturation. To assess the effects of RACK1 WD-40-derived peptides on insulin-induced PKC-mediated maturation, 50 nl of a 20 mM NaCl solution containing the indicated peptides [peptide I (SEQ ID NO:1; ●), peptide rVI (SEQ ID NO:7; ■), or injection solution (□)] (peptides at 50 μM) were microinjected into Xenopus oocytes. The symbols refer to symbols used in FIG. 5, which shows the data from this example. One hour following the peptide injections, the oocytes were exposed to a solution containing insulin (8.25 μg/ml) for 2 minutes (t=0). 10–15 oocytes were used for each sample.

The data, representative of three independent experiments, are expressed as the percent of oocytes with GVBD following insulin exposure and are plotted as a function of time in FIG. 5.

In oocytes injected with buffer or control peptide, onset of maturation was typically 4–5 hours after exposure to insulin. Following this delay, %GVBD followed an approximately exponential time-course, reaching a plateau of about 85–90% GVBD at about 10–12 hours. These data indicate that approximately 80–85% of sham-injected oocytes exposed to insulin at t=0 reach maturation, and that maturation is reached relatively quickly (within about 10 hours) relative to the time-course of the experiment (20 hours).

Oocytes injected with peptide I (SEQ ID NO:1) responded in a manner similar to control oocytes, except the plateau was at about 45–50% GVBD. These data suggest that injection of peptide I blocked maturation in approximately 40–45% of oocytes that would normally proceed to maturation, but had little effect on the kinetics or extent of maturation of the remaining (50–55%) oocytes.

Oocytes injected with peptide rVI (SEQ ID NO:7) responded with a slightly shorter delay (about 3–4 hours), but reached a higher plateau (about 95–100% GVBD) more quickly (within about 5 hours) than control oocytes. These data suggest that peptide rVI potentiates the effects of insulin on oocyte maturation, both in terms of the rate of maturation, and in the total fraction of oocytes that mature during the experiment. Injection of peptide rVI increases the maturing fraction to essentially 100%.

The effects of both peptides I and rVI on GVBD were dose-dependent between 5 µm–500 µM.

Since peptide rVI enhanced insulin-induced GVBD, experiments were performed to determine whether peptide rVI can induce GVBD in the absence of insulin. The data from these experiments are shown in FIG. 5B. Microinjection of peptide rVI (50 µM) alone, but not peptide I, control peptide or buffer, induced GVBD. Maturation initiated with a longer delay (about 6–7 hours) than in the control insulin-induced oocytes in FIG. 5A (about 4–5 hours), and reached a plateau of about 50% GVBD.

Together, the data above indicate that peptides homologous to the WD-40 region of RACK1 modulate the function of PKC. Peptide I inhibited PKC-mediated oocyte maturation by about 40%, whereas peptide rVI potentiated insulin-induced maturation, and resulted in a limited maturation response even in the absence of insulin. The latter result suggests that peptide rVI, under appropriate circumstances, may act to activate PKC in the absence of other activating substances.

EXAMPLE 8

Effects of RACK1 WD-40-derived Peptides on PKC Translocation in Xenopus Oocytes

A. Buffers

Homogenization buffer: 20 mM Tris HCl, pH 7.5, 10 mM EGTA, 2 mM EDTA, 0.25M sucrose, 10 µM phenylmethylsulfonyl fluoride, 20 µg/ml of each leupeptin and soybean trypsin inhibitor.

B. PKC Translocation in Oocytes

Insulin causes the translocation of βPKC, but not other PKC isozymes, from a cytosolic form to a membrane-associated form, as evidenced by the relative levels of PKC in the soluble vs. the particulate fraction of oocyte homogenate. To assess the effects of RACK1 WD-40-derived peptides on insulin-induced PKC translocation, 50 nl of a 20 mM NaCl solution containing the indicated peptides were microinjected into Xenopus oocytes. The oocytes were then homogenized, and the relative amount of PKC in the soluble and particulate fractions was assayed. The protocol followed was a modification of a method described by Smith, et al. (1992). The results are shown in FIG. 6.

Batches of 50 oocytes were microinjected with either peptide rVI (SEQ ID NO:7; 50 µM; lanes 3, 4), peptide I (SEQ ID NO:1; 50 µM, lanes 7, 8) or injection solution (NaCl 20 mM, lanes 1,2 and 5,6). Homogenates from each batch were prepared 60 minutes after microinjection (lanes 1–4) or 60 minutes after addition of insulin (lanes 5–8). The homogenates were centrifuged at 10,000 g for 3 minutes, the upper layer (containing fat and yolk) was removed, and the remainder was frozen at −70° C. Prior to use, the samples were thawed, 200 µl homogenization buffer was added and the samples were centrifuged at 100,000 g for 30 minutes at 4° C. The supernatants (soluble fraction) were removed and concentrated to 20 µl using "CENTRICON" concentrators (Amicon, Beverly, Mass.). The pellets (particulate fractions) were dissolved in 20 µl of homogenization buffer. The samples were resolved on an 8% SDS/PAGE gel and blotted onto nitrocellulose. The amount of PKC in each fraction was determined by Western blot using anti-βPKC antibodies (1:1000 dilution; Seikagaku Kogyo, Tokyo, Japan). Bound primary antibodies were detected by chemiluminescence as described in Example 3, part C.

The antibodies showed immunoreactivity with an ~80 kDa protein that corresponds to βPKC. Data are representative of three experiments.

The data are shown in FIG. 6. Lanes 1, 3, 5 and 7 contain particulate fractions (p), while lanes 2, 4, 6 and 8 contain soluble (cytosol) fractions (c). Peptide I (50 µM) did not affect βPKC distribution in untreated oocytes, but inhibited insulin-induced βPKC translocation (FIG. 3, lanes 7,8). In contrast, peptide rVI (50 µM) induced βPKC translocation in the absence of insulin treatment (FIG. 3, lanes 3,4).

The results above suggest that peptide I is an antagonist of insulin-induced PKC translocation, whereas peptide rVI is an agonist and an activator of PKC translocation. In light of the results presented in Example 7, the data also suggest that the inhibition of insulin-induced GVBD following microinjection of peptide I was due to an inhibition of βPKC translocation.

EXAMPLE 9

Effects of RACK1 WD-40-derived Peptides on Sensitivity of PKC to Arg-C Endopeptidase A. Buffers Sample buffer: 0.3 M Tris HCl, 5% SDS, 50% glycerol, 0.01% bromophenol blue and 5% β-mercaptoethanol.

B. Nicking of βPKC by Arg-C Endopeptidase

Upon activation of PKC, a pseudosubstrate autoinhibitory sequence at the N-terminus of the molecule dissociates from the catalytic site and becomes sensitive to endopeptidase Arg-C (Orr, et al.). In the absence of PKC activators, exposure of the 80 kDa βPKC to endopeptidase Arg-C has no effect on the enzyme (see FIG. 7, lane 1). In the presence of the PKC activators PS, DG and calcium, however, exposure of βPKC to Arg-C results in a "nicking" of the PKC (i.e. limited proteolysis generating a 78 kDa fragment and several small fragments (see FIG. 7, lane 2)). Continued exposure to Arg-C results in the disappearance of βPKC (Orr, et al.). The present experiment tests whether peptides derived from the WD-40 region of RACK1 alter the sensitivity of βPKC to endopeptidase Arg-C.

The methods used to assay Arg-C sensitivity are a modification of methods described by Orr, et al. Rat brain PKC (~5 nM) was incubated at room temperature in 500 µl of 20 mM Tris-HCl buffer (pH 7.5) alone or with Arg-C (5 units/ml) in the presence or absence of the indicated peptides (final concentration 10 µM or as indicated), PS, DG, and calcium (as indicated). 50 µl aliquots were removed into 20 µl of sample buffer during the reaction as indicated (samples in all the lanes were incubated for 30 minutes, except lanes 5, and 6, which were incubated for 5 and 15 minutes, respectively). The samples were boiled for 10 minutes at 80° C. and loaded onto 8% SDS-PAGE. βPKC was detected by Western blot analysis using anti-βPKC antibodies as described in Examples 6 and 8.

The results are shown in FIG. 7. PKC was incubated for the indicated time alone (lane 1) or in the presence of Arg-C (lanes 2–9), with DG (0.8 μg/ml), PS (50 μg/ml) and CaCl$_2$ (1 mM; lane 2), with PS (50 μg/ml) and CaCl$_2$ (1 mM; lane 3), with PS (2.5 μg/ml) and CaCl$_2$ (50 μM; lane 4); with PS (2.5 μg/ml), CaCl$_2$ (50 μM) and with either peptide rVI (SEQ ID NO:7; 10 μM; lanes 5–7), control peptide (SEQ ID NO:9; lane 8) or with peptide I (SEQ ID NO:1; lane 9).

Incubation of βPKC with Arg-C at low concentrations of activators (2.5 μg/ml PS and 50 μM CaCl$_2$) in the absence of added peptide did not result in appreciable nicking activity (FIG. 7, lane 4). Similarly, nicking of βPKC did not occur in the presence of this concentration of activators with peptide I (lane 9) or with control peptide (lane 8). However, incubation of βPKC with the same concentration of activators in the presence of peptide rVI resulted in a time-dependent appearance of the 78 kDa nicked PKC fragment (FIG. 4, lanes 5–7). Concentrations as low as 10 nM of peptide rVI were sufficient to result in nicking activity, indicative of βPKC activation. The results indicate that peptide rVI, but not peptide I, is effective to stabilize PKC in an activated conformation that renders it susceptible to Arg-C under conditions of low PKC activators that would otherwise not render the enzyme susceptible to Arg-C.

EXAMPLE 10

Effects of RACK1 WD-40-derived Peptides on PKC Autophosphorylation

Activated PKC is capable of autophosphorylation. Since peptide rVI (SEQ ID NO:7) was effective to induce PKC translocation and GVBD in the absence of an activator such as insulin, the ability of the peptide to induce PKC autophosphorylation in the absence of PKC activators was assessed.

PKC autophosphorylation in the presence of βPKC pseudosubstrate antibodies or the indicated peptides was carried out using a modification of the method described by Makowske, et al. Anti-pseudosubstrate antibodies, which were shown previously to induce autophosphorylation in the absence of PKC activators (Makowske, et al.) were used as a positive control. The results are shown in FIG. 8.

Rat brain PKC (~10 nM) was incubated with mild agitation in a final volume of 250 μl of overlay buffer, as in Example 1 either with anti-βPKC pseudosubstrate antibodies (1:10 dilution, Life Technologies, Gaithersburg, Md.) or with the indicated peptide (10 μM). Where indicated, PS (50 μg/ml), DG (0.8 μg/ml) and CaCl$_2$ (1 mM) were also added. The amount of autophosphorylation was determined after 2 hours for the reaction with the anti-pseudosubstrate antibodies, or after 15 minutes for the other samples. 50 μl of a buffer comprised of 20 mM Tris-HCl (pH 7.5), 20 mM MgCl$_2$, 20 μM ATP and 5 μci/ml [γ-$^{32}$P]ATP. The mixture was incubated for 15 minutes at room temperature and the reaction was stopped by adding 60 μl sample buffer (see Example 9). The samples were then boiled for 10 minutes, loaded onto a 10% SDS-PAGE mini gel and electrophoresed. The gel was fixed with 50% methanol and 10% acetic acid for 1 hour, and the autophosphorylation of PKC was determined by autoradiography.

The results in FIG. 8 show PKC autophosphorylation in the presence of DG, PS, and calcium (lane 1), in the presence of EGTA (lane 2), in the presence of anti-βPKC pseudosubstrate antibodies (diluted 1:10 in 20 mM Tris-HCl; lane 3), in the presence of peptide rVI (SEQ ID NO:7; 10 μM; lane 4), in the presence of peptide I (SEQ ID NO:1; 10 μM; lane 5), or in the presence of control peptide (SEQ ID NO:9; 10 μM; lane 6).

Peptide rVI in the absence of PKC activators induced PKC autophosphorylation to over 80% of the autophosphorylation obtained in the presence of optimal concentration of PS, DG, and calcium (compare FIG. 8 lane 1 (control) with lane 4 (peptide rVI). Neither peptide I nor control peptide induced PKC autophosphorylation in the absence of PKC activators (FIG. 8 lanes 5 and 6, respectively).

EXAMPLE 11

Effects of RACK1 WD-40-derived Peptides on Histone Phosphorylation by PKC

Incubation of PKC with peptide rVI (SEQ ID NO:7) induced histone phosphorylation by PKC. The method used was a modification of the protocol described by Mochly-Rosen, et al. (1987). The results are shown in FIG. 9.

Histone type IIIs (Sigma Chemical Company, St. Louis, Mo.) was phosphorylated by PKC (~10 nM) in the absence (lane 1) and presence of peptide rVI (10 μM) (lanes 2 and 3) and in the presence and absence of DG (0.8 μg/ml), PS (50 μg/ml) and CaCl$_2$ (1 mM) (lane 3). The results are expressed as percentage of control that is the amount of Histone phosphorylation by PKC in the presence of DG (0.8 μg/ml), PS (50 μg/ml) and CaCl$_2$ (1 mM). The results are the average ±SEM of two independent experiments. PKC was first incubated with the peptide rVI (10 μM) for 15 minutes in overlay buffer as described above. Histone type IIIs (40 μg/ml) was added in Tris-HCl (20 mM), MgCl$_2$ (20 mM), ATP (20 μM) and [γ-$^{32}$P]ATP (5 μci/ml) with or without PS (50 μg/ml), DG (0.8 μg/ml) and CaCl$_2$ (1 mM). Histone phosphorylation was determined by autoradiography as above.

PKC activators PS, DG, and calcium were not required for either peptide rVI-induced autophosphorylation or histone phosphorylation, suggesting that peptide rVI is an agonist of PKC activation.

In a related experiment, phosphorylation of histone type IIIs (25 μM) by PKC (10 nM) was not inhibited by RACK1; rather, a 4.5±0.1 fold increase of histone phosphorylation occurred when co-incubated with ~100 nM RACK1 (n=2).

What is claimed is:

1. A method to identify a compound which will modulate the localized enzymatic activity of a first target protein that interacts with a second protein containing at least one WD-40 region which method comprises
   determining the interaction of said first and second protein containing at least one WD-40 region in the presence and absence of a candidate compound;
   comparing the level of interaction of said first and second protein in the presence and absence of said candidate compound; and
   identifying as a successful candidate a compound which modifies the level of interaction of said first and second protein in its presence as opposed to its absence, wherein the first target protein is selected from the group consisting of protein kinase C (PKC) and β adrenergic receptor kinase (βARK) and wherein the WD40 region has the amino acid sequence set forth in SEQ ID NO:69–SEQ ID NO:75, the sequence set forth in SEQ ID NO:28–SEQ ID NO:68 or the sequence set forth in SEQ ID NO:128–SEQ ID NO:134.

2. The method of claim 1 wherein the first target protein is a protein kinase C (PKC).

3. The method of claim 1 wherein the first target protein is a β adrenergic receptor kinase (βARK).

4. The method of claim 1 wherein the second protein is a receptor for activated protein kinase C (RACK).

5. The method of claim 4 wherein the second protein has the sequence represented by SEQ ID NO:27.

6. A method to identify a compound which modulates the localized enzymatic activity of a first target protein which interacts with a second protein containing at least one WD-40 region which method comprises
   determining the interaction between said first target protein and a peptide of 4–50 amino acids, said peptide having an amino acid sequence derived from the amino acid sequence of the same length in said WD-40 region of said second protein, in the presence and absence of a candidate compound;
   comparing the level of interaction of said first and second protein in the presence and absence of said candidate compound; and
   identifying as a successful candidate a compound which modifies the level of said interaction in its presence as compared to its absence, wherein the first target protein is selected from the group consisting of protein kinase C (PKC) and β adrenergic receptor kinase (βARK) and wherein the WD-40 region has the amino acid sequence set forth in SEQ ID NO:69–SEQ ID NO:75, the sequence set forth in SEQ ID NO:28–SEQ ID NO:68 or the sequence set forth in SEQ ID NO:128–SEQ ID NO:134.

7. The method of claim 6 wherein the first target protein is a protein kinase C (PKC).

8. The method of claim 6 wherein the first target protein is a β adrenergic receptor kinase (βARK).

9. The method of claim 6 wherein the WD-40 region has the amino acid sequence set forth in SEQ ID NO:69–SEQ ID NO:75.

10. The method of claim 6 wherein the WD-40 region has the amino acid sequence set forth in SEQ ID NO:28–SEQ ID NO:68.

11. The method of claim 6 wherein the WD-40 region has the amino acid sequence set forth in SEQ ID NO:128–SEQ ID NO:134.

12. The method of claim 6 wherein the peptide has the amino acid sequence set forth in SEQ ID NO:13–SEQ ID NO:18.

13. The method of claim 6 wherein the peptide has the amino acid sequence set forth in SEQ ID NO:4 or SEQ ID NO:7.

* * * * *